United States Patent
Dubcovsky et al.

(10) Patent No.: US 7,462,706 B2
(45) Date of Patent: Dec. 9, 2008

(54) GENES RESPONSIBLE FOR VERNALIZATION REGULATION IN TEMPERATE GRASSES AND USES THEREOF

(75) Inventors: Jorge Dubcovsky, Davis, CA (US); Liuling Yan, Davis, CA (US); Artem Loukoianov, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 34 days.

(21) Appl. No.: 10/723,947

(22) Filed: Nov. 26, 2003

(65) Prior Publication Data

US 2004/0205848 A1  Oct. 14, 2004

Related U.S. Application Data

(63) Continuation-in-part of application No. 10/412,137, filed on Apr. 11, 2003, now abandoned.

(51) Int. Cl.
*C12N 15/29* (2006.01)
(52) U.S. Cl. .................................... 536/23.6; 536/24.1
(58) Field of Classification Search ................ 536/23.1, 536/23.6, 24.1; 800/287, 298, 278, 290; 435/320.1, 410, 419, 468
See application file for complete search history.

(56) References Cited

U.S. PATENT DOCUMENTS 6,077,994 A   6/2000   Coupland et al.

FOREIGN PATENT DOCUMENTS

| WO | WO 00/44918 | 8/2000 |
|---|---|---|
| WO | WO 01/21822 A1 | 3/2001 |

OTHER PUBLICATIONS

Kano-Murakami et al (1993, FEBS 334:365-368).*
Bowie et al, Science 247:1306-1310, 1990,*
McConnell et al, Nature 411 (6838):709-713, 2001.*
Schomburg, Fritz M. et al. (Jun. 2001) "FPA, a Gene Involved in Floral Induction in Arabidopsis, Encodes a Protein Containing RNA-Recognition Motifs," The Plant Cell, 13: 1427-1436.
Dubcovsky, J. et al. (1998) "Comparative RFLP mapping of *Triticum monococcum* genes controlling vernalization requirement" *Theor. Appl. Genet.* 97: 968-975.
Dubcovsky, Jorge (2001) "Plant gene cloning may lead to better timing of flowering" *National Research Initiative Research Highlights*, United States Department of Agriculture, No. 2: 2 pages.
Fowler, D. B. et al. (1996) "Relationship between low-temperature tolerance and vernalization response in wheat and rye" *Canadian Journal of Plant Science* 76 (1): 37-42.
Holland, J. B. et al. (2002) "Genomic regions controlling vernalization and photoperiod responses in oat" *Theor. Appl. Genet.* 105: 113-126.
Johansen, Bo et al. (2002) "MADS-box gene evolution- structure and transcription patterns" *Molecular Phylogenetics and Evolution* 23: 458-480.
Murai, Koji et al. (1997) "Wheat MADS box genes, a multigene family dispersed throughout the genome" Genes Genet. Syst. 72: 317-321.
Murai, Koji et al. (2002) "Pistillody, homoeotic transformation of stamens into pistil-like structures, caused by nuclear-cytoplasm interaction in wheat" *The Plant Journal* 29 (2): 169-181.
Patnaik, Debasis and Pramijt Khurana. (2001) "Wheat biotechnology: A minireview" *Electronic Journal of Biotechnology*, Universidad Catolica de Valparaiso (from http://www.ejbiotechnology.info/content/vol4/issue2/full/4/bip/, Mar. 4, 2003: 4 pages).
Peña, Leandro et al. (2001) "Constitutive expression of *Arabidopsis* LEAFY or APETALA1 genes in citrus reduces their generation time" *Nature Biotechnology* 19: 263-267.
Schmitz, Jürgen et al. (2000) "Cloning, mapping and expression analysis of barley MADS-box genes" *Plant Molecular Biology* 42: 899-913.
Tranquilli, G. and J. Dubcovsky (2000) Epistatic Interaction Between Vernalization Genes $Vrn\text{-}A^{m}1$ and $Vrn\text{-}A^{m}2$ in Diploid Wheat. *The Journal of Heredity* 91(4): 304-306.
Yan, L., et al., "Positional Cloning of the Wheat Vernalization Gene VRN1", PNAS 100(10): 6263-6268 (2003).
Danyluk, Jean et al. (Aug. 2003) "TaVRT-1, a Putative Transcription Factor Associated with Vegetative to Reproductive Transition in Cereals" *Plant Physiology* 132: 1-12.
He Y, Michaels SD, Amasino RM (2003) "Regulation of flowering time by histone acetylation in Arabidopsis." Science 302:1751-1754.
Tadege, M. et al. (2001). "Control of Flowering Time by FLC Orthologues in Brassica Napus," *The Plant Journal* 28(5):545-553.

* cited by examiner

*Primary Examiner*—Stuart F. Baum
(74) *Attorney, Agent, or Firm*—Morrison & Foerster LLP

(57) ABSTRACT

Winter wheats require several weeks at low temperature to flower. This process called vernalization is controlled mainly by a pair of genes, VRN1 and VRN2. The present invention includes the sequences of the VRN1 and VRN2 genes, proteins and promoter regions, transgenic plants containing the genes and/or promoters and uses of the foregoing. Of particular interest are temperate cereals with modified vernalization responses or flowering times.

6 Claims, 21 Drawing Sheets

| F₂ family | G2528 | G1777 | AA | | AB | | BB | |
|---|---|---|---|---|---|---|---|---|
| | | | N | D | N | D | N | D |
| #1736 | 0 D | 45 D | 10 | -5/+1 | 16 | -5/0 | 10 | -5/+1 |
| #1897 | 0 D | 60 D | 7 | 35/40 | 22 | -5/0 | 8 | -5/0 |

Figure 7

G2528 (*Vrn1*) = DV92 (*vrn1*)

A. ATGGGGCGCGGGAAGGTGCAGCTGAAGCGGATCGAGAACAAGATCAACCGGCAGGTGACCTTCTCCAAG
CGCCGCTCGGGGCTTCTCAAGAAGGCGCACGAGATCTCCGTGCTCTGCGACGCCGAGGTCGGCCTCATC
ATCTTCTCCACCAAGGGAAAGCTCTACGAGTTCTCCACCGAGTCATGTATGGACAAAATTCTTGAACGG
TATGAGCGCTATTCTTATGCAGAAAAGGTTCTCGTTTCAAGTGAATCTGAAATTCAGGGAAACTGGTGT
CACGAATATAGGAAACTGAAGGCGAAGGTTGAGACAATACAGAAATGTCAAAAACATCTCATGGGAGAG
GATCTTGAATCTTTGAATCTCAAGGAGTTGCAGCAACTGGAGCAGCAGCTGGAAAGCTCACTGAAACAT
ATCAGATCCAGGAAGAACCAACTTATGCACGAATCCATTTCTGAGCTGCAGAAGAAGGAGAGGTCACTG
CAGGAGGAGAATAAAGTTCTCCAGAAGGAACTCGTGGAGAAGCAGAAGGCCCATGCGGCGCAGCAAGAT
CAAACTCAGCCTCAAACCAGCTCTTCTTCTTCTTCCTTCATGCTGAGGGATGCTCCCCCTGCCGCAAAT
ACCAGCATTCATCCAGCGGCGGCAGGCGAGAGGGCAGAGGATGCGGCAGTGCAGCCGCAGGCCCCACCC
CGGACGGGGCTTCCACCGTGGATGGTGAGCCACATCAACGGGTGA (SEQ ID NO: 5)

B. G1777 (*vrn1*) = G3116(*vrn1*)

ATGGGGCGCGGGAAGGTGCAGCTGAAGCGGATCGAGAACAAGATCAACCGGCAGGTGACCTTCTCCAAG
CGCCGCTCGGGGCTTCTCAAGAAGGCGCACGAGATCTCCGTGCTCTGCGACGCCGAGGTCGGCCTCATC
ATCTTCTCCACCAAGGGAAAGCTCTACGAGTTCTCCACCGAGTCATGTATGGACAAAATTCTTGAACGG
TATGAGCGCTATTCTTATGCAGAAAAGGTTCTCGTTTCAAGTGAATCTGAAATTCAGGGAAACTGGTGT
CACGAATATAGGAAACTGAAGGCGAAGGTTGAGACAATACAGAAATGTCAAAAACATCTCATGGGAGAG
GATCTTGAATCTTTGAATCTCAAGGAGTTGCAGCAACTGGAGCAGCAGCTGGAAAGCTCACTGAAACAT
ATCAGATCCAGGAAGAACCAACTTATGCAGGATCCATTTCTGAGCTGCAGAAGAAGGAGAGGTCACTGC
AGGAGGAGAATAAAGTTCTCCAGAAGGAACTCGTGGAGAAGCAGAAGGCCCATGCGGCGCAGCAAGATC
AAACTCAGCCTCAAACCAGCTCTTCTTCTTCTTCCTTCATGCTGAGGGATGCTCCCCCTGCCGCAAATA
CCAGCATTCATCCAGCGGCGGCAGGCGAGAGGGCAGAGGATGCGGCAGTGCAGCCGCAGGCCCCACCCC
GGACGGGGCTTCCACCGTGGATGGTGAGCCACATCAACGGGTGA (SEQ ID NO: 6)

Figure 8

A. G2528 (*Vrn1*) = DV92 (*vrn1*)
MGRGKVQLKRIENKINRQVTFSKRRSGLLKKAHEISVLCDAEVGLIIFSTKGKLYEFSTESCMDKILERYER
YSYAEKVLVSSESEIQGNWCHEYRKLKAKVETIQKCQKHLMGEDLESLNLKELQQLEQQLESSLKHIRSR
KNQLMHESISELQKKERSLQEENKVLQKELVEKQKAHAAQQDQTQPQTSSSSSSFMLRDAPPAANTSIHP
AAAGERAEDAAVQPQAPPRTGLPPWMVSHING* (SEQ ID NO: 7)

B. G1777 (*vrn1*) = G3116(*vrn1*)
MGRGKVQLKRIENKINRQVTFSKRRSGLLKKAHEISVLCDAEVGLIIFSTKGKLYEFSTESCMDKILERYER
YSYAEKVLVSSESEIQGNWCHEYRKLKAKVETIQKCQKHLMGEDLESLNLKELQQLEQQLESSLKHIRSR
KNQLMHGSISELQKKERSLQEENKVLQKELVEKQKAHAAQQDQTQPQTSSSSSSFMLRDAPPAANTSIHP
AAAGERAEDAAVQPQAPPRTGLPPWMVSHING* (SEQ ID NO. 8)

Figure 9A

```
G2528    1  ATTTGCCTCATGAGACGCTTGACAACAGTGTATTGATGGATGTCTGGTCGGTATACACGC
DV92     1  ATTTGCCTCATGAGACGCTTGACAACAGTGTATTGATGGATGTCTGGTCGGTATACACGC
G1777    1  ATTTGCCTCATGAGACGCTTGACAACAGTGTATTGATGGATGTCTGGTCGGTATACACGC
G3116    1  ATTTGCCTCATGAGACGCTTGACAACAGTGTATTGATGGATGTCTGGTCGGTATACACGC

G2528   61  ACAGCACAGTACCCCTACTCCTAGGACTGGCGAGTATCTTTCATTCATTCCAGAAATACG
DV92    61  ACAGCACAGTACCCCTACTCCTAGGACTGGCGAGTATCTTTCATTCATTCCAGAAATACG
G1777   61  ACAGCACAGTACCCCTACTCCTAGGACTGGCGAGTATCTTTCATTCATTCCAGAAATACG
G3116   61  ACAGCACAGTACCCCTACTCCTAGGACTGGCGAGTATCTTTCATTCATTCCAGAAATACG

G2528  121  CGGGTCGGCCAAAAGTAGAAAAATACACTGCGCCCACTCAATCCACGCAGCGCACTGCAC
DV92   121  CGGGTCGGCCAAAAGTAGAAAAATACACTGCGCCCACTCAATCCACGCAGCGCACTGCAC
G1777  121  CGGGTCGGCCAAAAGTAGAAAAATACACTGCGCCCACTCAATCCACGTAGCGCACTGCAC
G3116  121  CGGGTCGGCCAAAAGTAGAAAAATACACTGCGCCCACTCAATCCACGTAGCGCACTGCAC

G2528  181  TGCACAGCAACGCTTCATGTCAAAAGTCGAGCTCAAGCATGCACGCGATGGACGCGGCGC
DV92   181  TGCACAGCAACGCTTCATGTCAAAAGTCGAGCTCAAGCATGCACGCGATGGACGCGGCGC
G1777  181  TGCACAGCAACGCTTCATGTCAAAAGTCGAGCTCAAGCATGCACGCGATGGACGCGGCGC
G3116  181  TGCACAGCAACGCTTCATGTCAAAAGTCGAGCTCAAGCATGCACGCGATGGACGCGGCGC

G2528  241  GAATGACCCGGGCGGCACGACGCGAGTGCCCGCCGCGCCCGCCCGCCTGCCCCGCAGCCG
DV92   241  GAATGACCCGGGCGGCACGACGCGAGTGCCCGCCGCGCCCGCCCGCCTGCCCCGCAGCCG
G1777  241  GAATGACCCGGGCGGCACGACGCGAGTGCCCGCCGCGCCCGCCCGCCTGCCCCGCAGCCG
G3116  241  GAATGACCCGGGCGGCACGACGCGAGTGCCCGCCGCGCCCGCCCGCCTGCCCCGCAGCCG

G2528  301  ACCTCTTCCCAAACGGGACAAGCGAGACGGCCCAAAACGAGCAAGGAAAGCAGCCTCCTA
DV92   301  ACCTCT-CCCAAACGGGACAAGCGAGACGGCCCAAAACGAGCAAGGAAAGCAGCCTCCTA
G1777  301  ACCTCT-CCCAAACGGGACAAGCGAGACGGCCCAAAACGAGCAAGGAAAGCAGCCTCCTA
G3116  301  ACCTCT-CCCAAACGGGACAAGCGAGACGGCCCAAAACGAGCAAGGAAAGCAGCCTCCTA

G2528  361  CTGTGGCAGCCCGCCCCCACGACCGTCATCTCGCCTTCCATTCCATTTTCCCTGGACGGA
DV92   360  CTGTGGCAGCCCGCCCCCACGACCGTCATCTCGCCTTCCATTCCATTTTCCCTGGACGGA
G1777  360  CTGTGGCAGCCCGCCCCCACGACCGTCATCTCACCCTCCATTCCATTTTCCCTGGACGGA
G3116  360  CTGTGGCAGCCCGCCCCCACGACCGTCATCTCACCCTCCATTCCATTTTCCCTGGACGGA

G2528  421  CCAGACCCGTCCGAGCCGCCCTGACCTAGCCAGCCAGCATTTCCTCTTTCGTCCCCCGCC
DV92   420  CCAGACCCGTCCGAGCCGCCCTGACCTAGCCAGCCAGCATTTCCTCTTTCGTCCCCCGCC
G1777  420  CCAGACCCGTCCGAGCCGCCCTGACCTAGCCAGCCAGCATTTCCTCTTTCGTCCCCCGCC
G3116  420  CCAGACCCGTCCGAGCCGCCCTGACCTAGCCAGCCAGCATTTCCTCTTTCGTCCCCCGCC

G2528  481  GCCGTGACCAAAAAAGCAAAAAGGAAAAAGGGAAAATGCTAAAGGAAAAAACTCCGCTC
DV92   480  GCCGTGACCAAAAAAGCAAAAAGGAAAAAGGGAAAATGCTAAAGGAAAAAACTCCGCTC
G1777  480  GCCGTGACCAAAAAAGCAAAAAGGAAAAAGGGAAAATGCTAAAGGAAAAAACTCCGCTC
G3116  480  GCCGTGACCAAAAAAGCAAAAAGGAAAAAGGGAAAATGCTAAAGGAAAAAACTCCGCTC

G2528  541  TTTCCCTTCTTCTAGGCCTAGGGTACAGTAGAATATTATAAAAGGAAAAATTCTGCTCGT
DV92   540  TTTCCCTTCTTCTAGGCCTAGGGTACAGTAGAATATTATAAAAGGAAAAATTCTGCTCGT
G1777  540  TTTCCCTTCTTCTAGGCCTAGGGTACAGTAGAATATTATAAAAGGAAAAATTCTGCTCGT
G3116  540  TTTCCCTTCTTCTAGGCCTAGGGTACAGTAGAATATTATAAAAGGAAAAATTCTGCTCGT

G2528  601  TTTTTGCTCTGTGGTGTGTGTTTGTGGCGAGAGAAAATGATTTGGGGAAAGCAAAATCGG
DV92   600  TTTTTGCTCTGTGGTGTGTGTTTGTGGCGAGAGAAAATGATTTGGGGAAAGCAAAATCGG
G1777  600  TTTTTGCTCTGTGGTGTGTGTTTGTGGCGAGAGAAAATGATTTGGGGAAAGCAAAATCGG
G3116  600  TTTTTGCTCTGTGGTGTGTGTTTGTGGCGAGAGAAAATGATTTGGGGAAAGCAAAATCGG

G2528  661  GAGATTCGCACGTACGATCGTTCGACACGTCGACGCCCGGCGGGCCCGTGGTGGGGCATC
DV92   660  GAGATTCGCACGTACGATCGTTCGACACGTCGACGCCCGGCGGGCCCGTGGTGGGGCATC
G1777  660  GAGATTCGCACGTACGATCGTTCGACACGTCGACGCCCGGCGGGCCCGTGGTGGGGCATC
G3116  660  GAGATTCGCACGTACGATCGTTCGACACGTCGACGCCCGGCGGGCCCGTGGTGGGGCATC
```

Figure 9B

```
G2528    721  GTGTGGCTGCAGGACCGCGGGGCCCCGCGGGGCGGGCCGGGCCAATGGGTGCTCGACAGC
DV92     720  GTGTGGCTGCAGGACCGCGGGGCCCCGCGGGGCGGGCCGGGCCAATGGGTGCTCGACAGC
G1777    720  GTGTGGCTGCAGGACCGCGGGGCCCCGCGGGGCGGGCCGGGCCAATGGGTGCTCGACAGC
G3116    720  GTGTGGCTGCAGGACCGCGGGGCCCCGCGGGGCGGGCCGGGCCAATGGGTGCTCGACAGC

G2528    781  GGCTATGCTCCAGACCAGCCCGGTATTGCATACCGCGCTCGGGGCCAGATCCCTTTAAAA
DV92     780  GGCTATGCTCCAGACCAGCCCGGTATTGCATACCGCGCTCGGGGCCAGATCCCTTTAAAA
G1777    780  GGCTATGCTCCAGACCAGCCCGGTATTGCATACCGCGCTCGGGGCCAGATCCCTTTAAAA
G3116    780  GGCTATGCTCCAGACCAGCCCGGTATTGCATACCGCGCTCGGGGCCAGATCCCTTTAAAA

G2528    841  ACCC--------------------TCGTTTTGGCCTGGCCATCCTCCCTCTCCTCCCCTC
DV92     840  ACCCCTCCCCCCCTGCCGGAACCCTCGTTTTGGCCTGGCCATCCTCCCTCTCCTCCCCTC
G1777    840  ACCCCTCCCCCCCTGCCGGAACCCTCGTTTTGGCCTGGCCATCCTCCCTCTCCTCCCCTC
G3116    840  ACCCCTCCCCCCCTGCCGGAACCCTCGTTTTGGCCTGGCCATCCTCCCTCTCCTCCCCTC

G2528    881  TCTTCCACCTCACCCAACCACCTGATAGCCATGGCTCCGCCGCCTCGCCTCCGCCTGCGC
DV92     900  TCTTCCACCTCACCCAACCACCTGATAGCCATGGCTCCGCCGCCTCGCCTCCGCCTGCGC
G1777    900  TCTTCCACCTCACCCAACCACCTGATAGCCATGGCTCCGCCGCCTCGCCTCCGCCTGCGC
G3116    900  TCTTCCACCTCACCCAACCACCTGATAGCCATGGCTCCGCCGCCTCGCCTCCGCCTGCGC

G2528    941  CAGTCGGAGTAGCCGTCGCGGTCTGCGGGTGTTGGAGGGTAGGGGCGTAGGGTTGGCCCG
DV92     960  CAGTCGGAGTAGCCGTCGCGGTCTGCGGGTGTTGGAGGGTAGGGGCGTAGGGTTGGCCCG
G1777    960  CAGTCGGAGTAGCCGTCGCGGTCTGCGGGTGTTGGAGGGTAGGGGCGTAGGGTTGGCCCG
G3116    960  CAGTCGGAGTAGCCGTCGCGGTCTGCGGGTGTTGGAGGGTAGGGGCGTAGGGTTGGCCCG

G2528   1001  GTTCTCGAGCGGAGATG  Start codon (SEQ ID NO: 9)
DV92    1020  GTTCTCGAGCGGAGATG  Start codon (SEQ ID NO: 10)
G1777   1020  GTTCTCGAGCGGAGATG  Start codon (SEQ ID NO: 11)
G3116   1020  GTTCTCGAGCGGAGATG  Start codon (SEQ ID NO: 12)
```

Transgenic Jagger cDNAs

Transgenic Bobwhite cDNAs

| | | | |
|---|---|---|---|
| ZCCT1_TmDV92 | EREAKVMRYREKRKRRRYDKQIRYESRKAYAELRPVNGRFVKV | | (SEQ ID NO: 117) |
| ZCCT1_TmG3116 | EREAKVMRYREKRKRRRYDKQIRYESRKAYAELRPRVNGRFVKV | | (SEQ ID NO: 118) |
| ZCCT1_Td | EREAKVMRYREKRKRRRYDKQIRYESRKAYAELRPRVNGRFVKV | | (SEQ ID NO: 119) |
| ZCCT2_Tm | EREAKVMRYREKRKRRYDKQIRYESRKAYAELRPRVNGRFVKV | | (SEQ ID NO: 120) |
| ZCCT2_Td | EREAKVMRYREKRKRRYDKQIRYESRKAYAELRPRVNGRFVKV | | (SEQ ID NO: 121) |
| ZCCT2_Hb(Fan) | EREAKVMRYREKRKKRRYDKQIRYESRKAYAELRPRVNGRFVKV | | (SEQ ID NO: 122) |
| ZCCT2_Ha | EREAKVMRYREKRKRRRYDKQIRYESRKAYAELRPVNGRFVKV | ZCCT | (SEQ ID NO: 123) |
| OsI | EREAKVMRYVEKRKKRVEKQIRYVSRKAYAERPRVGRFVK | | (SEQ ID NO: 124) |
| HvCO9 | EREAKVMRYVEKRKRRYEKQIRYVSRKAYAERPVKGRFAKV | | (SEQ ID NO: 125) |
| OsH | EREAKVMRYVEKRKRRYVKQIRYASRKAYAERPRVKGRFAKV | Group IV | (SEQ ID NO: 126) |
| AtCO | EREAVVRYREKRKTRKEEKIIRYVSRKAYAELRPRVNGRFAKR | | (SEQ ID NO: 127) |
| OsHd1 | EREAKVRYREKKKARKEEKIIRYESRKAYABRPRIKGRFRKR | | (SEQ ID NO: 128) |
| HvCO1 | EREAKVERYVEKKKRKEEKVRYVRKAYABARPRIKGRFAKR | Group Ia | (SEQ ID NO: 129) |
| HvCO3 | DREARVIRYREKRKMRREEKIIRYASRKAYAELRPRIKGRFRKR | | (SEQ ID NO: 130) |
| OsB | DREAKVIRYREKRKIRREEKIIRYASRKAYAELRPRLKGRFRKR | Group Ib | (SEQ ID NO: 131) |
| HvCO4 | EREARIMRYREKRKQRREEKIIRYASRKAYAELRPRVKGRFAKR | | (SEQ ID NO: 132) |
| OsC | EREARIMRYREKRKRRLEKIIRYASRKAYAELRPRVKGRFAKR | | (SEQ ID NO: 133) |
| AtCOL3 | EREAKVIRYREKRKVRKEEKIIRYASRKAYAELRPRIKGRFAKR | Group Ic | (SEQ ID NO: 134) |
| HvCO7 | GREARIMRYREKRKIRRFEKIIRYASRKAYAESRPRVTGRFAKR | | (SEQ ID NO: 135) |
| OsF | GRLARIMRYREKRKIRRFEKIIRYASRKAYAELRPRVKGRFAKR | Group Id | (SEQ ID NO: 136) |
| HvCO8 | DLAARVMRYREKRKIRKDHKIIRYASRKAYAEARPRIKGRFVKR | | (SEQ ID NO: 137) |
| OsG | PREAKVMRYREKRKNKEFHKLIRYASRKAYAEARPRLKGRFVKR | Group Ie | (SEQ ID NO: 138) |
| AtCOL6 | GREARVSRYREKRRTRLLSKKIRYEVRKLNAEKRPRVKGRFVKR | | (SEQ ID NO: 139) |
| OsJ | EREAKVSRYREKRPTRLLAKKIRYEVRKLNAEKRPRVKGRFVKR | Group II | (SEQ ID NO: 140) |
| AtCOL9 | TRNNAVMRYLEKKKARKEDKRVRYASRKARADVRPRVKGRFVKA | | (SEQ ID NO: 141) |
| OsN | SRDNALIRYLEKKKRRIGDKKIRYASRKARADVRKRVKGRFVKA | Group III | (SEQ ID NO: 142) |

Tm=*T. monococcum*, Td=*T. dicoccoides* A genome, Hv=*Hordeum vulgare*, Os=*O. sativa.*

```
ZCCT1_Td_A      MSMSCGLCGANNCPRLMVSPIHHHHHHHQEHQL  Hx₃H position not certain
                                                        (SEQ ID NO: 143)
ZCCT1_DV92      MSMSCGLCGANNCPRLMVSPIHHHHHHHQEHQL  Hx₃H position not certain
                                                        (SEQ ID NO: 144)
ZCCT1_G3116     MSMSCGLCGANNCPRLMVSPIHHHHHHHQEHQL  Hx₃H position not certain
                                                        (SEQ ID NO: 145)
ZCCT-Hb(Fan)    MSMACGLCGASNCPYHMMSPVDLHHHHHQEHRL  Hx₃H position not certain
                                                        (SEQ ID NO: 146)
ZCCT-Ha         MSMSCGLCGASNCYHMMSPVEHHHHHQEHTL    Hx₃H position not certain
                                                        (SEQ ID NO: 147)
ZCCT2_Td_B      MSMSCGLCGASNCPHHMISPVQHHHHHQEHRL   Hx₃H position not certain
                                                        (SEQ ID NO: 148)
ZCCT2_DV92      MSMSCGLCGASDCPHHMISPVQHQEQHWEREY        (SEQ ID NO: 149)
ZCCT2_Td_A      MBMSCGLCGASDCPHHMISPVQHQEQHRLREY        (SEQ ID NO: 150)
```

*CO*-LIKE GROUP IV (Yellow highlight: similar ZCCT)

```
OsI  (SEQ ID NO: 151)  MGMANEESPNYQVKKGGRIPPRSSLIYPFMSMGPAAGEGCGLCGADGGGCCSRHRHD
OsH  (SEQ ID NO: 152)                               MSAASGAACGVCGGGVGECGCLLHQRRG
```

*CO*-LIKE Group I, II, III

```
HvCO1  (SEQ ID NO: 153)       MNCVSNGTVYEEAVGREGRWARLCDGCCTVPSVVYCRADSAYLCASCDA
HvCO3  (SEQ ID NO: 154)  MIKAEPDLRGQLRGSAGVGGMQLQQRCDSCRSAPCAFYCRADSAALCAACDA
HvCO4  (SEQ ID NO: 155)       MEGEEKPVVGGAYWGVGARACDSCATEAARLFCRADAAFLCAGCDA
       (SEQ ID NO: 156)           RAHGSGSRHARVWLCEVCEHAPAAVTCKADAAVLCASCDA
OsJ    (SEQ ID NO: 157)       MASAAAATGAALGARTARACDGCMRRRARWHCPADDAFLCQACDA
OsN    (SEQ ID NO: 158)  MDALCDFCREQRSMVYCRSDAASLCLSCDRNVHSANALSRRHTRTLLCDRCVGQ
       (SEQ ID NO: 159)           PAAVRCLEENTSLCQNCDWNGHGAASSAAGHKRQTINCYSGCP
```

US 7,462,706 B2

GENES RESPONSIBLE FOR VERNALIZATION REGULATION IN TEMPERATE GRASSES AND USES THEREOF

RELATED APPLICATIONS

This application is a continuation-in-part application of U.S. application Ser. No. 10/412,137, filed Apr. 11, 2003, which is incorporated by reference herein its entirety.

GOVERNMENT INTEREST

This invention was made with Government support under Grant (or Contract) No. 00-35300-9565 awarded by the USDA-NRI. The Government has certain rights in the invention.

FIELD OF THE INVENTION

This invention is in the field of plant breeding and plant molecular biology. In particular, this invention relates to non-naturally occurring plants with an altered response to vernalization or flowering time, and to molecular markers for the natural occurring alleles of the vernalization genes.

BACKGROUND OF THE INVENTION

Little is known about the molecular regulation of the vernalization response in grasses. If the molecular mechanism of the vernalization response was better understood, the response could be engineered to alter a plant's response to vernalization to improve flowering, growth efficiency and, ultimately, yield. Also, being able to control flowering may allow better control over breeding of plants. There is thus a tremendous need to identify molecular factors involved with a plant's response to vernalization. In addition, there is a need to identify promoters involved in the vernalization response and factors that regulate such promoters.

SUMMARY OF THE INVENTION

In order to meet these needs, the present invention is directed to the finding that the AP1 promoter controls the vernalization response in wheat. The "AP1 promoter sequence" as defined herein refers to any sequence that hybridizes to the nucleic acid molecule of SEQ ID NO:12 (FIG. 9) or the complement thereof under at least low stringency, preferably moderate, high or very high stringency conditions, or any sequence that includes the critical regulatory recognition sites for vernalization present in SEQ ID NO:12, including the CCTCGTTTTGG (SEQ ID NO:23) sequence located −162 to −172 bp upstream from the start codon of the AP1gene. This 11-bp region will be referred hereafter as the "CArG-box". In addition, the "AP1 promoter sequence" may also include sequences sharing at least 75%, 80%, 85%, 90%, 95%, or 97% identity with SEQ ID NO:12. The present invention is thus directed to a recombinant AP1 promoter sequence such as those depicted in FIGS. 9A-B and 11. In particular, the present invention is directed to recombinant AP1 promoters and their use in plant molecular biology and plant breeding. In a first format, the recombinant AP1 promoter sequence with all or a portion of the CArG box may be operably linked to any heterologous protein coding sequence and introduced into a plant to regulate the expression of the protein by vernalization.

In a second format, the AP1 promoter with or without part or all of the CArG box may be operably linked to an AP1 protein encoding sequence and introduced into a plant to modify flowering time or the vernalization requirement in the plant. The AP1 protein encoding sequences of the invention include those sequences that hybridize under high stringency conditions to a nucleic acid selected from SEQ ID NO:5, SEQ ID NO:6, SEQ ID NO:18 and SEQ ID NO:22. The AP1 protein coding sequences may encode AP1 proteins such as those having polypeptide sequences selected from SEQ ID NO: 7, 8, 19, 20 and 21.

The recombinant AP1 promoter sequences of the invention may be cloned into a vector. The vector may be introduced into a cell. The cell may be a prokaryotic cell or a eukaryotic cell. In a preferred format, the cell is a plant cell.

The recombinant AP1 promoter sequences may be introduced into a transgenic plant. The transgenic plant may be transgenic wheat, barley, rye, oats, or forage grasses. The invention is further directed to seed from the transgenic plants of the invention.

The present invention is further directed to a method for altering a plant's response to vernalization or its flowering time. A plant's response to vernalization is said to be altered when the requirement of vernalization or the effect of vernalization in the acceleration of flowering is modified by the expression of a heterologous protein in the plant. The method of the invention includes, as a first step, transforming a plant or plant tissue with a genetic construct having a recombinant AP1 promoter sequence operably linked to a recombinant heterologous protein sequence. The AP1 promoter sequence may lack all or a portion of nucleotides −162 to −172 upstream of the start codon of SEQ ID NO:12. In the method of the invention, the recombinant protein sequence may be an AP1 protein-encoding sequence or any other useful heterologous protein. The method includes, as a second step, expressing the genetic construct in the plant to alter the plant's response to vernalization or its flowering time independently of vernalization. The plant may be selected from wheat, barley, rye, oats and forage grasses.

The present invention is further directed to molecular markers for Vrn1 derived from a gene selected from the group of genes depicted in FIG. 1.

Another aspect of the present invention is the Vrn2 gene and the ZCCT1 protein produced from the gene. This gene is a repressor of flowering and its RNA abundance decreases during vernalization (FIG. 14). The gene may be in a vector or transgenically expressed in plants. The gene is preferably operably linked to a promoter that may be an inducible promoter, a regulated promoter, or a constitutive promoter. The ZCCT1 coding sequences and flanking regulatory sequences of the invention include those sequences that hybridize under at least low stringency and preferably moderate, high, or very high stringency conditions to a nucleic acid selected from SEQ ID NO:74, 75, 78, and 79. In another embodiment of the presenting invention, the ZCCT1 coding sequences and flanking sequences also include those sequences with at least 75% sequence identity and preferably at least 80%, at least 85%, at least 90%, or at least 95% sequence identity with a nucleotide sequence selected from SEQ ID NO:74, 75, 78, and 79. The present invention also includes the protein sequences selected from SEQ ID NO:76, 77, and 80 as well as protein sequences with at least 75% sequence identity and preferably at least 80%, at least 85%, at least 90%, or at least 95% sequence identity with a protein sequence selected from SEQ ID NO:76, 77, and 80. The present invention further includes nucleic acid sequences encoding the above protein sequences.

Yet another aspect of the present invention includes ZCCT-related proteins and nucleic acids encoding such proteins.

The ZCCT-related proteins are proteins with structural homology to ZCCT1 proteins that have at least one ZCCT1 activity including the ability to repress expression of AP1 in temperate grasses, the ability to interfere with the endogenous ZCCT1 activity such as by competitively binding the ZCCT1 DNA binding site or having the repressor activity of ZCCT1. Nucleic acids encoding ZCCT-related proteins may be in a vector or transgenically expressed in plants. Such nucleic acids are preferably operably linked to a promoter that may be an inducible promoter, a regulated promoter, or a constitutive promoter. The ZCCT-related protein coding sequences and flanking regulatory sequences of the invention include those sequences that hybridize under at least low stringency and preferably moderate, high, or very high stringency conditions to a nucleic acid selected from SEQ ID NO:74, 75, 78, 79, 81, 82, 84, 85, 87, 88, 90, and 91. In another embodiment of the presenting invention, the ZCCT-related protein coding sequences and flanking sequences also include those sequences with at least 75% sequence identity and preferably at least 80%, at least 85%, at least 90%, or at least 95% sequence identity with a nucleotide sequence selected from SEQ ID NO: 74, 75, 78, 79, 81, 82, 84, 85, 87, 88, 90, and 91. The present invention also includes the protein sequences selected from SEQ ID NO:76, 77, 80, 83, 86, 89, and 92 as well as protein sequences with at least 75% sequence identity and preferably at least 80%, at least 85%, at least 90%, or at least 95% sequence identity with a protein sequence selected from SEQ ID NO: 76, 77, 80, 83, 86, 89, and 92. The present invention further includes nucleic acid sequences encoding the above protein sequences.

In still another aspect, the promoter regions from ZCCT1 or ZCCT-related protein encoding genes as described above may be operably linked to a heterologous gene. Such constructs may be in a vector. The vector may be introduced into a cell. The cell may be a prokaryotic cell or a eukaryotic cell. In a preferred format, the cell is a plant cell.

In another aspect, flowering in wheat or other temperate grasses may be regulated by stimuli other than vernalization. This may be achieved by replacement of the endogenous AP1 gene with an AP1 gene operably linked to an inducible promoter. Thus, expression of the AP1 gene may be induced in response to exposure to a particular stimulus such as pathogen exposure, wounding, heat exposure, chemical exposure, etc. so that the plant will flower at a controlled time or under certain conditions. In addition, controlled flowering may be achieved by addition of a ZCCT-related protein coding gene operably linked to an inducible promoter. Then removal of the stimulus that increases expression of the ZCCT1 repressor can stimulate flowering by derepression of AP1. In yet another embodiment, the expression of the AP1 gene or the ZCCT1 gene may be regulated by RNAi or antisense gene operably linked to an inducible promoter.

In yet another aspect of the present invention, a plant that normally requires vernalization, such as winter wheat, may be modified to no longer require vernalization in order to flower. Such plants may be generated by a number of methods. In one embodiment, the plant may be supplied with an AP1 promoter that is not repressed prior to vernalization operably linked to an AP1 gene. In another embodiment, the plant's endogenous ZCCT1 activity may be inhibited. The ZCCT1 activity may be inhibited by a wide variety of methods. Examples include repression with RNAi or antisense gene expression, knockout of the ZCCT1 gene or promoter, overexpression of a repression defective ZCCT-related protein that competes with the endogenous ZCCT1 for the ZCCT1 DNA binding site, overexpression of a DNA binding defective ZCCT-related protein that competes with the endogenous ZCCT1 for associated proteins involved in repressing AP1, or replacement of the endogenous ZCCT1 protein with a defective ZCCT1 protein by homologous recombination for example.

In still another aspect, plants that never flower may be generated for use as forage or in situations where flowing is not desired such as golf courses. Such plants may be generated by expression of a ZCCT-related protein operably linked to a constitutive promoter. In another embodiment, the AP1 activity may be permanently repressed by RNAi or antisense gene expression.

BRIEF DESCRIPTION OF THE DRAWINGS

FIG. 1A depicts a genetic map of the VRN1 region on chromosome 5A$^m$ of $T.$ $monococcum$. Genetic distances are in cM (6,190 gametes). FIG. 1B-D depict physical maps of the collinear VRN1 regions in rice, sorghum, and wheat. Regions indicated in red have been sequenced. Double dot lines indicate gaps in the current physical maps. FIG. 1B shows the sequence of the collinear region in rice chromosome 3. FIG. 1C shows $S.$ $bicolor$ BACs 170F8 (AF503433) and 17E12 (AY188330). FIG. 1D shows a $T.$ $monococcum$ physical map. BAC clones order from left to right is: 49I16, 115G1, 136F13, 133P9, 116F2, 89E14, 160C18, 491M20, 328O3, 609E6, 393O11, 719C13, 454P4, 54K21, 579P2, 601A24, 231A16, 638J12, 52F19, 242A12, 668L22, 539M19, and 309P20 (bold letters indicate sequenced BACs). Black dots indicate validation of BAC connections by hybridization. FIG. 1E shows the gene structure of two MADS-box genes completely linked to the VRN1 gene (AY188331, AY188333). Bars represent exons. FIG. 1F shows the sequence comparison of the AP1 promoter regions from genotypes carrying the Vrn1 and vrn1 alleles, and from two $T.$ $monococcum$ accessions with additional deletions (SEQ ID NO:1-4). Deletions in the promoters in SEQ ID 2 and 3 have been found to be completely linked to the Vrn1 allele for spring growth habit. Linkage between SEQ ID 4 and the Vrn1 allele for spring growth habit has not been determined yet. Numbers indicate distances from the start codon. A putative MADS-box protein-binding site (CArG-box) is highlighted.

FIG. 7A-7B depicts allelic variation in the diploid wheat AP1 DNA sequences. The bolded and underlined nucleotide indicates the only polymorphism in the coding region. FIG. 7A depicts the sequence of G2528 (vrn1)=DV92 (vrn1) (SEQ ID NO:5). FIG. 7B depicts the sequence of G1777 (vrn1)=G3116 (vrn1) (SEQ ID NO:6).

FIG. 8A-8B depicts allelic variation in the wheat AP1 protein sequence. The bolded and underlined amino acid indicates a difference in the sequence. FIG. 8A depicts the sequence of G2528 (vrn1)=DV92 (vrn1) (SEQ ID NO:7). FIG. 8B depicts the sequence of G1777(vrn1)=G3116 (vrn1) (SEQ ID NO:8).

FIGS. 9A and 9B depict allelic variation in the AP1 promoter region. G2528: Vrn1 allele (SEQ ID NO:9), DV92=G1777=G3116=vrn1 allele (SEQ ID NO:10-12); ATTTGCCT End of the 401-bp repetitive element; GA host duplication created by the insertion of the repetitive element Highlighted: differences between Vrn1 and vrn1 genotypes. Underlined: 5' UTR based on alignment with ESTs BF429319 and BF484655

In FIG. 14D, plants were moved to the light after 24 h in the dark. In FIG. 14E, plants were moved to the dark after 8 h in the light. Units for the Y-axis in the quantitative PCR experiments (B, C, D, and E) are linearized values using the $2^{(-\Delta\Delta C_T)}$ method, where $C_T$ is the threshold cycle.

FIG. 15A bottom shows RT-PCR with primers for the translated PolyA region from the vector used in the RNAi transformation. RNA was extracted from transgenic winter wheat Jagger transformed with an RNA interference construct for ZCCT1. The primers were designed for the translated PolyA region from the vector used in the RNAi transformation. Progeny from the transgenic plant (34 positive and 11 negative) showed perfect cosegregation of the presence of the transgene and early flowering.

FIG. 18A shows a comparison of CCT domains from ZCCT and CO-like genes. Light blue indicates amino acids mainly conserved in the ZCCT genes and green indicates amino acids conserved mainly in the CO-like proteins. The arrowhead indicates the location of the EMS mutation in *Arabidopsis* co-7 and the R to W mutation in DV92.

FIG. 18B shows a comparison of putative Zinc fingers. Underlined indicates primer sequence, light blue indicate putative zinc fingers.

BRIEF DESCRIPTION OF THE SEQUENCE LISTING

Figure 1:
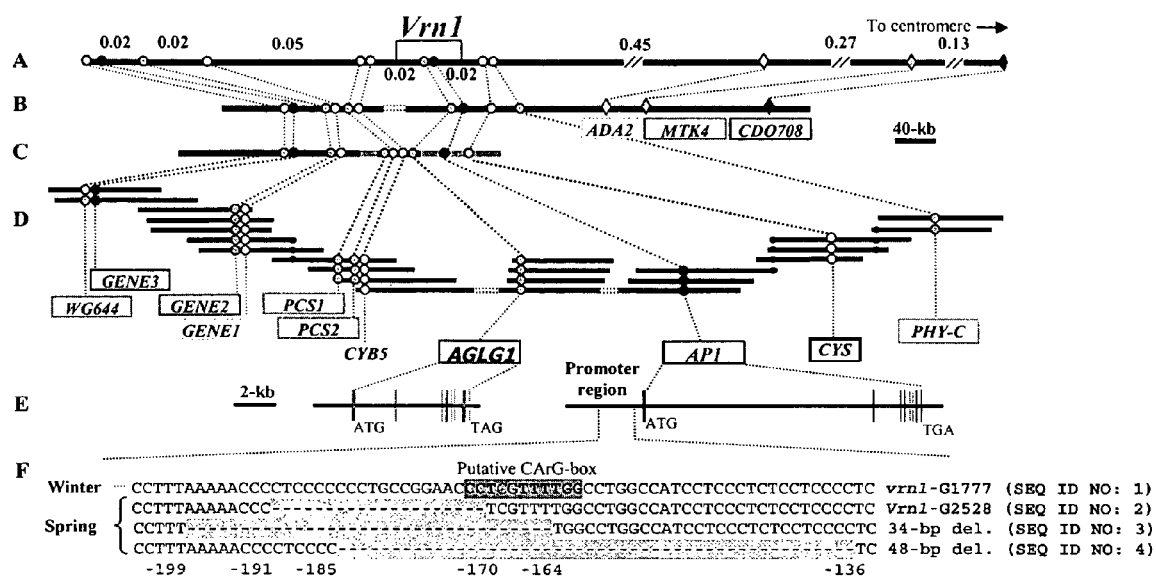
FIG. 1A-1F depicts physical maps of the VRN1 regions of various plants.

The following list of sequences are grouped according to the nature of the sequence. The list does not include sequences used as PCR primers or sequences used in sequence comparisons.

SEQ ID NO:5 is the protein encoding nucleotide sequence of the AP1 from wheat DV92.

SEQ ID NO:6 is the protein encoding nucleotide sequence of the AP1 from wheat G3116.

SEQ ID NO:7 is the protein sequence of the AP1 from wheat DV92.

SEQ ID NO:8 is the protein sequence of the AP1 from wheat G3116.

SEQ ID NO:9 is the nucleotide sequence of the AP1 promoter region from wheat G2528.

SEQ ID NO:10 is the nucleotide sequence of the AP1 promoter region from wheat DV92.

SEQ ID NO:11 is the nucleotide sequence of the AP1 promoter region from wheat G1777.

SEQ ID NO:12 is the nucleotide sequence of the AP1 promoter region from wheat G3116.

SEQ ID NOs:13-17 are the nucleotide sequences from the AP1 promoter regions from *T. monococcum* including winter recessive G1777 and spring growth accessions G2528, PI 349049, PI355515, and PI503874.

SEQ ID NOs:109-116 are the nucleotide sequences from the AP1 promoter regions of the genomes -A, -B, and -D of the winter Triple Dirk line, the spring cultivar Anza (duplication of promoter regions with SEQ ID 112 and 113), Marquis PI94548, *T. dicoccoides* (Accession FA15-3), and *T. timopheevii*.

SEQ ID NO:18 is the protein encoding nucleotide sequence of the AP1 from barley.

SEQ ID NO:19 is the protein sequence of the AP1 from barley.

SEQ ID NO:20 is the protein sequence of the AP1 from hexaploid wheat.

SEQ ID NO:21 is the protein sequence of the AP1 from *Lolium temulentum*.

SEQ ID NO:22 is the protein encoding nucleotide sequence of the AP1 from *Lolium temulentum*.

SEQ ID NO:23 is the nucleotide sequence of the CArG-box from the AP1 promoter.

SEQ ID NO:74 is the genomic DNA sequence including the promoter region of ZCCT1 from *T. monococcum* DV92.

SEQ ID NO:75 is the predicted cDNA sequence of ZCCT1 from *T. monococcum* DV92.

SEQ ID NO:76 is the protein sequence of a nonfunctional ZCCT1 with a R to W mutation from *T. monococcum* DV92.

SEQ ID NO:77 is the protein sequence of a functional ZCCT1 from *T. monococcum* G3116.

SEQ ID NO:78 is the genomic DNA sequence including the promoter region of ZCCT1 from Langdon (tetraploid wheat).

SEQ ID NO:79 is the predicted cDNA sequence of ZCCT1 from Langdon (tetraploid wheat).

SEQ ID NO:80 is the protein sequence ZCCT1 from Langdon (tetraploid wheat).

SEQ ID NO:81 is the genomic DNA sequence including the promoter region of ZCCT2 from *T. monococcum* DV92.

SEQ ID NO:82 is the predicted cDNA sequence of ZCCT2 from *T. monococcum* DV92.

SEQ ID NO:83 is the protein sequence of ZCCT2 from *T. monococcum* DV92.

SEQ ID NO:84 is the genomic DNA sequence including the promoter region of ZCCT2 from Langdon (tetraploid wheat).

SEQ ID NO:85 is the predicted cDNA sequence of ZCCT2 from Langdon (tetraploid wheat).

SEQ ID NO:86 is the protein sequence of ZCCT2 from Langdon (tetraploid wheat).

SEQ ID NO:87 is the genomic DNA sequence including the promoter region of ZCCT-Ha from winter barley (Dairokkaku).

SEQ ID NO:88 is the predicted cDNA sequence of ZCCT-Ha from winter barley (Dairokkaku).

SEQ ID NO:89 is the protein sequence of ZCCT-Ha from winter barley (Dairokkaku).

SEQ ID NO:90 is the genomic DNA sequence including the promoter region of ZCCT-Hb from winter barley (Dairokkaku).

SEQ ID NO:91 is the predicted cDNA sequence of ZCCT-Hb from winter barley (Dairokkaku).

SEQ ID NO:92 is the protein sequence of ZCCT-Hb from winter barley (Dairokkaku).

DETAILED DESCRIPTION OF THE INVENTION

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Throughout this disclosure, various publications, patents and published patent specifications are referenced. The disclosures of these publications, patents and published patent specifications are hereby incorporated by reference into the present disclosure to more fully describe the state of the art to which this invention pertains. The practice of the present invention will employ, unless otherwise indicated, conventional techniques of plant breeding, immunology, molecular biology, microbiology, cell biology and recombinant DNA, which are within the skill of the art. See, e.g., Sambrook et al. (1989), Ausubel et al. (1987), Hayward et al. (1993), Coligan et al. (1995), MacPherson et al. (1995), Harlow and Lane (1988) and Freshney (1987).

Unless otherwise noted, technical terms are used according to conventional usage. Definitions of common terms in molecular biology may be found in Lewin (1994); Kendrew et al. (1994); Meyers (1995); Ausubel et al. (1987); and Sambrook et al (1989).

In order to facilitate review of the various embodiments of the invention, the following definitions are provided:

AP1 protein or AP1 polypeptide: An AP1 protein or AP1 polypeptide is a protein encoded by the floral meristem identity gene APETALA1 (AP1). In *Arabidopsis*, mutations in AP1 result in replacement of a few basal flowers by inflorescence shoots that are not subtended by leaves. An apical flower produced in an ap1 mutant has an indeterminate structure in which a flower arises within a flower.

The present invention may be practiced using nucleic acid sequences that encode full length AP1 proteins as well as AP1 derived proteins that retain AP1 activity. The preferred AP1 proteins are wheat derived. AP1 derived proteins which retain AP1 biological activity include fragments of AP1, generated either by chemical (e.g. enzymatic) digestion or genetic engineering means; chemically functionalized protein molecules obtained starting with the exemplified protein or nucleic acid sequences, and protein sequence variants, for example allelic variants and mutational variants, such as those produced by in vitro mutagenesis techniques, such as gene shuffling (Stemmer et al, 1994a, 1994b). Thus, the term "AP1 protein" encompasses full-length AP1 proteins, as well as such AP1 derived proteins that retain AP1 activity.

Representative but non-limiting AP1 sequences useful in the invention include the wheat AP1 DNA sequences depicted in FIGS. 7A and 7B and the corresponding protein sequences depicted in FIGS. 8A and 8B.

Also encompassed within the definition of AP1 sequences include the barley AP1 protein (BM5 AJ249144) encoded by the following sequence:

```
ATGGGGCGCAGGAAGGTGCAGCTGAAGCGGATCGAGAACAAGATCAACCGCCAGGTCACCTTCTCCAAGCGC    (SEQ ID NO: 18)

CGCTCGGGGCTGCTCAAGAAGGCGCACGAGATCTCCGTGCTCTACGACGCCGAGGTCGGCCTCATCATCTTCT

CCACCAAGGGAAAGCTCTACGAGTTCTCCACCGAGTCATGTATGGACAAAATTCTTGAACGGTATGAGCGCTA

CTCTTATGCAGAAAAGGTTCTCGTTTCAAGTGAATCTGAAATTCAGGGAAACTGGTGTCACGAATATAGGAAA

CTGAAGGCGAAGGTTGAGACAATACAGAAATGTCAAAAGCATCTCATGGGAGAGGATCTTGAATCTTTGAATC

TCAAGGAGTTGCAGCAACTGGAGCAGCAGCTGGAAAGCTCACTGAAACATATCAGAGCCAGGAAGAACCAACT

TATGCACGAATCCATTTCTGAGCTTCAGAAGAAGGAGAGGTCACTGCAGGAGGAGAATAAAGTTCTCCAGAAG

GAACTTGTGGAGAAGCAGAAGGCCCAGGCGGCGCAGCAAGATCAAACTCAGCCTCAAACCAGCTCTTCTTCTT

CTTCCTTCATGATGAGGGATGCTCCCCCTGTCGCAGATACCAGCAATCACCCAGCGGCGGCAGGCGAGAGGG

CAGAGGATGTGGCAGTGCAGCCTCAGGTCCCACTCCGGACGGCGCTTCCACTGTGGATGGTGAGCCACATCA

ACGGCTGA
```

The corresponding barley AP1 protein (Hv BM5 CAB97352.1 AJ249144) sequence is:

```
MGRRKVQLKRIENKINRQVTFSKRRSGLLKKAHEISVLYDAEVGLIIFSTKGKLYEFSTESCMDKILERYERYSYAE    (SEQ ID NO: 19)

KVLVSSESEIQGNWCHEYRKLKAKVETIQKCQKHLMGEDLESLNLKELQQLEQQLESSLKHIRARKNQLMHESISEL

QKKERSLQEENKVLQKELVEKQKAQAAQQDQTQPQTSSSSSSFMMRDAPPVADTSNHPAAAGERAEDVAVQPQ

VPLRTALPLWMVSHING
```

Also encompassed within the definition of AP1 sequences include the hexaploid wheat AP1 protein (Ta AP1 BAA33457 MADS) sequence is:

```
MGRGKVQLKRIENKINRQVTFSKRRSGLLKKAHEISVLCDAEVGLIIFSTKGKLYEFSTESCMDKILERYERYSYAE    (SEQ ID NO: 20)

KVLVSSESEIQGNWCHEYRKLKAKVETIQKCQKHLMGEDLESLNLKELQQLEQQLESSLKHIRSRKNQLMHESISE

LQKKERSLQEENKVLQKELVEKQKAQAAQQDQTQPQTSSSSSSFMMRDAPPAAATSIHPMAGERAGDAAVQPQ

APPRTGLPLWMVSHING
```

Included within the definition of AP1 sequences for this invention is the *Lolium temulentum* AP1 protein sequence which is:

MGRGKVQLKRIENKINRQVTFSKRRSGLLKKAHEISVLCDAEVGLIIFSTKGKLYEFATDSCMDKILERYERYSYAE    (SEQ ID NO: 21)

KVLISTESEIQGNWCHEYRKLKAKVETIQRCQKHLMGEDLESLNLKELQQLEQQLESSLKHIRSRKSQLMHESISE

LQKKERSLQEENKILQKELIEKQKAHTQQAQLEQTQPQTSSSSSSFMMGEATPATNRSNPPAAASDRAEDATGQP

PARTVLPPWMVSHLNNG

The corresponding *Lolium temulentum* AP1 DNA sequence (AF035378) encoding the protein sequence is:

CTCTCTTCTTCCCCACTGGACGCACGCCATGACACCGGCCCCACGGCTCCACCTGCACCCTCGGGACTAGCCG    (SEQ ID NO: 22)

TCGCCGTCGCCGTCCGGGCGGGTTGTCGATTAGGGTTTGGTCTGCTCTTCCAGGGAGGGAGGCGAGATGGG

GCGCGGCAAGGTGCAGCTCAAGCGGATCGAGAACAAGATCAACCGCCAGGTCACCTTCTCCAAGCGCCGCTC

AGGCCTGCTCAAGAAGGCGCACGAGATCTCCGTGCTCTGCGACGCAGAGGTCGGGCTCATCATCTTCTCCACC

AAGGGAAAGCTCTACGAGTTCGCCACCGACTCATGTATGGACAAAATTCTTGAGCGGTATGAGCGCTACTCCT

ATGCAGAGAAAGTGCTCATTTCAACTGAATCTGAAATTCAGGGAAACTGGTGTCATGAATATAGGAAACTGAA

GGCGAAGGTTGAGACAATACAGAGATGTCAAAAGCATCTAATGGGAGAGGATCTTGAATCATTGAATCTCAAG

GAGTTGCAGCAACTAGAGCAGCAGCTGGAAAGTTCACTGAAACATATTAGATCCAGAAAGAGCCAGCTTATGC

ACGAATCCATATCTGAGCTTCAAAAGAAGGAGAGGTCACTGCAAGAGGAGAATAAAATTCTCCAGAAGGAACT

CATAGAGAAGCAGAAGGCCCACACGCAGCAAGCGCAGTTGGAGCAAACTCAGCCCCAAACCAGCTCTTCCTCC

TCCTCCTTTATGATGGGGGAAGCTACCCCAGCAACAAATCGCAGTAATCCCCCAGCAGCGGCCAGCGACAGAG

CAGAGGATGCGACGGGGCAGCCTCCAGCTCGCACGGTGCTTCCACCATGGATGGTGAGTCACCTCAACAATG

GCTGAAGGGTCCTTCCACTCCATCTAAACGTATTATTCAGTACGTGTAGCGAGCTGCACCGGCCTGTCTTGTG

GTTGCCTAGCAAGCTGACCCTCCTGCGTGAGCTGACTTCACGTAAGGTAGCAGGTTGCAATGTGTATATTTCA

CTCTGTTCTGCTCAGTTTCCCTCCTGCGTGAGCTGACTTCACGTAAGAGTTATTTAACTTGTAATACATGTGTA

GCGTGAGTGACAAATTTTCCACTTTCTACGACCCTCTTGGGTACCGTCTGTTTCTGTGAATTAAACTATCCAAT

ATCAGTATTATGTATATTGTGATTGTTGAAAAAAAAAAAA

The coding region start and stop sites are bold and underlined.

The maize and *Arabidopsis* AP1 sequences are also included within the definition of AP1 protein and are disclosed in U.S. Pat. No. 6,355,863 which is hereby incorporated by reference.

AP1 Promoter: An AP1 promoter is a promoter for the APETALA1 (AP1) gene. AP1 promoters are generally found 5' to the AP1 protein coding sequence and regulate expression of the AP1 gene. AP1 promoter sequences as defined herein include those sequences that hybridize under high stringency conditions to the nucleic acid of SEQ ID NO:12 (FIG. 9). Such sequences can be synthesized chemically or they can be isolated from plants. AP1 promoters can be spring or winter AP1 promoters, for example, spring wheat or winter wheat AP1 promoters. Representative plants from which AP1 promoters can be isolated include wheat (spring and winter), barley, rye, triticale, oat and forage grasses. A spring AP1 promoter sequence as defined herein includes nucleic acids that hybridize to the nucleic acid molecule of SEQ ID NO:12 or the complement thereof under high stringency conditions wherein the AP1 promoter sequence lacks all or a portion of nucleotides −162 to −172 upstream of the starting ATG, CCTCGTTTTGG (SEQ ID NO:23) or has similar deletions to those indicated in SEQ ID NO: 14, 15, 16, 17, 112, and 114. An AP1 promoter sequence is said to lack all or a portion of SEQ ID NO:23 if 1, 2, 3, 4, 5, 6, 7, 8, 9, 10, 11 of the nucleotides of SEQ ID NO:23 are missing, changed or altered. A spring AP1 promoter sequence also includes any insertion or deletion in the proximity of the CArG box that alter its binding with the repressor (e.g. SEQ ID NO:112 and 113). A winter AP1 promoter sequence as defined herein includes nucleic acids that hybridize to the nucleic acid of SEQ ID NO:12 or the complement thereof under high stringency conditions and that is transcriptionally up regulated by vernalization. Also included in the definition of AP1 promoter are additional natural or synthetic sequences that might not hybridize with SEQ ID NO: 12 but that include the CArG box CCTCGTTTTGG or a related motif that act as a recognition site for the vernalization signal.

Vernalization: Vernalization is the exposure of plants to cold to trigger flowering. For example, winter wheats typically require 4 to 8 weeks at 4° C. to flower.

Sequence Identity: The similarity between two nucleic acid sequences, or two amino acid sequences is expressed in terms of sequence identity (or, for proteins, also in terms of sequence similarity). Sequence identity is frequently measured in terms of percentage identity; the higher the percentage, the more similar the two sequences are. As described herein, homologs and variants of the AP1 nucleic acid molecules may be used in the present invention. Homologs and variants of these nucleic acid molecules will possess a relatively high degree of sequence identity when aligned using standard methods. Such homologs and variants will hybridize under high stringency conditions to one another.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblasbx. It can be accessed at the NCBI Website. A description of how to determine sequence identity using this program is available at the NCBI website.

Homologs of the disclosed protein and nucleic acid sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%,z at least about 90% or at least about 95% sequence identity.

The alignment may include the introduction of gaps in the sequences to be aligned. In addition, for sequences which contain either more or fewer amino acids than the protein encoded by the sequences in the figures, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleotides, frameshifts, unknown nucleotides, or other types of sequencing errors in any of the sequences; however, the correct sequences will fall within the homology and stringency definitions herein.

Very High Stringency: Very high stringency conditions refers to hybridization to filter-bound DNA in 5×SSC, 2% sodium dodecyl sulfate (SDS), 100 ug/ml single stranded DNA at 55-65° C. for 8 hours, and washing in 0.1×SSC and 0.1% SDS at 60-65° C. for thirty minutes.

High Stringency: High stringency conditions refers to hybridization to filter-bound DNA in 5×SSC, 2% sodium dodecyl sulfate (SDS), 100 ug/ml single stranded DNA at 55-65° C. for 8 hours, and washing in 0.2×SSC and 0.2% SDS at 60-65° C. for thirty minutes.

Moderate Stringency: Moderate stringency conditions refers to hybridization to filter-bound DNA in 5×SSC, 2% sodium dodecyl sulfate (SDS), 100 ug/ml single stranded DNA at 55-65° C. for 8 hours, and washing in 0.2×SSC and 0.2% SDS at 50-55° C. for thirty minutes.

Low Stringency: Low stringency conditions refers to hybridization to filter-bound DNA in 5×SSC, 2% sodium dodecyl sulfate (SDS), 100 ug/ml single stranded DNA at 55-65° C. for 8 hours, and washing in 2.0×SSC and 0.2% SDS at 50-55° C. for thirty minutes.

Vector: A nucleic acid molecule as introduced into a host cell, thereby producing a transformed host cell. A vector may include one or more nucleic acid sequences that permit it to replicate in one or more host cells, such as origin(s) of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by *Agrobacterium*, with plasmid vectors, and introduction of naked DNA by electroporation, lipofection, and particle gun acceleration and includes transient as well as stable transformants.

Isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below. As an example, a gene in a large fragment such as a contig is not sufficiently purified away from other biological components to be considered isolated due to the relatively large amount of extra DNA found in the average contig.

Operably linked: A first nucleic acid sequence is operably linked with a second nucleic acid sequence when the first nucleic acid sequence is placed in a functional relationship with the second nucleic acid sequence. For instance, a promoter is operably linked to a protein coding sequence if the promoter affects the transcription or expression of the protein coding sequence. Generally, operably linked DNA sequences are contiguous and, where necessary, join two protein-coding regions in the same reading frame. With respect to polypeptides, two polypeptide sequences may be operably linked by covalent linkage, such as through peptide bonds or disulfide bonds.

Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell, however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated" as described above. A gene in a large fragment such as a contig would not be a "recombinant nucleic acid" given that artificial combination does not relate to the gene. However, if sequences around or within a gene in a contig have been manipulated for purposes relating to that gene (i.e., not merely because the gene is near the end of the contig), then such a gene in a contig would constitute a "recombinant nucleic acid" due to the relative proximity of the recombinant portion of the nucleic acid to the gene in question.

Non-naturally Occurring Plant: A non-naturally occurring plant is a plant that does not occur in nature without human intervention. Non-naturally occurring plants include transgenic plants and plants produced by non transgenic means such as plant breeding.

Transgenic plant: As used herein, this term refers to a plant or tree that contains recombinant genetic material not normally found in plants or trees of this type and which has been introduced into the plant in question (or into progenitors of the plant) by human manipulation. For the avoidance of doubt, introduction of a nucleic acid isolated from a plant or tree back into the plant or tree by human manipulation still generates a transgenic plant. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems etc.

Inducible promoter: As used herein, this term refers to any promoter functional in a plant that may provide differential expression levels in response to externally supplied stimuli. This includes both promoters that increase expression and promoters that decrease expression in response to stimuli or changed external conditions.

External stimuli that may effect transcription by inducible promoters include, without limitation, pathogen attack, anaerobic conditions, the presence or absence of light, heat or cold stress, osmotic stress, toxic metal stress, steroid responsive promoters, and chemically inducible promoters. Examples of inducible promoters are the AdhI promoter, which is inducible by hypoxia or cold stress, the Hsp70 promoter, which is inducible by heat stress, and the PPDK promoter, which is inducible by light. Examples of pathogen-inducible promoters include those from proteins, which are induced following infection by a pathogen; e.g., PR proteins, SAR proteins, beta-1,3-glucanase, chitinase, etc. See, for example, Redolfi et al. (1983); Uknes et al. (1992); Van Loon (1985); PCT Publication No. WO 99/43819.

Also of interest are promoters that are expressed locally at or near the site of pathogen infection. See, for example, Marineau, et al. (1987); Matton, et al. (1987); Somssich et al. (1986); Somssich et al. (1988); Yang (1996). See also, Chen, et al. (1996); Zhang and Sing (1994); Warner et al. (1993), and Siebertz et al. (1989), all of which are herein incorporated by reference.

Additionally, inducible promoters include wound inducible promoters. Such wound inducible promoters include potato proteinase inhibitor (pin II) gene (Ryan (1990); Duan et al. (1996)); wun1 and wun 2, U.S. Pat. No. 5,428,148; win1 and win2 (Stanford et al. (1989)); systemin (McGurl et al. (1992)); WIP1 (Rohmeier et al. (1993); Eckelkamp et al. (1993)); MPI gene (Cordero et al. (1994)); and the like, herein incorporated by reference.

Both heterologous and non-heterologous (i.e. endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in wheat, operably linked to a polynucleotide of the present invention. Promoters useful in these embodiments include the endogenous promoters driving expression of a polypeptide of the present invention.

Regulated promoter: As used herein, this term refers to any promoter functional in a plant that provides differential expression levels in response to stimuli internal to the plant such as developmental signals. This includes both promoters that increase expression and promoters that decrease expression in response to stimuli or changed external conditions. Many promoters that are regulated promoters are also inducible promoters. For example, promoters that are responsive to auxin are both because they will change levels of expression in response to developmental changes in auxin levels and in response to externally supplied auxin.

Examples of regulated promoters under developmental control include promoters that initiate transcription only, or preferentially, in certain tissues, such as leaves, roots,. fruit, seeds, or flowers. Exemplary promoters include the anther specific promoter 5126 (U.S. Pat. Nos. 5,689,049 and 5,689,051), glob-1 promoter, and gamma-zein promoter. An exemplary promoter for leaf- and stalk-preferred expression is MS8-15 (WO 98/00533). Examples of seed-preferred promoters included, but are not limited to, 27 kD gamma zein promoter and waxy promoter (Boronat et al. (1986); Reina et al. (1990); and Kloesgen et al. (1986)). Promoters that express in the embryo, pericarp, and endosperm are disclosed in U.S. applications Ser. No. 60/097,233 filed Aug. 20, 1998 and U.S. applications Ser. No. 60/098,230 filed Aug. 28, 1998 both of which are hereby incorporated by reference. The operation of a promoter may also vary depending on its location in the genome. Thus, a developmentally regulated promoter may become fully or partially constitutive in certain locations. A developmentally regulated promoter can also be modified, if necessary, for weak expression.

Ortholog: Two nucleotide or amino acid sequences are orthologs of each other if they share a common ancestral sequence and diverged when a species carrying that ancestral sequence split into two species, sub-species, or cultivars. Orthologous sequences are also homologous sequences. Orthologous sequences hybridize to one another under high-stringency conditions. The term "polynucleotide", "oligonucleotide", or "nucleic acid" refers to a polymeric form of nucleotides of any length, either deoxyribonucleotides or ribonucleotides, or analogs thereof. The terms "polynucleotide" and "nucleotide" as used herein are used interchangeably. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A "fragment" or "segment" of a nucleic acid is a small piece of that nucleic acid.

ZCCT1 protein or ZCCT1 polypeptide: A ZCCT1 protein or ZCCT1 polypeptide is a protein encoded by the VRN2 gene in temperate grasses. In wheat, deletions or mutations in ZCCT1 result in a shift from a winter wheat phenotype, which requires vernalization, to a spring wheat phenotype, which does not need vernalization in order to flower.

The present invention may be practiced using nucleic acid sequences that encode full length ZCCT1 proteins as well as ZCCT1 derived proteins that retain ZCCT1 activity. The ZCCT1 activity depends upon the intended use of the ZCCT1 derived proteins. For example, ZCCT1 activity may be full activity in its ability to repress expression of AP1 in temperate grasses. ZCCT1 activity may also be the ability of the ZCCT1 derived protein to interfere with the endogenous ZCCT1 activity, which could include ZCCT1 DNA binding activity without repression so that the ZCCT1 derived protein competes with the endogenous ZCCT1 for its DNA binding site. By competing with the endogenous ZCCT1, the fragment could be used to prevent the endogenous ZCCT1 protein from repressing the AP1 gene and any other gene that the ZCCT1 protein may repress. Also, ZCCT1 activity could be the repressor activity without the DNA binding activity. Overexpression of the repressor will interfere with the endogenous ZCCT1 activity by competing with accessory proteins that bind to ZCCT1 and enable repression of AP1. This again would prevent the endogenous ZCCT1 protein from repressing the AP1 gene and any other genes that ZCCT1 represses. ZCCT1 derived proteins which retain ZCCT1 biological activity include fragments of ZCCT1, generated either by chemical (e.g. enzymatic) digestion or genetic engineering means; chemically functionalized protein molecules obtained starting with the exemplified protein or nucleic acid sequences, and protein sequence variants, for example allelic variants and mutational variants, such as those produced by in vitro mutagenesis techniques, such as gene shuffling (Stemmer, 1994a, 1994b). Thus, the term "ZCCT1 protein" encompasses full-length ZCCT1 proteins, as well as such ZCCT1 derived proteins that retain the desired ZCCT1 activity.

Representative but non-limiting ZCCT1 sequences useful in the invention include the wheat ZCCT1 DNA sequences and the corresponding protein sequences.

Examples of such sequences include the genomic ZCCT1 DNA sequence from *T. monococcum* DV92 encoded by the following sequence (Exon 1 and 2 are in bold with the stop codon underlined):

```
GAAAGCGGTGCCCACCCACGCAACCATCGCCAACATCGACTCCGGCCGAACACAAGCTTTTGCCTAGACCTAGACAC    (SEQ ID NO: 74)

AACCGCTCTACCAAACCCTCGGAATAGTCTGGCCTAGCTAACAACCAACATCGCCCCTCCCTACTCCGACCAAACAT

GATGAAGTACTAACTGACAATGCCTCCAAGGAGTAGAATGGCATCCTCAAGCGTCATCATCGCCGAAGAATCAAACT

TTCGCCCAGAGCCTTACACCTCTCCACATCCACAGACCCCAAGGAAGGAGCCAAGCTACAACGAACATGTGAGGCCA

AGCCGCGACTCCACTCGATCCAACAACAACGAACCAGTCCAGTTGGATCAGAAGGACACCACGACCACCTGTATCAC

CATGGTAGGCTACCTGTGTCGATGCCAACACCAACCCAACACTACAACCAGGATGCCTGGCAAATGCAGTCCTTGCC

GTCGAGGAGAACGCGGGCCCAAAATGCCCCCCTAGCCACAAATTGCCCACTATGATAAAAAAACACAAGCCAGAGCC

GCTGGTAAGTAGTCGCCTTGTGTCGTGGGCCACATAGGCTCACATGCACCGACGGCGGCACCTAAGCCGCCATGAGC

CACCACCGCGCACAAGAGCAGCAGACACCTAGACCAGGCTGACATGAGACCTGTCACCACTACATGTTGTCGCATCA

CAACAGGCCATCAGACATCAGTAGGTCGCCGCACCTCAGAAGCACCTCCGTCCCGCAGCCAACACGAAGCACCCAAT

TCGAGATCCTTCAGCAAACTCCCCTACGTGCGAGTGGCCGCGAGCCGACGAGAAGAGTAGGCCACGCCACCTCCGGA

TCGGCGCGGGCTTCACTAGGCAGAGCCCATTGGCAATAGCGAGGGGAGGGGGGCGGTCTAAGAGGGATTGAGCCGC

CGCCCGGGTGGACCCGGGGAGGGAACAATATTGCAAGTTTTTTTTACAATGAGCACACACCCAGTCTCTGCATAGTT

AGGATGATATAGCCAACACCAACTCACACACATACGAAAACACGCTGACAACTAGCAACGTCACATAAGACCAATGA

TGTTCGTTGGCAAGAAAAAAATGCCGCAAAACAATCAGATTTGTGATTGACAAACTACAATAATGACCATATCCACA

CCAATCATCTCATAAAACCACACTGACGATGAGGTCTTCGATAGCAATGCCTTTAGGAAGGGAGCGACACTCAAGCA

CCACCATCACTAGATCCAACCACAAGGCCAAAATGTAGGTTTTCATCCCGAAGAATCAGTCCAAGCATATTCGAGCA

ATGCATTCGACAAGGTAAGAATGTAAGAAAAACATCGCCTTTTCCAGGTATAAACTGTTGGTTCTGACCTAGGCTTT
```

-continued

```
TGCCCCTGAGGTCGAGACCGGGTGCTCGAGTAGCAACACCATCGAAGTCGCTCATGTGTTGTCATCACCACTTTTCC
GTGATTCTAGCAGCAACATGTGATGCAACTGCTGCCACTGCACACCCATCCCTTTGCATCAAGCCGTCGTCCATAAT
TTGTATCTCATCACTGAAGTTAACCACTGGATCAGGAGAGATGACCCCTCCCAGGGACCATTCAATGACCACTGCCG
TCGTGGAGTCCTAGGAAGTAGTTGCAGTATAGTTTGCAGCAACACCATCTGGCAGGTCAGATCTGGATCACCACCAC
CAACCCATGGATCTTAGCGCCGCCAACCAGCCACCGCACACGTGGAAAGCCAGCACCTCGCAGCAACAGTCCTCATC
CAATAGAAAGACCGACGCCAAATCCGATCGGATCTTGCCGGAGTCCACCCACATAGTGAGTCACCACCACAATAAGG
GACGCGCCTCTAGCCATGGTAGCGAGTGACCCGCACAACCAGTCTCACCTGCCGTGAAGAAATATGCGTGCTCCCGG
TTGCTGTAGGATGGGACATATGGTTCCCATGACAAGGGAGCGGTAGAGGGACGAGAGGATGTGAATATAAATATATT
TTTTTGAAAAGGGGGATATCCCCCAGCGTGTGCATCCAAAAGATGCATGTGACCATATTATTAAAGCAGTTGCAGCA
AAAAACAAGGTCTGGTATCCAAATATATCTCGCAAAAGGAGCAAAAATAAGTAAAAGCTAAGAAAGATAAACATAGC
CACAACCCGCAGGATGAGAGGATTAGAATATGCCAAACGAAAAAAAGATGGGATGCGGAAGCATCCTGCCGCCGCCG
TCCGGCCACCGGTGGTTTCCTCTCGCAACAGCGAGGGGTTGGGTGGCTGGTGGGGGGAGGGTTGGGTGGGGAGGGTT
GGGTGTGGCAGCGTGGGCACCTCCGGAGTCGACAACGGCGATCCAGGAGGCCGGTTAAGCTTGGGGGAGAAGAGTCC
TCGCTGGTTCTCATTCTAGAGTTTAGTTTCCATGCCCATGATAATAGCATGGATGCCCATGACGAAAATTGTTTCA
CAGCTGGTAGTACTTTTCTATTTTAGTATTGGCATGGTTTCCATTTTGTTGTTTTTGTCTCCCTCGGACTTTTGTGT
TAGCATCTCCTTTTTGTTTTGACGCTGACCAAAAAAAGCTACACAAATATCTAGCAGTGGCCTTGTGTGGACATAAG
ATCATGTGGGGATTCCCGGCAAGCAAGGTCTGCATGGCTCCGGCTCCTCCGCGTAAGAAAGAAAGAAATCAACGAT
GGATCGAGGGATCATATCTATTCCGACCCACTCATTAGTTGGGTCTATTTGATTTGATCTATCATATTTTGATAGTT
GCCATATCGAATCTTTTTTCTGGCCTGAGAGCTCACGGCTGCCTATATGCAGTGCATGTGAGAGAGACACAGTACGG
CCCTAGCTACTACTACAAGTACCTTGGTAGTTACTGGTACTCATAACTGCCTCTTCTTCTTCCTCGACGTCTCTCCT
CCTCGGCTCCTCCACGCACCAGACCACACCAGAAAAAACAAACAAGCAAGCAAACCTTGGAGCTAGCTAGCAGT**ATG
TCCATGTCATGCGGTTTGTGCGGCGCCAACAACTGCCCGCGCCTCATGGTCTCGCCCATTCACCATCATCATCACCA
TCATCAGGAGCACCAGCTGTGTGAGTACCAGTTCTTCGCCCATGGCAACCACCACCACCACCACCATGGCTCGGCAG
CAGACTACCCAGTGCCACCGCCGCCAGACAACTTCGACCACCGCAGAACATGGACCAGACCATTTCATGAAACAGCA
GCGGCAGGGAACAGCAGCAGGCTCACGCTGGAGGTGGGCGCAGGCGGCCAACACATGGCTCACCTAGTGCAGCCACC
GGCAAGAGCCCACATC**GTAAGTAGTACTACTGCTTAATTGTTTCATCTCTTGCCGATGGATGCGTCCATGGCTTCCT
CCTTAAAAATCCCCACCTAATTAATGTCCATCTGACTACACCCACTACAAAAAAGTAGCACCATGTAACCATTTCAT
ATATTTCTCACATAATTCTGTTAATTTACGCTGCTCGATTGTTCTCCTGAAAAAGATATACGGGAATGGATCTGGAT
ATTCTTTAATTTTCTATGGAGGCATAGAGTTTGTGTTTTGTATTAGTTGATGCAGAATTGTATGGGTTGTCAAATCA
TCAGTCATACATATATACTTATTTCTTTTTTTTTGACCAACAAGAAGGTAATCAGTCATACATGCATACTGAAAATT
AGACTTGTGTGCAATAACTAACTAACCAACTCGACCGGCACAGCTGGGGGAAGACTTTAATCAAGCTGCTAGCTAGA
GCTTAATAATATAACATATCTCTTTATGGGATCAAGCAATACATATGCGCTCAATTCTCAACTTGTCAATATCTATC
TGGAGTCCACACTTTATGGTAATTAATTGACAAAGTTTTGTGAAATGGACAATATACATACTGGATCGATGCACCCT
TTTTCTCATTTTATGTGGTCATTATAATTGATTGTTATTTAGTATTTCAATTTTATCTTGAGCTAGTTTTGCAAGTC
TGTAGCTCATATATAACTGATACTACTCCCCACGATAGCTTGCGTAGTGGCCGGGTGATCGATCTACCGAGTTCATA
AAACTGATCGAGATCGGGTCCAAAAAAGAACAAACCCATACAAAATGGAAAGAAGATCCTTGTTTAGTTAGTTTGCA
TCAGAAAATTGCCTAATTAGTTACTTGCTATCAATCTTTTGAACATGGCATGTTCACCCCAAACGGACCCAGATCAC
AATTATTGATGAAGTTACGCCTTTTAAAAACTCATAAAACTGTACATACATGTACAGGGCTACACACATGTACATAA
TACACCTAATTAAAACGTATATTTGTAGACCAATTGATTTTGGACGGTGCGCATCTTTGGAAAAAAAATGCCAGAGG
AGTTGTTAGCTTCCACTGTCCAGAAATAGAATAGTTACAATCAAGTGCATCTCTGAATGAAAATGGATCATTTTCTA
```

GTTAATTAGAGACCAATTAGATACTTCATAAACAGGGGAGTATCAAGTACGTATCTGCTACCCATAAGAAAGTACAT

AACTGCGATCTTATGATTATTTTCCTCTTGATGTTCAGGTGCCATTTCACGGAGGTGCATTCACCAACACTATTAGC

AATGAAGCAATCATGACTATTGACACAGAGATGATGGTGGGGCCTGCCCATTATCCCACAATGCAGGAGAGAGCAGC

GAAGGTGATGAGGTATAGGGAGAAGAGGAAGAGGCGGCGCTATGACAAGCAAATCCGATACGAGTCCAGAAAAGCTT

ACGCTGAGCTTCGGCCATGGGTCAACGGCCGCTTTGTCAAGGTACCCGAAGCCATGGCATCGCCATCATCTCCAGCT

TCGCCCTATGATCCTAGTAAACTTCACCTCGGATGGTTCCGGTAATTTATAGCACAAGCCAGATAAAATGATAACAT

ATTTCCTTCTGATTGATCCACCCGTGAAGCAGTTGTTCCTCAAAGTAAAATAAGTCGGTTAGTGATTGATCGATTGG

AGCCATTATGTTGACTTGACTATTTAAAATGGTCAGCAGATCAATCAAACAAAATGTATTTATTGAAACAAGTCTTG

TTATACTACGTGTTGATTTAAACATGTAATTTCAAGAGGATAGCTACTTTGATGTGTAATAAAATTGTCTCAAAATT

GGTGACAAGTGCGATTGTTGTTGTGATTTATATGGAATTATGTCAATCATACTGGAAAAATAATATGTAACCAGTTG

AATTAAGTCATCGCCGACTCAAAATTAAATACGAATGAGGCTTTTATGTATAAAGTTTGTTATTTTATCCTGAGGAC

TTCTCTAGGGGTGGAAAACGGATTGAGAAAGTACACCATCACGATTGCCGAACATGTACAATGCTTATCTTGAGAAA

GAAAATTATATTTCATTCACCAAATATGAGGTGAACCTTGCAACCACATGTATATTAAAAAGCTATGTGTCAGCTAA

CTAATTTGTGGACTTATCATAGGTTAAATACCTCCAATGTGTACGAATGAGGAACTTGAGTAGAATATGTGAAGTTG

CATGGAAAACTGTGAACATATCAAATTATCAAGACATCACTACAGATGTACATCATCCGAAGTTCATGTATTATATT

GAAATTGTGTGTTCCTTATGTTGTTGGATGTACTTATTGAAGTGATCCTTCATCTATGAGGTAAGTATTAATTAATT

TGTCCATCGTTTGATCAATCATGTGTATTTAATTAGTTTGTTGGATGTACTAAGTTTTAATTAGTTTGTTGGATGTA

CTGAGTATTAATTAGTTTGTCCATCCCAAGCTTCATCTATAACCCAATGACAAAGGTGACAACGCTATGCACACATA

CATACACATGATTGATCAAACGATGGACAAACTACCAATGACAAAGGTGACAACGCTATGCACACATACATACACAA

ATAGATGAAGCTTGGAATACGGCACGGGTGGCAGCCTCGAACCTCAAGCTGGTGCGAACCCAATGAGCTAGACAAGA

TAACAATGTCTGTCCAAGATAAGGGGAAGCTATTGTTGACTGCCATGATCTAATAGGTTGCCAAATACTAATTGTCA

TGAGATTTATTTAGTCCAATGTGTTGGGTTTAGTCCCACTTCAGTTGTGGGGGAGACATAACATGATTTATAAGGG

CAGGGGTGTCCCCTCCTAACAGGCTAGTCCTTTGGAGGGAGAGGGCCCAAGACCTCTCATAAGTCGGTGTTACTCTC

TGGTTGAGCCTGGTTGACGCATGTGGGTCGGAAATGCTAGTGTTAGCGGACCCGAAATTGCGTAACAAGTGGTACCA

TGAGCTAGGTTGTTCGAGGTTGCGATTGTTAATTCAGAGGAGGTCGTGTTCAATCGACGGAGGCGCTGCGAGGGTTT

GCCAGGTGCCTGCGGTGAGATCGAAGTTGTCCGATTGAAGGTCAACGGAAAGATCAAAAGCAGTCAAAGCTGGATCG

GTTTGGCAGAGGCAGCAGGCCGAGCAAGCTGCGGGACGCGCAGGCCAAGCAGGACCCAAGTGCGGGTGACTGGCCT

GGTAAAGCACGCGGCTGCTAGTAGACAGGAGCGCGTATGCGGCAGCCAGACAAGCGGATGCGGTCTGCGATGTGGCA

CTTGGCAGAGGCTGTTTGGTACGTGGTTGGCTCAAGGAATGGCCTATTGATGCTGCTGGTGTGAGCACAAAGAGGCG

AGATTTCACGGGCAAGTTTGGCTGATTCTTGGAGAAGCGGTGTTGCATATAAAAGTCTGTTTGTTGATGTGCTTAAA

GACTGTACCAAGAAGCAAGTTGACGGGTCAAAAAAAGAAGCAAGTTGAGAACATTACCAAGGGTAGTGACAAGGCA

AGGACGACAACGTGCGATAAGGCTTGAAGCAAGAGTCTGGAGCTTGTCGTGGCAGGATCATGCATACACAGGGCGTC

AAGCAATGCACGGAGATGTGCGGGGCGGACACGGCGCAGAGTGGAGCATGGTTGCAGTCGAACATACACGGCTGGCT

TGGACTGGATTGTTTAATGGACTGGCATGGAGGTTGGTCAAAGC

Also encompassed within the definition of ZCCT1 DNA sequences is the ZCCT1 protein coding cDNA sequence from *T. monococcum* DV92 encoded by the following sequence (the coding sequence is in bold with the stop codon underlined):

```
TAACTGCCTCTTCTTCTTCCTCGACGTCTCTCCTCCTCGGCTCCTCCACGCACCAGACCACACCAGAAAAAACAAAC   (SEQ ID NO: 75)

AAGCAAGCAAACCTTGGAGCTAGCTAGCAGTATGTCCATGTCATGCGGTTTGTGCGGCGCCAACAACTGCCCGCGCC

TCATGGTCTCGCCCATTCACCATCATCATCACCATCATCAGGAGCACCAGCTGTGTGAGTACCAGTTCTTCGCCCAT

GGCAACCACCACCACCACCACCATGGCTCGGCAGCAGACTACCCAGTGCCACCGCCGCCAGACAACTTCGACCACCG

CAGAACATGGACCAGACCATTTCATGAAACAGCAGCGGCAGGGAACAGCAGCAGGCTCACGCTGGAGGTGGGCGCAG

GCGGCCAACACATGGCTCACCTAGTGCAGCCACCGGCAAGAGCCCACATCGTGCCATTTCACGGAGGTGCATTCACC

AACACTATTAGCAATGAAGCAATCATGACTATTGACACAGAGATGATGGTGGGGCCTGCCCATTATCCCACAATGCA

GGAGAGAGCAGCGAAGGTGATGAGGTATAGGGAGAAGAGGAAGAGGCGGCGCTATGACAAGCAAATCCGATACGAGT

CCAGAAAAGCTTACGCTGAGCTTCGGCCATGGGTCAACGGCCGCTTTGTCAAGGTACCCGAAGCCATGGCATCGCCA

TCATCTCCAGCTTCGCCCTATGATCCTAGTAAACTTCACCTCGGATGGTTCCGGTAATTTATAGCACAAGCCAGATA

AAATGATAACATATTTCCTTCTGATTGATCCACCCGTGAAGCAGTTGTTCCTCAAAGTAAAATAAGTCGGTTAGTGA

TTGATCGATTGGAGCCATTATGTTGACTTGACTATTTAAAATGGTCAGCAGATCAATCAAACAAAATGTATTTATTG

AAACAAGTCTTGTTATACTACGTGTTGATTTAAACATGTAATTTCAAGAGGATAGCTACTTTGATGTGTAAT
```

The sequence of the *T. monococcum* DV92 ZCCT1 protein is as follows (Non-functional with R to W mutation in bold).

```
MSMSCGLCGANNCPRLMVSPIHHHHHHHQEHQLCEYQFFAHGNHHHHHHGSAADYPVPPPPDNFDHRRTWTRPFHET   (SEQ ID NO: 76)

AAAGNSSRLTLEVGAGGQHMAHLVQPPARAHIVPFHGGAFTNTISNEAIMTIDTEMMVGPAHYPTMQERAAKVMRYR

EKRKRRRYDKQIRYESRKAYAELRPWVNGRFVKVPEAMASPSSPASPYDPSKLHLGWFR*
```

The protein sequence of the *T. monococcum* G3116 functional winter allele of ZCCT1 is:

```
MSMSCGLCGANNCPRLMVSPIHHHHHHHQEHQLCEYQFFAHGNHHHHHHGSAADYPVPPPPDNFDHRRTWTRPFHET   (SEQ ID NO: 77)

AAAGNSSRLTLEVGAGGQHMAHLVQPPARAHIVPFYGGAFTNTISNEAIMTIDTEMMVGPAHYPTMQERAAKVMRYR

EKRKRRRYDKQIRYESRKAYAELRPRVNGRFVK
```

Also encompassed within the definition of ZCCT1 DNA sequences are the genomic ZCCT1 DNA sequence from Langdon (tetraploid wheat) ZCCT-A1 encoded by the following sequence (Exon 1 and 2 are in bold with the stop codon underlined):

```
GAGTTTAGTTTCCATGCCCATGATAATAGCATGGATGCCCCATGACGAAAATTGTTTCACAGCTGGTAGTACTTTTC   (SEQ ID NO: 78)

TATTTTAGTATTGGCATGGTTTCCATTTTGTTGTTTTTGTCTCCCTCGGACTTTTGTGTTAGCATCTCCTTTTTGTT

TTGACGCTGACCAAAAAAAGCTACACAAATATCTAGCAGTGGCCTTGTGTGGACATAAGATCATGTGGGGGATTCCC

AGCAAGCAAGGTCTGCATGGCTCCGGCTCCTCCGCGTAAGAAAGAAAGAAATCAACGATGGATCGAGGGATCATATC

TATTCCGACCCACTCATTAGTTGAGCAATATTTTGATAGTTGCCATATCGAATATTTTTCTGGCCTGAGAGCTCAC

GGCTGCCTATATGCAGTGCATGTGAGAGAGACACAGTACGGCCCTAGCTACTACTACAAGTACCTTGGTAGTTACTG

GTACTCATAACTGCCTCTTCTTCTTCCTCGACATCTCTCCTCCTCGGCTTCTCCACGCACCAGACCACAGCAGAAAA

AACAAAAAAGCAAGCAAACCTTGGAGCTAGCTAGCAGTATGTCCATGTCATGCGGTTTGTGCGGCGCCAACAACTGC

CCGCGCCTCATGGTCTCGCCCATTCATCATCGTCATCACCATCATCAGGAGCACCAGCTGCGTCAGCACCAGTTCTT
```

-continued

```
CGCCCAAGGCAACCACCACCACCACCACCCAGTGCCACTGCCGCCAGCCAACTTCGACCATAGCAGAACATGGACCA
CACCATTTCATGAAACAGCAGCTGCAGGGAACAGCAGCAGGCTCACGCTGGAGGTGGGCGCAGGCGGCCGACCCATG
GCTCACCTAGTGCAGCCACCGGCAAGAGCCCACATCGTAAGTAGTAGTACCGCTTAATTGTTTCATCTCTTGCCGAT
GGATGCGTCCCTGGCTTCCTCCTTAAAAATCCCCACCTAATTTATGTCCATCTATACCCACTACAAAAAAATAGCAC
CATGTAACCATCTCATATATCTGTCACATAATTCTGTTAATGTACGCTGCTCAATTGTTCTCCTGAAAAAGATATGC
GGGAATGGATCTTGATATTCTTTAATTTTCTATGGAGGCATATATAGAGTTTGTGTTTTGTATTAGTTGATGCAGAA
TTGTATGGGTTGTCAAATCATCAGTCATACATATAAACTTATTTCATTTTATTTGACCAACAACAAGGTAATCAGTC
ATACATGCATACTGAAAATTTGACTTGTGTTCAATAACTAACCAACTCGACCGGCACAGCTGGGGGAAGACTTTAAT
CAAGCTGCTAGCTAGAGCTTAATAATATAACATATCTCTTTATGGGATCAAGCAATACATATGCGCTCAATTCTCAA
CTTGTCAATATCTATCTGGAGTCCACACTTTATGGTAATTAATTGACAAAGTTTTGTGAAATGGACAATATACATAC
TGGATCGATGCACCCTTTTTCTCATTTTATGTGGTCATTATGAATTTGATTGTTATTTAGTATTTCAATTTTATCTT
GAGCTAGTTTTGCAAGTCTGTAGCTCATATATAACTGATACTACTCCCCACGATAGCTTGCGTAGTGGCCGGGTGAT
CGATCTACCGAGTTCATAAAACTGATCGAGATCGGGTCCAAAAAAGAACAAACCCATACAAAATGGAAAGAAGATCC
TTGTTTAGTTAGTTTGCATCAGAAAATTGCCTAATTAGTTACTTGCTATCAATCTTTTGAACATGGCATGTTCACCC
CAAACGGACTCAGATCACAATTATTGATCAAGTTACCCCTTTTAAAAACTCATAAAACTGTACATACATGTACAGGG
CTACACACATGTACATAATACACCTAATTAAAACGTATATTCGTAGACCAATTGTTTTGGACGGTGCACATCTTTGA
AAAAAAATGCCAGAGGAGTTGTTAGCTTCCACTGTCCAGAAATAGAATAGTTACAATCAAGTGCATCTCTGAATGAA
AATGGATCATTTTCTAGTTAATTAGAGACCAATTAGATACTTCATAAACAGGGGAGTATCAAGTACGTATCTGCTAC
CCTAAGAAAGTACATAACTGCGATCTTATGATTATTTTCCTCTTGATGTTCAG**GTGCCATTTTACGGAGGTGCATTC
ACCAACACTATTAGCAATGAAGCAATCATGACTATTGACACAGAGATGATGGTGGGGCCTGCCCATTATCCCACAAT
GCAGGAGAGAGCAGCGAAGGTGATGAGGTATAGGGAGAAGAGGAAGAGGCGGCGCTATGACAAGCAAATCAGATACG
AGTCCAGAAAAGCTTACGCTGAGCTTCGGCCACGGGTCAACGGCTGCTTTGTCAAGGTACCCGAAGCCATGGCGTCG
CCATCATCTCCAGCTTCGCCCTATGATCCTAGTAAACTTCACCTCGGATGGTTCCGGTAA**TTTATAGCACAAGCCAG
ATAAAATGATAACATATTTCCTTCTGATTGATCCACCCGTGAAGCAGTTGTTCCTCAAAGTAAAATAAGTCGGTTAG
TGATTGATCGATTGGAGCCATTATGTTGACTTGACTATTTAAAATGGTCAGCAGATCAATCAAACAAATGTATTTA
TTGAAACAAGTCTTGTTATACTACGTGTTGATTTAAACATGTAATTTCAAGAGGATAGCTACTTTGATGTGTAATAA
AATTGTCTCAAAATTGGTGACAAGTGCGATTGTTGTTGTGATTTATATGGAATTATGTCAATCATATTGGAAAAATA
ATTAACCAGTTGAATTAAGTCATCGCCAACTCAAAATTAAATACGAATGAGGCTTTTATGTATAAAGTTTGTTATTT
TATCTTGAGGACTTCTCTAGGGGTGGAAAACGGATTGAGAAAGTACACCATCACGATTGCCGAA
```

Also encompassed within the definition of ZCCT1 DNA sequences include the ZCCT1 cDNA sequence from Langdon (tetraploid wheat) ZCCT-A1 encoded by the following sequence (the protein coding region is in bold with the stop codon underlined):

```
TAACTGCCTCTTCTTCTTCCTCGACATCTCTCCTCCTCGGCTTCTCCACGCACCAGACCACAGCAGAAAAAACAAAA    (SEQ ID NO: 79)
AAGCAAGCAAACCTTGGAGCTAGCTAGCAGT**ATGTCCATGTCATGCGGTTTGTGCGGCGCCAACAACTGCCCGCGCC
TCATGGTCTCGCCCATTCATCATCGTCATCACCATCATCAGGAGCACCAGCTGCGTCAGCACCAGTTCTTCGCCCAA
GGCAACCACCACCACCACCACCCAGTGCCACTGCCGCCAGCCAACTTCGACCATAGCAGAACATGGACCACACCATT
TCATGAAACAGCAGCTGCAGGGAACAGCAGCAGGCTCACGCTGGAGGTGGGCGCAGGCGGCCGACCCATGGCTCACC
TAGTGCAGCCACCGGCAAGAGCCCACATCGTGCCATTTTACGGAGGTGCATTCACCAACACTATTAGCAATGAAGCA**
```

```
ATCATGACTATTGACACAGAGATGATGGTGGGGCCTGCCCATTATCCCACAATGCAGGAGAGAGCAGCGAAGGTGAT

GAGGTATAGGGAGAAGAGGAAGAGGCGGCGCTATGACAAGCAAATCAGATACGAGTCCAGAAAAGCTTACGCTGAGC

TTCGGCCACGGGTCAACGGCTGCTTTGTCAAGGTACCCGAAGCCATGGCGTCGCCATCATCTCCAGCTTCGCCCTAT

GATCCTAGTAAACTTCACCTCGGATGGTTCCGGTAATTTATAGCACAAGCCAGATAAAATGATAACATATTTCCTTC

TGATTGATCCACCCGTGAAGCAGTTGTTCCTCAAAGTAAAATAAGTCGGTTAGTGATTGATCGATTGGAGCCATTAT

GTTGACTTGACTATTTAAAATGGTCAGCAGATCAATCAAACAAAATGTATTTATTGAAACAAGTCTTGTTATACTAC

GTGTTGATTTAAACATGTAATTTCAAGAGGATAGCTACTTTGATGTGTAAT
```

The sequence of the Langdon ZCCT-A1 protein (with normal R amino acid in bold) is as follows:

```
MSMSCGLCGANNCPRLMVSPIHHRHHHHQEHQLRQHQFFAQGNHHHHHPVPLPPANFDHSRTWTTPFHETAAAGNSS    (SEQ ID NO: 80)

RLTLEVGAGGRPMAHLVQPPARAHIVPFYGGAFTNTISNEAIMTIDTEMMVGPAHYPTMQERAAKVMRYREKRKRRR

YDKQIRYESRKAYAELRPRVNGCFVKVPEAMASPSSPASPYDPSKLHLGWFR*
```

ZCCT-related protein or ZCCT-related polypeptide: A ZCCT-related protein or ZCCT-related polypeptide is a protein encoded by the VRN2 gene or genes of related function in temperate grasses. ZCCT-related proteins are defined by their structural homology to ZCCT1 proteins and their conserved function. As discussed above, the ZCCT-related protein activity depends upon the intended use of the ZCCT-related protein. For example, ZCCT-related protein may be full activity in its ability to repress expression of AP1 in temperate grasses. ZCCT-related protein activity may also be the ability of the ZCCT-related protein to interfere with the endogenous ZCCT1 activity, which could include ZCCT1 DNA binding activity without repression so that the ZCCT-related protein competes with the endogenous ZCCT1 or ZCCT-related protein for its DNA binding site. Also, ZCCT-related protein activity could be the repressor activity without the DNA binding activity. Overexpression of the repressor will interfere with the endogenous ZCCT1 or ZCCT-related protein activity by competing with accessory proteins that bind to ZCCT1 or ZCCT-related protein and enable repression of AP1.

The ZCCT-related proteins include the wheat ZCCT2 protein. The nucleotide sequence for the *T. monococcum* ZCCT2 genomic DNA including the promoter region (2,588 bp upstream from start codon and 1415-bp downstream from stop codon. Exon 1 and 2 are in bold) is as follows:

```
TTTTCACCAAAAGTAATTACCTATGTACTATATGTATACTTTTTTCTGTGTGATTTTCATGACCGATCTTGTCGATAG    (SEQ ID NO: 81)

CTAGCTAGGATGAGAGAAGTCAATGCATAATGTGTGTGATATGTAGCTAGCTAGCCAGTCCTAAAAGATCAAACATGT

AATGGATTGTGCTGTGTGTGTGGCAGTCTGCATCACGCCATCAGATGACAAAAATATTCTCTACCTAGCTAGTTCACA

TGAACTTGCTGGCCTGCATCTATACATATACACACCAGAACAAAGAATACTTGGCTTTTCTTTCTTTTTGTAGCATAG

CCTTTGTTTCTACTTCAGGGCAGAAGAAGATGAATCGCCTGTGTGGTGGTCCGAGATAGCTTAGATGCATAGATCTGT

GTGGTAGCCCGCAGGGTGTGGTGCTGATGAGGTCGCCCACGCGGGCTACTCCTGCGAGCTCAGGATTGTGTGGACTGT

CTGGCCCTGCTTTATGCAAAGGAGGAAATGGCGGCGGATTCCAACGCTCCATGGCTCCAGACTCTCCCGCTGCTTCTT

GCGCTTTTCGCTGCCCAGAAAGATCGACCACATGTGTATCTGGATTGAAATGTGCTAGCTAATGGTTGTTTCGTTCTT

GATTTTTGCTCCTTTTCATGTGCTCCACATGTACACAATAGAAAGATCTTGAAAACGACTCCGCTGCCGGTGATACCT

CGATTTGTGGATCAGAGTTGGTCGCACAGACAAGGGATCGATCGAGATATATGCTTGCCAATGGCCATCCAAATACAT

AAATGGTTCCATGTCACCGATGTGCGTGCAAGATAGCAAACATGATCAAATTGACTGTTTAATCTCTTCGTCTGGTTT

AATTATGAAACTAGTATATTTTCGAACCCTCAACTATATATTTTGTGTGGTGAACTTTTGTTGGTTCTCATTTTACAG

CTAAATTAATTTCCACGCCCATACGTAACGCTTTGTTACGAGGGGAGGCTCACACAATTGAAAAAGCCTAGCCGCCTT

TCCCATCGCCTTCCTTTCTCGCCGCCACGCAGGTTCAGGAGCAGCTTACTGGGGAAGTTTTGAAGGTCTTGGGGGGTT

GTTGTAGCTTGACAAGGAGATGAAGGCTCGAGTGGAGGTTTCCATCAGGGAGTGTTCAACAGCAGCATTTGTGAATCC

GGCGGCGCCCGAACCAACCCAACATGGTGAGCTTCTACGCGGCGCAGCTTGGCTAGGCCATCGGAGAAGATGATGTG
```

-continued

```
GATGCATGGCCCTGGAGGGCGGCGAGTTCGATCTCAGGTCCAGACTTGGCGTACAACAGCGTGATAATTTTGTCTCAT

GCATTCTTTATGCTGTCTTCGTGTTTTGTTAGGTATGGCTTGCCGGCTGCGCTCCCCCCTGTTGAAAGAAATGTTGTC

CCCGTCTTGCCCCCTGCTGATGTGCTCACCACCGATGGAGGGTGTGTGTTTTTGTGTCTCCGTCGATGGGTCTTCCGG

GATCCAGACGGTTTAGGTTTTCCATGGATTCGCCCGATTCGGCCAGCTTTCGTGATCTTCAGAGTTTCTACAAGTCCT

TATCGATGTTCTCTTCTCTGGGGTGGCGGTTTGCTTTGCGGATCACAGTCTCGCCGACGTCTCTTGGTCTGCGTCAAC

GAGTTCCTACTCGTTGCCTCTGCAAGCTCCTGGGTTTGAAAAAAGGTTCGCTACATCAAGGCCGAGACCCAAAAACAG

CACCGAGCTTTCATAGTGCGCCGCCGATGTATGCATGACGAAGAAGACTTCGGCACCCTTGAAGTGTTGATTGTAATT

TTTCTTTGTATATGGCTGTGTTTGTAAGGTCCTATGATTCTTAATATATGGTTTTAAGCCTCTTTGCCAAAAAAAAGT

TCAACGCCCATCACATTACTATTTTTATGATGAAGAGTGTTTTTGTTAACTTAAAATGTAGCGTCAAATGGATACAGA

GCATGATGAGCAACACGCGGCCTTTGCAATACCAACTGTCTGTCCAAACTAAAAAAAAACTGACATATTGACAATGCT

AAAGTCATATAGGACCAACACTACACCATTAATTGTTCCACAACTTGTACTTTTCTGTTTTAGTATTGCCATGGTTTC

CACTGTGTTGTGTTTGTCTCCCTCGGACCTTTGTGTTAGCATCTCCTTTTTGTTTGACAGTGACCAAAAAAGCTACAA

ATATCTAGCAGTGGCCTTGCGTGGACATAAGATCATGTGGGAGATTCCCGGCAAGCAAGGCGTGCATGGGTCCAGCTC

CTCCGCGTAAGAAAGAAAGAAATAAAAAATGAATCGAGGGGTAGTATCTATTCCGACGCACTCATTAGTTGGGCCTAT

TTGATTTGATCCATCATCTTTTGCTAATTCTCAGATCGAATCTTTTGCCTGGTCTGCAGCTCACTGCTGCATATATGC

AGTGCAGTGGAGGAGGGAGAGACACAACACAACCCTAGCTATTTCAAGGTGCCTTAGTAGTTAGTACTCGTCGTCGTC

TCTTCTTCTTCCTCGACATCTCTCCCCCTCCACGCGCCAAACCACACCAGAAACAAACAAGCAAGCAATCAAACGTAG

GGGCTAGCTGCAGTATGTCCATGTCATGCGGTTTGTGCGGCGCAAGCGACTGCCCGCACCACATGATCTCGCCCGTT

CTTCAGCATCAGGAACAACACTGGCTGCGCGAGTACCAGTTCTTCACCCAAGGCCACCACCACCACCACGGCGC

GGCGGCGGACTACCCACCGCCACCGCCACCGTCGGCCAATTGCCACCACTGCAGATCATGGACCACACCGTTTCATGA

AACAGCAGCTGCAGGGAACAGCAGCAGACTCACGCTGGAGGTAGATGCAGGCGGCCAAAACATGGCTCACCTGCTGC

AGCCACCGGCACGGCCAAGAACCACCATCGTGAGTAGTACTACTGCTTAATTGTTCCAGCTCTTGCCGATCGCTGGG

GCCTCCTTGTAACAAAAGTTCCCTTTTACGTAATCTCCATCTACTCCCCCCCCCCCCCCCCCCCCCCCGCCCCCTCC

CCGCATCTCAAAAAAAGTTAGCGCCATGTAACCAGCTCATATATCTGTCACATAATTCTGTTAATTTATGCTGGTCAA

TTATAATCTCCCAAGGCAGAAAGTTTGTGTTTTGTATCAGTTGATGAACAAGAATGGGAACTCACATCATCAGTTACA

CATACATACTTATTTCATTTTATTTGACTAACAAGGTAATCAGTTAATTCCTTTATGGGAACAAGCAATACATATGTC

CACGCCTTCATGTTAATTCCTTGACAAAGTTTGTGAAATGGACAATATATATACTGGATCAATGCACCCTCTTTCTCA

TTTTATGTGGTCATTTATGAATTTTAGTGCTATTTTATATTTAAATTTTCTCTTAAGCTTGTTTTGTAAGCTTATAGC

TCATGTATAACAGATACTACTCCCCATAATTGCTTCCGTAGTGGCCGGGTGATCAATCTACCGAGTTCATAAAACTGA

TCGGGATCAGATCCAAAACAGACCAAAACCTCACGAAATAGAAACAAGATCCTTGTTTAATAAGTTTGCACCAGGAAA

TTGCCTACTTAATTACTTTCTATCAATCTTATGAACATGGCATGTTTCTCACATATGGTGACCCAGATCACAATTGTT

GACGGAGTTAAACATTTTTAGCAATTCATAAAACCATGCACAGATGTACAGGGCTACGCGTATGCACATACATAATAC

ACCTAATTAAAACATATATTCATAGAGCGATTGAGTTTGGACTGTGCGCTTCTTTGGACACAAAGGCCCGGGAAGTTG

TTCTCTTCCATTGTCTAGAAAAATAGAACAGTTACAATCAAGTGCACCACTGAATGAAAATGGGTCAACTCTGGTTAA

TAAGAGACCAACTGTACTTCATAAACAGGGAATATCATGTACATATCTGCAACCCACAGGAAAGTACAGAGCTGCAC

TCTTACAGTTATTTTCCTCTTCATGTTCAGGTGCCATTCTGCGGGCTGCATTCACCAGCACTATTAGCAATGCAACA

ATCATGACTATTGATACAGAGATGATGGTGGGGGCTGCCCATAATCTGACGATGCAGGAGAGAGAGGCGAAGGTGATG

AGGTACAGGGAGAAGAGGAAGAGGCGGTGCTATGACAAGCAAATCCGCTACGAGTCCAGAAAAGCTTACGCCGAGCTC

AGGCCACGGGTCAATGGCTGCTTTGTCAAGGTACCAGAAGCCGCTGCATCGTCGTCACCCCCAGCTTCGCCCTATGAT

CCTAGTAAACTTCACCTCGGATGGTTCCAGTAGTTTTTCATCAAAGTAAAATAAGTTGGTTATTGATTGACCGACGGG
```

-continued

```
AGGAGTTATGTTGATTTGACTATTTCAAAAGGTCAGCAAACCAATCAAAGAAAATGTATTTGTTGAAACAAGTATTGT

TATGCTTTATGTTAATTTAAGCATGTAATTTGAGGAGGCTAGCTACTTAGATGTGTTTATTGTATGCAACCAATTGAA

TCAAGTCATCACCAACTCAAAGTTAAATACGGACGAGCTTTTTATGTATAAAGTTGTTGTTTTATCTTGACGACTTAT

CAAGAGTGAAAAATGGATTGGGAGTTATGAGTAAACCATCACGACCGCCAAAGATGTACAATGCTTATTTTGAGAGAG

AAAATTATATTTCACTCACCAAATATGAGTTGAACCTTGTAACCACATGTATATTACAAAGCTGTGTGTCACCTAACT

AATTTGAGGCCTTATCATAGGTAAAATACCTCCAATCTGCACGAATGAGTCACTTTAAAAGAATATGTCACGTTGCAT

GGAAAACTGTAAACATGTGTAGACAGCATAATATATAGCTGCAAATCATCCAAAGCTTGTGTACTATATTATAATTAT

GAGTTCCTTATGCTGTTGCATGTACTTATTGAAGTGATCCTTCGTCTATGAGGTAAGTTTGTACATTCATTCATCCAT

TTAACCTCGCGAATATAGATAGCTAGTTAATTCGTTTGATCGATCATGTGTATGTGTGCGTCCATAGTGTCACCGCCT

TTATCACTGGGAGATGGCACACGGTGGCAGCCTCCAACCTCAAGCTGGTGCAAACCAGATCAGCTAGACAAGATAACA

ATGTTTGTCCAAGATAAAGGGAAGCTATTGTTGACTACCATGATCCAGCAAGTTGCCAAATACTAGGGGCCAGTTCTT

TTGTTGGCTTCCAAAATAAGCTGCCCCCTATCTAGCTTTTTCTAAAAGCCCAACCAAATTAATTTTTTAGAAGCTTAC

TAATTAAGACTTGATAGTAGGCTTCTAAAAAGTATTTTTGGTTGGGCTTCTAGAATAAGCTGGGTAGGGGGCCGCTTA

TTCTAGAAGCCCAAAAAACCACTAAAAGAACTGACCCTAATTGTCATGAGATTTATTAAGTCCAAAGCTCGATGGAAG

TGACTAGATTAATTGTTTGTTCCTAAATTCATGGGCGGATGCCATGGGTGAAGGCAAAGTAAGTTTAACTATATACTT

AACACTAGTTATCTAATAAGTTAATGCTACTAGCTATTTGTTGATATCATGATAATATTTAGACTGAATTATATTATG

GAGTGTAAAATTTCACAATATTTCAGCAGCGGCACCCCGGATATTAAGATCCTAGGTCCTTCACCGCCTTAATTAATA

TCAATTCCCCTGAACAAGTTATTACTTGGTTGTTCCATCTTGTA
```

The predicted cDNA sequence for *T. monococcum* ZCCT2 is as follows

```
ATGTCCATGTCATGCGGTTTGTGCGGCGCAAGCGACTGCCCGCACCACATGATCTCGCCCGTTCTTCAGCATCAGGA    (SEQ ID NO: 82)

ACAACACTGGCTGCGCGAGTACCAGTTCTTCACCCAAGGCCACCACCACCACCACCACGGCGCGGCGGCGGACTACC

CACCGCCACCGCCACCGTCGGCCAATTGCCACCACTGCAGATCATGGACCACACCGTTTCATGAAACAGCAGCTGCA

GGGAACAGCAGCAGACTCACGCTGGAGGTAGATGCAGGCGGCCAAAACATGGCTCACCTGCTGCAGCCACCGGCACG

GCCAAGAACCACCATCGTGCCATTCTGCGGGGCTGCATTCACCAGCACTATTAGCAATGCAACAATCATGACTATTG

ATACAGAGATGATGGTGGGGGCTGCCCATAATCTGACGATGCAGGAGAGAGAGGCGAAGGTGATGAGGTACAGGGAG

AAGAGGAAGAGGCGGTGCTATGACAAGCAAATCCGCTACGAGTCCAGAAAAGCTTACGCCGAGCTCAGGCCACGGGT

CAATGGCTGCTTTGTCAAGGTACCAGAAGCCGCTGCATCGTCGTCACCCCCAGCTTCGCCCTATGATCCTAGTAAAC

TTCACCTCGGATGGTTCCAGTAG
```

The protein sequence for *T. monococcum* ZCCT2 from DV92 is as follows:

```
MSMSCGLCGASDCPHHMISPVLQHQEQHWLREYQFFTQGHHHHHHGAAADYPPPPPPSANCHHCRSWTTPFHETAAAG    (SEQ ID NO: 83)

NSSRLTLEVDAGGQNMAHLLQPPARPRTTIVPFCGAAFTSTISNATIMTIDTEMMVGAAHNLTMQEREAKVMRYREKR

KRRCYDKQIRYESRKAYAELRPRVNGCFVKVPEAAASSSPPASPYDPSKLHLGWFQ*
```

The genomic DNA sequence for the Langdon ZCCT2 gene is as follows:

```
TGTTTTGTTAGGTATGGCGTGCCGGCTGTGCTCCCCCCTGTTGAAAGAAATGTTGTCCCCATCCTGCCCCCTGGCGA    (SEQ ID NO: 84)
TGTGCTCACCACCGATGGAGGGTGTGTGTTTTTGTGTCTCCGTCGATGGGTCTTCTGGGATCCGGTCGGTTTAGGTT
TCCCATGGATTCGCCCGAATTCGGCCAGCTTTCGTGATCTTCAGAGTTTCTACAAGTCCTTATCGACGTTCTCTTCT
CTGGGGTGGCGGTTTGCTTTGCGGATCACAGTCTCGCCGACGTCTCTTGGTCTGCGTCGACGAGTTCCTACTCGTTG
CCTCTGCAAGCTCCTGGGTTTCAAAAAAGGTTTGCTACATCAAGGCGGAGACCCAAAGACAGCACCGAGCTTTCATA
GTGCGCCGCCGATGTATGCATGACGAAGAAGACTTCGGCACCCCTAAAGTTTTGATTGTAATTTTTCTTTGTATATG
GGTGTATTTGTAAGGTCCTATGATTCTTAATATATGGTTTTAAGCCTCTTTGCCAAAAAAAAAGTTCAACACCCAT
CACATTACTATTTTTACGATGAAGAGTGTTTTTGTTAACTTAAAATGTAGCGTCAAATGGATACAGAGCATGATGAG
CAACACGCGGCCTTTGCAATACCAAGTGTCTGTCCAAACTAAAAAAAACTGACATATTGACAATGCTAAAGTCATAT
AGGACCAACACTACACCACTAAATGTTCCACAACTTGTACTTTTCTGTTTAGTATTGCCATGGTTTCCATTGTGTTG
TGTTTGTCTCCCTCGGACCTTTGTGTTAGCATCTCCTTTTTGTTTGACAGTGACCAAAAAAGCTACAAATATCTAGC
AGTGGCCTTGCGTGGACATAAGATCATGTGGGAGATTCCCGGCAAGCAAGGTGTGCATGGCTCCAGCTCCTCCGCGT
AAGAAAGAAATAAAAAATGAATCGAGGGGTAGTATCTATTCCGACGCACTCATTAGTTGGGCCTATTTGATTT
GATCCATCATCTTTTGCTAATTCTCAGATCGAATCTTTTGCCTGGTCTGCAGCTCACTGCTGCATACATGCAGTGCA
GTGGAGGAGGGAGAGACACAACACAACCCTAGCTATTTCAAGGTGCCTTAGTAGTTAGTACTCGTCGTTGTCTCTTC
TTCTTCCTCGACATCTCTCCCCCTCCACGCACCAAACCACACCAGAAACAAACAAGCAAGCAAGCAAACGTAGGAGC
TAGCTGCAGT**ATGCCCATGTCATGCGGTTTGTGCGGCGCAAGCGACTGCCCGCACCACATGATCTCGCCCGTTCTTC
AGCATCAGGAACAACACCGGCTGCGCGAGTACCAGTTCTTCACCCAAGGCCACCACCACCACCACGACGCGGCG
GCGGACTACCCACCGCCACCGCCACCGTCAGCCAATTGCCACCACTGCAGATCATGGACCACACCGTTTCATGAAAC
AGCAGCTGCAGGGAACAGCAGCAGGCTCACGCTGGAGGTAGACGCAGGCGGCCAAAACATGGCTCACCTGCTGCAGC
CACCGGCACGGCCAAGAACCACCATC**GTGAGTAGTACTACTGCTTAATTGTTCCAGCTCTTGCCGATCGCTTGGGCC
TCCTTCTAACAAAAGTTCCCTTTTACGTAATCTCCATCTACTCCCCCCCCCCCCCCCCCGGCATCTCAAAAAAAG
TTAGCGCCATGTAACCAGCTCATATATCTGTCACGTAATTCTGTTAATTTATGCTGGTTGAATATAATCTCCCAAGG
CAGAGTGTTTGTGTTTTGTATCAGTTGATGCACAAGAATGGGCACTCACATCATCAGTTACATACATACTTATTT
CATTTTATTTGACTAACAAGGTAATCAGTTAATTCCTTTATGGGAACAAGCAATACATATGTCCACGCCTTCATGTT
AATTCCTTGACAAAGTTTGTGAAATGGACAATATATATACTGGATCAGTGCACCATCTTTTTCATTTTATGTGGTCA
TTTATGAATTTTAGTGCTATTTTGTATTTAAAATTTTCTCTTAAGCTTGTTTTGTAAGCTTATAGCTCAAGTATAAC
AGATACTACTCCCCATAATTGCTTCCGTAGTGGCCGGGTGATCAATCTACCGAGTTCATAAAACTGATCGAAATCAG
ATCCAAAACAGACCAAAACCTCACGAAATAGAAACAAGATCCTTGTTTAATTAGTTTGCACCAGGAAATTGCCTACT
TAATTACTTTCTATCAATCTTATGAAGATGGTATGTTTCTCACATATGGTGATCCAGATCACAATTGTTGACGGAGT
TAAACATTTTTAGCAATTCATAAAACCGTGCACAGATGTACAGGGCTACGCGTATGCACATACATAATACACCTAAT
TAAAACATATATTCATAGAGCGATTGAGTTTGGACTGTGCGCTTCTTTGGACACAAAGGCCCGGGAAGTTGTTCTCT
TCCATTGTCTAGAAAAATAGAACAGTTACAATCAAGTGCACCACTGAATGAAAATGGGTCAATTCTGGTTAATAAGA
GACCAACTGTACTTCATAAACAGGGAATATCATGTACATATCTGCAACCCACAGGAAAAGTACAGAACTGCACTCTT
ACGATTATTTTCCTCTTCATGTTCAG**GTGCCATTCTGCGGGGCTGCATTCACCAGCACTATTAGCAATGCAACGATC
ATGACTATTGATACAGAGATGATGGTGGGGGCTGCCCATAATCTGACGATGCAGGAGAGAGAGGCGAAGGTGATGAG
GTACAGGGAGAAGAGGAAGAGGCGGTGCTATGACAAGCAAATCCGCTATGAGTCCAGAAAAAGCTTACGCCGAGCTCA
GGCCACGGGTCAATGGCCGCTTTGTCAAGGTACCAGAAGCCGCTGCATCGTCGTCACCCCCAGCTTCGCCCTATGAT**
```

```
CCTAGTAAACTTCACCTCGGATGGTTCCGGTAGTTTTTCATCAAAGTAAAATAAGTTGGTTATTGTTTGACCGATGG

GAGGAGTTATGTTGATTTGACTATTTCAAAAGGTCAGCAGACCAATCAAAGAAAATGTATTTGTTGAAACAAGTATT

GTTATGCTTTATGTTAATTTAAGCATGTAGTTTGAGGAGGCTAGCTACTTAGATGTGTTTATTGTATGCAACCAATT

GAATCAAGTCATCACCAACTCAAAGTTAAATACGGACAAGCTTTTTATGTATAAAGTTGTTATTTTATCTTGACGAC

TTATCAAGAGTGAAAAATGGATTGGGAGTTATGAGTAAACCATCACGACCGCCAAAGATGTACAATGCTTATTTTGA

GAGAGAAAAATTATATTTCACTCACCAAATATGAGTTGAACCTTGTAACCACATGTATATTACAAAGCTGTGTGTCA

CCTAACTAATTTGAGGCCTTATCATAGGTAAAATACCTCCAATCTGCACGAATGAGGCACTTTAAA
```

The predicted cDNA sequence for the Langdon ZCCT2 gene is as follows:

```
ATGCCCATGTCATGCGGTTTGTGCGGCGCAAGCGACTGCCCGCACCACATGATCTCGCCCGTTCTTCAGCATCAGGA    (SEQ ID NO: 85)

ACAACACCGGCTGCGCGAGTACCAGTTCTTCACCCAAGGCCACCACCACCACCACCACGACGCGGCGGCGGACTACC

CACCGCCACCGCCACCGTCAGCCAATTGCCACCACTGCAGATCATGGACCACACCGTTTCATGAAACAGCAGCTGCA

GGGAACAGCAGCAGGCTCACGCTGGAGGTAGACGCAGGCGGCCAAAACATGGCTCACCTGCTGCAGCCACCGGCACG

GCCAAGAACCACCATCGTGCCATTCTGCGGGGCTGCATTCACCAGCACTATTAGCAATGCAACGATCATGACTATTG

ATACAGAGATGATGGTGGGGGCTGCCCATAATCTGACGATGCAGGAGAGAGAGGCGAAGGTGATGAGGTACAGGGAG

AAGAGGAAGAGGCGGTGCTATGACAAGCAAATCCGCTATGAGTCCAGAAAAGCTTACGCCGAGCTCAGGCCACGGGT

CAATGGCCGCTTTGTCAAGGTACCAGAAGCCGCTGCATCGTCGTCACCCCCAGCTTCGCCCTATGATCCTAGTAAAC

TTCACCTCGGATGGTTCCGGTAG
```

The protein sequence for the Langdon ZCCT2 is as follows:

```
MPMSCGLCGASDCPHHMISPVLQHQEQHRLREYQFFTQGHHHHHHDAAADYPPPPPPSANCHHCRSWTTPFHETAAAG    (SEQ ID NO: 86)

NSSRLTLEVDAGGQNMAHLLQPPARPRTTIVPFCGAAFTSTISNATIMTIDTEMMVGAAHNLTMQEREAKVMRYREKR

KRRCYDKQIRYESRKAYAELRPRVNGRFVKVPEAAASSSPPASPYDPSKLHLGWFR*
```

Also encompassed within the definition of ZCCT-related proteins are the winter barley ZCCT-Ha/Hb proteins. The ZCCT-Ha Dairokkaku Genomic sequence is as follows (exon 1 and 2 are in bold):

```
CCTCCGCGTAAGGAAGAAATAAATCAAAAATGCATCGAGGGACCGTATCTATTCCGACGCGCTCATTAGTTGGGCCT    (SEQ ID NO: 87)

ATTTGATTTGATTTGATCCATCGTTTTGCTAATTCTCAGGTCGAATCTTTTGTTTGGCCTGCAGCTCAGTGCTGCA

TATATGCAGTGCAGTGCAGTGCAGGAGGGAGAGACACAATACAGCCCTAGCTTCTTCAAGGTGTTAGTAGCTAGCAC

TCATCGCTGTCTCTTCTTCTTCCTCGACATCTCTCTTCCACGCACCAGACCACACCAGAAACAAACAAACTAGCAAA

CAAGCAAACGTTGGAGTTAGCTGCAGTATGTCCATGTCATGTGGTTTGTGCGGCGCCAGCAACTGCGCGTACCACAT

GATGTCGCCCGTTCTTCTTCATCATCACCATCATCAGGAACACCCACTGCACGAGTACCAGTTCTTCGCCCAAGGTC

ACCACCACCACCAGCGCGGCAGCGGACTACCCACCACCACCGCCACCGCCAGACAATTGCCACCACCACAGATCA

TGGACCACGCCGTTTCATGAAACAGCAGCTCCAGAGAACAGCACCAGGCTCACACGGGAGGTGGACGCAGGCGGCCA

ACACATGGCTCACCTGCTGCAGCCACCGGCGCCGCCAAGAGCCACCATCGTGAGTAGTACTACTGCTTAATTTTTCT

ATCTCTTGCCGATCGATGGGACCTGCTAACAAAAATCACACTTTCTTAATTTCCATCTCAAAAAAAGCTACCGCCAT
```

-continued

```
GTGACCAGCTCATATATATGCCACATAACTCCTTTAATTTATTCTGGTCGATTGTAATTTACCAAGGCAGAAAGCTT
GTATTTTGTATCAGTTGATGCACAAGAATGGGCGCTCACGTCATCAGTCGCACATACTATATACTTATTTCATTTTA
TTTGACTAACAAGGTAACTAGTTAATTCCTTTATGGGGTCAAGCAATACATATGTGCACGCCTTCATGTTAATTCCT
TGACAAAGTTTGTGAAGTGGAAAATATATTTACTTTATCAATGCACCTACTCTCATTTTATGTGGTCATTTATGAAT
TTTATTAATTTTCTGTTGAGCTAGTTTTGTATGCTTATAGCTCATATATAACTGATACTACTCCCCATAATTTTTCC
GTAGTGGTCGGGTGATCGATCTACCTAGTTCATAAACTTATCGAGATCAGGTCCAAAACAGACCAAAACCTCACGAA
ATGGAAACAAGATCCTTGTTTAATTAGTTTGCATCAGGAAATTGCTTATTACTTGCTGTCAATCTTATGAAGATGGT
ATTTTCCTCACAAATGGATCCAGTCACAATTGTTGATGAAGTTAAACATTTTTGGCAATTCATAAAACCGTGCATAG
ATGTCCGGCTACACGCACACAAGTACATAATACACCTAGTTAAAACATATATCCATAGAGCAATTGAGTTTGGACTA
TGCGCTTCATTGGACACAAAGGCCCGGGAAGTTGTTCTCTTCCATTGTCTAAAAAAATAGAACAGTTACAGTCAAGT
GCAACACTGAATGAAAATGGATCAAGTTTTGGTTAACAAGAGACCAACTTATACTTCATAAACAAGGAATATCAAGT
ACATATCTGCTACCCACAAGAAAGTACACCTTATGACTATTTTCTTCTTGATGTTCAGGTGCCATTCTGCGAGAGT
GCATTCGCCAGCACTATTAGCAACGCAACGATCATGACTATTGATACAGAAATGATGGTGGGGCCTGCCTATAATCC
AACGATGCAGGAGAGAGAGGCGAAGGTGATGAGGTACAGGGAGAAGAGGAAGAGGCGGCGCTATGACAAGCAAATCC
GCTACGAGTCCAGAAAAGCTTACGCCGAGCTCAGGCCACGGGTCAATGGCCGCTTTGCCAAGGTGCCCGAAGCCGTT
GTGTCTCCATCACCCCCAACTTCCCCCCATGATCCTAGTAAACTTCACCTCGGATGGTTC
```

The predicted cDNA sequence for the ZCCT-Ha Dairokkaku gene is as follows:

```
ATGTCCATGTCATGTGGTTTGTGCGGCGCCAGCAACTGCGCGTACCACATGATGTCGCCCGTTCTTCTTCA          (SEQ ID NO: 88)
TCATCACCATCATCAGGAACACCCACTGCACGAGTACCAGTTCTTCGCCCAAGGTCACCACCACCACCACAGCGCGG
CAGCGGACTACCCACCACCACCGCCACCGCCAGACAATTGCCACCACCACAGATCATGGACCACGCCGTTTCATGAA
ACAGCAGCTCCAGAGAACAGCACCAGGCTCACACGGGAGGTGGACGCAGGCGGCCAACACATGGCTCACCTGCTGCA
GCCACCGGCGCCGCCAAGAGCCACCATCGTGCCATTCTGCGAGAGTGCATTCGCCAGCACTATTAGCAACGCAACGA
TCATGACTATTGATACAGAAATGATGGTGGGGCCTGCCTATAATCCAACGATGCAGGAGAGAGAGGCGAAGGTGATG
AGGTACAGGGAGAAGAGGAAGAGGCGGCGCTATGACAAGCAAATCCGCTACGAGTCCAGAAAAGCTTACGCCGAGCT
CAGGCCACGGGTCAATGGCCGCTTTGCCAAGGTGCCCGAAGCCGTTGTGTCTCCATCACCCCCAACTTCCCCCCATG
ATCCTAGTAAACTTCACCTCGGATGGTTC
```

The protein sequence for the ZCCT-Ha Dairokkaku is as follows:

```
MSMSCGLCGASNCAYHMMSPVLLHHHHHQEHPLHEYQFFAQGHHHHHSAAADYPPPPPPPDNCHHHRSWTTPFHETA   (SEQ ID NO: 89)
APENSTRLTREVDAGGQHMAHLLQPPAPPRATIVPFCESAFASTISNATIMTIDTEMMVGPAYNPTMQEREAKVMRY
REKRKRRRYDKQIRYESRKAYAELRPRVNGRFAKVPEAVVSPSPPTSPHDPSKLHLGWF
```

The genomic DNA sequence of the barley ZCCT1-Hb from Dairokkaku is as follows (exon 1 and 2 are in bold):

```
TCAAATATTCTAGCAGTGGCCTTGCGTGGACATAAGATCATGTGGTAGATTCCCGGCAAGCAAGGTGTGCA         (SEQ ID NO: 90)
TGGCTCCAACTCCTCCGCGTAAGGAAGAAATAAATCAAAAATGCATCGAGGGACCGTATCTATTCCGACGCACTCAT
```

```
TAGTTGGATTTATCTGATTTGATTTTATCCATCGTCTTTTGCTAATTCTCAGATCGAATCTTTTGTCTGGTCTGCAG

CTCACTGCTGCATATATGCAGTGCAGTGCAGGAGGGAGAGACACAATACAGCCCTAGCTTCTTCAAGGTGCTTTAGT

AGCTAGCACTCATCGCTGTCTCTTCTTCTTCCTCGACATCTCTCTTCCACGCACCAGACCACACCAGAAACAAACAG

ACAAGCAAGCAAGCAAGCAAACGTTGGAGCTAGCTGCAGTATGTCCATGGCATGCGGTTTGTGCGGCGCCAGCAATT

GCCCGTATCACATGATGTCGCCCGTTCTTCTTCATCATCACCATCATCAGGAACATCGGCAGCGCGAGTACCAGTTC

TTCGCCCAAGGTCACCACCACCACCACCACGGCGCGGCAGCAGACTACCCACCGCCACAGCCACCGCCGGCCAATTG

CCACCACCGCAGATCATGGGCCACGCTGTTTCATGAAACAGCAGCTCCAGTGAATAGCACCAGGCTCACACAAGAGG

TGGACGCAGGCGGCCAACAGATGGCTCACCTGCTGCAGCCACCGGCGCCGCCAAGAGCCACCATCGTGAGTACTACT

GCTTAATCGTTCCATCTCTTCCCGATCGATGTGACTCCTTCTAACAAAAATCACACTTTCTTAATTTCCATCTCAAA

AAAAGCTAGCGCCATGTGACCAGCTCATATATCTGTCACATAACTCCGTTAATTTATGCTGGTCGATTGTAATTTAC

CAAGGCAGAAAGTTTGTGTTTTGTATCAGTTGATGCACAAGACTGGATGCTCAGATCATCAGTCACACATACTATAT

ATTTATTTCATTTTATTTGACTAACAAGGTAATCAGTTAATTCCTTTATGGGGTCAAGCAACATATGTCCACGCCTT

CATGTTAATTCCTTGGCAGAGTTTGTGAAATAGAAGATATATATTGGGATCAATGCACCCTACCTCTTTCTCATTTT

ATGTGGTCATTTAAGAATTTGAATGCTATTTTGTATTTAAATTTTCTCTTGAGCTAGTGTGTAAGCTTATAGCTCAT

ATATAACTGATACTACTCCCCATATTGCTTCCATAGTGGCCGGGTGATTGATCTACCGAGTTCATGAAACTGATCAA

GATCAGGTCCAAAACAGGCCAAAACCTCACGAAATGGAATTACGATCCTTGTTTAATTAGTTTGCATCAGGAAATTG

GCTACTTAATTACTTGCTACCAATCTTATGAAGATGGCATGTTTCCTCACAAATGGATCCAGCTCACAATTTTTGGT

GAAGTTAAACATTTTTTAGCAATTCATAAAAGGTGCATAGATGTACAGGGCTACACGTACACACGCACATAATACGC

CTAGTTAAAACATATATGCATAGAGCAATTGAGTTTGGACAATGCGCTTCTTTGGACATAATGGCCCGGGAAATTGT

TCTCTTCCATTGTCTAAAAACATAGAACAGTTAGAATCAAGTGCACCACTGAATGAGAATGGGTCAATTTTTGGTTA

ACGAGAGACCAACTATACGTTATAAACACTGTACTACTCTCACCATTGTTTTCCTCTCGATGTTCAGGTGCCATTCC

GCCGGAGTGCATTCACCAACACTATTAGCAACGCAACGATCATGACTATTGATACAGAGATGATGGCGGGGACTGCC

TATAGTCCAACGATGCAGGAAAGAGAAGCAAAGGTGATGAGGTACAGGGAGAAGAGGAAGAAGCGGCGCTATGACAA

GCAAATCCGCTACGAGTCCAGAAAAGCTTACGCCGAGCTTAGGCCACGGGTCAACGGCCGCTTTGTCAAGGTACCTG

AAGCCGCTGCGTCACCATCACCCCCAGCTTCGCCCCATGATCCTAGTGAACTTCACCTCGGATGGTTC
```

The predicted cDNA sequence for the barley ZCCT1-Hb from Dairokkaku is as follows:

```
ATGTCCATGGCATGCGGTTTGTGCGGCGCCAGCAATTGCCCGTATCACATGATGTCGCCCGTTCTTCTTCATCATCA   (SEQ ID NO: 91)

CCATCATCAGGAACATCGGCAGCGCGAGTACCAGTTCTTCGCCCAAGGTCACCACCACCACCACCACGGCGCGGCAG

CAGACTACCCACCGCCACAGCCACCGCCGGCCAATTGCCACCACCGCAGATCATGGGCCACGCTGTTTCATGAAACA

GCAGCTCCAGTGAATAGCACCAGGCTCACACAAGAGGTGGACGCAGGCGGCCAACAGATGGCTCACCTGCTGCAGCC

ACCGGCGCCGCCAAGAGCCACCATCGTGCCATTCCGCCGGAGTGCATTCACCAACACTATTAGCAACGCAACGATCA

TGACTATTGATACAGAGATGATGGCGGGGACTGCCTATAGTCCAACGATGCAGGAAAGAGAAGCAAAGGTGATGAGG

TACAGGGAGAAGAGGAAGAAGCGGCGCTATGACAAGCAAATCCGCTACGAGTCCAGAAAAGCTTACGCCGAGCTTAG

GCCACGGGTCAACGGCCGCTTTGTCAAGGTACCTGAAGCCGCTGCGTCACCATCACCCCCAGCTTCGCCCCATGATC

CTAGTGAACTTCACCTCGGATGGTTC
```

The protein sequence for the barley ZCCT-Hb Dairokkaku (which alone is not sufficient alone to generate a vernalization requirement) is as follows:

MSMACGLCGASNCPYHMMSPVLLHHHHHQEHRQREYQFFAQGHHHHHHGAAADYPPPQPPPANCHHRRSWATLFHET (SEQ ID NO: 92)

AAPVNSTRLTQEVDAGGQQMAHLLQPPAPPRATIVPFRRSAFTNTISNATIMTIDTEMMAGTAYSPTMQEREAKVMR

YREKRKKRRYDKQIRYESRKAYAELRPRVNGRFVKVPEAAASPSPPASPHDPSELHLGWF

ZCCT1 Promoter: A ZCCT1 promoter is a promoter from the ZCCT1 gene. ZCCT1 promoters are generally found 5' to the ZCCT1 protein coding sequence and regulate expression of the ZCCT1 gene. ZCCT1 promoter sequences as defined herein include those sequences that hybridize under high stringency conditions to promoter regions contained in the nucleic acids of SEQ ID NO:74 and 78. Such sequences can be synthesized chemically or they can be isolated from plants. ZCCT1 promoters can be spring or winter ZCCT1 promoters, for example, spring wheat or winter wheat ZCCT1 promoters. Representative plants from which ZCCT1 promoters can be isolated include wheat (spring and winter). Functional ZCCT1 promoters are preferred for their responsiveness to vernalization. However, non-functional ZCCT1 promoters are included and may be used for example as probes for detecting spring phenotype or as part of a nucleotide used for homologous recombination to convert winter varieties to spring varieties.

ZCCT-related Promoter: A ZCCT-related promoter is a promoter from a ZCCT1 gene or a ZCCT-related protein gene. ZCCT-related proteins promoters are generally found 5' to the ZCCT1 protein coding sequence or ZCCT-related protein coding sequence and regulate expression of the operably linked gene. ZCCT-1 related promoters are characterized by their down-regulation in response to vernalization. ZCCT-related promoter sequences as defined herein include those sequences that hybridize under high stringency conditions to promoter regions contained in the nucleic acids of SEQ ID NO:74, 78, 81, 84, 87, and 90. Such sequences can be synthesized chemically or they can be isolated from plants. Representative plants from which ZCCT1 promoters can be isolated include wheat, barley, rye, triticale, oat and forage grasses.

Taking into account these definitions, the present invention is directed to the finding that differences in the sequence of the wheat AP1 promoter and/or the wheat ZCCT1 protein are the determining factors in distinguishing winter wheat from spring wheat. Mutations in one or both of these two regions eliminate the requirement for vernalization to flower. This has been demonstrated in wheat and barley and is inferred to be common to all temperate grasses that have a vernalization response. Winter wheats require several weeks at low temperature to flower. This process called vernalization is controlled mainly by the VRN1 gene which in turn is repressed directly or indirectly by the gene product of the VRN2 gene. As detailed in Example 1, using 6,190 gametes VRN1 was found to be completely linked to MADS-box genes AP1 and AGLG1 in a 0.03-cM interval flanked by genes Cysteine and Cytochrome B5. No additional genes were found between the last two genes in 324-kb of wheat sequence or in the colinear regions in rice and sorghum. Example 1 further shows that AP1 transcription is regulated by vernalization in both apices and leaves, and the progressive increase of AP1 transcription was consistent with the progressive effect of vernalization on flowering time. In addition, Example 1 indicates that vernalization is required for AP1 transcription in apices and leaves in winter wheat but not in spring wheat. No differences were detected between genotypes with different VRN1 alleles in the AP1 and AGLG1 coding regions, but three independent deletions were found in the promoter region of AP1.

In particular, all accessions with deletions that affect all, a portion or an adjacent region to the CArG box region (SEQ ID NO:23) in the wheat AP1 promoter sequence have a spring growth habit. These results and the relatively later expression of AGLG1 during the flowering process demonstrate that AP1 is a better candidate for VRN1 than AGLG1.

Figure 12:
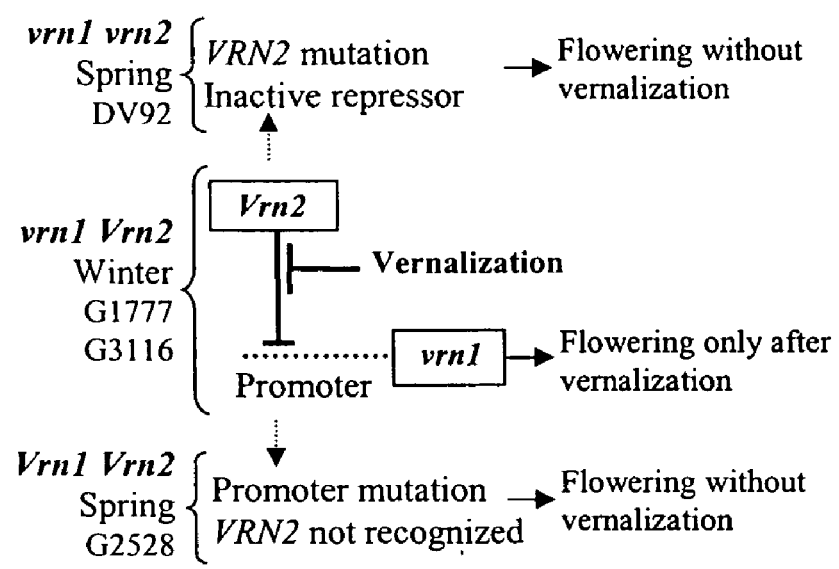
FIG. 12 shows a model of the regulation of flowering initiation by vernalization in diploid wheat.

The epistatic interactions between vernalization genes VRN1 and VRN2 suggested a model in which VRN2 would repress directly or indirectly the expression of AP1 (FIG. 12). As explained in detail below, a mutation in the CAr-G section of the promoter region of AP1 or adjacent regions would result in the lack of recognition of the repressor and in a dominant spring growth habit. The present invention is directed to this finding and the finding that ZCCT1 acts to repress the AP1 gene and their application to plant molecular biology and plant breeding.

As detailed in Example 2, VRN2 was found to be completely linked to ZCCT1 and ZCCT2, two closely related homologs. Vernalization resulted in a gradual and stable repression of ZCCT1 transcription in leaves and apices. ZCCT2 was not detected in the apices. The identity between ZCCT1 and VRN2 was confirmed by the association of the vrn2 allele for spring growth phenotype with four independent ZCCT1 mutations, and by the elimination of the vernalization requirement in transgenic winter wheat by RNA interference as illustrated in Example 2.

The AP1 Promoter

The isolation and sequence analysis of the wheat AP1 promoter and the determination that it is the controlling factor in distinguishing winter wheat from spring wheat has broad applications in plant molecular biology and plant breeding.

Figure 11:
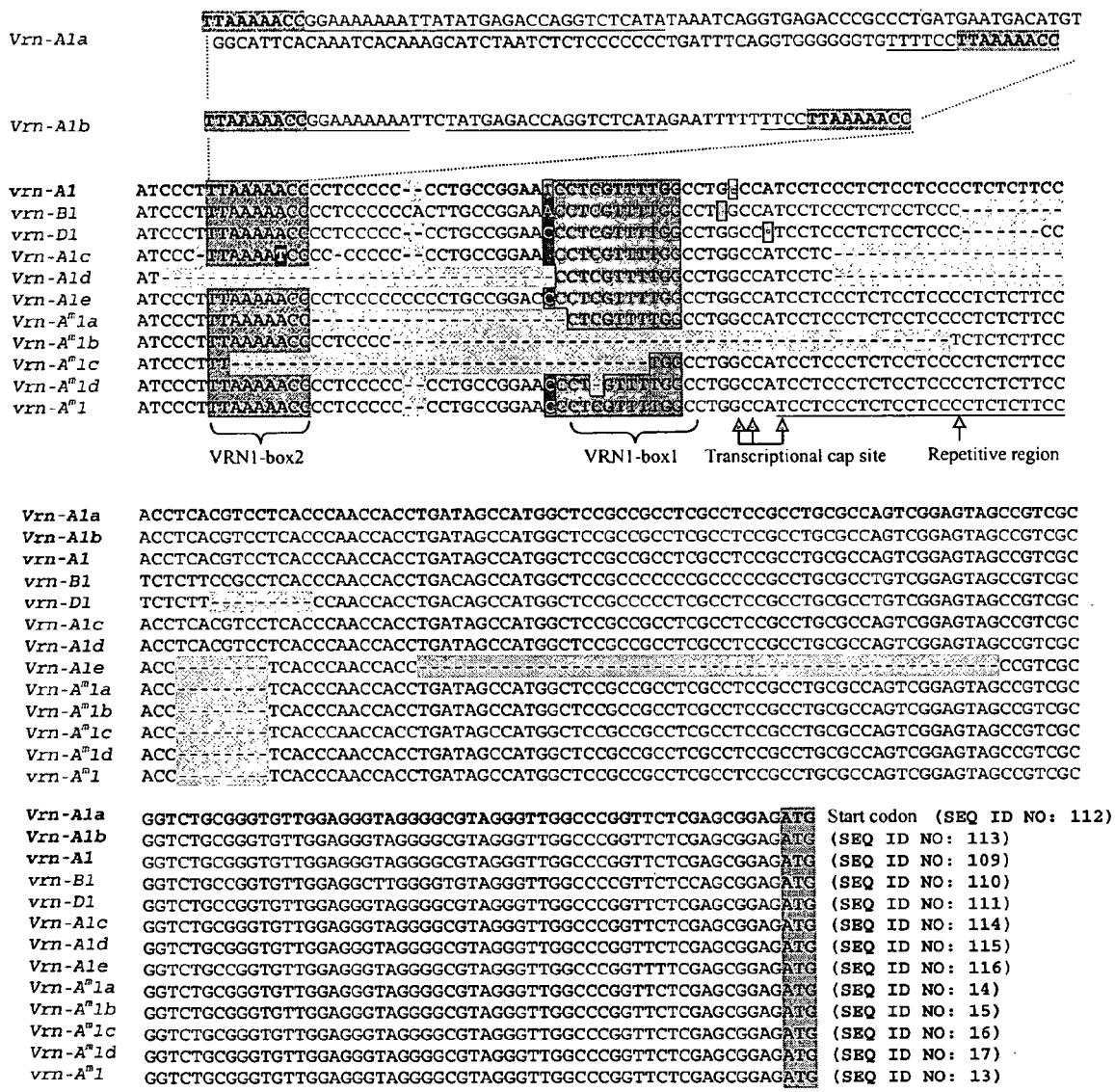
FIG. 11 shows the sequence alignment of the VRN-1 promoter sequences from hexaploid, tetraploid and diploid wheat. Section of the VRN-1 promoter amplified with genome-specific primers. The recessive vrn-A1(SEQ ID NO:109), vrn-B1(SEQ ID NO: 110) and vrn-D1 (SEQ ID NO: 111) were amplified from genomes-A, -B and -D of the common wheat winter Triple Dirk line. Vrn-A1a and Vrn-A1b are two duplicated regions of the VRN-A1 promoter including the large and short foldback elements respectively. This duplication was from the spring Triple Dirk line (SEQ ID NO:112 and SEQ ID NO:113). This duplication with the inserted foldback elements was found in spring cultivar Anza and in approximately half of the spring varieties from Argentina and from California. On the top line, only the sequence of the inserted foldback element is indicated (the rest of the sequence is identical to vrn-A1). The 9-bp host duplication is highlighted in light blue. Bases that are part of a perfect inverted repeat are indicated in blue. Conserved bases between the two duplications are underlined. Outside the foldback element, the 9-bp host duplication is highlighted in light blue and the CArG-box1 in green, but its putative variable border in red. Vrn-A1c: Marquis (PI 94548, SEQ ID NO:114), Vrn-A1d: *T. dicoccoides* (accession FA15-3, SEQ ID NO:115) and Vrn-A1e from *T. timopheevii*, (SEQ ID NO:116). Alleles from *T. monococcum* are indicated by the Am genome (blue letters). The winter recessive vrn-Am1 allele was from accession G1777 (SEQ ID NO:13). The alleles for spring growth habit are Vrn-A$^m$1a: G2528 (SEQ ID NO:14), Vrn-A$^m$1b: PI349049 (SEQ ID NO:15), Vrn-A$^m$1c: PI355515 (SEQ ID NO:16), and Vrn-A$^m$1d: PI 503874 (SEQ ID NO:17). The transcriptional initiation sites were deduced based on the sequence of the wheat EST clone and are indicated in pink highlight (vrn-A1, vrn-B1 and vrn-D1). A variable TC-rich repetitive region of the UTR is underlined. Deletions are indicated by dashes highlighted in yellow. Polymorphic bases are indicated in red.

As a first embodiment, the present invention is directed to the AP1 promoter isolated from spring wheat. The winter wheat AP1 promoter sequence, G3116, depicted in FIG. 9 (SEQ ID NO:12) contains a core CArG box sequence CCTCGTTTTGG (SEQ ID NO:23). The spring wheat AP1 promoter sequence lacks all, a portion, or adjacent sequence to this core sequence. As such, the present invention is directed to a recombinant AP1 promoter sequence wherein the AP1 promoter sequence hybridizes to the nucleic acid molecule of SEQ ID NO:12 or the complement thereof under high stringency conditions wherein the AP1 promoter sequence lacks all or a portion of nucleotides −162 to −172 upstream the start codon of SEQ ID NO: 9, CCTCGTTTTGG (SEQ ID NO:23). Representative, but non-limiting spring wheat AP1 sequences are depicted in FIG. 11 as SEQ ID NO:14-17 wherein a portion of the CCTCGTTTTGG sequence is deleted or altered. An AP1 promoter sequence is said to lack all or a portion of the CCTCGTTTTGG sequence if 1, 2, 3, 4, 5, 6, 7, 8, 9, 10, or 11 of the nucleotides of SEQ ID NO:23 are missing, absent, mutated, or subject to a sequence change or a deletion has been introduced in the sequence. The mutation may be an inversion, a reversion or other alteration in the sequence.

Alteration of the region close the putative TATA box upstream of the CArG box also result in a spring growth habit in polyploid species of wheat (FIG. 11, SEQ ID NO:112, 113, 114, 115, 116).

Vectors

The promoters or the coding regions of the AP1 and ZCCT genes of the present invention may be cloned into a suitable vector. Expression vectors are well known in the art and provide a means to transfer and express an exogenous nucleic acid molecule into a host cell. Thus, an expression vector contains, for example, transcription start and stop sites such as a TATA sequence and a poly-A signal sequence, as well as a translation start site such as a ribosome binding site and a stop codon, if not present in the coding sequence. A vector can be a cloning vector or an expression vector and provides a means to transfer an exogenous nucleic acid molecule into a host cell, which can be a prokaryotic or eukaryotic cell. Such vectors include plasmids, cosmids, phage vectors and viral vectors. Various vectors and methods for introducing such vectors into a cell are described, for example, by Sambrook et al. 1989.

The invention also provides an expression vector containing an AP1 promoter nucleic acid molecule operably linked to a protein coding sequence. For this construct, the AP1 promoter may be from any temperate grass but is preferably from a winter wheat or a spring wheat. In another format, the present invention is directed to a recombinant AP1 promoter sequence linked to an AP1 protein.

The invention also provides an expression vector containing a ZCCT1 or ZCCT1 derived protein coding sequence operably linked to a promoter. The promoter may be constitutive or inducible.

The invention further provides an expression vector containing a ZCCT1 promoter nucleic acid molecule operably linked to a protein coding sequence. For this construct, the ZCCT1 promoter may be from any temperate grass but is preferably from a winter wheat or a spring wheat.

In the constructs of the invention, each component is operably linked to the next. For example, where the construct comprises the spring wheat AP1 promoter, and protein encoding sequence, preferably, the wheat AP1 protein, the AP1 promoter is operably linked to the 5' end of the wheat AP1 protein encoding sequence or open reading frame.

The AP1 coding sequence may be from wheat or other AP1 protein coding sequences as defined herein. The protein coding sequence linked to the AP1 promoter may be an AP1 protein sequence or another heterologous protein. The heterologous proteins which find use in the invention include those that provide resistance to plant pests, facilitate translocation of nutrients, provide resistance to stresses typical of the summer: heat and dehydration, etc.

The constructs of the invention may be introduced into transgenic plants. A number of recombinant vectors suitable for stable transformation of plant cells or for the establishment of transgenic plants have been described including those described in Weissbach and Weissbach (1988), and Gelvin et al. (1990). Typically, plant transformation vectors include one or more open reading frames (ORFs) under the transcriptional control of 5' and 3' regulatory sequences and a dominant selectable marker with 5' and 3' regulatory sequences. Dominant selectable marker genes that allow for the ready selection of transformants include those encoding antibiotic resistance genes (e.g., resistance to hygromycin, kanamycin, bleomycin, G418, streptomycin or spectinomycin) and herbicide resistance genes (e.g., phosphinothricin acetyltransferase).

Standard molecular biology methods, such as the polymerase chain reaction, restriction enzyme digestion, and/or ligation may be employed to produce these constructs.

Transgenic Plants

Standard molecular biology methods and plant transformation techniques can be used to produce transgenic plants that produce plants having a recombinant AP1 promoter.

Introduction of the selected construct into plants is typically achieved using standard transformation techniques. The basic approach is to: (a) clone the construct into a transformation vector, which (b) is then introduced into plant cells by one of a number of techniques (e.g., electroporation, microparticle bombardment, *Agrobacterium* infection); (c) identify the transformed plant cells; (d) regenerate whole plants from the identified plant cells, and (d) select progeny plants containing the introduced construct.

Preferably all or part of the transformation vector will stably integrate into the genome of the plant cell. That part of the transformation vector which integrates into the plant cell and which contains the introduced recombinant sequence may be referred to as the recombinant expression cassette.

Selection of progeny plants containing the introduced transgene may be made based upon the detection of the recombinant AP1 promoter in transgenic plants, upon the detection of the recombinant ZCCT-related protein coding sequence or upon enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include: U.S. Pat. No. 5,571,706 ("Plant Virus Resistance Gene and Methods"); U.S. Pat. No. 5,677,175 ("Plant Pathogen Induced Proteins"); U.S. Pat. No. 5,510,471 ("Chimeric Gene for the Transformation of Plants"); U.S. Pat. No. 5,750,386 ("Pathogen-Resistant Transgenic Plants"); U.S. Pat. No. 5,597,945 ("Plants Genetically Enhanced for Disease Resistance"); U.S. Pat. No. 5,589,615 ("Process for the Production of Transgenic Plants with Increased Nutritional Value Via the Expression of Modified 2S Storage Albumins"); U.S. Pat. No. 5,750,871 ("Transformation and Foreign Gene Expression in *Brassica* Species"); U.S. Pat. No. 5,268,526 ("Overexpression of Phytochrome in Transgenic Plants"); U.S. Pat. No. 5,780,708 ("Fertile Transgenic Corn Plants"); U.S. Pat. No. 5,538,880 ("Method for Preparing Fertile Transgenic Corn Plants"); U.S. Pat. No. 5,773,269 ("Fertile Transgenic Oat Plants"); U.S. Pat. No. 5,736,369 ("Method for Producing Transgenic Cereal Plants"); U.S. Pat. No. 5,610,049 ("Methods for Stable Transformation of Wheat"); U.S. Pat. No. 6,235,529 ("Compositions and Methods for Plant Transformation and Regeneration") all of which are hereby incorporated by reference in their entirety. These examples include descriptions of transformation vector selection, transformation techniques and the construction of constructs designed to express an introduced transgene.

The transgene-expressing constructs of the present invention may be usefully expressed in a wide range of higher plants where an altered response to vernalization is useful. The invention is expected to be particularly applicable to monocotyledonous cereal plants including barley, wheat, rye, triticale, oat and forage grasses.

Methods for the transformation and regeneration of monocotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG-mediated transformation); transformation using viruses; micro-injection of plant cells; micro-projectile bombardment of plant cells; vacuum infiltration; and Agrobacterium-mediated transformation. Typical procedures for transforming and regenerating plants are described in the patent documents listed above.

Following transformation, transformants are preferably selected using a dominant selectable marker. Typically, such a marker will confer antibiotic or herbicide resistance on the seedlings of transformed plants, and selection of transformants can be accomplished by exposing the seedlings to appropriate concentrations of the antibiotic or herbicide. After transformed plants are selected and grown the plant can be assayed for expression of recombinant proteins.

Uses of the Transgenic Plants of the Invention

The transgenic plants of the invention are useful in that they exhibit an altered response to vernalization or altered flowering time. An altered flowering time means that the transformed plant will flower at a different time than the untransformed plant or may not flower at all. As defined herein, an altered response to vernalization means that the transgenic plant will respond differently to vernalization than a comparable non-transgenic plant. In one embodiment, a transgenic winter wheat expressing a recombinant spring wheat AP1 promoter operably coupled to an AP1 polypeptide sequence will exhibit an altered response to vernalization in that the recombinant AP1 protein will be expressed in the absence of vernalization and the plant will flower without the requirement of vernalization. In other words, a winter genotype would be transformed into a spring phenotype. Such expression contrasts with the expression of the endogenous (non-recombinant) AP1 protein in the transgenic plant, which requires vernalization for expression.

The protein coding sequence linked to the AP1 promoter or ZCCT1 promoter may be also any heterologous protein. Heterologous proteins useful in the invention include proteins encoded by polynucleotides from any source, natural or synthetic. Suitable coding regions encode animal RNAs or polypeptides, as well as variants, fragments and derivatives thereof. The encoded products may be recovered for use outside the host plant cell (e.g., therapeutically active products) or they may alter the phenotype of the host plant cell (e.g., conferring disease resistance, the ability to survive or grow in the presence of particular substrates). Examples of such coding regions include polynucleotides derived from vertebrates, such as mammalian coding regions for RNAs (e.g., anti-sense RNAs, ribozymes, and chimeric RNAs having ribozyme structure and activity) or polypeptides (e.g., human polypeptide coding regions). Other coding regions useful in the inventive methods are derived from invertebrates (e.g., insects), plants (e.g., crop plants), and other life forms such as yeast, fungi and bacteria. The heterologous proteins which find particular use in the invention include those that provide resistance to plant pests, facilitate translocation of nutrients, provide resistance to stresses typical of the summer: heat and dehydration, etc. Such protein sequences are available in the literature and known to those of skill in the art. Representative proteins of interest are described and disclosed in Lea and Leegood (1998); Grierson and Covey (1991); and Buchanan et al. (2001), all of which are hereby incorporated by reference in their entirety.

In another embodiment, a transgenic plant will express any protein only after vernalization or flowering if linked to the AP1 promoter or only before vernalization if linked to the ZCCT1 promoter. This could be useful to avoid the expression of the transgene during the vegetative growth and to direct its expression to the flowering period of the plant. Alternatively, this could be used to express the transgene during the vegetative growth phase but not during the flowering period of the plant. For example, a transgene could be operatively linked to the AP1 promoter. Such a construct in winter wheat would only be expressed after vernalization.

In another embodiment, flowering in wheat or other temperate grasses may be regulated by stimuli other than vernalization. This may be achieved by replacement of the endogenous AP1 gene with an AP1 gene operably linked to an inducible promoter. Thus, expression of the AP1 gene may be induced in response to exposure to a particular stimulus such as pathogen exposure, wounding, heat exposure, chemical exposure, etc. so that the plant will flower at a controlled time or under certain conditions. In addition, controlled vernalization may be achieved by addition of a ZCCT-related protein coding gene operably linked to an inducible promoter. Then removal of the stimulus that increases expression or addition of the stimulus that induces repression can stimulate flowering by derepression of AP1. In yet another embodiment, the expression of the AP1 gene or the ZCCT1 gene may be regulated by RNAi or antisense gene operably linked to an inducible promoter.

Figure 15A:
FIG. 15A shows a transgenic winter wheat transformed with an RNA interference construct for ZCCT1 which flowered 23 days earlier than the negative control.
Figure 15B:
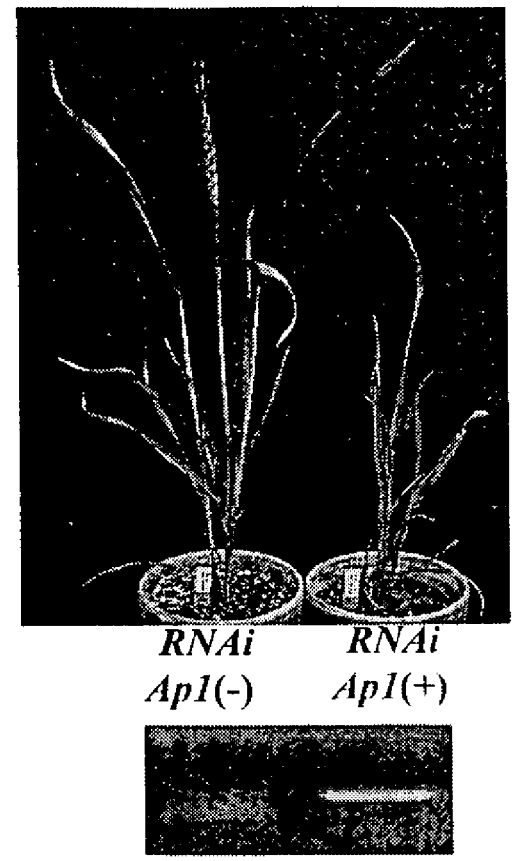
FIG. 15B shows a transgenic spring wheat transformed with an RNA interference construct for AP1 which flowered 23 days earlier than the negative control.
Figure 15C:
FIG. 15C shows RT-PCR with primers for a transcribed region from the vector used in the RNAi transformation. RNA was extracted from transgenic spring wheat Bobwhite transformed with an RNA interference construct for AP1. The primers were designed for a transcribed region from the vector used in the RNAi transformation. Progeny from the transgenic plant (7 positive and 8 negative) showed perfect cosegregation of the presence of the transgene and lat flowering.
Figure 16:
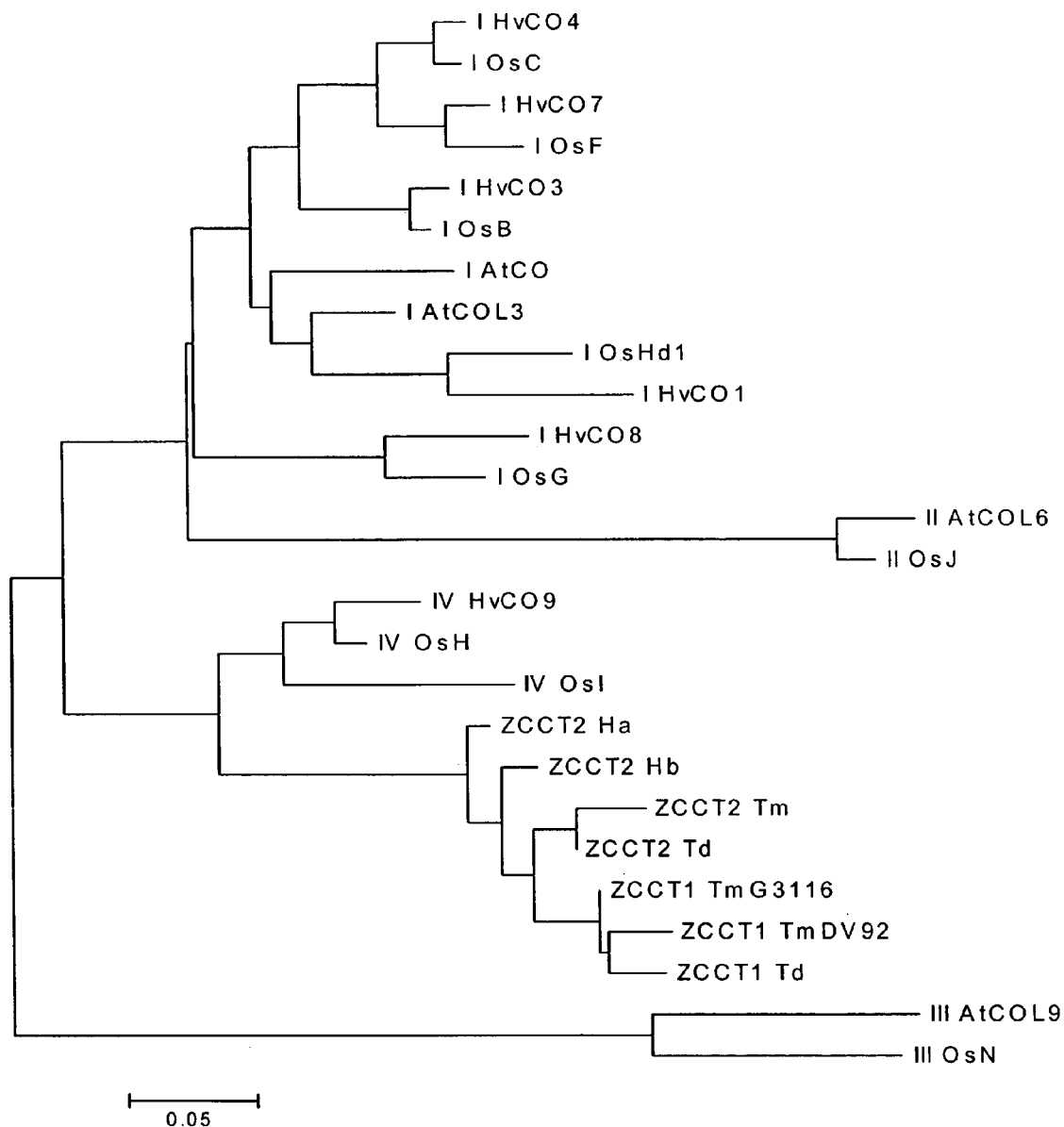
FIG. 16 shows the Best Neighbor Joining tree based on CCT domains. Bosstrap values >50 based on 1000 replications are indicated in their respective nodes. Roman numbers in front of the gene names indicate the CO-like group according to Griffiths et al. (2003).

Both delay of flowering by RNAi repression of AP1, and acceleration of flowering by RNAi repression of ZCCT1 have been confirmed experimentally. In both cases the variation in flowering time observed in a T0 plant, cosegregated with the transgene in the T1 progeny (FIG. 15).

In yet another aspect of the present invention, a plant that normally requires vernalization, such as winter wheat, may be modified to no longer require vernalization in order to flower. Such plants may be generated by a number of methods. In one embodiment, the plant may be supplied with an AP1 promoter that is not repressed prior to vernalization operably linked to an AP1 gene. In another embodiment, the plant's endogenous ZCCT1 activity may be inhibited. The ZCCT1 activity may be inhibited by a wide variety of methods. Examples include repression with RNAi (FIG. 15A) or antisense gene expression, knockout of the ZCCT1 gene or promoter, overexpression of a repression defective ZCCT-related protein that competes with the endogenous ZCCT1 for the ZCCT1 DNA binding site, overexpression of a DNA binding defective ZCCT-related protein that competes with the endogenous ZCCT1 for associated proteins involved in repressing AP1, or replacement of the endogenous ZCCT1 protein with a defective ZCCT1 protein by homologous recombination for example.

In still another aspect, temperate grasses that never flower or have a long delayed flowering may be generated for use as forage or in situations where flowing is not desired such as golf courses. Such plants may be generated by expression of a ZCCT-related protein operably linked to a constitutive promoter. In another embodiment, the AP1 activity may be permanently or greatly repressed by RNAi or antisense gene expression.

Plants Produced by Plant Breeding

Results presented here demonstrated that the allelic variation at the AP1 gene is responsible for the allelic variation at the Vrn1 gene from wheat. Therefore allelic variation at the AP1 gene can be used as a molecular marker for the Vrn1 gene in marker assisted selection programs. Similarly, the allelic variation at the ZCCT1 gene is responsible for the allelic variation at the Vrn2 gene from diploid wheat. Therefore allelic variation at the ZCCT1 gene can be used as a molecular marker for the Vrn2 gene in marker assisted selection programs. Marker-assisted breeding is a procedure well known in the art as described in Hayward, et al. (1993).

These markers can be used to transfer different Vrn1 and/or Vrn2 alleles into different germplasm by marker-assisted selection. They can also be used to determine the different haplotypes present in this region in the cultivated wheats and to establish a classification of the different haplotypes. This characterization will be useful to determine the adaptive value of the different haplotypes to different environments.

Figure 13:
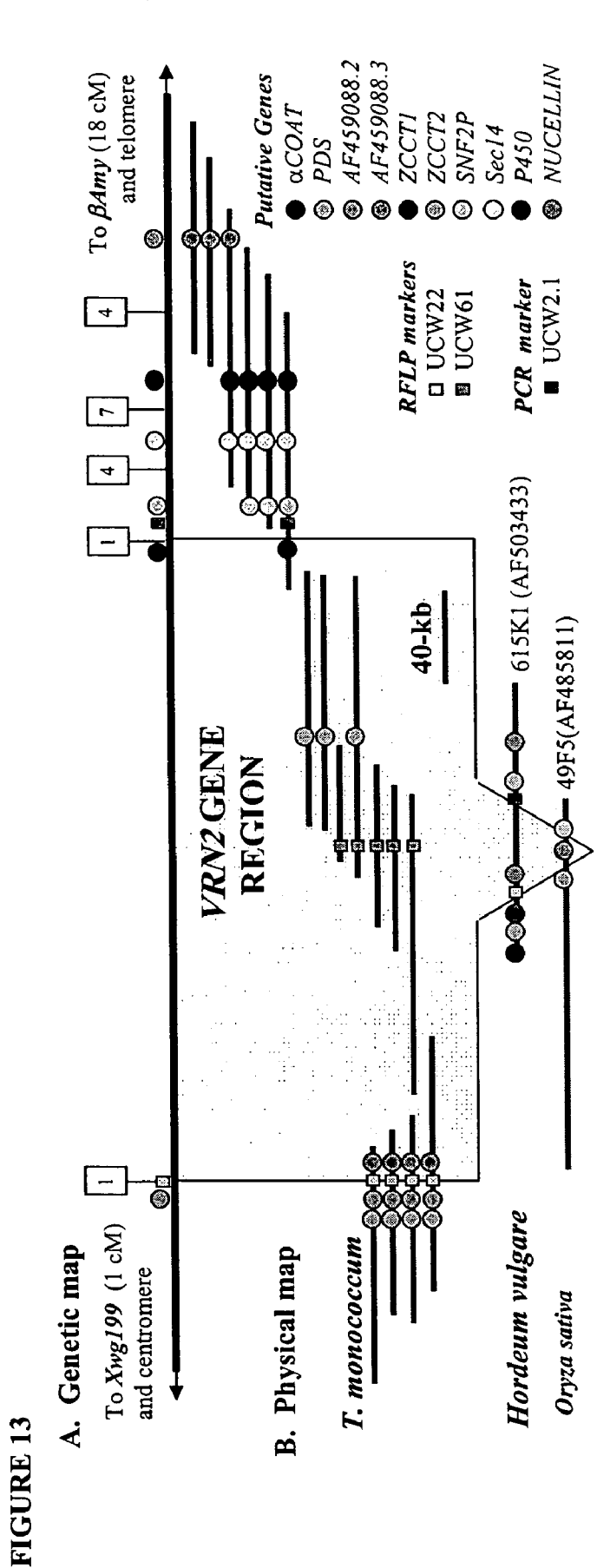
FIG. 13A shows a genetic map of the VRN2 region on chromosome 5A$^m$ of *T. monococcum* based on 5,698 gametes. Numbers of crossovers in the critical recombinant plants are indicated in boxes.
FIG. 13B shows a physical map of the wheat VRN2 gene region in *T. monococcum* and in colinear regions from barley and rice. BAC clones indicated in red have been sequenced (438,828-bp, AF459088). BAC clones order from left to right are: 374A18, 94E8, 304H18, 258C22, 301G15, 615O6, 650N20, 405L8, 271O11, 275P20, 157P20, 455C17, 322L23, 702K8, 32A1, 533H16 and 324G2 (bold letters indicate sequenced BACs).

This invention relates to the use of allelic variation at any of the genes present in FIG. 1 as molecular markers for the Vrn1 gene or in FIG. 13 as molecular markers for the Vrn2 gene.

This invention will be better understood by reference to the following non-limiting examples.

EXAMPLE 1

Background

VRN1 and VRN2 (unrelated to the genes with similar names in *Arabidopsis*) are the main genes involved in the vernalization response in diploid wheat *Triticum monococcum* (Dubcovsky, J., et al. (1998), Tranquilli, G. E., et al. (1999)). (Full citations for the references cited herein are provided before the claims.) However, most of the variation in the vernalization requirement in the economically important polyploid species of wheat is controlled by the VRN1 locus (Tranquilli, G. E., et al. (1999), Law, C. N., et al. (1975)). This gene is critical in polyploid wheats for their adaptation to autumn sowing and divides wheat varieties into the winter and spring market classes.

The VRN1 gene has been mapped in colinear regions of the long arm of chromosomes 5A (Dubcovsky, J., et al. (1998), Law, C. N., et al. (1975), Galiba, G., et al. (1995)), 5B (Iwaki, K., et al. (2002), Barrett, B., et al. (2002)) and 5D (Law, C. N., et al. (1975)). This region of wheat chromosome 5 is colinear with a region from rice chromosome 3 that includes the HD-6 QTL for heading date (Kato, K., et al. (1999)). However, it was recently demonstrated that VRN1 and HD-6 are different genes (Kato, K., et al. (2002)).

In spite of the progress made in the elucidation of the vernalization pathway in *Arabidopsis*, little progress has been made in the characterization of wheat vernalization genes. The two main genes involved in the vernalization pathway in *Arabidopsis*, FRI and FLC (Michaels, S. D., et al. (1999), Sheldon, C. C., et al. (2000), Johanson, U., et al. (2000)), have no clear homologues in the complete draft sequences of the rice. genome (Goff, S. A., et al. (2002)). This may not be surprising considering that rice is a subtropical species that has no vernalization requirement. Since no clear orthologues of the *Arabidopsis* vernalization genes were found in rice or among the wheat or barley ESTs, a map based cloning project for the wheat VRN1 gene was initiated.

Chromosome walking in wheat is not a trivial exercise because of the large size of its genomes (5,600 Mb per haploid genome) and the abundance of repetitive elements (Wicker, T., et al. (2001), SanMiguel, P., et al. (2002)). To minimize the probability that these repetitive elements would stop the chromosome walking, simultaneous efforts were initiated in the orthologous regions in rice, sorghum, and wheat. The initial sequencing of rice, sorghum, and wheat BACs selected with RFLP marker WG644 (0.1 cM from VRN1) showed good microcollinearity among these genera (SanMiguel, P., et al. (2002), Dubcovsky, J., et al. (2001), Ramakrishna, W., et al. (2002)). The low gene density observed in the wheat region and the large ratio of physical to genetic distances (SanMiguel, P., et al. (2002)) suggested that large mapping populations and comparative physical maps would be necessary for a successful positional cloning of VRN1.

Materials and Methods

Mapping Population

The high-density map was based on 3,095 $F_2$ plants from the cross between *T. monococcum* ssp. aegilopoides accessions G2528 (spring, VRN1) with G1777 (winter, vrn1 ). These two lines have the same dominant allele at the VRN2 locus and therefore, plants from this cross segregate only for VRN1 in a clear 3:1 ratio (Dubcovsky, J., et al. (1998), Tranquilli, G. E., et al. (1999)).

Plants were grown in a greenhouse at 20-25° C. without vernalization and under long photoperiod (16-h light). Under these conditions, winter plants flowered one to two months later than spring plants. $F_2$ plants are analyzed for molecular markers flanking VRN1, and progeny tests are performed for plants showing recombination between these markers. The 20-25 individual $F_3$ plants from each progeny test were characterized with molecular markers flanking the crossover to confirm that the observed segregation in growth habit was determined by variation at the VRN1 locus. G2528 and G1777 were included as controls in each progeny test.

For studies to confirm that the CArG-box is the critical site for the recognition of the vernalization signal the following steps were taken. PI503874 (spring wheat with a single bp deletion in the CArG box SEQ 17) was crossed G3116 (winter wheat). An F1 plant was produced with spring flowering habits (no vernalization requirement) indicative of a dominant spring growth habit. F1 plants were self-pollinated to produce 144 F2 seeds. The 144 F2 seeds were planted in cones and grown without vernalization in the green house under long day conditions. DNA was extracted from each of the plants and the promoter region was amplified by PCR. The amplified PCR fragment was digested with a restriction enzyme that cut only the sequence without the one base pair deletion.

Procedures for genomic DNA extraction, Southern blots, and hybridizations were described before (Dubcovsy, J., et al (1994)). The first 500 $F_2$ plants were screened with flanking RFLP markers CDO708 and WG644, which were later replaced by closer PCR markers to screen the complete mapping population. Additional markers were developed for the eight genes present between the PCR markers as detailed below.

Molecular Markers

Molecular markers were developed for the high-density map of the *Triticum monococcum* Vrn1 vernalization gene as depicted in FIGS. 1-2. The information is organized by the order of genes in FIG. 1. All primers are 5' to 3'. The Cleavage Amplification Polymorphic Sequence (CAPS) markers show PCR products digested with the polymorphic restriction enzyme. The PCR products are detectable by gel electrophoresis.

a) RFLP Marker WG644

Sequence of the WG644 showed that this RFLP marker was part of GENE4 (putative ABC transporter gene) present in *T. monococcum* BAC clone 115G10 (AF459639). This wheat RFLP marker was polymorphic between G1777 and G2528 with restriction enzyme DraI.

b) GENE1 (Putative Mitochondrial Carrier Protein, AF459639)

```
GENE1-F    CCAGCGTATGATTTGGAGGT    (SEQ ID NO: 24)
GENE1-R    TTGGCATTATTGGACCATCA    (SEQ ID NO: 25)
```

Sequence of the G1777 (AY244503) and G2528 (AY244504) alleles showed a polymorphic Taq I restriction site. This polymorphism was used to develop a CAPS marker.

c) PCS1 (Phytochelatin Synthetase)

```
PCS1-F    CTGACCTGGGGCCTTGAGAG    (SEQ ID NO: 26)
PCS1-R    CTTCGCATCAGCAGCTGTAT    (SEQ ID NO: 27)
```

These primers amplified a 507 bp region of the Phytochelatin Synthetase pseudogene (AY188332). This wheat RFLP marker was polymorphic between G1777 and G2528 with restriction enzyme DraI.

d) PCS2 (Phytochelatin Synthetase)

```
PCS2-F    CCATGGATAATCATCGGGAG    (SEQ ID NO:28)
PCS2-R    GTCACCATCACCAACTTCAA    (SEQ ID NO:29)
```

Primers were used to amplify a region of the Phytochelatin Synthetase 2 gene (Exons 3-4) from barley variety Morex (AY244504). This RFLP marker was polymorphic between G1777 and G2528 with restriction enzyme Eco RI.

e) CYB5(Cytochrome B5)

```
CYB5-F    GACTGCGTATTTGGACGACC    (SEQ ID NO:30)
CYB5-R    CCACGGCTGATATCCCGACTG   (SEQ ID NO:31)
```

These primers amplify a 373-bp region of Cytochrome B5 gene (Exons 2-3) from *T. monococcum* BAC clone 609E06 (AY188332). This RFLP marker was polymorphic between G1777 and G2528 with restriction enzyme Eco RI.

f) AGLG1(MADS-box)

```
AGLG1-F    GACCCTCGAGAGGTACCAG    (SEQ ID NO:32)
AGLG1-R    CATCTACACTACGATCTAGC   (SEQ ID NO:33)
```

These primers amplified exon2 and intron 2 of AGLG1 from *T. monococcum* BAC 719C13. Sequence of the G1777 (YA244506) and G2528 (YA244507) alleles showed two polymorphic Dpn II restriction sites. A cDNA from this gene (BE430753) was also mapped by RFLP using Eco RI to delimit the region of the crossover between AGLG1 and CYB5.

g) PHY-C(Phytochrome-C)

Primers based on barley EST BE060096

```
PHY-C-F    GAAAATGTCTGAACAAGCTGCT    (SEQ ID NO:34)
PHY-C-R    TCTAGATGAGCAATCTGCAT      (SEQ ID NO:35)
```

These primers were used to amplify a 750-bp product form G1777 (AY244514) that was used as an RFLP probe to map a Hha I polymorphism.

h) ADA2(Transcriptional Adaptor, *Zea mays* AJ430205)

Primers based on *T. aestivum* EST BJ309328

```
ADA2-F    GAAGATGCACTTGGAGAAGG    (SEQ ID NO:36)
ADA2-R    GTCTCTTTGCATTGTACCCA    (SEQ ID NO:37)
```

These primers were used to amplify a 700-bp product from G1777 (AY244515) that was used as an RFLP probe to map an Rsa I polymorphism.

i) MTK4 (Tousled-like Kinase, AC091811)

Primers

```
MTK4_F    GGTAAAAGATGAGCAAGGAG        (SEQ ID NO:38)
MTK4-R    TCTATCTATGGTGAACTCTTACTTC   (SEQ ID NO:39)
```

Sequencing of G1777 (AY244512) and G2528 (AY244513) alleles with these primers showed a polymorphic Dpn II restriction site that was used to develop a CAPS marker.

j) CDO708 (Putative RNA-binding Protein, AC091811)

The CDO708 clone was sequenced with primer M13 Forward. This sequence had a high homology to putative RNA-binding protein ML58954.1 from rice BAC AC091811. This clone was used as an RFLP probe to map a Hha I polymorphism between G1777 and G2528.

Contig Construction and BAC Sequencing

High-density filters for the BAC libraries from *T. monococcum* accession DV92 (Lijavetzky, D., et al. (1999)), *Oryza sativa* var. *Nipponbare* (Zhang, H.-B., et al. (1996)), and *Sorghum bicolor* (Woo, S. S., et al. (1994)) were screened with segments from the different genes indicated in FIG. 1. Contigs were assembled using Hind III fingerprinting and confirmed by hybridization of BAC ends obtained by plasmid rescue, inverse PCR (Woo, S. S., et al. (1994)) or BAC sequencing. Restriction maps using single and double digestions with eight-cutter restriction enzymes, pulse field electrophoresis, and hybridization of the Southern blots with different genes, were used to order genes within the BACs, to select the fragment sequenced from the sorghum BAC, and to confirm the assembly results from the BAC sequencing. Shotgun libraries for BAC sequencing were constructed as described before (Ducovsky, J., et al. (2001)). Complete *T. monococcum* BACs 609E06, 719C13, and 231A16 and a 24-kb fragment from sorghum BAC 17E12 were sequenced. Genes were identified by a combination of comparative genomic analysis, BLAST searches and gene-finding programs.

Phylogenetic Analysis

Figure 3:
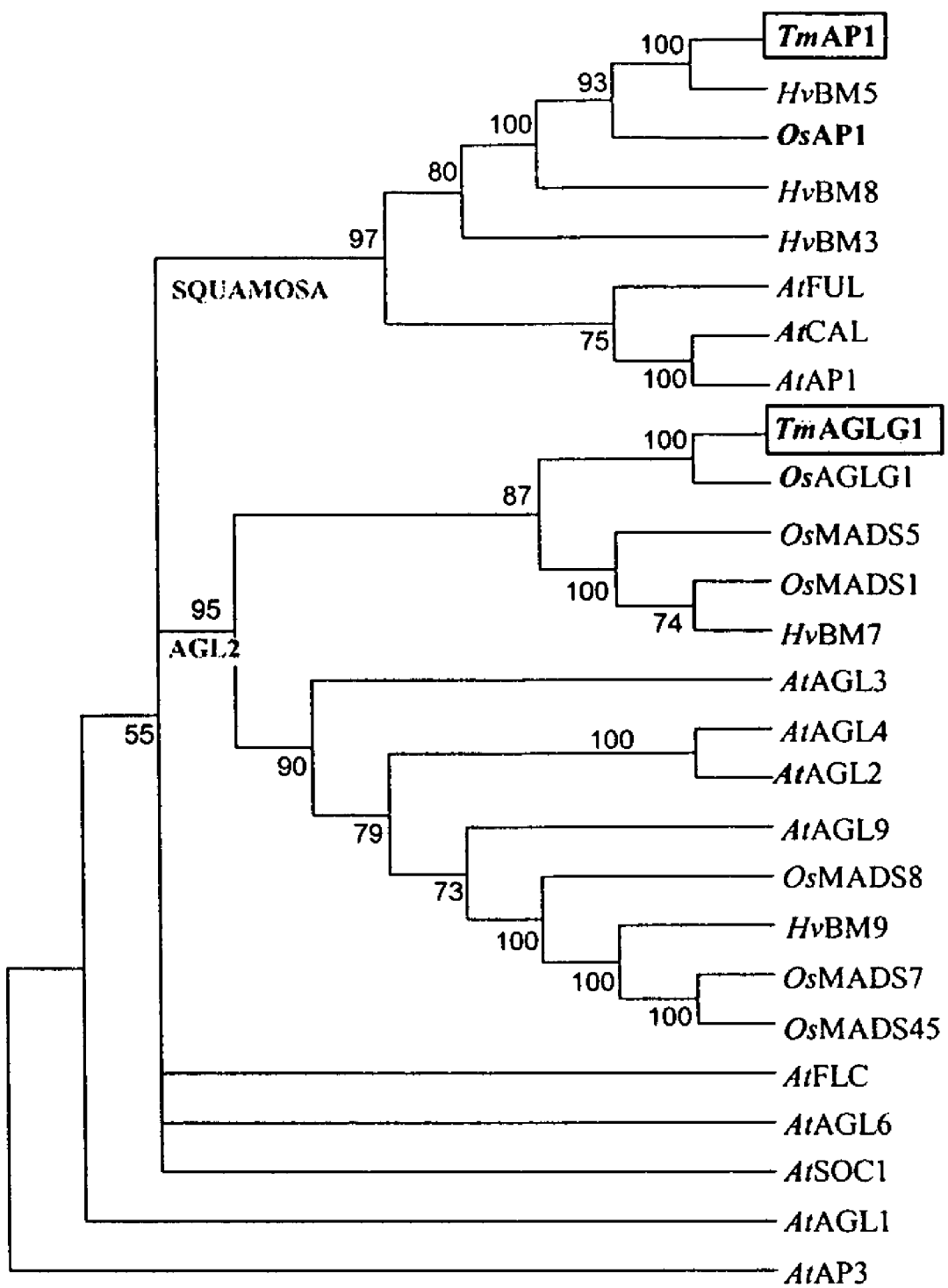
FIG. 3 depicts the relationship between wheat proteins AP1 and AGLG1 and other plant MADS-box proteins in a Neighbor-joining tree. Confidence values on the branches are based on 1000 bootstraps. Tm=$Triticum$ $monococcum,$ Hv=$Hordeum$ $vulgare,$ Os=$Oryza$ $sativa,$ At=$Arabidopsis$ $thaliana.$

A phylogenetic study was performed using the two wheat MADS-box genes found in this study and 24 additional MADS-box genes (FIG. 3). Phylogenetic trees were generated from the ClustalW sequence alignments of the complete proteins using multiple distance- and parsimony-based methods available in the MEGA2.1 computer software package (Kumar, S., et al. (1994)). Distances between each pair of proteins were calculated and a tree was constructed using the Neighbor-Joining algorithm. The consensus tree and the confidence values for the nodes were calculated using 1000 bootstraps (MEGA2.1). GenBank accessions used in the study were SQUAMOSA: HvBM5 (CAB97352.1), OsAP1 (AAM34398.1), HvBM8 (CAB97354.1), HvBM3 (CAB97351.1), AtFUL (Q38876), AtCAL (NP_564243.1), AtAP1 (CAA78909.1); AGL2: OsAGLE21 (AAM34397.1), OsMADS5 (AAB71434.1), OsMADS1 (AAA66187.1), HvBM7 (CAB97353.1), AtAGL3 (AAB38975.1), AtAGL4 (AAA32734.1), AtAGL2 (AAA32732.1), AtAGL9 (AAB67832.1), OsMADS8 (AAC49817.1), HvBM9 (CAB97355.1), OsMADS7 (AAC49816.1), OsMADS45 (AAB50180.1); OTHER: AtFLC (AAD21249.1), AtAGL6 (AAA79328.1), AtSOC1 (AAG16297.1), AtAGL1 (AAA32730.1), AtAP3 (AAA32740.1).

RT-PCR and Quantitative PCR

RNA from leaves, undifferentiated apices, and young spikes was extracted using the TRIZOL method (INVITROGEN). RT-PCR procedures were performed as described before (Yan, L., et al. (2002)). Quantitative PCR experiments were performed in an ABI7700 using three TaqMan® systems for *T. monococcum* AP1 and for ACTIN and UBIQUITIN as endogenous controls. RT-PCR and Quantitative PCR experiments for *Triticum monococcum* AP1 gene. All probes and primers are indicated in 5' to 3' orientation. RT-PCR reactions were performed using Superscript II (Invitrogen®) and primed with oligo(dT)$_{12-18}$.

The $2^{-\Delta\Delta}{}_T$ method (Livak, K. J., et al. (2001)) was used to normalize and calibrate the $C_T$ values of wheat AP1 relative to the endogenous controls. For the vernalization time course, RNA was extracted from the youngest fully expanded leaf of five winter *T. monococcum* plants (1 month old) immediately before moving the plants into the cold room, and then after 2, 4, and 6 weeks of vernalization (4° C.). The last sample was collected two weeks after moving plants to the greenhouse (20° C.). Plants kept in the greenhouse were sampled as controls at each time point simultaneously with the plants from the cold room (5 plants per time point).

a) RT-PCR

RT-PCR reactions were performed using superscript II (Invitrogen®) and primed with oligol ($^{dT}$) 12-18. AM probes and primers are indicated in the 5' to 3' orientation.

AP1

The Left primer, Exon 3 was GGAAACTGGTGTCAC-GAATA (SEQ ID NO:40). The Right primer 5' UTR was CAAGGGGTCAGGCGTGCTAG (SEQ ID NO:41)

The cDNA product: 571-bp and the Genomic DNA product was 1262-bp. The AP1-specificity of the 5' UTR primer was confirmed by sequencing the PCR amplification products. Hybridization of the PCR product with Southern blots of *T. monococcum* indicated that AP1 was a single copy gene in *T. monococcum*.

AGLG1

The Left primer Exon 2 was GAGGATTTGGCTCCACT-GAG (SEQ ID NO:42). The Right primer. Exon 7 outside K-box was TCTAGGGCCTGGAAGMGTG (SEQ ID NO:43).

The cDNA product was 302-bp in length. The Genomic DNA product was 901-bp.

The AGLG1-specificity of these primers was confirmed by sequencing the PCR amplification products. Hybridization of the PCR product with Southern blots of *T. monococcum* indicated that AGLG1 was a single copy gene in *T. monococcum*.

ACTIN

The Left primer, Exon 3 was ATGTGGATATCAG-GAAGGA (SEQ ID NO:44). The Right primer, Exon 3 was CTCATACGGTCAGCAATAC (SEQ ID NO:45)

The cDNA product: 85-bp b) Quantitative PCR

Tests for amplification efficiency were performed. Six 2-fold dilutions were tested in triplicate; 1:1, 1:2, 1:4, 1:8, 1:16, 1:32. Standard curves were plotted with ng RNA on the X-axis and $\Delta C_T$ on the y-axis. The slope and the differences in slopes with the 18S standard curve were determined. The criteria for passed test was set as the differences of slopes being <0.1. The calculation of the efficiency based on the slope was also plotted.

ACTIN TaqMan System

The Left primer was: ATGGAAGCTGCTGGAATCCAT (SEQ ID NO:46). The Probe (reverse orientation) was CCT-TCCTGATATCCACATCACACTTCATGATAGAGT (SEQ ID NO:47)

The Right primer is: CCTTGCTCATACGGTCAG-CAATAC (SEQ ID NO:48)

The sequence of Actin exon 3 is:

```
GAGAAGAGCTATGAGCTGCCTGATGGGCAGGTGATCACCATTGGGGCAGAGAGGTTCCGTTG    (SEQ ID NO:49)

CCCTGAGGTCCTTTTCCAGCCATCTTTCATTGGTATGGAAGCTGCTGGAATCCATGAGACCAC

CTACAACTCTATCATGAAGTGTGATGTGGATATCAGGAAGGATCTGTATGGTAACATCGTGCT

CAGTGGTGGCTCAACTATGTTCCCGGGTATTGCTGACCGTATGAGCAAGGAGATCACTGCCCT

TGCACCAAGCAGCATGAAGATCAAGGTGGTGGCACCGCCTGAGAGGAAGTACAGTGTCTGGA

TTGGAGGGTCGATTCTTGCCTCCCTTAGTACCTTCCAACAG
```

The differences of the slopes with 18S was determined to be 0.0352. The actin system passed the efficiency test with an efficiency of 99.1.

AP1 TaqMan System

The Left primer was: AACTCAGCCTCAAAC-CAGCTCTT (SEQ ID NO:50). The Probe (reverse orientation) was CATGCTGAGGGATGCTCCCCCTG (SEQ ID NO:51). The Right primer was CTGGATGAATGCTGG-TATTTGC (SEQ ID NO:52).

The AP1 *T. monococcum* sequence is:

```
CTCGTGGAGAAGCAGAAGGCCCATGCGGCGCAGCAAGATCAAACTCAGCCTCAAACCAGCTCT    (SEQ ID NO:53)

TCTTCTTCTTCCTTCATGCTGAGGGATGCTCCCCCTGCCGCAAATACCAGCATTCATCCAGCGG

CGGCAGGCGAGAGGGCAGAGGATGCGGCAGTGCAGCCGCAGGCCCCACCCCGGACGGGGCTT

CCACCGTGGATGGTGAGCCACATCAACGGGTGA
```

The differences of the slopes with 18S was determined to be 0.0056. The actin system passed the efficiency test with an efficiency of 96.3.

UBIQUITIN TaqMan System

```
The Left primer was:  ATGCAGATCTTTGTGAAGACCCTTAC.    (SEQ ID NO:54)

The Probe was:        CAAGACCATCACTCTGGAGGTTGAGAGCTC. (SEQ ID NO:55)

The Right primer      GTCCTGGATCTTGGCCTTGA            (SEQ ID NO:56)
```

The sequence of Ubiquitin is:

```
ATGCAGATCTTTGTGAAGACCCTTACTGGCAAGACCATCACTCTGGAGGTTGAGAGCTCAGAC   (SEQ ID NO: 57)
ACCATCGACAATGTCAAGGCCAAGATCCAGGACAAGGAGGGCATCCCCCCGGACCAGCAGCGC
CTCATCTTCGCAGGAAAGCAGCTGGAGGATGGCCGCACTCTTGCTGACTACAACATCCAGAAG
GAGTCCACTCTTCACCTTGTCCTGCGTCTTCGTGGCGGT
```

The differences of the slopes with 18S was determined to be 0.0292. The actin system passed the efficiency test with an efficiency of 99.4.

Additional Deletions in the Promoter Region of AP1

PCR primers for the promoter region flanking the 20-bp deletion present in the spring genotype G2528 were used to screen a collection of 65 accessions of cultivated *T. monococcum* ssp. *monococcum*. None of the winter accessions showed deletions in this region. Among the accessions with spring growth habit, three (PI-349049, PI326317, and PI 418582) showed a 34-bp deletion, one (PI-355515) showed a 48-bp deletion and one showed a 1 nucleotide change in the CArG box (FIG. 11).

The Primers used to screen the *T. monococcum* collection were: AP1_ProDel_F1: ACAGCGGCTATGCTCCAG (SEQ ID NO:58) and AP1_ProDel_R1: TATCAGGTGGTTGGGT-GAGG (SEQ ID NO:59). The expected size without deletion is 152 bp Deletions are illustrated in FIG. 11. Accessions carrying the new deletions can be crossed with winter *T. monococcum* ssp. *boeticum* G3116 to determine the linkage between these deletions and growth habit. A detailed sequence analysis of the allelic variation at the Vrn1 and Vrn2 loci in this collection can be prepared by procedures available to those of skill in the art.

The CArG-box was confirmed as a critical site for the recognition of the vernalization signal. The sequence of spring *Triticum monococcum* accession number PI503874 showed the presence of a 1-pb deletion in the CArG-box of the promoter of the AP1 gene. The normal CArG box is CCCTCGTTTTGG and the sequence in PI503874 was CCCT-GTTTTGG. The sequence of the promoter region *T. monococcum* PI 503874 is provided in FIG. 11 (SEQ ID No:17). This one base pair deletion was the only observed difference with the promoters from other *T. monococcum* accessions with winter growth habit. Thirty-four plants were winter and 110 were spring. All the spring plants were homozygous or heterozygous for the presence of the one-base pair deletion, whereas the 34 winter plants were all homozygous for the absence of the one-bp deletion. This confirms complete linkage between the 1-bp deletion and the spring growth habit.

Marker Development

In the initial genetic map (Dubcovsky, J., et al. (1998)) the VRN1 gene was flanked in the distal side by WG644 and in the proximal side by CDO708. These markers were used as anchor points to the rice genome sequence to find additional markers.

Figures 2A, 2B:
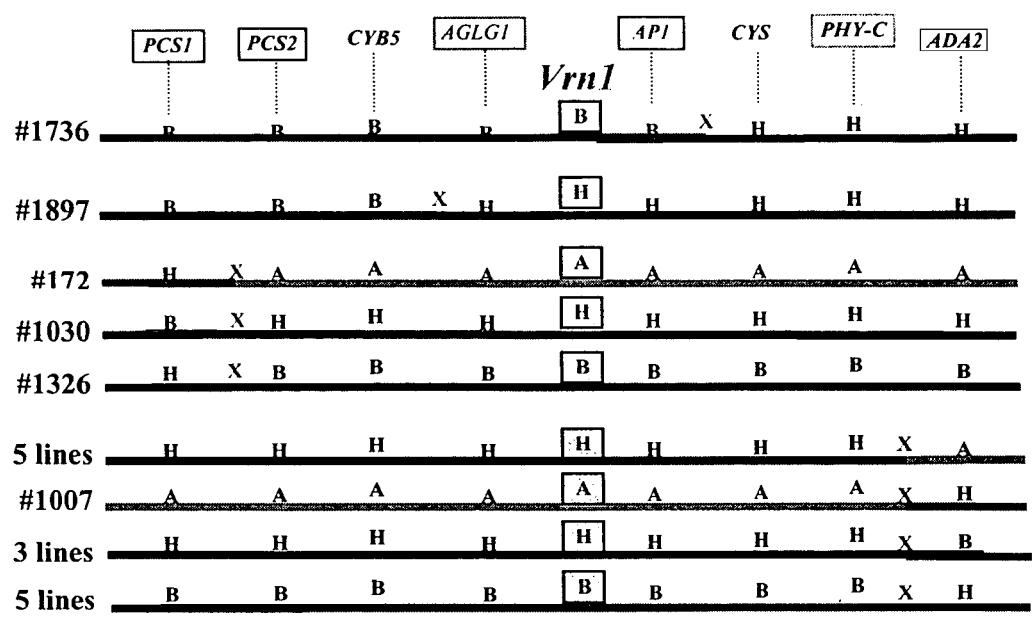
FIG. 2A identifies plants with critical crossovers flanking VRN1. A: homozygous for G1777 (vrn1); B: homozygous for G2528 (Vrn1 ); H: heterozygous. X: crossover between two markers. $F_2$ Vrn1 genotype inferred from $F_3$ progeny test. The names of marker genes are the same as indicated in FIG. 1.
FIG. 2B depicts Progeny tests for plants with critical recombination events as determined by the closest heterozygous molecular marker to AP1. "N" indicates the number of plants in each class. "D" indicates the range of heading dates of the unvernalized plants with a particular genotype after the heading date of the of control spring parent G2528 used as zero.

Distal region: WG644 was previously used to identify rice BAC 36I5 that included GENE1 at its proximal end (Dubcovsky, J., et al (2001). BLASTN searches of the different rice genome projects using GENE1 and the end sequence of BAC 36I5 (AY013245) identified the connected contig CLO13482.168 (Goff, S. A., et al. (2002)). Two additional genes, Phytochelatin synthetase (PCS, *Zea mays* MF24189.1) and Cytochrome B5(CYB5, NP_173958.1), were discovered and annotated in this new contig. These genes were mapped in wheat by RFLP (FIGS. 1 and 2A-2B).

Proximal region: RFLP marker CDO708 was mapped 0.9 cM proximal to VRN1 in the *T. monococcum* map. The sequence of this clone showed a high homology to a putative RNA-binding protein (AAL58954.1) located in rice BAC AC091811. The end of this rice BAC also included gene MTK4 (putative protein kinase tousled, AAL58952. 1) that was converted into a PCR marker and was mapped in wheat (FIG. 1). Rice BAC sequence AC091811 was then connected through contigs CL039395.93, CL039395.83, and CL018222.111.1 (Goff, S. A., et al. (2002)) to rice BAC sequences AC092556 and AF377947. BAC sequence AC092556 included a Transcriptional Adaptor gene (ADA2, AJ430205) that was mapped in *T. monococcum* 0.5 cM from the VRN1 gene (FIG. 1). The last rice BAC sequence AF377947 included genes Phytochrome-C(PHY-C, AAM34402.1), Cysteine proteinase (CYS, AAM34401.1) and MADS-box genes AAM34398.1 and AAM34397.1, designated hereafter AP1 and AGLG1 (AGL-like gene from Grasses). The rice proximal region included 318-kb of contiguous sequence.

High-density Genetic Maps of the VRN1 Region

The PCR markers developed for GENE1 and MTK4 were used to screen 6,190 chromosomes for recombination. Fifty-one recombinant events were detected, and those plants were further characterized using molecular markers for all the genes present between these two markers in rice (FIG. 1 and FIGS. 2A-2B). Progeny tests were performed for 30 of the 51 $F_2$ plants, to determine the VRN1 genotype of the parental $F_2$ plants. Based on the mapping information, the VRN1 locus was completely linked to AP1 and AGLG1.

On the proximal side, genes PHY-C and CYS flanked the VRN1 locus. The last two genes were completely linked to each other and separated from VRN1 by a single crossover (FIG. 1, FIGS. 2A-2B). On the distal side, the CYB5 gene was also separated from VRN1 by a single crossover. Comparison of genotypic and phenotypic data from all the $F_3$ plants used in the 30 progeny tests confirmed that the observed segregation in growth habit was determined by variation at the VRN1 locus. Unvernalized plants homozygous for the G1777 AP1 allele flowered 1-2 months later than G2528 whereas the other plants flowered only one week before or after the G2528 control. These results confirmed the simple Mendelian segregation for vernalization requirement in this cross (Dubcovsky, J., et al. (1998)).

Physical Maps

Distal contig: Genes CYB5 and GENE1 were used to screen the BAC libraries from *T. monococcum*, rice and sorghum. *Triticum monococcum* BAC clone 609E6 selected with the CYB5 gene was connected to previously sequenced 116F2 (AF459639) by four BACs (FIG. 1). The PCS gene hybridized with two fragments from BAC 609E06 (PCS1 and PCS2, FIG. 1) whereas only one PCS copy was found in the colinear region in rice. No single copy probes were found in BACs 609E6 or in the unique Hind III fragments from the most proximal BAC 393O11 to continue the chromosome walking towards the proximal region.

Proximal contig. Screening of the *T. monococcum* BAC library with PHY-C, CYS, AP1, and AGLG1 yielded twelve BACs organized in two contigs. The largest contig included eight BACs that hybridized with genes PHY-C, CYS, and AP1. The four additional BACs hybridized only with the AGLG1 gene (FIG. 1). The location of the AGLG1 contig within the physical map was determined by the complete linkage between the single copy genes AGLG1 and AP1 and the proximal location of AGLG1 relative to single copy gene CYB5. No additional single copy probes were found to close the gaps flanking the AGLG1 contig.

The proximal gap between AGLG1 and AP1 was covered by the current rice sequence. However, the distal gap between CYB5 and AGLG1 was also present in the different rice genome sequencing projects. The screening of the Nipponbare BAC libraries with probe CYB5 failed to extend the rice region because of the presence of a gap in the current rice physical maps. Fortunately, sorghum BAC 17E12 included GENE1, PCS1, PCS2, and CYB5 genes from the distal contig, and AGLG1, AP1, and the CYS genes from the proximal contig, bridging the gap present in the rice and wheat contigs (FIG. 1). A restriction map of sorghum BAC 17E12 (FIG. 6) indicated that the sorghum genes were in the same order as previously found in rice and wheat and that a 24-kb Swa I-Swa I restriction fragment spanned the region of the rice and wheat gap between CYB5 and AGLG1.

Sequence Analysis

Annotated sequences from the three *T. monococcum* BACs (AY188331, AY188332, AY188333) and the partial sequence of the sorghum BAC 17E12 (AY188330) were deposited in GenBank. Including BACs 115G01 and 116F02 (AF459639) a total of 550-kb were sequenced. Multiple retrotransposons organized in up to four layers of nested elements were the most abundant features, similar to wheat regions analyzed before (Wicker, T., et al. (2001), SanMiguel, P., et al. (2002)). Retrotransposons and other repetitive elements accounted for 78.4% of the annotated sequence whereas genes represented only 8.5% of the total. The genes detected in this sequence were in the same order as the ones present in the corresponding regions in rice and sorghum, indicating an almost perfect microcollinearity. The only exception was the duplication of the PCS gene in sorghum and wheat relative to the presence of a single PCS gene in the colinear rice region (FIG. 1).

Figure 6:
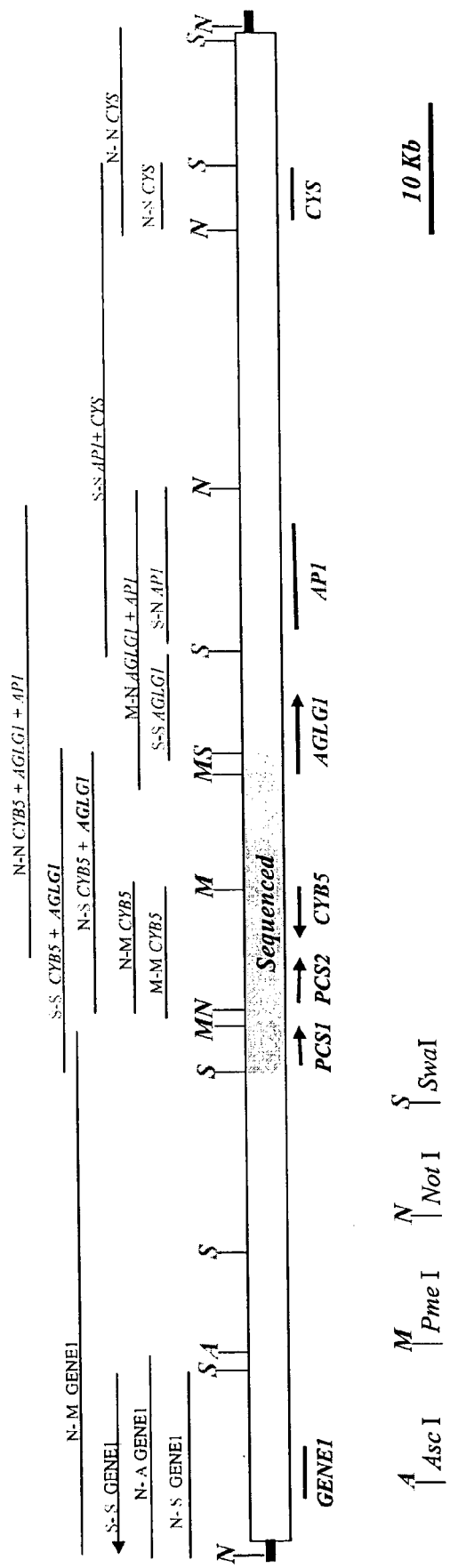
FIG. 6 shows a restriction map of sorghum BAC 17E12. The horizontal lines indicate the fragment detected by hybridization of the Southern blots of the restriction maps with the probe indicated above.

No additional genes were found in the rice sequence between the two MADS-box genes corresponding to one of the two gaps in the wheat physical map. These two genes were also adjacent in sorghum (FIG. 1, and FIG. 6). Similarly, no new genes were found between CYB5 and AGLG1 in the sequence of the 24-kb Swa I-Swa I restriction fragment from sorghum BAC 17E12 (AY188330) that covered the other gap in the wheat physical map. The four genes present in the sorghum sequence were in the same order and orientation as previously found in rice and wheat (FIG. 6). FIG. 6 shows: 1) No additional genes were detected between CYB5 and AGLG1. 2) No similar sequences were detected between the intergenic regions in sorghum and the colinear sequences in rice or wheat. 3) Genes in sorghum were in the same order as in wheat and rice.

The absence of new genes in the colinear regions of rice and sorghum, together with the excellent microcollinearity detected in this region, suggested that it would be unlikely to find additional genes in the current gaps of the wheat physical map. This assumption was also supported by the absence of any new gene in the 324-kb of wheat sequence flanking these gaps. The presence of almost uninterrupted series of nested retrotransposons flanking the gaps also explained the failure to find single copy probes to close the two gaps.

Classification of the Two MADS-box Genes

The AP1 and AGLG1 proteins have MADS-box and K domains characteristic of homeotic genes involved in the flowering process and similar exon structure (FIG. 1, FIG. 6) (Ng, M., et al. (2001)). The consensus tree for 26 plant MADS-box proteins (FIG. 3) showed that the closest proteins to wheat AP1 and AGLG1 belonged to the SQUAMOSA (bootstrap 97) and AGL2 groups (bootstrap 95) respectively.

The closest *Arabidopsis* MADS-box proteins to wheat AP1 were the proteins coded by the three related meristem identity genes AP1, CAL and FUL (FIG. 3). Two separate clusters were observed in the SQUAMOSA group dividing the *Arabidopsis* and grass proteins. A similar separation between the monocot and dicot proteins was found in more detailed studies of this group (Johansen, B., et al. (2002)). The AP1 protein from *T. monococcum* was 98.4% similar to previously described *T. aestivum* WAP1, formerly TaMADS#11 (Murai, K., et al. (1997), Murai, K., et al. (2002)), and 96.0% similar to barley BM5 (Schmitz, J., et al (2000)). These two putative orthologous genes were described in papers characterizing the MADS-box family in wheat and barley, but were not mapped or associated with the VRN1 gene.

The wheat AGLG1 protein was clustered with members of the AGL2 subgroup and was closely related with the rice AGLG1 orthologue and with rice OSMADS5, OsMADS1 and barley BM7 proteins (bootstrap 87, FIG. 3).

Expression Profiles

No AP1 transcripts were detected in apices from unvernalized plants of *T. monococcum* with strong winter growth habit (G3116) even after ten months in the greenhouse under long day conditions. However, AP1 transcription was detected in the apices of plants from the same genotype after six weeks of vernalization (FIG. 4A, lanes 6 and 7). The same result was obtained in three independent experiments. These apices were morphologically at vegetative stage zero according to the developmental scale of Gardner et al. (1985). In *T. monococcum* accessions with spring growth habit, AP1 transcripts were observed in the apices without the need of previous vernalization.

Developmental Stage of the Apexes Used in the RT-PCR Experiment

After six weeks of vernalization the shoot apexes did not show any morphological sign of differentiation from the vegetative shoot apex stage as observed before vernalization. An apex from winter *T. monococcum* accession G3116 after six weeks of vernalization was visualized. The results showed that the expression of Ap1 in the apices precedes the differentiation of the apex.

Transcripts of AP1 were also detected in the leaves, as previously reported for WAP1 (Murai, K., et al. (1997)) and BM5(Schmitz, J., (2000)). A quantitative PCR experiment using the endogenous controls ACTIN and UBIQUITIN demonstrated that transcription of AP1 in the leaves of the winter genotypes was also regulated by vernalization.

| Effect of vernalization on ACTIN and UBIQUITIN transcription levels Average threshold cycle ($C_T$) | | | | |
|---|---|---|---|---|
| | n | Cold room $C_T$ | n | Greenhouse $C_T$ | ANOVA |
| ACTIN | 15 | 17.4 | 30 | 17.5 | P = 0.99 |
| UBIQUITIN | 14 | 15.1 | 29 | 15.3 | P = 0.55 |

No significant differences were detected between plants in the greenhouse and plants in the cold room in the $C_T$ values of ACTIN and UBIQUITIN. The abundance of AP1 transcripts started to increase after the first two weeks of vernalization and continue increasing during the four additional weeks of the vernalization process (FIG. 4B).

Figure 5:
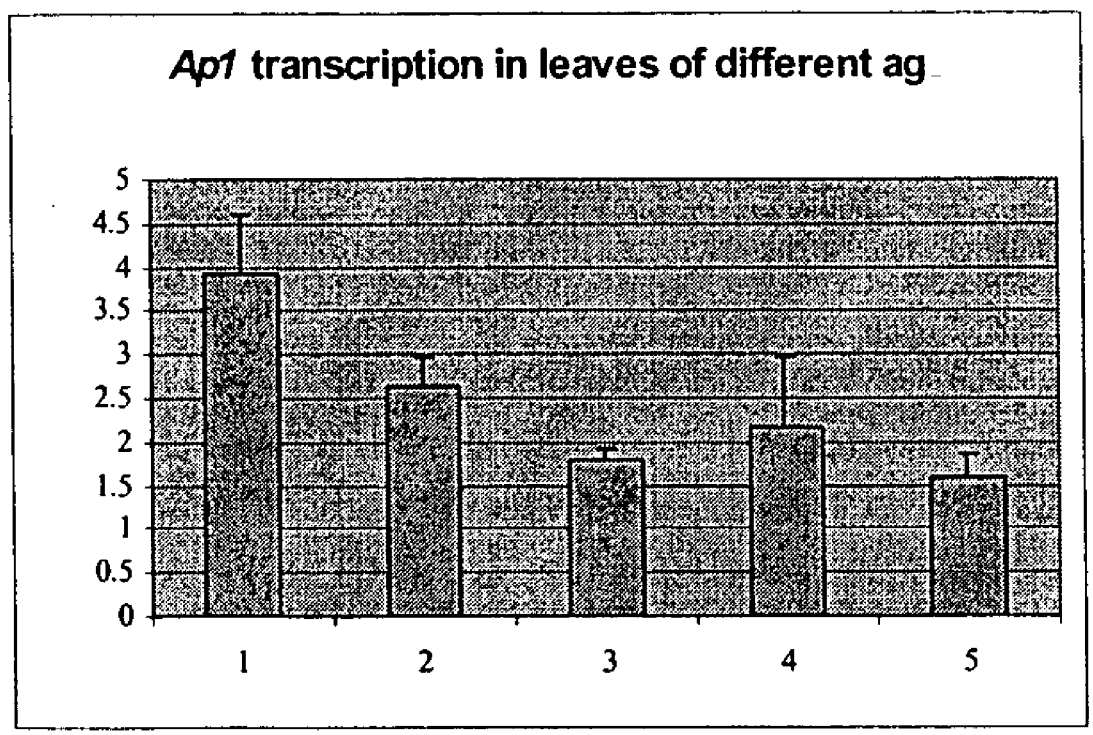
FIG. 5 shows AP1 transcription in leaves of different age. The numbers on the x-axis represent different leaves from the same tiller from the youngest (1) to the oldest (5). The numbers on the y-axis represent linearized values using the $2^{(-\Delta\Delta CT)}$ method, where CT is the threshold cycle

The AP1 transcription levels relative to ubiquitin are presented in FIG. 5. Samples were extracted from the emerging and first fully expanded leaves of *Triticum monococcum* G3116 (winter growth habit) 1) Before vernalization, 2) 2 weeks in the cold room, 3) 4 weeks in the cold room, 4) 6 weeks in the cold room, 5) two weeks after the vernalized plants were returned to the greenhouse. Units are linearized values using the $2^{(-\Delta\Delta CT)}$ method, where CT is the threshold cycle. The results show that AP1 transcripts were also present in the leaves from vernalized plants two weeks after their transfer to the greenhouse.

Control plants kept in the greenhouse showed very low level of AP1 transcription during the eight weeks of the vernalization experiment (FIG. 4B). In the genotypes with a spring growth habit, AP1 transcripts were observed in the leaves of unvernalized plants that were initiating the transition to flowering.

AP1 transcription levels in leaves of different ages are shown in FIG. 5. One-month-old G3116 plants were vernalized for six weeks and then transferred to the greenhouse for two weeks under long day conditions. RNA was extracted from each of the five green leaves from the main stem and one secondary tiller from two plants. In FIG. 5, number 1 indicates the youngest leaf (not fully emerged from the sheath) and number 5 the oldest green leaf. Bars represent standard errors of the means. Ubiquitin was used as an internal control. Units are linearized values using the $2^{(-\Delta\Delta CT)}$ method, where CT is the threshold cycle. The results show that AP1 transcripts were detected in young and old green leaves.

A relatively high level of expression of Ap1 was observed in all the leaves. Average $C_T$ values for Ap1 (24.1) were only two cycles higher than for Ubiquitin (22.0). This result confirmed that Ap1 induction by vernalization was not restricted to the youngest leaves. Marginally significant differences (ANOVA, P=0.05) were observed between leaves of different ages, with the highest value for leaf 1

AGLG1 transcripts were detected only in young spikes (FIG. 4A, lane 8), but were not observed in the same cDNA samples from apices after six weeks of vernalization where the AP1 transcripts were already present (FIG. 4A). This indicates that AGLG1 transcription is initiated later than AP1. Transcripts from AGLG1 were not detected in the leaves (FIG. 4A).

The expression results together with the known role of the AP1 homologues in *Arabidopsis* as meristem identity genes, suggested that AP1 was a better candidate gene for VRN1 than AGLG1.

Allelic Variation

Four AP1 genes were sequenced from *T. monococcum* accessions G1777, G3116, and DV92 carrying the vrn1 allele and G2528 carrying the Vrn1 allele. The nucleotide sequences for G2528 and DV92 are presented in FIG. 7. The predicted proteins from DV92 and G2528 were identical and differed from the predicted proteins from G3116 and G1777 by a single amino acid (FIG. 8).

Analysis of the 1024-bp region upstream from the AP1 start-codon and up to the insertion point of a large repetitive element (AY188331) showed the presence of five polymorphic sites. Two of them differentiated G2528 from the three accessions carrying the vrn1 allele for winter growth habit. One was a one bp insertion located 728-bp upstream from the start codon and the other one was a 20-bp deletion located 176-bp upstream from the start codon (FIG. 1, FIGS. 9A-9B, 11). No difference were detected in the first 600-bp of the AP1 3' region between the vrn1 and Vrn1 alleles.

Figure 10:
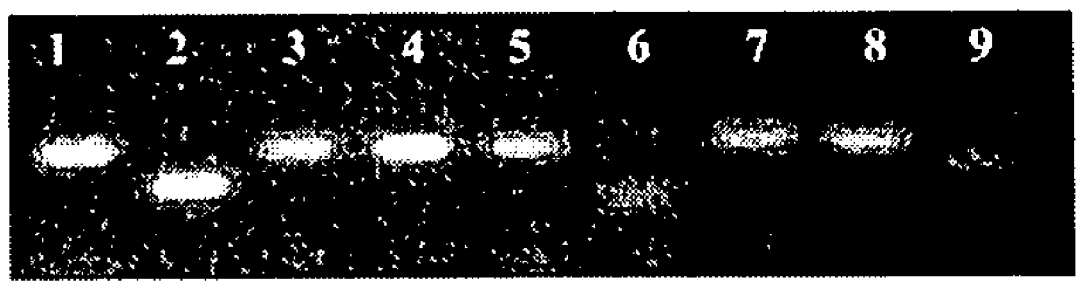
FIG. 10 depicts a gel showing the 34 and 48 bp deletions in the AP1 promoter region. Lines 1, 3, 4, and 5 (PI355516, PI352473, PI272561, PI573529): cultivated *T. monococcum* accessions with winter growth habit. Line 2 (PI349049): 34-dp deletion, spring growth habit. Line 6 (PI355515): 48-bp deletion, spring growth habit. Line 7: G3116, vrn1. Lines 8: G1777, vrn1. Line 9: G2528, Vrn1 (20-bp deletion).

A PCR screening of a collection of cultivated *T. monococcum* accessions with primers flanking the 20-bp deletion region revealed the presence of deletions of different sizes in agarose gels (FIG. 10). Sequencing of these lines showed the presence of two new deletions of 34-bp and 48-bp that overlapped with the 20-bp deletion from G2528. These new deletions included a putative MADS-box protein-binding site adjacent to the 20-bp deletion (FIG. 1, FIG. 11). A 1-bp deletion within the CArG box (FIG. 11) was found in 7 *T. monococcum* accessions with spring growth habit. We confirmed by genetic analysis of segregating F2 populations that the 34-bp and 1-bp deletion were completely linked with the spring growth habit. New crosses have been made to analyze the 48-bp deletion.

No DNA differences were detected between accessions DV92 (vrn1) and G2528 (Vrn1) in the coding region, or the 5' (365-bp) and 3' (583-bp) untranslated regions of the AGLG1 gene.

Discussion

Genetic and Physical Maps of the VRN1 Region

Only eight genes were found in the 556-kb of sequence from the *T. monococcum* VRN1 region, resulting in an estimated gene density of one gene per 70-kb. The low gene density observed in this region was paralleled by a high ratio between physical and genetic distances. Excluding the two gaps in the physical map, a minimum ratio of 6,250-kb cM$^{-1}$ was estimated for the region between WG644 and PHY-C This value is two times larger than the average genome-wide estimate of 3,000-kb cM$^{-1}$ (Bennett, M. D., et al. (1991)) and four times larger than the 1,400-kb cM$^{-1}$ reported for the telomeric region of chromosome 1A (Stein, N., et al. (2000)). Previous cytogenetic studies demonstrated that recombination in the wheat chromosomes decrease exponentially with distance from the telomere (Dvorak, J., et al. (1984), Lukaszewski, A. J., et al. (1993)), predicting an increase of the ratio between physical and genetic distance in the same direction. The region studied here is located between the breakpoints in deletion lines 5AL-6 (FL 0.68) and 5AL-17 (FL 0.78), in a more proximal location than regions used before to estimate ratios between physical and genetic distances in wheat. This result suggests that positional cloning projects in the proximal regions of wheat will be difficult and would greatly benefit from the use of the rice genomic sequence to jump over large blocks of repetitive elements.

In spite of the low recombination rate found in this region, the large number of evaluated gametes was sufficient to find crossovers between most of the genes or at least between pairs of adjacent genes. This detailed genetic study showed that the variation in growth habit determined by the VRN1 gene was completely linked to only two genes. Although the possibility that additional genes would be found in the two current gaps and unsequenced regions of our *T. monococcum* physical maps cannot be ruled out, this seems unlikely based on the comparative studies with rice and sorghum and the absence of any additional genes in the 324-kb of wheat sequence between CYB5 and CYS.

The genetic data reduced the problem of the identification of VRN1 to the question of which of the two MADS-box genes was the correct candidate. However, since no recombination was found between AGLG1 and AP1 it was not possible to answer this question based on the available genetic results. Therefore, the relationship between AGLG1 and AP1 with MADS-box genes from other species was established as a first step to predict their function from the known function of the related genes.

Phylogenetic Relationships of the VRN1 Candidate Genes

The similarity between the wheat AP1 gene and the *Arabidopsis* meristem identity genes AP1, CAL, and FUL provided a first indication that the wheat AP1 gene was a good candidate for VRN1. These *Arabidopsis* genes are expressed in the apices and are required for the transition between the vegetative and reproductive phases (Ferrandiz, C., et al. (2000)). The triple *Arabidopsis* mutant ap1-cal-ful never flowers under standard growing conditions. In wheat, the VRN1 gene is also responsible, directly or indirectly, for the transition between vegetative and reproductive apices. This transition is greatly accelerated by vernalization in the wheat plants carrying the vrn1 allele for winter growth habit. Therefore, it is reasonable to speculate that the sequence similarity between the wheat AP1 gene and the *Arabidopsis* meristem identity genes may indicate similar functions. An evolutionary change in the promoter region of AP1 may be sufficient to explain the regulation of AP1 by vernalization in wheat (see model below).

The close relationship of wheat AGLG1 to members of the AGL2 subgroup suggested that AGLG1 was a less likely candidate for VRN1 than AP1 because transcripts from genes included in this group are usually not observed in the apices in the vegetative phase (Johansen, B., et al. (2002)). Expression of *Arabidopsis* AGL2, AGL4 and AGL9 begins after the onset of expression of floral meristem identity genes but before the activation of floral organ identity genes suggesting that members of the AGL2 clade may act as intermediaries between the meristem identity genes and the organ identity genes (Flanagan, C. A., et al. (1994), Savidge, B., et al. (1995), Mandel, M. A., et al. (1998)). This seems to be valid also for OsMADS1, which is more closely related to AGLG1 than the *Arabidopsis* members of the AGL2 lade. In situ hybridization experiments of young rice inflorescences with OsMADS1, showed strong hybridization signals in flower primordia but not in other tissues (Chung, Y. Y., et al. (1994)).

If the functions of wheat AP1 and AGLG1 were similar to the function of the related genes from *Arabidopsis*, the initiation of transcription of AP1 should precede the initiation of transcription of AGLG1 in wheat.

Transcription Profiles of the VRN1 Candidate Genes

RT-PCR experiments using RNA samples from vernalized apices showed transcription of AP1 but not of AGLG1 (FIG. 4A) indicating that transcription of AGLG1 occurs after the initiation of transcription of AP1. The similar timing and order of transcription suggests that the wheat genes might perform similar functions to the related *Arabidopsis* genes.

It could be argued that any gene in the flowering regulatory pathway would be up regulated by the initiation of flowering caused by the vernalization process. However, the up regulation of AP1 transcription in the leaves by vernalization (FIG. 4B) indicated a more direct role of the vernalization pathway in the regulation of wheat AP1 gene. Four additional characteristics of the transcription profile of AP1 paralleled the predicted expression of a vernalization gene. First, vernalization was required to initiate AP1 transcription in the plants with winter growth habit but not in the plants with spring growth habit. Second, AP1 transcription was initiated only after two weeks in the cold room, and a minimum of two weeks of vernalization is required by many winter wheat varieties to produce any significant acceleration of flowering (Limin, A. E., et al. (2002)). Third, the progressive increase of AP1 transcripts after the second week of vernalization (FIG. 4B) is consistent with the progressive effect of the length of the vernalization period in the acceleration of flowering time. Finally, a high level of AP1 transcripts was observed after the plants were moved from the cold to room temperature indicating that AP1 is not just a cold stress induced gene.

Allelic Variation

No differences were found in the AGLG1 coding region or in its 5' and 3' regions between *T. monococcum* accessions G2528 (Vrn1) and DV92 (vrn1) confirming that AGLG1 was not a good candidate to explain the observed differences in growth habit.

Figure 4:
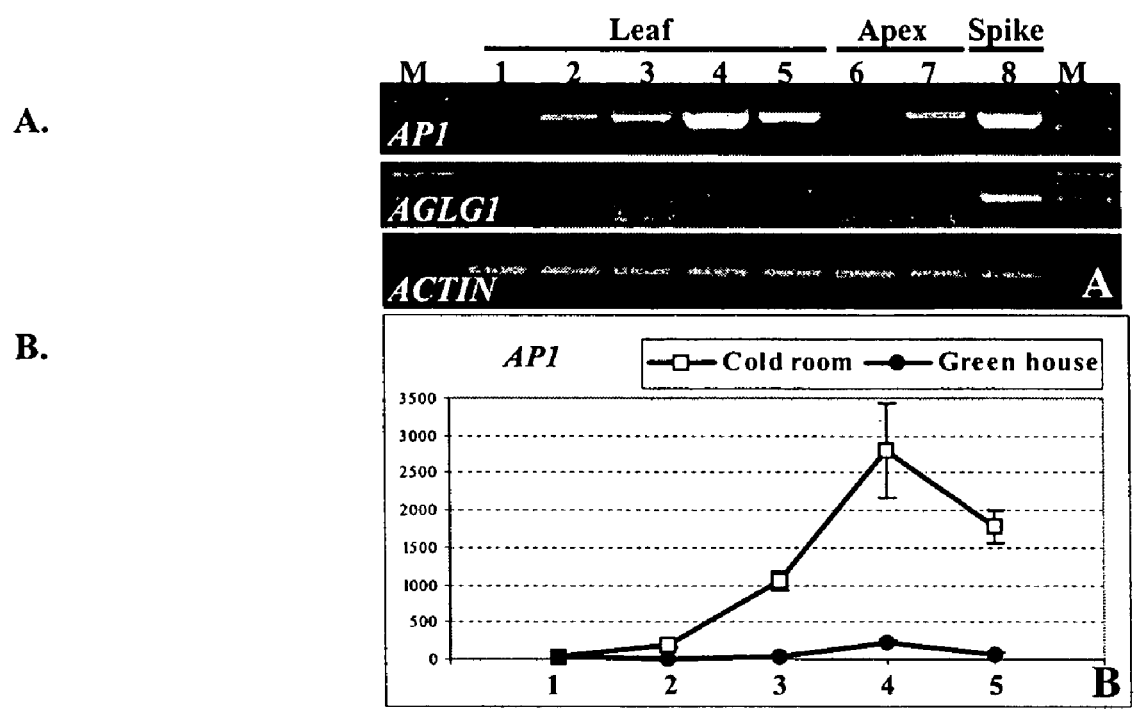
FIG. 4A shows a Reverse Transcription Polymerase Chain Reaction (RT PCR) experiment using $T.$ $monococcum$ G3116 (winter growth habit) and AP1, AGLG1 and ACTIN specific primers. The PCR reactions for the three genes were performed using the same cDNA samples. Leaves 1-5): Leaves 1) Before vernalization; 2-4) 2, 4 and 6 weeks of vernalization; 5) two weeks after vernalized plants were returned to the greenhouse; 6) unvernalized apices; 7) 6-weeks vernalized apices; 8) young spikes.
FIG. 4B shows the AP1 transcription levels in leaves relative to ACTIN measured by quantitative PCR. 1-5) Leaves from plants at the same vernalization stage as samples 1-5 in 4A. Units are linearized values using the $2^{(-\Delta\Delta CT)}$ method, where CT is the threshold cycle.

Although no differences were detected in the AP1 coding sequences and 3' region, the spring and winter accessions differed in their promoter sequence. The first 600-bp upstream from the start codon were identical among the four genotypes analyzed in this study except for a 20-bp deletion located close to the start of transcription and adjacent to a putative MADS-box protein binding site (CArG-box) in G2528 (Tilly, J. J., et al. (1998)) (FIG. 4). Two additional overlapping deletions were discovered in the same region of the promoter in spring accessions of cultivated *T. monococcum* (FIG. 11) and a 1-bp deletion was found by sequencing accession PI503874 (SEQ ID NO: 17). The presence of a putative CArG-box in this region suggests the possibility that a trans-acting factor may bind to this site and repress AP1 transcription until vernalization occurs. This is similar to the case for FLC in *Arabidopsis*, which was recently shown to bind to MADS-box gene SOC1 and repress its transcription prior to vernalization (Hepworth, S. R., et al. (2002)).

A model for the Regulation of Flowering by Vernalization in Wheat

The results presented in this study can be included in an integrated model (FIG. 12) based on the known epistatic interactions between VRN1 and VRN2 (Tranquilli, G. E., et al. (1999)) and the available information about the evolution of the vernalization requirement in the Triticeae. The significant epistatic interactions observed between VRN1 and VRN2 indicate that these two genes act in the same pathway. According to the model presented here (FIG. 12), VRN2 codes for a dominant repressor of flowering that acts directly or indirectly to repress VRN1. As the vernalization process reduces the abundance of the VRN2 gene product, VRN1 transcription gradually increases leading to the competence to flower (FIG. 13, center).

The growth habit of plants homozygous for the recessive vrn2 allele for spring growth habit (FIG. 12, upper panel) is independent of variation at the VRN1 locus. According to this model, the vrn2 allele represents a null or defective repressor that cannot interact with the VRN1 promoter. Therefore, variation in the promoter of the VRN1 gene would have no effect on flowering time in homozygous vrn2 plants. This can be illustrated by the expression pattern of AP1 in *T. monococcum* DV92 (vrn1 vrn2). In this genotype, the initiation of AP1 transcription in leaves and apices did not require vernalization in spite of the presence of a recessive vrn1 allele. This result indicated that the VRN1 gene acts downstream of VRN2 (FIG. 12).

Conversely, plants homozygous for the Vrn1 allele for spring growth habit showed no significant effects of the VRN2 gene on flowering time. According to the model in FIG. 12 (lower panel), the VRN2 repressor will have no effect on flowering in genotypes carrying the Vrn1 allele because of the lack of the recognition site in the VRN1 promoter region. This part of the model can be used to explain the AP1 expression profile of G2528 (Vrn1 Vrn2). In this genotype, transcription of AP1 in leaves and apices is initiated without a requirement for vernalization in spite of the presence of an active VRN2 repressor. This suggested that the active repressor could not interact with the G2528 AP1 promoter region, possibly because of the presence of the 20-bp deletion.

This model also provides an explanation for the parallel evolution of VRN1 spring alleles in three different Triticeae lineages. A vernalization gene with a dominant spring growth habit has been mapped in the same map location in diploid wheat (Dubcovsky, J., et al. (1998)), barley (Laurie, D. A., et al. (1995)), and rye (Plaschke, J., et al. (1993)). Most of the wild Triticeae have a winter growth habit suggesting that the recessive vrn1 allele is the ancestral character (Kihara, H., et al. (1958), Halloran, G. M., et al. (1967), Goncharov, N. P., et al. (1998)). This is also supported by the fact that it is unlikely that a vernalization requirement would be developed independently at the same locus in the three different lineages from an ancestral spring genotype. According to the model presented here, independent mutations in the promoter regions of winter wheat, barley, and rye genotypes have resulted in the loss of the recognition site of the VRN2 repressor (or an intermediate gene) and therefore, in a dominant spring growth habit (Vrn1 allele). Since this is a loss rather of a gain of a new function it is easier to explain its recurrent occurrence in the different Triticeae lineages.

In summary, this invention presents the delimitation of the candidate genes for Vrn1 to AP1 and AGLG1 by a high-density genetic map, and the identification of AP1 as the most likely candidate based on its similar sequence to meristem identity genes, its transcription profile, and its natural allelic variation. The model is presented to integrate the results from this study with the previous knowledge about the epistatic interactions between vernalization genes and the evolution of vernalization in the Triticeae.

EXAMPLE 2

Introduction

Genes controlling vernalization requirement prevent flower development during the cold months of winter, providing protection for the environmentally sensitive floral organs. The proper timing of the transition from the vegetative to the reproductive stage is critical to the reproductive success of a species and is under the regulation of a complex gene network (G. G. Simpson et al. (2002), A. Mouradov et al. (2002)).

The vernalization pathway is an important part of this regulatory network, and has been studied with great detail in *Arabidopsis*. The FLC gene plays a central role in this pathway by integrating the signals from the extended cold treatment with signals from the autonomous flowering pathway (S. D. Michaels, et al. (1999), C. C. Sheldon, et al. (1999)). A high level of FLC expression is required to maintain a vegetative status. Another important gene in the *Arabidopsis* vernalization pathway is FRI, which upregulates FLC transcription (S. D. Michaels, et al. (1999), U. Johanson et al. (2000)). Vernalization produces the opposite effect, and results in the permanent downregulated of FLC(S. D. Michaels, et al. (1999), C. C. Sheldon, et al. (1999)). Two genes, recently designated VRN1 and VRN2 are required to keep FLC in its repressed status, but not for its initial repression by cold (A. R. Gendal et al. (2002)). We suggest renaming the *Arabidopsis* genes as $VRN1^{At}$ and $VRN2^{At}$ to avoid confusion with the main vernalization loci in wheat, VRN1 and VRN2, which correspond to different genes (See Example 1) and were assigned these names before (R. A. McIntosh, et al. (1998)). The signals from the vernalization pathway converge with those from the photoperiod pathways at the regulatory regions of the SOC1 and FT genes (G. G. Simpson, et al. (2002), A. Mouradov, et al. (2002)). FLC binds to the promoter of SOC1 and impairs its activation by CO (S. R. Hepworth, et al. (2002)), a central gene in the photoperiod pathway (P. Suarez-Lopez, et al. (2001)). CO activates SOC1 and FT (S. R. Hepworth, et al. (2002)), which then interact with other genes to induce the meristem identity gene AP1, initiating the transition between the vegetative and reproductive apex.

CO has different functions in rice and *Arabidopsis*. This gene promotes flowering under long days in *Arabidopsis* but it represses flowering under this conditions in rice (P. Suarez-Lopez, et al. (2001)). In addition, no clear homologues for FRI or FLC were found in the rice genome (S. A. Goff et al. (2002)). Although this may be expected based on lack of a vernalization requirement in rice, the absence of FRI and FLC homologues in the extensive wheat and barley EST collections (≈770,000) suggested the possibility that the temperate grasses used a different set of genes to develop their vernalization requirement. Since temperate cereals evolved from subtropical primitive grasses (W. D. Clayton, et al. (1986)) it is possible that the development of the vernalization pathway in the winter cereals evolved independently of the vernalization requirement in *Arabidopsis*. In this Example, we demonstrate the positional cloning and characterization of wheat VRN2 gene, and demonstrate that the genes included in the vernalization pathway in the temperate cereals are different from those in *Arabidopsis*.

Positional Cloning of Wheat Vernalization Gene VRN2

In a previous study we mapped wheat vernalization gene VRN2 in the long arm of chromosome 5A using a segregating population from the cross between *T. monococcum* DV92 (vrn1vrn2, spring) and G3116 (vrn1Vrn2, winter) (J. Dubcovsky, et al. (1998)). We found strong epistatic interactions between this gene and VRN1, indicating that both genes were part of the same regulatory pathway (G. E. Tranquilli, et al. (1999)). Similar epistatic interactions were found in barley (R. Takahashi, et al. (1971)) and both genes were mapped in colinear chromosome locations, suggesting that wheat and barley vernalization genes were orthologous (J. Dubcovsky, et al. (1998), D. A. Laurie, et al. (2002)).

In this Example, we developed a high-density map based on 2,849 unvernalized $F_2$ plants from the DV92×G3116 cross, as a first step for the positional cloning of VRN2. We used VRN2 flanking markers NUCELLIN and UCW22 to determine the genotype of each of the $F_2$ plants and to find 18 recombination events within this region (FIG. 13). Note: Probe Nucellin is a 832-bp region between exons 4 and 6 amplified by primers NucellinEx6L (CTTCACGAAGAGG-TAGTTTTGAGG (SEQ ID NO: 72)) and NucellinEx4U (TGGGTACAAGCAGGAGGAGC (SEQ ID NO: 73)) AF459084 (92-814-93,645) and probe UCw22 is a 719-bp Sau3A I fragment (AF459088: 24,701-25,419) located between genes AF459088.2 and AF459088.3. The 2,831 plants that did not show recombination between the critical markers were used to confirm the location of VRN2 within the NUCELLIN-UCW22 region. All plants homozygous for the DV92 allele showed a spring growth habit, whereas plants carrying G3116 alleles had a strong vernalization requirement when grown under long day conditions without vernalization. The simple Mendelian segregation of VRN2 in this mapping population facilitated the precise mapping of VRN2. We generated additional markers from the BAC clones included in the physical map (FIG. 13) to define precisely the location of the two crossovers flanking the vernalization gene. The VRN2 gene was finally mapped into a 0.04-cM interval flanked by RFLP marker UCW22 and PCR marker UCW2.1 (FIG. 13). Note: Probe UCW2.1 is a 620-bp fragment with primers C171L (AGTGGCATCGTTTTCAG-GAT (SEQ ID NO: 64)) and C171R (GCCATGCCGAT-AGCTGACTA (SEQ ID NO: 65)) (AF459088: 338,499-339, 118). The product from accession G3116 is digested into 505-bp and 115-bp fragments, whereas the DV92 PCR product is not digested.

We constructed a complete physical map of the VRN2 region using the BAC library of *T. monococcum* accession DV92 (D. Lijavetzky, et al. (1999)) and two steps of chromosome walking (FIG. 13). BACs 258C22, 301G15, 405L8, and 455C17 were completely sequenced and annotated using procedures described before (P. SanMiguel, et al. (2002)). Note: Probe UCW61 is a 452-bp fragment amplified by primers V2L8F2 (TGCATGGAACACTTCCGATT (SEQ ID NO: 60)) and V2L8R2 (CTTCCTCGACCTCTCCACAG (SEQ ID NO: 61)) (AF459088: 191,044-191,496). It hybridized with a single copy fragment in genomic DNA of *T. monococcum*. UCW61 was not included in the linkage map but was used to screen the *T. monococcum* BAC library and to select BAC 301G15 that closed the contig. The complete 438,828-bp annotated sequence was deposited in GeneBank under accession AF459088. We also sequenced the orthologous BAC 615K1 from barley variety Morex (AF459084) and BAC 49F5 from rice Nipponbare (AF485811).

Additional probes were as follows: A PCR marker for the second exon of the ZCCT1 gene comprising a 231-bp fragment amplified with primers R3C1N3 (GCAATCATGAC-TATTGACACA (SEQ ID NO: 62)) and RACEC1N1 (GGGCGAAGCTGGAGATGATG (SEQ ID NO: 63)) (AF459088: 330,948-331,178). The PCR product from accession DV92 is digested by restriction enzyme Nco I into 189-bp and 42-bp fragments, whereas the G3116 PCR products is not digested. A SNF2P gene (encoding a global transcriptional regulator (L. Yan, et al. (2002)) probe comprising a 1,091-bp fragment between exon 14 and 15 with amplified with primers SNF2PEx14F (GGGTCATGGAGGAAT-GTTTG (SEQ ID NO: 66)) and SNF2PEx15R (TTGGCT-TCTGCAGAGAGGAT (SEQ ID NO: 67)) (AF459088: 351, 083-352,173). The PCR product from accession G3116 is digested by restriction enzyme EcoR I into 900-bp and 200-bp fragments, whereas the DV92 PCR product is not digested. A SEC14 gene (AF459088.7-encoding a protein similar to rice phosphatidylinositol/phosphatidylcholine transfer protein (AA020076.1) and *Candida Glabrata* SEC14 cytosolic factor (CAA65985)) probe comprising a 305-bp fragment from the last exon of the SEC14 gene amplified with primers TmSEC14F (GTTACGTGAACTGTGACATC (SEQ ID NO: 68))and TmSEC14R (TCAGTTGCATGTCGACGAAGG (SEQ ID NO: 69)) (AF459088: 406,207-406,511). The resulting PCR product digested with restriction enzyme BamH I produces a smaller fragment in DV92 than in G3116. A P450 gene (encoding a Cytochrome P450 protein) probe comprising a 376-bp fragment amplified with primers TmP450P3 (CGACGATGCCCTTCCAAATG (SEQ ID NO: 70)) and TmP450P4 (TCAAGCAGCTGCTGCCTCCC (SEQ ID NO: 71)) (AF459088: 432,795-433,170). The resulting PCR product digested with restriction enzyme Sac I produces a larger fragment in DV92 than in G3116.

Eight genes and one pseudogene were detected in the non-repetitive regions of the *T. monococcum* sequence, representing a gene density of one gene per 55-kb and a ratio of genetic to physical distances of approximately 2.1-Mb per cM. Five of these genes where found in the same order and orientation in the barley BAC, and three in the rice BAC confirming the collinearity of these sequences (FIG. 13). The closest common genes flanking the VRN2 gene, PDS and SNF2P, were 7-kb apart in rice, 26-kb apart in barley, and 328-kb apart in *T. monococcum* (FIG. 13).

The sequences from markers UCW22 and UCW2.1 flanking the VRN2 gene in the genetic map (FIG. 13) were used to delimit a 315-kb candidate region within AF459088. Seventy-five percent of the sequence from this region was annotated as repetitive elements. We found only three genes completely linked to the VRN2 gene. The first gene, designated AF459088.3, encoded a 254-amino acid protein that was 87% and 96% similar to the orthologous proteins in rice and barley colinear BACs respectively (FIG. 13). The AF459088.3 protein was 76% similar to *Arabidopsis* expressed protein MD32834.1, which was close to SNF2P(11-kb), as in the three grass species suggesting the conservation of a small colinear segment across the monocot-dicot divide. The AF459088.3 gene includes a conserved domain designated DUF614 (pfam04749.2, $E=2e^{-22}$) that is present in different eukaryotic proteins of unknown function.

We named the two other genes ZCCT1 and ZCCT2 based on the presence of a putative zinc finger in the first exon and a CCT domain in the second exon. The CCT domain was named after CO, CO-like, and TOC1 (J. Putterill, et al. (1995)), and is sufficient and necessary for the nuclear localization of CO in *Arabidopsis* (F. Robson, et al. (2001)). The proteins coded by the two other genes found in the VRN2 region were 76% identical, suggesting a duplication event that occurred approximately 14±3 million years ago. Alignment of ZCCT1 and ZCCT2 DNA sequences resulted in 629 aligned base pairs. We found 22 transitions and 11 transversions in the 209 aligned base pairs at the third position. Using the average synonymous substitution rate of 6.5×10-9 substitutions/synonymous site/year calculated from the divergence of the adh1 and adh2 genes in grasses (B. S. Gaut, et al. (1996)), we calculated that the duplication time of ZCCT gene in diploid wheat occurred approximately 13.9±2.5 million years ago.

A search of the *Arabidopsis* genome with the wheat ZCCT proteins showed that CO and CO-like proteins were the most similar, but this similarity was restricted to the CCT domain ($E=2e^{-11}$). A similar search was performed in the rice genome, and CO-related proteins AP005307 (OsI, $E=3e^{-16}$) and AAL79780 (OsH, $E=2e^{-16}$) showed the highest similarity values. The partial similarity of the ZCCT proteins to CO-like proteins involved in the regulation of flowering time was the first indication of the potential of the ZCCT genes as candidates for VRN2.

Evolutionary Relationships Between the ZCCT and CO-like Genes

Besides two ZCCT genes cloned from *T. monococcum*, we isolated additional ZCCT genes from the A genome of tetraploid wheat and from winter barley variety Diarokkaku, and compared their CCT domains with those from CO-like genes in other plant species (FIG. 18A). A recent study of the CO-like gene family identified 17 proteins in *Arabidopsis*, 16 in rice, and 9 in barley that were grouped in four major classes (I to IV) (S. Griffiths, et a. (2003)). We performed a Neighbor Joining cluster analysis using the 44-amino acids CCT motifs from the ZCCT proteins and from members of each of the different classes of CO-like proteins. CCT motifs from Group III (AtCOL9 and OsN) were very different and were used as an outgroup. The ZCCT proteins formed a separate group that was distantly related to members of Group IV proteins (HvCO9, OsI, OsH). These two groups were separated (bootstrap 73) from Groups I (AtCO, Hd1) and II (AtCOL6, OsJ), which included genes with known effects on the regulation of flowering by photoperiod. No *Arabidopsis* protein was found within the ZCCT or Group IV clusters suggesting that this group of genes originated after the monocot-dicot divergence. In addition, no genes were found in the rice genome within the ZCCT cluster (FIG. 18B). The absence of ZCCT genes in the colinear rice region flanked by genes AF459088.3 and SNF2P (FIG. 13) supports the results from the cluster analysis suggesting that these genes were originated in the temperate cereals after the divergence with rice.

Analysis of the putative zinc fingers confirmed the classification based on the CCT domains (FIG. 18B). CO-like proteins from groups II and I have one or two B-box zinc fingers with a conserved $Cx_2Cx_{15-16}Cx_2C$ structure whereas the ZCCT proteins showed a single $C_2H_2$ zinc finger with a conserved $Cx_2Cx_{15-16}Hx_3H$ structure. Zinc fingers from Group IV proteins were more similar, although not identical, to the zinc fingers from the ZCCT proteins. These observations suggest that the ZCCT genes probably originated from an ancestral CO-like protein from Group IV. However, their particular zinc finger motifs, differentiated CCT domains, and unique function justify the inclusion of these genes into a new gene group.

Expression Studies of the Candidate Genes

Transcription levels of AF459088.3 were not affected by vernalization (FIG. 14A), and no differences in expression were observed between spring and winter genotypes. Numerous Triticeae ESTs from dormant embryos, seedlings, roots, and young spikelets cDNA libraries showed significant similarity (E<e-100) to AF459088.3 suggesting a relatively high level of expression in numerous tissues.

On the contrary, the absence of any ESTs corresponding to the ZCCT genes in the extensive wheat and barley collections (≈870,000 ESTs as of October 2003) suggested low transcription levels. We developed the following TaqMan systems for ZCCT1 and ZCCT2 and used available ACTIN and UBIQUITIN systems as endogenous controls (Example 1). TaqMan probes for ZCCT1 and ZCCT2 were located in the junction between exon 1 and exon 2 to avoid genomic DNA amplification. The specificity of the two systems was confirmed by repeated experiments using as a substrate the cDNA clones from ZCCT1 and ZCCT2.

Test for Amplification Efficiency for TaqMan Systems

Tests for amplification efficiency were performed. Six 2-fold dilutions tested in triplicate; 1:1, 1:2, 1:4, 1:8, 1:16, 1:32. Standard curves were plotted with and slope and the differences between the slopes with the 18S standard curve were calculated. Criteria for passed test: differences of slopes <0.1. The efficiency based on the slope was also calculated.

```
ZCCT1 TaqMan System

Left primer:                    CCAACACATGGCTCACCTAGTG      (SEQ ID NO: 93)

Probe (reverse orientation):    AAATGGCACGATGTGGGCTCTTGCC   (SEQ ID NO: 94)

Right primer:                   TTGCTTCATTGCTAATAGTGTTGGT   (SEQ ID NO: 95)
```

Amplification efficiency—ZCCT1
Differences of the slopes with 18S: 0.027: ZCCT1 system passed efficiency test
Efficiency 99.8

```
ZCCT2 TaqMan System

Left primer:                    CCACCACTGCAGATCATGGA        (SEQ ID NO: 96)

Probe (reverse orientation):    CCAAGAACCACCATCGTGCCATTCTG  (SEQ ID NO: 97)

Right primer:                   TTGCTAATAGTGCTGGTGAATGC     (SEQ ID NO: 98)
```

Amplification Efficiency—ZCCT2
Differences of the slopes with 18S: 0.023: ZCCT2 system passed efficiency test
Efficiency 99.6

Figure 17:
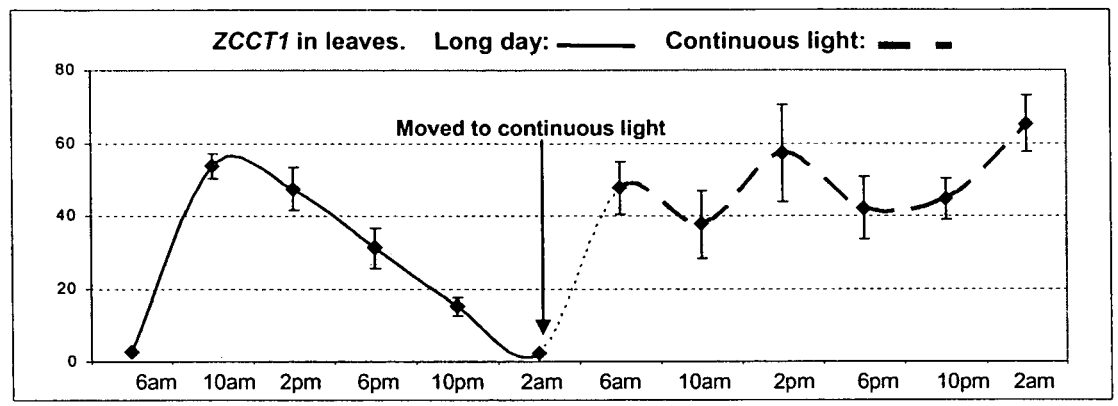
FIG. 17 shows the time course expression of ZCCT1 under long day and continuous light. Samples were extracted from leaves of unvernalized *Triticum monococcum* G3116 every 4 hours. The first 6 samples were extracted from plants located in the greenhouse under long day conditions. After the 2AM sampling plants were transferred to a growth chamber under continuous light. Values are averages of ten plants ±SE. Units are linearized values using the 2 $(^{-\Delta\Delta}CT)$ method, where CT is the threshold cycle. No significant differences in ZCCT1 linearized values were detected among the different collection times under continuous light (P=0.25) and highly significant differences were detected under the long day conditions (P<0.0001).

Time Course Expression of ZCCT1 Under Long Day and Continuous Light (See FIG. 17)

Samples were extracted from leaves of unvernalized *Triticum monococcum* G3116 every 4 hours. The first 6 samples were extracted from plants located in the greenhouse under long day conditions. After the 2 am sampling plants were transferred to a growth chamber under continuous light. Values are averages of ten plants ±SE. Units are linearized values using the $2^{(-\Delta\Delta C_T)}$ method, where $C_T$ is the threshold cycle. No significant differences in ZCCT1 linearized values were detected among the different collection times under continuous light (P=0.25) and highly significant differences were detected under the long day conditions (P<0.0001).

Figure 14:
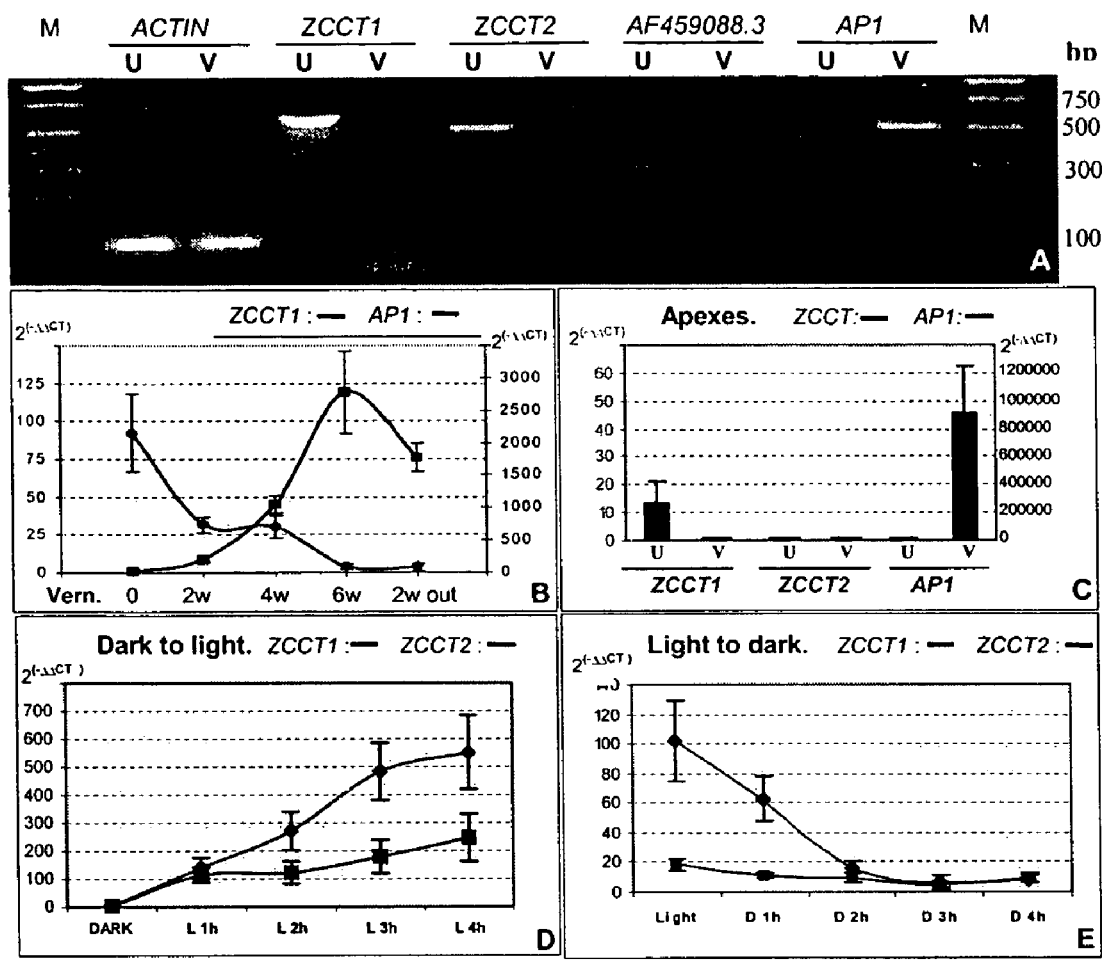
FIG. 14A shows RT-PCR from leaves of G3116 2-month old plants unvernalized (U) or 5 days at room temperature after 6 weeks of vernalization (V). B-E) Quantitative PCR.
FIG. 14B shows transcript levels in leaves of ZCCT1 (red scale) and AP1 (blue scale) relative to ACTIN in G3116 (averages of 5 plants±SE): 0: before 4° C.; 2 w, 4 w, 6 w: weeks at 4° C.; 2 w out: 2 weeks in greenhouse after vernalization.
FIG. 14C shows transcript levels in apexes of ZCCT1, ZCCT2 and AP1 relative to ACTIN in G3116 (averages of 3 pools of apexes from 5 plants each±SE). U=unvernalized, V=3-5 days at room temperature after 6 weeks of vernalization.
FIGS. 14D and 14E show the effect of light on transcript levels of ZCCT1 relative to UBIQUITIN in leaves from unvernalized G3116 (measured every hour, averages of 10 plants±SE).

During the eight weeks of the vernalization experiment (16 h of light), we observed a progressive decrease of both ZCCT transcripts in the leaves relative to ACTIN (FIG. 14B) or UBIQUITIN. Plants kept in the greenhouse showed stable transcript levels during all the experiment. An important observation was that ZCCT transcription was not restored after removing the vernalized plants from the cold room and returning them to the greenhouse (FIG. 14, 2 w out). A similar stable repression of transcription by vernalization was observed in the unrelated *Arabidopsis* MADS-box gene FLC, suggesting that the ZCCT genes may play a similar central role in the repression of flowering in cereals.

The downregulation of ZCCT1 during vernalization was paralleled by an increase of AP1 transcription (FIG. 14B). We have previously shown that AP1 is the wheat VRN1 gene (Example 1) and that there are strong epistatic interactions between VRN1 and VRN2 (G. E. Tranquilli, et al. (1999)). The model for these epistatic interactions predicted the opposite transcription profiles observed in FIG. 14. According to this model the VRN2 gene acts as a repressor of flowering, which directly or indirectly represses AP1 transcription (Example 1).

Quantitative PCR analysis of the transcription of the ZCCT genes in the apices provided the first evidence that ZCCT1 was a better candidate for VRN2 than ZCCT2. ZCCT1 transcripts were present in the apices from the unvernalized winter plants but after six weeks of vernalization were reduced to undetectable levels. AP1 transcripts showed the opposite pattern, being greatly induced after vernalization (FIG. 14C). We were not able to detect transcripts of ZCCT2 in the same RNA samples where we detected ZCCT1 and AP1. Transcripts from ZCCT2 were detected in positive controls from leaves. These results suggested that ZCCT2 was either not expressed in the apices or its transcription level was below our detection threshold. Since apices are the critical points for the transition between the vegetative and reproductive phases, these experiments suggested that ZCCT1 was a better candidate for VRN2 than ZCCT2.

An interesting observation was that the transcript level of ZCCT1 and ZCCT2 varied significantly during the day. However, no significant variation was observed when plants were transferred from the long day conditions (16 h light) to continuous light, suggesting that the circadian clock was not involved in the regulation of ZCCT transcription. We found that ZCCT transcription was rapidly upregulated when plants were moved from the dark to the light (FIG. 14D), and downregulated when moved from the light to the dark (FIG. 14E). The role of this dual regulation of the VRN2 candidate gene by vernalization and light is still not clear, but it is tempting to speculate that this phenomenon might be related to the integration of photoperiod and vernalization signals in the regulation of flowering in temperate cereals.

ZCCT1 transcription was downregulated during vernalization in both winter G3116 and spring DV92 plants, suggesting that the differences in growth habit were not originated by differences in the transcriptional regulation of ZCCT1. To test this hypothesis we compared the sequences of the promoter and coding regions from different VRN2 candidate genes between spring and winter accessions of cultivated *T. monococcum* from different parts of the world. We sequenced the complete coding region of ZCCT1 from seven winter accessions, PI355522, PI277133, PI272561, PI573529, PI221413, PI355522, and G3116. None of the winter accessions carry the R to W mutation identified in DV92.

The primers used to amplify cDNA of the ZCCT1 gene were:

```
C1Out3F1:   GGCTCCAATCGATCAATCAC  (SEQ ID NO: 99)
C1Out5R1:   TTCTTCCTCGACGTCTCTCC  (SEQ ID NO: 100)
```

Allelic Variation Among Cultivated Diploid *Triticum monococcum*

We observed no differences in the AF459088.3 protein between vrn2-spring accession DV92 and Vrn2-winter accessions PI355532 and PI277133. Similarly, no differences were found in the predicted ZCCT2 proteins between vrn2-spring accession DV92 and Vrn2-winter accessions PI272561 and PI277133. The promoter region (1,098-bp) and the 3' region (736-bp) of the ZCCT2 gene from winter accession PI272561 were also identical to DV92. These results suggested that the differences in vernalization requirement were not associated to differences in the coding sequences of these two genes or in the regulatory sequences of ZCCT2.

No differences were found either for the promoter region of ZCCT1 between DV92 and winter accession PI272561. We compared the 638-bp promoter region downstream from the start codon of the ZCCT1 in spring accession DV92 with the same region in winter accessions G3116, PI272561, and PI573529. The promoter sequence of DV92 was identical to the sequence of winter accession PI272561 confirming that the differences detected between Vrn2 and vrn2 alleles was determined by differences in the ZCCT1 protein rather than differences in its transcriptional regulation.

Primers used to amplify the promoter region:

```
C1ProF1:   TGAGGCGCGGGCAGTTGTTG   (SEQ ID NO: 101)
C1ProR1:   GGTTAAGCTTGGGGGAGAAG   (SEQ ID NO: 102)
```

However, comparison of the ZCCT1 coding region from DV92 with cultivated *T. monococcum* accessions with a winter growth habit provided good evidence that ZCCT1 was the VRN2 gene. The spring accession DV92 carried a point mutation at position 35 of the CCT domain that replaced an Arg (R) amino acid by a Trp (W). This R amino acid was conserved in all the ZCCT proteins (FIG. 29A) and in all the CO-like proteins from *Arabidopsis*, rice and barley (S. Griffiths, et al. (2003)). A point mutation at the same position in the CCT domain from CO in *Arabidopsis* EMS mutant co-7 did not affect the nuclear localization of the CO protein but produced a severe effect on flowering time (F. Robson, et al. (2001)). Kurup et al. (2000) suggested that the CCT domain might be involved in protein-protein interactions, and therefore, a mutation within this domain can disrupt these interactions and the function of the involved proteins. The conservation of the 35-R amino acid in all the CCT domains, and the strong effect of its mutation on flowering time indicate that this amino acid is essential for the correct function of the CCT domain and that the point mutation observed in DV92-ZCCT1 provides a good explanation for its spring growth habit.

The Arg/Trp mutation in DV92 determined a unique Nco I restriction site, which was absent in the wild allele (the probe for this polymorphism is described above). This polymorphism was used to screen a germplasm collection of 65 accessions of cultivated *T. monococcum* from different parts of the world. The Arg/Trp mutation was absent in all 16 winter accessions, but present in 22 of the 49 spring accessions. Screening of the remaining 27 spring accessions by hybridization with ZCCT1 showed that 17 accessions had a complete deletion of ZCCT1 and ZCCT2. Seven of the remaining spring accessions showed a 1-bp deletion in the VRN1 promoter that explained their spring growth habit (SEQ ID NO:17). We have initiated crosses between the last three spring accessions and tester lines DV92 and G3116 to determine the location of the gene responsible for the spring growth habit in these lines. It is interesting to point out that these three accessions originated from the eastern border of the *T. monococcum* distribution (Bulgaria, Romania, and Russia).

We confirmed experimentally that the complete ZCCT deletion was allelic to the vrn2 allele from DV92. The $F_1$ hybrid between accession PI190915 carrying the complete deletion and winter accession G3116 had a winter growth habit whereas the cross with DV92 showed a spring growth habit. In addition, all the $F_2$ plants from the cross PI190915× DV92 had a spring growth habit. In summary, the described mutations at the ZCCT1 and VRN1 genes were sufficient to explain the spring growth habit of 92%, of the cultivated *T. monococcum* accessions analyzed in this study.

This provides supporting evidence to the importance of AP1 and ZCCT1 genes in the determination of growth habit in diploid wheat Allelic Variation in Barley The absence of both ZCCT genes in the orthologous BAC from barley variety Morex (FIG. 13), suggested that this variety carries a recessive vrn2 allele. Hybridization of barley genomic DNA with wheat ZCCT1 clone (UCW39) showed no fragments in Morex, but three XbaI-fragments in winter *Hordeum spontaneum*. These three RFLP fragments were completely linked to SNF2P in 102 $F_2$ plants from the cross between Morex and *H. spontaneum*, demonstrating that barley Morex has a recessive vrn-H2 allele completely linked to the ZCCT deletion.

We cloned and sequenced two ZCCT genes from winter barley Dairokkaku. A Neighbor Joining cluster analysis of the complete wheat and barley proteins showed that the two barley genes were more similar to each other than to wheat ZCCT1 or ZCCT2 genes. This lack of correspondence between the wheat and barley genes was expected because the divergence time between wheat and barley (11-15 million years ago (W. Ramakrishna, et al. (2002))) was close to the time of the duplication of the ZCCT genes (11-16 mya). The two barley genes were designated ZCCT-Ha and ZCCT-Hb To study the distribution of the deletion of the ZCCT genes in barley and its association to the vrn2 allele, we screened a collection of 85 barley varieties from different parts of the world that were previously characterized genetically for their vernalization alleles (R. Takahashi, (1956)). Hybridization of Southern blots with DNAs from these varieties with the ZCCT1 probe showed the presence of three Dra I fragments in the 23 winter varieties, and their absence in 61 vrn-H2-spring barley varieties (C.-L. Chen (2002)). The vrn-H2 spring barley variety 'Fan' was the only exception, showing a single Dra I fragment when hybridized with ZCCT1. Sequencing of part of Fan ZCCT gene showed that it was identical to ZCCT-Hb from winter variety Dairokkaku. In summary, a perfect association was observed in barley between the presence of ZCCT deletions and the vrn-H2 allele.

Validation of ZCCT1 as VRN2 by RNAi Transgenic Wheats

We transformed winter bread-wheat variety Jagger with an RNA interference (RNAi) construct including a 347-bp segment from *T. monococcum* ZCCT1 gene. Three positive T0 plants from three independent transformation events were identified by PCR. However, only one of the three T0 transgenics flowered earlier (23 days) than the negative control. An RT-PCR experiment using primers for the transcribed PolyA region from the vector confirmed the expression of the RNAi transgene in the early flowering transgenic plant and its absence in the negative controls (FIG. 15A).

RNA Interference

The RNAi construct was made in the binary vector pMCG161 (available on the Internet at the website for the Plant Chromatin Database, ChromDB) This vector contains a cassette designed for making inverted repeat transcripts of a gene, flanking a loop, which should efficiently produce a double stranded RNA. Expression of the transgene is driven by the 35S promoter followed by the Adh1intron.

We cloned a 361-bp segment from ZCCT1 (90-bp to 436-bp, excluding the CCT domain and the Zinc finger) in sense orientation between restriction sites AscI-AvrII and in antisense orientation between restriction sites Sgf I-Spe I. The engineered recombinant plasmid was co-transformed with UBI:BAR into immature-embryos of Jagger, a hard red winter wheat, by microprojectile bombardment as described before (P. A. Okubara, et al. (2002)). Jagger is less responsive to tissue culture and more sensitive to bialaphos than Bobwhite, the cultivar used in previous work, and therefore the following additions were made to the post-bombardment callus maintenance and regeneration media: 5 uM cupric sulfate and 0.1 mg/L benzyladenopurine as suggested by Cho et al. (M. J. Cho, et al. (1998)). Selection of transformants was done by addition of 3 mg/L bialaphos to shoot regeneration and 1 mg/L bialaphos to rooting media. Positive plants were confirmed by PCR using primers designed based on the vector sequence flanking the sense and antisense insertions.

```
Ri_S_F:     GTTGAGTGGCCCTGTTTCTC   (SEQ ID NO: 103)

Ri_S_R:     CATTGATCAGCCTAACCAAACA (SEQ ID NO: 104)

Expected product: 741-bp

Ri_AntiS_F: CAAATTCTAATCCCCAATCCAA (SEQ ID NO: 105)

Ri_AntiS_R: GGCGGTAAGGATCTGAGCTA   (SEQ ID NO: 106)

Expected product: 632-bp
```

Transcription of the transgene in the three selected transgenic plants was confirmed by RT-PCR using primers for the transcribed Octopine Synthetase PolyA region of the pMCG161 vector. No amplification was detected in the control plants.

```
OCS-PolyA_F: AGTGGGTCTAGAGTCCTGCTT (SEQ ID NO: 107)

Ri_AntiS_R:  GGCGGTAAGGATCTGAGCTA  (SEQ ID NO: 108)

Expected product: 124-bp
```

Transcription level of ZCCT1 was tested using the ZCCT1 TaqMan system. To avoid amplification from the transgene, the reverse transcription was performed with primer Race_C12F1 that is outside the 361-bp region included in the vector. As a control, ACTIN primer Actin_L was also included in the reverse transcription reaction. Transcription level of AP1 in the transgenic plants was evaluated using the AP1 TaqMan system (See Example 1).

Quantitative PCR experiments showed that only one of the early flowering transgenic plants showed a downregulation of ZCCT1 and upregulation of AP1 in the leaves (FIG. 15A). This plant flowered 23 days earlier than the negative control (FIG. 15A).

We self-pollinated the early flowering transgenic T0 plant and determined the presence or absence of the transgene in 45 plants from the T1 progeny by Southern blots. Hybridization of genomic DNA with the 35S promoter from the vector showed a single fragment that segregated in a perfect 3:1 ratio (34 plants present vs. 11 plants absent). All plants carrying the transgene flowered earlier (3-5 weeks) than the 11 plants homozygous for the absence of the transgene. This experiment confirmed that the reduction of the RNA level of ZCCT1 is directly associated with the acceleration of flowering time.

A new Vernalization Pathway

The complete linkage between ZCCT1 and VRN2 in a large mapping population, its gradual and stable transcriptional downregulation during vernalization, its opposite transcription profile to AP1, the association between natural allelic variation at ZCCT1 and spring growth habit in four independent mutation events, and the elimination of the requirement of vernalization by RNAi of ZCCT1 transcripts, demonstrated that ZCCT1 is the VRN2 gene.

Therefore, the central repressor of flowering in the vernalization pathway in temperate cereals is a gene that is not present in *Arabidopsis*. The vernalization pathway in the temperate cereals also differs from that in *Arabidopsis* in the direct regulation of AP1 transcription by vernalization (Example 1). Therefore, we conclude that the temperate grasses developed a vernalization pathway de novo, using a different set of genes than *Arabidopsis*.

*Arabidopsis* has been recently compared to the Rosetta stone because of its huge contribution to our understanding of the "language of flowering" (G. G. Simpson, et al. (2002)). However, there are more human written languages than those included in the Rosetta stone. In a similar way, this Example shows that there might be also multiple "languages of flowering" that will require dedicated research efforts to be deciphered. This is particularly important for the crops that feed our world.

REFERENCES

The following references cited herein are hereby incorporated by reference in their entirety.

Altschul, S. F. et al. (1990) J. Mol. Bio. 215:403-410.
Altschul, S. F. et al. (1994) Nat. Genet. 6(2):119-29.
Ausubel, F. M. et al. eds. (1987) CURRENT PROTOCOLS IN MOLECULAR BIOLOGY, Green Publishing.
Barrett, B., Bayram, M. & Kidwell, K. (2002) *Pl. Breed.* 121, 400-406.
Bennett, M. D. & Smith, J. B. (1991) *Phil Trans Roy Soc London B* 334, 309-345.
Boronat et al. (1986) Plant Sci 47: 95-102.
Buchanan, Bob B., Wilhelm Gruissem, and Russell L. Jones, eds. (2001) Biochemistry & Molecular Biology of Plants; John Wiley and Sons, Publishers.
Chen, F. Q., M. R. Foolad (1997) *Pl. Mol. Biol* 35: 821-831.
Chen, et al. (1996) Plant J 10: 955-966.
Chen, C.-L., MS, University of California (2002).
Cho, M. J., W. Jiang, P. G. Lemaux (1998) *Plant Sci.* 138, 229-244.
Chung, Y. Y., Kim, S. R., Finkel, D., Yanofsky, M. F. & An, G. H. (1994) *Pl. Mol. Biol.* 26, 657-665.
Clayton, W. D., S. A. Renvoize (1986) *Genera Graminum. Grasses of the world.* (Kew, London: Royal Botanic Gardens.
Coligan, Dunn, Ploegh, Speicher and Wingfeld, eds. (1995) CURRENT PROTOCOLS IN PROTEIN SCIENCE (John Wiley & Sons, Inc.).
Cordero, et al. (1994) The Plant J 6(2): 141-150.
Corpet, F. (1988) Nucleic Acids Res. 16:10881-10890
Duan, et al. (1996) Nat Biotech 14: 494-498.
Dubcovsky, J., Galvez, A. F. & Dvorak, J. (1994) *Theor. Appl. Genet* 87, 957-964.
Dubcovsky, J., Lijavetzky, D., Appendino, L. & Tranquilli, G. (1998) *Theor. Appl. Genet.* 97, 968-975.
Dubcovsky, J., Ramakrishna, W., SanMiguel, P., Busso, C., Yan, L., Shiloff, B. & Bennetzen, J. (2001) *Plant Physiol.* 125, 1342-1353.
Dubcovsky, J., L. Yan (2003) Allelic variation in the promoter of Ap1, the candidate gene for Vrn-1, N. Pogna, Ed., X International Wheat Genetics Symposium., Paestum, Italy.
Dvorak, J. & Chen, K.-C. (1984) *Genetics* 106, 325-333.
Eckelkamp, et al. (1993) FEB Letters 323: 73-76.
Ferrandiz, C., Gu, Q., Martienssen, R. & Yanofsky, M. F. (2000) *Development* 127, 725-734.
Flanagan, C. A. & Ma, H. (1994) *Pl. Mol. Biol.* 26, 581-595.
Freshney, R. I., ed. (1987) ANIMAL CELL CULTURE.
Galiba, G., Quarrie, S. A., Sutka, J. & Morgounov, A. (1995) *Theor. Appl. Genet.* 90, 1174-1179.
Gardner, J. S., Hess, W. M. & Trione, E. J. (1985) *Amer. J. Bot.* 72, 548-559.
Gaut, B. S., B. R. Morton, B. C. McCaig, M. T. Clegg, *Proc Nat Acad Sci USA* 93, 10274-10279 (1996).
Gelvin, S. B., Habeck, L. L. (1990) Bacteriol. 172(3):1600-8.
Gendall, A. R, Y. Y. Levy, A. Wilson, C. Dean, *Cell* 107, 525-535 (2001)
Goff, S. A., Ricke, D., Lan, T. H., Presting, G., Wang, R. L., Dunn, M., Glazebrook, J., Sessions, A., Oeller, P., Varma, H., Hadley, D., Hutchinson, D., Martin, C., Katagiri, F., Lange, B. M., Moughamer, T., Xia, Y., Budworth, P., Zhong, J. P., Miguel, T., Paszkowski, U., Zhang, S. P., Colbert, M., Sun, W. L., Chen, L. L., Cooper, B., Park, S., Wood, T. C., Mao, L., Quail, P., Wing, R., Dean, R., Yu, Y. S., Zharkikh, A., Shen, R., Sahasrabudhe, S., Thomas, A., Cannings, R., Gutin, A., Pruss, D., Reid, J., Tavtigian, S., Mitchell, J., Eldredge, G., Scholl, T., Miller, R. M., Bhatnagar, S., Adey, N., Rubano, T., Tusneem, N., Robinson, R., Feldhaus, J., Macalma, T., Oliphant, A. & Briggs, S. (2002) *Science* 296, 92-100.
Goncharov, N. P. (1998) *Euphytica* 100, 371-376.
Grierson, D. and S. N. Covey (April 1991) Plant Molecular Biology-Second Edition, John Innes Institute, Norwich, UK Kluwer Academic Publishers, Dordrecht.
Griffiths, S., R. P. Dunford, G. Coupland, D. A. Laurie, *Plant Physiol.* 131, 1855-1867 (2003).
Halloran, G. M. (1967) *Genetics* 57, 401-407.
Harlow and Lane, eds. (1988) ANTIBODIES, A LABORATORY MANUAL.
Hayama, R., S. Yokoi, S. Tamaki, M. Yano, K. Shimamoto, *Nature* 422, 719-722 (2003).
Hayward, M. D., N. O. Bosemark, I. Romagosa (1993) PLANT BREEDING: PRINCIPLES AND PROSPECTS (Plant Breeding, Vol 1) Chapman & Hall.
Hepworth, S. R., Valverde, F., Ravenscroft, D., Mouradov, A. & Coupland, G. (2002) *EMBO J.* 21, 4327-4337.
Higgins, D. G. and Sharp, P. M. (1988) Gene 73(1):237-44.
Higgins, D. G. and Sharp, P. M. (1989) Comput Appl Biosci. 5(2):151-3.
Huang X. et al. (1992) Comput. Appl. Biosci. 8(2):155-65.
Iwaki, K., Nishida, J., Yanagisawa, T., Yoshida, H. & Kato, K. (2002) *Theor. Appl. Genet.* 104, 571-576.
Johansen, B., Pedersen, L. B., Skipper, M. & Frederiksen, S. (2002) *Mol. Phylogenet Evol.* 23, 458-480.
Johanson, U., West, I., Lister, C., Michaels, S., Amasino, R. & Dean, C. (2000) *Science* 290, 344-347.

Kato, K., Miura, H. & Sawada, S. (1999) *Genome* 42, 204-209.

Kato, K., Kidou, S., Miura, H. & Sawada, S. (2002) *Theor. Appl. Genet.* 104, 1071-1077.

Kendrew et al., eds. (1994) The Encyclopedia of Molecular Biology, published by Blackwell Science Ltd. (SBN 0-632-02182-9).

Kihara, H. & Tanaka, M. (1958) *Preslia* 30, 241-251.

Kloesgen, et al. (1986) Mol Gen Genet 203: 237-244.

Kumar, S., Tamura, K. & Nei, M. (1994) *Comput Appl Biosci* 10, 189-191.

Kurup, S., H. D. Jones, M. J. Holdsworth, *Plant J.* 21, 143-155 (2000).

Law, C. N., Worland, A. J. & Giorgi, B. (1975) *Heredity* 36, 49-58.

Lea, Peter and Richard C. Leegood, eds. (1998) Plant Biochemistry and Molecular Biology, 2nd Edition.

Levy, Y. Y., S. Mesnage, J. S. Mylne, A. R. Gendall, C. Dean (2002) *Science* 297, 243-246.

Lewin (1994) Genes V, published by Oxford University Press (SBN 0-19-854287-9).

Lijavetzky, D., Muzzi, G., Wicker, T., Keller, B., Wing, R. & Dubcovsky, J. (1999) *Genome* 42, 1176-1182.

Limin, A. E. & Fowler, D. B. (2002) *Annals of Botany* 89, 579-585.

Livak, K. J. & Schmittgen, T. D. (2001) *Methods* 25, 402-408.

Lukaszewski, A. J. & Curtis, C. A. (1993) *Theor. Appl. Genet.* 84, 121-127.

MacPherson, M. J., Hames, B. D., and G. R. Taylor eds. (1995) the series METHODS IN ENZYMOLOGY (Academic Press, Inc.): PCR 2: A PRACTICAL APPROACH.

Mandel, M. A. & Yanofsky, M. F. (1998) *Sex Plant Reprod* 11, 22-28.

Marineau, et al. (1987) Plant Mol Biol 9: 335-342.

Matton, et al. (1987) Molecular Plant-Microbe Interacions 2: 325-342.

McGurl, et al. (1992) Science 225: 1570-1573.

McIntosh, R. A., G. E. Hart, K. M. Devos, M. D. Gale, W. J. Rogers (1998) Catalogue of Gene Symbols for Wheat., Proc. 9th Int. Wheat Genetics Symp., Saskatchewan, Canada.

Meyer, Robert A., ed. (1995) Molecular Biology and Biotechnology, a Comprehensive Desk Reference, published by VCH Publishers, Inc. (ISBN 1-56081-569-8).

Michaels, S. D. & Amasino, R. M. (1999) *Plant Cell* 1, 949-956.

Mouradov, A., F. Cremer, G. Coupland (2002) *Plant Cell* 14, S111-S130.

Murai, K., Murai, R. & Ogihara, Y. (1997) *Genes Genet Syst* 72, 317-321.

Murai, K., Takumi, S., Koga, H. & Ogihara, Y. (2002) *Plant J.* 29, 169-181.

Needleman, S. B. and Wunsch, C. D. (1970) J. Mol. Biol. 48:443-453.

Ng, M. & Yanofsky, M. F. (2001) *Nat Rev Genet* 2, 186-195.

Okubara, P. A. et al. (2002) *Theor. Appl. Genet.* 106, 74-83.

Pearson, W. R., Lipman, D. J., (1988) *PNAS USA* 85:2444-8.

Pearson W R. (1994) Methods Mol. Biol. 24:307-31.

Plaschke, J., Börner, A., Xie, D. X., Koebner, R. M. D., Schlegel, R. & Gale, M. D. (1993) *Theor. Appl. Genet.* 85, 1049-1054.

Putterill, J., F. Robson, K. Lee, R. Simon, G. Coupland (1995) *Cell* 80, 847-857.

Ramakrishna, W., Dubcovsky, J., Park, Y. J., Busso, C. S., Emberton, J., SanMiguel, P. & Bennetzen, J. L. (2002) *Genetics* 162: 1389-1400.

Redolfi et al. (1983) Meth J. Plant Pathol. 89: 245-254.

Reina et al. (1990) Nucleic Acids Res 18 (21): 6426.

Robson, F. et al. (2001) *Plant J.* 28, 619-631.

Rohmeier, et al. (1993) Plant Mol Biol 22: 783-792.

Ryan (1990) Annu Rev Phytopath 28: 425-449.

Sambrook, Fritsch and Maniatis, (1989) MOLECULAR CLONING: A LABORATORY MANUAL, 2nd edition, Cold Spring Harbor, N.Y.

SanMiguel, P., Ramakrishna, W., Bennetzen, J. L., Busso, C. S. & Dubcovsky, J. (2002) *Functional and Integrative Genomics* 2, 70-80.

Savidge, B., Rounsley, S. D. & Yanofsky, M. F. (1995) *Plant Cell* 7, 721-733.

Schmitz, J., Franzen, R., Ngyuen, T. H., Garcia-Maroto, F., Pozzi, C., Salamini, F. & Rohde, W. (2000) *Pl. Mol. Biol.* 42, 899-913.

Sheldon, C. C., et al. (1999) *Plant Cell* 11, 445-458.

Sheldon, C. C., Rouse, D. T., Finnegan, E. J., Peacock, W. J. & Dennis, E. S. (2000) *Proc Nat Acad Sci USA* 97, 3753-3758.

Siebertz, et al. (1989) Plant Cell 1: 961-968.

Simpson, G. G., C. Dean (2002) *Science* 296: 285-289.

Smith, T. F. and Waterman, M. S. (1981) J. Mol. Biol. 147: 195-197

Somssich et al. (1986) Proc Natl Acad Sci USA 83: 2427-2430.

Somssich et al. (1988) Mole Gen Genetics 2: 93-98.

Stanford et al. (1989) Mol Gen Genet 215: 200-208.

Stein, N., Feuillet, C., Wicker, T., Schlagenhauf, E. & Keller, B. (2000) *Proc Nat Acad Sci USA* 97, 13436-13441.

Stemmer, W. P. (1994) Nature 370(6488):389-91.

Stemmer, W. P. (1994) Proc. Natl. Acad. Sci., U.S.A. 91(22): 10747-51.

Suarez-Lopez, P., et al. (2001), *Nature* 410, 1116-1120.

Takahashi, R. (1956) "Catalogue of the barley germplasm preserved in Okayama University" (Institute of Agricultural and Biological Sciences, Okayama University, 1983); R. Takahashi, S. Yasuda, *Ber.Ohara Inst Landw.Biol., Okayama University*. 10, 245-308.

Takahashi, R., S. Yasuda, Genetics of earliness and growth habit in barley, R. A. Nilan, Ed., Proceedings of the 2nd International Barley Genetics Symposium, Washington (Washington State University Press, 1971).

Tilly, J. J., Allen, D. W. & Jack, T. (1998) *Development* 125, 1647-1657.

Tranquilli, G. E. & Dubcovsky, J. (1999) *J. Hered.* 91, 304-306.

Uknes et al. (1992) The Plant Cell 4: 645-656.

Van Loon (1985) Plant Mol. Virol. 4: 111-116.

Warner, et al. (1993) Plant J 3: 191-201.

Weissbach, A. and Weissbach, H. (eds.) (1988) Methods for Plant Molecular Biology.

Wicker, T., Stein, N., Albar, L., Feuillet, C., Schlagenhauf, E. & Keller, B. (2001) *Plant J.* 26, 307-316.

Woo, S. S., Jiang, J., Gill, B. S., Paterson, A. H. & Wing, R. A. (1994) *Nucleic Acid Research* 22, 4922-4931.

Yan, L., Echenique, V., Busso, C., SanMiguel, P., Ramakrishna, W., Bennetzen, J. L., Harrington, S. & Dubcovsky, J. (2002) *Mol. Gener. Genomics* 268, 488-499.

Yang (1996) Proc Natl Acad Sci USA 93: 14972-14977.

Zhang and Sing (1994) Proc Natl Acad Sci USA 91: 2507-2511.

Zhang, H.-B., Choi, S., Woo, S. S., Li, Z. & Wing, R. A. (1996) *Mol Breeding* 2, 11-24.

We claim:

1. An isolated nucleic acid comprising the sequence of SEQ ID NO: 75.

2. The isolated nucleic acid of claim 1, wherein the nucleic acid is operably linked to a promoter.

3. The isolated nucleic acid of claim 2, wherein the promoter is a heterologous promoter.

4. The isolated nucleic acid of claim 2, wherein the promoter is a inducible promoter.

5. The isolated nucleic acid of claim 2, wherein the promoter is a regulated promoter.

6. The isolated nucleic acid of claim 2, wherein the promoter is a constitutive promoter.

* * * * *

SEQUENCE LISTING

<160> NUMBER OF SEQ ID NOS: 159

<210> SEQ ID NO 1
<211> LENGTH: 69
<212> TYPE: DNA
<213> ORGANISM: Triticum monococcum

<400> SEQUENCE: 1
cctttaaaaa cccctccccc cctgccggaa ccctcgtttt ggcctggcca tcctccctct    60
cctcccctc                                                            69

<210> SEQ ID NO 2
<211> LENGTH: 49
<212> TYPE: DNA
<213> ORGANISM: Triticum monococcum

<400> SEQUENCE: 2
cctttaaaaa ccctcgtttt ggcctggcca tcctccctct cctcccctc                49

<210> SEQ ID NO 3
<211> LENGTH: 35
<212> TYPE: DNA
<213> ORGANISM: Triticum monococcum

<400> SEQUENCE: 3 cctttttggcc tggccatcct ccctctcctc ccctc                              35

<210> SEQ ID NO 4
<211> LENGTH: 21
<212> TYPE: DNA
<213> ORGANISM: Triticum monococcum

<400> SEQUENCE: 4
cctttaaaaa cccctcccct c                                              21

<210> SEQ ID NO 5
<211> LENGTH: 735
<212> TYPE: DNA
<213> ORGANISM: Triticum monococcum

<400> SEQUENCE: 5
atggggcgcg ggaaggtgca gctgaagcgg atcgagaaca agatcaaccg gcaggtgacc    60
ttctccaagc gccgctcggg gcttctcaag aaggcgcacg agatctccgt gctctgcgac   120
gccgaggtcg gcctcatcat cttctccacc aagggaaagc tctacgagtt ctccaccgag   180
tcatgtatgg acaaaattct tgaacggtat gagcgctatt cttatgcaga aaaggttctc   240
gtttcaagtg aatctgaaat tcagggaaac tggtgtcacg aatataggaa actgaaggcg   300
aaggttgaga caatacagaa atgtcaaaaa catctcatgg gagaggatct tgaatctttg   360
aatctcaagg agttgcagca actggagcag cagctggaaa gctcactgaa acatatcaga   420
tccaggaaga accaacttat gcacgaatcc atttctgagc tgcagaagaa ggagaggtca   480
ctgcaggagg agaataaagt tctccagaag gaactcgtgg agaagcagaa ggcccatgcg   540
gcgcagcaag atcaaactca gcctcaaacc agctcttctt cttcttcctt catgctgagg   600
gatgctcccc ctgccgcaaa taccagcatt catccagcgg cggcaggcga gagggcagag   660
gatgcggcag tgcagccgca ggccccaccc cggacggggc ttccaccgtg gatggtgagc   720
cacatcaacg ggtga                                                    735

<210> SEQ ID NO 6
<211> LENGTH: 734
<212> TYPE: DNA
<213> ORGANISM: Triticum monococcum

<400> SEQUENCE: 6

```
atggggcgcg ggaaggtgca gctgaagcgg atcgagaaca agatcaaccg gcaggtgacc        60
ttctccaagc gccgctcggg gcttctcaag aaggcgcacg agatctccgt gctctgcgac       120
gccgaggtcg gcctcatcat cttctccacc aagggaaagc tctacgagtt ctccaccgag       180
tcatgtatgg acaaaattct tgaacggtat gagcgctatt cttatgcaga aaaggttctc       240
gtttcaagtg aatctgaaat tcagggaaac tggtgtcacg aatataggaa actgaaggcg       300
aaggttgaga caatacagaa atgtcaaaaa catctcatgg agaggatctt gaatctttg        360
aatctcaagg agttgcagca actggagcag cagctggaaa gctcactgaa acatatcaga       420
tccaggaaga accaacttat gcaggatcca tttctgagct gcagaagaag gagaggtcac       480
tgcaggagga gaataaagtt ctccagaagg aactcgtgga gaagcagaag gcccatgcgg       540
cgcagcaaga tcaaactcag cctcaaacca gctcttcttc ttcttccttc atgctgaggg       600
atgctccccc tgccgcaaat accagcattc atccagcggc ggcaggcgag agggcagagg       660
atgcggcagt gcagccgcag gccccacccc ggacggggct tccaccgtgg atggtgagcc       720
acatcaacgg gtga                                                         734
```

<210> SEQ ID NO 7
<211> LENGTH: 244
<212> TYPE: PRT
<213> ORGANISM: Triticum monococcum

<400> SEQUENCE: 7

```
Met Gly Arg Gly Lys Val Gln Leu Lys Arg Ile Glu Asn Lys Ile Asn
  1               5                  10                  15

Arg Gln Val Thr Phe Ser Lys Arg Arg Ser Gly Leu Leu Lys Lys Ala
             20                  25                  30

His Glu Ile Ser Val Leu Cys Asp Ala Glu Val Gly Leu Ile Ile Phe
         35                  40                  45

Ser Thr Lys Gly Lys Leu Tyr Glu Phe Ser Thr Glu Ser Cys Met Asp
     50                  55                  60

Lys Ile Leu Glu Arg Tyr Glu Arg Tyr Ser Tyr Ala Glu Lys Val Leu
 65                  70                  75                  80

Val Ser Ser Glu Ser Glu Ile Gln Gly Asn Trp Cys His Glu Tyr Arg
                 85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala His Ala Ala Gln Gln Asp Gln Thr Gln Pro Gln Thr Ser Ser
            180                 185                 190
```

```
Ser Ser Ser Ser Phe Met Leu Arg Asp Ala Pro Pro Ala Ala Asn Thr
        195                 200                 205

Ser Ile His Pro Ala Ala Ala Gly Glu Arg Ala Glu Asp Ala Ala Val
        210                 215                 220

Gln Pro Gln Ala Pro Pro Arg Thr Gly Leu Pro Pro Trp Met Val Ser
225                 230                 235                 240

His Ile Asn Gly

<210> SEQ ID NO 8
<211> LENGTH: 244
<212> TYPE: PRT
<213> ORGANISM: Triticum monococcum

<400> SEQUENCE: 8

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ser Thr Glu Ser Cys Met Asp
    50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Asn
    130                 135                 140

Gln Leu Met His Gly Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala His Ala Ala Gln Gln Asp Gln Thr Gln Pro Gln Thr Ser Ser
            180                 185                 190

Ser Ser Ser Ser Phe Met Leu Arg Asp Ala Pro Pro Ala Ala Asn Thr
        195                 200                 205

Ser Ile His Pro Ala Ala Ala Gly Glu Arg Ala Glu Asp Ala Ala Val
        210                 215                 220

Gln Pro Gln Ala Pro Pro Arg Thr Gly Leu Pro Pro Trp Met Val Ser
225                 230                 235                 240

His Ile Asn Gly

<210> SEQ ID NO 9
<211> LENGTH: 1017
<212> TYPE: DNA
<213> ORGANISM: Triticum monococcum

<400> SEQUENCE: 9
atttgcctga tgagacgctt gacaacagtg tattgatgga tgtctggtcg gtatacacgc    60
acagcacagt acccctactc ctaggactgg cgagtatctt tcattcattc cagaaatacg   120
cgggtcggcc aaaagtagaa aaatacactg cgcccactca atccacgcag cgcactgcac   180
```

```
tgcacagcaa cgcttcatgt caaaagtcga gctcaagcat gcacgcgatg gacgcggcgc    240
gaatgacccg ggcggcacga cgcgagtgcc cgccgcgccc gcccgcctgc cccgcagccg    300
acctcttccc aaacgggaca agcgagacgg cccaaaacga gcaaggaaag cagcctccta    360
ctgtggcagc ccgcccccac gaccgtcatc tcgccttcca ttccattttc cctggacgga    420
ccagacccgt ccgagccgcc ctgacctagc cagccagcat ttcctctttc gtccccgcc     480 gccgtgacca aaaagcaaaa aaggaaaaa gggaaatgc taaaggaaaa actccgctc      540 tttcccttct tctaggccta gggtacagta gaatattata aaggaaaaa ttctgctcgt     600 ttttgctct gtggtgtgtg tttgtggcga gagaaaatga tttggggaaa gcaaaatcgg     660
gagattcgca cgtacgatcg ttcgacacgt cgacgcccgg cgggcccgtg gtggggcatc    720
gtgtggctgc aggaccgcgg ggccccgcgg ggcgggccgg gccaatgggt gctcgacagc    780
ggctatgctc cagaccagcc cggtattgca taccgcgctc ggggccagat ccctttaaaa    840
accctcgttt tggcctggcc atcctccctc tcctcccctc tcttccacct cacccaacca    900
cctgatagcc atggctccgc cgcctcgcct ccgcctgcgc cagtcggagt agccgtcgcg    960
gtctgcgggt gttggagggt aggggcgtag ggttggcccg gttctcgagc ggagatg      1017

<210> SEQ ID NO 10
<211> LENGTH: 1036
<212> TYPE: DNA
<213> ORGANISM: Triticum monococcum

<400> SEQUENCE: 10
atttgcctga tgagacgctt gacaacagtg tattgatgga tgtctggtcg gtatacacgc    60
acagcacagt accctactc ctaggactgg cgagtatctt tcattcattc cagaaatacg     120
cgggtcggcc aaaagtagaa aaatacactg cgcccactca atccacgcag cgcactgcac    180
tgcacagcaa cgcttcatgt caaaagtcga gctcaagcat gcacgcgatg gacgcggcgc    240
gaatgacccg ggcggcacga cgcgagtgcc cgccgcgccc gcccgcctgc cccgcagccg    300
acctctccca aacgggacaa gcgagacggc caaaacgag caaggaaagc agcctcctac    360
tgtggcagcc cgcccccacg accgtcatct cgccttccat tccattttcc ctggacggac    420
cagacccgtc cgagccgccc tgacctagcc agccagcatt tcctctttcg tccccgccg    480 ccgtgaccaa aaagcaaaa aggaaaaag ggaaatgct aaaggaaaaa actccgctct      540
ttcccttctt ctaggcctag ggtacagtag aatattataa aggaaaaat tctgctcgtt    600 ttttgctctg tggtgtgtgt ttgtggcgag agaaaatgat ttggggaaag caaaatcggg    660
agattcgcac gtacgatcgt tcgacacgtc gacgcccggc gggcccgtgg tgggcatcg    720 tgtggctgca ggaccgcggg gcccgcggg gcgggccggg ccaatgggtg ctcgacagcg    780
gctatgctcc agaccagccc ggtattgcat accgcgctcg gggccagatc cctttaaaaa    840
cccctccccc cctgccggaa ccctcgtttt ggcctggcca tcctccctct cctccctct     900 cttccacctc acccaaccac ctgatagcca tggctccgcc gcctcgcctc cgcctgcgcc    960
agtcggagta gccgtcgcgg tctgcgggtg ttggagggta ggggcgtagg gttggcccgg    1020
ttctcgagcg gagatg                                                    1036

<210> SEQ ID NO 11
<211> LENGTH: 1036
<212> TYPE: DNA
<213> ORGANISM: Triticum monococcum
```

<400> SEQUENCE: 11

```
atttgcctga tgagacgctt gacaacagtg tattgatgga tgtctggtcg gtatacacgc      60
acagcacagt acccctactc ctaggactgg cgagtatctt tcattcattc cagaaatacg     120
cgggtcggcc aaaagtagaa aaatacactg cgcccactca atccacgtag cgcactgcac     180
tgcacagcaa cgcttcatgt caaaagtcga gctcaagcat gcacgcgatg gacgcggcgc     240
gaatgacccg ggcggcacga cgcgagtgcc cgccgcgccc gccgcctgc cccgcagccg      300
acctctccca acgggacaa gcgagacggc ccaaaacgag caaggaaagc agcctcctac      360
tgtggcagcc cgcccccacg accgtcatct caccctccat tccatttcc ctggacggac      420
cagacccgtc cgagccgccc tgacctagcc agccagcatt tcctctttcg tccccgccg      480
ccgtgaccaa aaaagcaaaa aaggaaaaag ggaaaatgct aaaggaaaaa actccgctct     540
ttcccttctt ctaggcctag ggtacagtag aatattataa aaggaaaaat tctgctcgtt     600
ttttgctctg tggtgtgtgt ttgtggcgag agaaaatgat ttggggaaag caaaatcggg     660
agattcgcac gtacgatcgt tcgacacgtc gacgcccggc gggcccgtgg tggggcatcg     720
tgtggctgca ggaccgcggg gccccgcggg gcgggccggg ccaatgggtg ctcgacagcg     780
gctatgctcc agaccagccc ggtattgcat accgcgctcg gggccagatc cctttaaaaa     840
cccctccccc cctgccggaa ccctcgtttt ggcctggcca tcctccctct cctcccctct     900
cttccacctc acccaaccac ctgatagcca tggctccgcc gcctcgcctc cgcctgcgcc     960
agtcggagta gccgtcgcgg tctgcgggtg ttggagggta ggggcgtagg gttggcccgg    1020
ttctcgagcg gagatg                                                    1036
```

<210> SEQ ID NO 12
<211> LENGTH: 1036
<212> TYPE: DNA
<213> ORGANISM: Triticum monococcum

<400> SEQUENCE: 12

```
atttgcctga tgagacgctt gacaacagtg tattgatgga tgtctggtcg gtatacacgc      60
acagcacagt acccctactc ctaggactgg cgagtatctt tcattcattc cagaaatacg     120
cgggtcggcc aaaagtagaa aaatacactg cgcccactca atccacgtag cgcactgcac     180
tgcacagcaa cgcttcatgt caaaagtcga gctcaagcat gcacgcgatg gacgcggcgc     240
gaatgacccg ggcggcacga cgcgagtgcc cgccgcgccc gccgcctgc cccgcagccg      300
acctctccca acgggacaa gcgagacggc ccaaaacgag caaggaaagc agcctcctac      360
tgtggcagcc cgcccccacg accgtcatct caccttccat tccatttcc ctggacggac      420
cagacccgtc cgagccgccc tgacctagcc agccagcatt tcctctttcg tccccgccg      480
ccgtgaccaa aaaagcaaaa aaggaaaaag ggaaaatgct aaaggaaaaa actccgctct     540
ttcccttctt ctaggcctag ggtacagtag aatattataa aaggaaaaat tctgctcgtt     600
ttttgctctg tggtgtgtgt ttgtggcgag agaaaatgat ttggggaaag caaaatcggg     660
agattcgcac gtacgatcgt tcgacacgtc gacgcccggc gggcccgtgg tggggcatcg     720
tgtggctgca ggaccgcggg gccccgcggg gcgggccggg ccaatgggtg ctcgacagcg     780
gctatgctcc agaccagccc ggtattgcat accgcgctcg gggccagatc cctttaaaaa     840
cccctccccc cctgccggaa ccctcgtttt ggcctggcca tcctccctct cctcccctct     900
cttccacctc acccaaccac ctgatagcca tggctccgcc gcctcgcctc cgcctgcgcc     960
agtcggagta gccgtcgcgg tctgcgggtg ttggagggta ggggcgtagg gttggcccgg    1020
```

```
ttctcgagcg gagatg                                                   1036

<210> SEQ ID NO 13
<211> LENGTH: 209
<212> TYPE: DNA
<213> ORGANISM: Triticum monococcum

<400> SEQUENCE: 13
atccctttaa aaacccctcc ccccctgccg aaccctcgt tttggcctgg ccatcctccc      60
tctcctcccc tctcttccac ctcacccaac cacctgatag ccatggctcc gccgcctcgc    120
ctccgcctgc gccagtcgga gtagccgtcg cggtctgcgg gtgttggagg gtagggcgt    180 agggttggcc cggttctcga gcggagatg                                      209

<210> SEQ ID NO 14
<211> LENGTH: 189
<212> TYPE: DNA
<213> ORGANISM: Triticum monococcum

<400> SEQUENCE: 14
atccctttaa aaaccctcgt tttggcctgg ccatcctccc tctcctcccc tctcttccac     60
ctcacccaac cacctgatag ccatggctcc gccgcctcgc ctccgcctgc gccagtcgga    120
gtagccgtcg cggtctgcgg gtgttggagg gtagggcgt agggttggcc cggttctcga    180
gcggagatg                                                           189

<210> SEQ ID NO 15
<211> LENGTH: 162
<212> TYPE: DNA
<213> ORGANISM: Triticum monococcum

<400> SEQUENCE: 15
atccctttaa aaaccccctcc cctctctctt cacctcaccc aaccacctga tagccatggc     60
tccgccgcct cgcctccgcc tgcgccagtc ggagtagccg tcgcggtctg cgggtgttgg    120
agggtagggg cgtagggttg gcccggttct cgagcggaga tg                       162

<210> SEQ ID NO 16
<211> LENGTH: 175
<212> TYPE: DNA
<213> ORGANISM: Triticum monococcum

<400> SEQUENCE: 16
atcccttttg gcctggccat cctccctctc ctccctctc ttccacctca cccaaccacc     60
tgatagccat ggctccgccg cctcgcctcc gcctgcgcca gtcggagtag ccgtcgcggt    120
ctgcgggtgt tggagggtag gggcgtaggg ttggcccggt tctcgagcgg agatg        175

<210> SEQ ID NO 17
<211> LENGTH: 208
<212> TYPE: DNA
<213> ORGANISM: Triticum monococcum

<400> SEQUENCE: 17
atccctttaa aaaccccctcc ccccctgccg aaccctgtt ttggcctggc catcctccct    60
ctcctcccct ctcttccacc tcacccaacc acctgatag catggctccg ccgcctcgcc    120
tccgcctgcg ccagtcggag tagccgtcg ggtctgcggg tgttggaggg tagggcgta    180 gggttggccc ggttctcgag cggagatg                                      208
```

<210> SEQ ID NO 18
<211> LENGTH: 735
<212> TYPE: DNA
<213> ORGANISM: Hordeum vulgare

<400> SEQUENCE: 18

```
atggggcgca ggaaggtgca gctgaagcgg atcgagaaca agatcaaccg ccaggtcacc      60
ttctccaagc gccgctcggg gctgctcaag aaggcgcacg agatctccgt gctctacgac     120
gccgaggtcg gcctcatcat cttctccacc aagggaaagc tctacgagtt ctccaccgag     180
tcatgtatgg acaaaattct gaacggtat gagcgctact cttatgcaga aaaggttctc      240
gtttcaagtg aatctgaaat tcagggaaac tggtgtcacg aatataggaa actgaaggcg     300
aaggttgaga caatacagaa atgtcaaaag catctcatgg gagaggatct tgaatctttg     360
aatctcaagg agttgcagca actggagcag cagctggaaa gctcactgaa acatatcaga     420
gccaggaaga accaacttat gcacgaatcc atttctgagc ttcagaagaa ggagaggtca     480
ctgcaggagg agaataaagt tctccagaag gaacttgtgg agaagcagaa ggcccaggcg     540
gcgcagcaag atcaaactca gcctcaaacc agctcttctt cttcttcctt catgatgagg     600
gatgctcccc ctgtcgcaga taccagcaat cacccagcgg cggcaggcga gagggcagag     660
gatgtggcag tgcagcctca ggtcccactc cggacggcgc ttccactgtg gatggtgagc     720
cacatcaacg gctga                                                      735
```

<210> SEQ ID NO 19
<211> LENGTH: 244
<212> TYPE: PRT
<213> ORGANISM: Hordeum vulgare

<400> SEQUENCE: 19

```
Met Gly Arg Arg Lys Val Gln Leu Lys Arg Ile Glu Asn Lys Ile Asn
 1               5                  10                  15

Arg Gln Val Thr Phe Ser Lys Arg Arg Ser Gly Leu Leu Lys Lys Ala
            20                  25                  30

His Glu Ile Ser Val Leu Tyr Asp Ala Glu Val Gly Leu Ile Ile Phe
        35                  40                  45

Ser Thr Lys Gly Lys Leu Tyr Glu Phe Ser Thr Glu Ser Cys Met Asp
    50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ala Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala Gln Ala Ala Gln Gln Asp Gln Thr Gln Pro Gln Thr Ser Ser
            180                 185                 190

Ser Ser Ser Ser Phe Met Met Arg Asp Ala Pro Pro Val Ala Asp Thr
```

-continued

```
                195                 200                 205
Ser Asn His Pro Ala Ala Gly Glu Arg Ala Glu Asp Val Ala Val
    210                 215                 220

Gln Pro Gln Val Pro Leu Arg Thr Ala Leu Pro Leu Trp Met Val Ser
225                 230                 235                 240

His Ile Asn Gly

<210> SEQ ID NO 20
<211> LENGTH: 244
<212> TYPE: PRT
<213> ORGANISM: Triticum monococcum

<400> SEQUENCE: 20

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Gly Leu Ile Ile Phe
            35                  40                  45

Ser Thr Lys Gly Lys Leu Tyr Glu Phe Ser Thr Glu Ser Cys Met Asp
50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
                100                 105                 110

Met Gly Glu Asp Leu Glu Ser Leu Asn Leu Lys Glu Leu Gln Gln Leu
            115                 120                 125

Glu Gln Gln Leu Glu Ser Ser Leu Lys His Ile Arg Ser Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala Gln Ala Ala Gln Gln Asp Gln Thr Gln Pro Gln Thr Ser Ser
            180                 185                 190

Ser Ser Ser Ser Phe Met Met Arg Asp Ala Pro Ala Ala Ala Thr
    195                 200                 205

Ser Ile His Pro Ala Ala Gly Glu Arg Ala Gly Asp Ala Ala Val
    210                 215                 220

Gln Pro Gln Ala Pro Arg Thr Gly Leu Pro Leu Trp Met Val Ser
225                 230                 235                 240

His Ile Asn Gly

<210> SEQ ID NO 21
<211> LENGTH: 245
<212> TYPE: PRT
<213> ORGANISM: Lolium temulentum

<400> SEQUENCE: 21

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30
```

-continued

```
His Glu Ile Ser Val Leu Cys Asp Ala Glu Val Gly Leu Ile Ile Phe
            35                  40                  45

Ser Thr Lys Gly Lys Leu Tyr Glu Phe Ala Thr Asp Ser Cys Met Asp
 50                  55                  60

Lys Ile Leu Glu Arg Tyr Glu Arg Tyr Ser Tyr Ala Glu Lys Val Leu
 65                  70                  75                  80

Ile Ser Thr Glu Ser Glu Ile Gln Gly Asn Trp Cys His Glu Tyr Arg
                 85                  90                  95

Lys Leu Lys Ala Lys Val Glu Thr Ile Gln Arg Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

Gln Leu Met His Glu Ser Ile Ser Glu Leu Gln Lys Lys Glu Arg Ser
145                 150                 155                 160

Leu Gln Glu Glu Asn Lys Ile Leu Gln Lys Glu Leu Ile Glu Lys Gln
                165                 170                 175

Lys Ala His Thr Gln Gln Ala Gln Leu Glu Gln Thr Gln Pro Gln Thr
            180                 185                 190

Ser Ser Ser Ser Ser Ser Phe Met Met Gly Glu Ala Thr Pro Ala Thr
        195                 200                 205

Asn Arg Ser Asn Pro Pro Ala Ala Ala Ser Asp Arg Ala Glu Asp Ala
    210                 215                 220

Thr Gly Gln Pro Pro Ala Arg Thr Val Leu Pro Pro Trp Met Val Ser
225                 230                 235                 240

His Leu Asn Asn Gly
                245

<210> SEQ ID NO 22
<211> LENGTH: 1207
<212> TYPE: DNA
<213> ORGANISM: Lolium temulentum

<400> SEQUENCE: 22
ctctcttctt ccccactgga cgcacgccat gacaccggcc ccacggctcc acctgcaccc      60
tcgggactag ccgtcgccgt cgccgtccgg gcgggttgtc gattagggtt tggtctgctc     120
ttccagggag ggaggcgaga tggggcgcgg caaggtgcag ctcaagcgga tcgagaacaa     180
gatcaaccgc caggtcacct tctccaagcg ccgctcaggc ctgctcaaga aggcgcacga     240
gatctccgtg ctctgcgacg cagaggtcgg gctcatcatc ttctccacca agggaaagct     300
ctacgagttc gccaccgact catgtatgga caaaattctt gagcggtatg agcgctactc     360
ctatgcagag aaagtgctca tttcaactga atctgaaatt cagggaaact ggtgtcatga     420
atataggaaa ctgaaggcga aggttgagac aatacagaga tgtcaaaagc atctaatggg     480
agaggatctt gaatcattga atctcaagga gttgcagcaa ctagagcagc agctggaaag     540
ttcactgaaa catattagat ccagaaagag ccagcttatg cacgaatcca tatctgagct     600
tcaaaagaag gagaggtcac tgcaagagga gaataaaatt ctccagaagg aactcataga     660
gaagcagaag gcccacacgc agcaagcgca gttggagcaa actcagcccc aaaccagctc     720
ttcctcctcc tcctttatga tgggggaagc taccccagca acaaatcgca gtaatccccc     780
agcagcggcc agcgacagag cagaggatgc gacgggcag cctccagctc gcacggtgct     840
tccaccatgg atggtgagtc acctcaacaa tggctgaagg gtccttccac tccatctaaa     900
```

-continued

```
cgtattattc agtacgtgta gcgagctgca ccggcctgtc ttgtggttgc ctagcaagct    960
gaccctcctg cgtgagctga cttcacgtaa ggtagcaggt tgcaatgtgt atatttcact   1020
ctgttctgct cagtttccct cctgcgtgag ctgacttcac gtaagagtta tttaacttgt   1080
aatacatgtg tagcgtgagt gacaaatttt ccactttcta cgaccctctt gggtaccgtc   1140
tgtttctgtg aattaaacta tccaatatca gtattatgta tattgtgatt gttgaaaaaa   1200
aaaaaaa                                                             1207
```

<210> SEQ ID NO 23
<211> LENGTH: 11
<212> TYPE: DNA
<213> ORGANISM: T. monococcum

<400> SEQUENCE: 23

```
cctcgttttg g                                                          11
```

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24

```
ccagcgtatg atttggaggt                                                 20
```

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25

```
ttggcattat tggaccatca                                                 20
```

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26

```
ctgacctggg gccttgagag                                                 20
```

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27

```
cttcgcatca gcagctctat                                                 20
```

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ccatggataa tcatcgggag                                          20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
gtcaccatca ccaacttcaa                                          20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gactgcgtat ttggacgacc                                          20

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
ccacggctga tatcccgact g                                        21

<210> SEQ ID NO 32
<211> LENGTH: 19
<212> TYPE: DNA
<213> ORGANISM: Artificial Sequence
<220> FEATURE:
<223> OTHER INFORMATION: Primer

<400> SEQUENCE: 32
gaccctcgag aggtaccag                                           19

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
catctacact acgatctagc                                          20

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
gaaaatgtct gaacaagctg ct                                       22

<210> SEQ ID NO 35
<211> LENGTH: 20

```
<212> TYPE: DNA
<213> ORGANISM: Artificial Sequence
<220> FEATURE:
<223> OTHER INFORMATION: Primer

<400> SEQUENCE: 35
tctagatgag caatctgcat                                              20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gaagatgcac ttggagaagg                                              20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
gtctctttgc attgtaccca                                              20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
ggtaaaagat gagcaaggag                                              20

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
tctatctatg gtgaactctt acttc                                        25

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
ggaaactggt gtcacgaata                                              20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
```

| | |
|---|---|
| caaggggtca ggcgtgctag | 20 |

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42

| | |
|---|---|
| gaggatttgg ctccactgag | 20 |

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43

| | |
|---|---|
| tctagggcct ggaagaagtg | 20 |

<210> SEQ ID NO 44
<211> LENGTH: 19
<212> TYPE: DNA
<213> ORGANISM: Artificial Sequence
<220> FEATURE:
<223> OTHER INFORMATION: Primer

<400> SEQUENCE: 44

| | |
|---|---|
| atgtggatat caggaagga | 19 |

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45

| | |
|---|---|
| ctcatacggt cagcaatac | 19 |

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46

| | |
|---|---|
| atggaagctg ctggaatcca t | 21 |

<210> SEQ ID NO 47
<211> LENGTH: 36
<212> TYPE: DNA
<213> ORGANISM: Artificial Sequence
<220> FEATURE:
<223> OTHER INFORMATION: Probe

<400> SEQUENCE: 47

| | |
|---|---|
| ccttcctgat atccacatca cacttcatga tagagt | 36 |

<210> SEQ ID NO 48
<211> LENGTH: 24
<212> TYPE: DNA
<213> ORGANISM: Artificial Sequence

```
<220> FEATURE:
<223> OTHER INFORMATION: Primer

<400> SEQUENCE: 48
ccttgctcat acggtcagca atac                                              24

<210> SEQ ID NO 49
<211> LENGTH: 354
<212> TYPE: DNA
<213> ORGANISM: Triticum monococcum

<400> SEQUENCE: 49
gagaagagct atgagctgcc tgatgggcag gtgatcacca ttggggcaga gaggttccgt       60
tgccctgagg tccttttcca gccatctttc attggtatgg aagctgctgg aatccatgag      120
accacctaca actctatcat gaagtgtgat gtggatatca ggaaggatct gtatggtaac      180
atcgtgctca gtggtggctc aactatgttc ccgggtattg ctgaccgtat gagcaaggag      240
atcactgccc ttgcaccaag cagcatgaag atcaaggtgg tggcaccgcc tgagaggaag      300
tacagtgtct ggattggagg gtcgattctt gcctccctta gtaccttcca acag            354

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
aactcagcct caaaccagct ctt                                               23

<210> SEQ ID NO 51
<211> LENGTH: 23
<212> TYPE: DNA
<213> ORGANISM: Artificial Sequence
<220> FEATURE:
<223> OTHER INFORMATION: Probe

<400> SEQUENCE: 51
catgctgagg gatgctcccc ctg                                               23

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
ctggatgaat gctggtattt gc                                                22

<210> SEQ ID NO 53
<211> LENGTH: 222
<212> TYPE: DNA
<213> ORGANISM: Triticum monococcum

<400> SEQUENCE: 53
ctcgtggaga agcagaaggc ccatgcggcg cagcaagatc aaactcagcc tcaaaccagc       60
tcttcttctt cttccttcat gctgaggat gctcccctg ccgcaaatac cagcattcat       120
ccagcggcgg caggcgagag ggcagaggat gcggcagtgc agccgcaggc cccaccccgg      180
acggggcttc caccgtggat ggtgagccac atcaacgggt ga                         222
```

```
<210> SEQ ID NO 54
<211> LENGTH: 26
<212> TYPE: DNA
<213> ORGANISM: Artificial Sequence
<220> FEATURE:
<223> OTHER INFORMATION: Primer

<400> SEQUENCE: 54
atgcagatct ttgtgaagac ccttac                                            26

<210> SEQ ID NO 55
<211> LENGTH: 30
<212> TYPE: DNA
<213> ORGANISM: Artificial Sequence
<220> FEATURE:
<223> OTHER INFORMATION: Probe

<400> SEQUENCE: 55
caagaccatc actctggagg ttgagagctc                                        30

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
gtcctggatc ttggccttga                                                   20

<210> SEQ ID NO 57
<211> LENGTH: 228
<212> TYPE: DNA
<213> ORGANISM: Triticum monococcum

<400> SEQUENCE: 57
atgcagatct ttgtgaagac ccttactggc aagaccatca ctctggaggt tgagagctca       60
gacaccatcg acaatgtcaa ggccaagatc caggacaagg agggcatccc cccggaccag      120
cagcgcctca tcttcgcagg aaagcagctg gaggatggcc gcactcttgc tgactacaac      180
atccagaagg agtccactct tcaccttgtc ctgcgtcttc gtggcggt                    228

<210> SEQ ID NO 58
<211> LENGTH: 18
<212> TYPE: DNA
<213> ORGANISM: Artificial Sequence
<220> FEATURE:
<223> OTHER INFORMATION: Primer

<400> SEQUENCE: 58
acagcggcta tgctccag                                                     18

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
tatcaggtgg ttgggtgagg                                                   20

<210> SEQ ID NO 60
<211> LENGTH: 20
```

```
<212> TYPE: DNA
<213> ORGANISM: Artificial Sequence
<220> FEATURE:
<223> OTHER INFORMATION: Primer

<400> SEQUENCE: 60
tgcatggaac acttccgatt                                              20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
cttcctcgac ctctccacag                                              20

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
gcaatcatga ctattgacac a                                            21

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
gggcgaagct ggagatgatg                                              20

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
agtggcatcg ttttcaggat                                              20

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
gccatgccga tagctgacta                                              20

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
```

```
gggtcatgga ggaatgtttg                                               20
```

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67

```
ttggcttctg cagagaggat                                               20
```

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68

```
gttacgtgaa ctgtgacatc                                               20
```

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69

```
tcagttgcat gtcgacgaag g                                             21
```

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70

```
cgacgatgcc cttccaaatg                                               20
```

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71

```
tcaagcagct gctgcctccc                                               20
```

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72

```
cttcacgaag aggtagtttt gagg                                          24
```

<210> SEQ ID NO 73
<211> LENGTH: 20
<212> TYPE: DNA
<213> ORGANISM: Artificial Sequence

```
<220> FEATURE:
<223> OTHER INFORMATION: Primer

<400> SEQUENCE: 73
tgggtacaag caggaggagc                                                    20

<210> SEQ ID NO 74
<211> LENGTH: 7051
<212> TYPE: DNA
<213> ORGANISM: Triticum monococcum

<400> SEQUENCE: 74
gaaagcggtg cccacccacg caaccatcgc caacatcgac tccggccgaa cacaagcttt        60
tgcctagacc tagacacaac cgctctacca aaccctcgga atagtctggc ctagctaaca       120
accaacatcg cccctcccta ctccgaccaa acatgatgaa gtactaactg acaatgcctc       180
caaggagtag aatggcatcc tcaagcgtca tcatcgccga agaatcaaac tttcgcccag       240
agccttacac ctctccacat ccacagaccc caaggaagga gccaagctac aacgaacatg       300
tgaggccaag ccgcgactcc actcgatcca acaacaacga accagtccag ttggatcaga       360
aggacaccac gaccacctgt atcaccatgg taggctacct gtgtcgatgc aacaccaac        420 ccaacactac aaccaggatg cctggcaaat gcagtccttg ccgtcgagga aacgcgggc        480 ccaaaatgcc cccctagcca caaattgccc actatgataa aaaacacaa gccagagccg        540 ctggtaagta gtcgccttgt gtcgtgggcc acataggctc acatgcaccg acggcggcac       600
ctaagccgcc atgagccacc accgcgcaca agagcagcag acacctagac caggctgaca       660
tgagacctgt caccactaca tgttgtcgca tcacaacagg ccatcagaca tcagtaggtc       720
gccgcacctc agaagcacct ccgtcccgca gccaacacga agcacccaat tcgagatcct       780
tcagcaaact cccctacgtg cgagtggccg cgagccgacg agaagagtag gccacgccac       840
ctccggatcg gcgcgggctt cactaggcag agcccattgg caatagcgag gggaggggg        900 gcggtctaag agggattgag ccgccgcccg ggtggacccg gggagggaac aatattgcaa       960
gtttttttta caatgagcac acacccagtc tctgcatagt taggatgata tagccaacac      1020
caactcacac acatacgaaa acacgctgac aactagcaac gtcacataag accaatgatg      1080
ttcgttggca agaaaaaaat gccgcaaaac aatcagattt gtgattgaca aactacaata      1140
atgaccatat ccacaccaat catctcataa aaccacactg acgatgaggt cttcgatagc      1200
aatgccttta ggaagggagc gacactcaag caccaccatc actagatcca accacaaggc      1260
caaaatgtag gttttcatcc cgaagaatca gtccaagcat attcgagcaa tgcattcgac      1320
aaggtaagaa tgtaagaaaa acatcgcctt ttccaggtat aaactgttgg ttctgaccta      1380
ggcttttgcc cctgaggtcg agaccgggtg ctcgagtagc aacaccatcg aagtcgctca      1440
tgtgttgtca tcaccacttt tccgtgattc tagcagcaac atgtgatgca actgctgcca      1500
ctgcacaccc atccctttgc atcaagccgt cgtccataat ttgtatctca tcactgaagt      1560
taaccactgg atcaggagag atgacccctc ccagggacca ttcaatgacc actgccgtcg      1620
tggagtccta ggaagtagtt gcagtatagt ttgcagcaac accatctggc aggtcagatc      1680
tggatcacca ccaccaaccc atggatctta gcgccgccaa ccagccaccg cacacgtgga      1740
aagccagcac ctcgcagcaa cagtcctcat ccaatagaaa gaccgacgcc aaatccgatc      1800
ggatcttgcc ggagtccacc cacatagtga gtcaccacca caataaggga cgcgcctcta      1860
gccatggtag cgagtgaccc gcacaaccag tctcacctgc cgtgaagaaa tatgcgtgct      1920
```

-continued

```
cccggttgct gtaggatggg acatatggtt cccatgacaa gggagcggta gagggacgag    1980
aggatgtgaa tataaatata ttttttttgaa aaggggggata tccccccagcg tgtgcatcca    2040
aaagatgcat gtgaccatat tattaaagca gttgcagcaa aaaacaaggt ctggtatcca    2100
aatatatctc gcaaaaggag caaaaataag taaaagctaa gaaagataaa catagccaca    2160
acccgcagga tgagaggatt agaatatgcc aaacgaaaaa aagatgggat gcggaagcat    2220
cctgccgccg ccgtccggcc accggtggtt tcctctcgca acagcgaggg gttgggtggc    2280
tggtgggggg agggttgggt ggggagggtt gggtgtggca gcgtgggcac ctccggagtc    2340
gacaacggcg atccaggagg ccggttaagc ttgggggaga agagtcctcg ctggttctca    2400
ttctagagtt tagttttccat gcccatgata atagcatgga tgccccatga cgaaaattgt    2460
ttcacagctg gtagtacttt tctattttag tattggcatg gtttccattt tgttgttttt    2520
gtctccctcg gacttttgtg ttagcatctc cttttttgttt tgacgctgac caaaaaaagc    2580
tacacaaata tctagcagtg gccttgtgtg gacataagat catgtggggg attcccggca    2640
agcaaggtct gcatggctcc ggctcctccg cgtaagaaag aaagaaatca acgatggatc    2700
gagggatcat atctattccg acccactcat tagttgggtc tatttgattt gatctatcat    2760
attttgatag ttgccatatc gaatctttt tctggcctga gagctcacgg ctgcctatat    2820
gcagtgcatg tgagagagac acagtacggc cctagctact actacaagta ccttggtagt    2880
tactggtact cataactgcc tcttcttctt cctcgacgtc tctcctcctc ggctcctcca    2940
cgcaccagac cacaccagaa aaacaaaca agcaagcaaa ccttggagct agctagcagt    3000
atgtccatgt catgcggttt gtgcggcgcc aacaactgcc cgcgcctcat ggtctcgccc    3060
attcaccatc atcatcacca tcatcaggag caccagctgt gtgagtacca gttcttcgcc    3120
catggcaacc accaccacca ccaccatggc tcggcagcag actacccagt gccaccgccg    3180
ccagacaact tcgaccaccg cagaacatgg accagaccat tcatgaaaac agcagcggca    3240
gggaacagca gcaggctcac gctggaggtg ggcgcaggcg gccaacacat ggctcaccta    3300
gtgcagccac cggcaagagc ccacatcgta agtagtacta ctgcttaatt gtttcatctc    3360
ttgccgatgg atgcgtccat ggcttcctcc ttaaaaatcc ccacctaatt aatgtccatc    3420
tgactacacc cactacaaaa aagtagcacc atgtaaccat ttcatatatt tctcacataa    3480
ttctgttaat ttacgctgct cgattgttct cctgaaaaag atatacggga atggatctgg    3540
atattcttta attttctatg gaggcataga gtttgtgttt tgtattagtt gatgcagaat    3600
tgtatgggtt gtcaaatcat cagtcataca tatatactta ttctttttt tttgaccaac    3660
aagaaggtaa tcagtcatac atgcatactg aaaattagac ttgtgtgcaa taactaacta    3720
accaactcga ccggcacagc tggggaaga ctttaatcaa gctgctagct agagcttaat    3780
aatataacat atctctttat gggatcaagc aatacatatg cgctcaattc tcaacttgtc    3840
aatatctatc tggagtccac actttatggt aattaattga caaagttttg tgaaatggac    3900
aatatacata ctggatcgat gcacccttt tctcatttta tgtggtcatt ataattgatt    3960
gttatttagt atttcaattt tatcttgagc tagttttgca agtctgtagc tcatatataa    4020
ctgatactac tccccacgat agcttgcgta gtggccgggt gatcgatcta ccgagttcat    4080
aaaactgatc gagatcgggt ccaaaaaaga acaaacccat acaaaatgga aagaagatcc    4140
ttgtttagtt agtttgcatc agaaaattgc ctaattagtt acttgctatc aatctttga    4200
acatggcatg ttcaccccaa acggaccccag atcacaatta ttgatgaagt tacgccttt    4260
aaaaactcat aaaactgtac atacatgtac agggctacac acatgtacat aatacaccta    4320
```

```
attaaaacgt atatttgtag accaattgat tttggacggt gcgcatcttt ggaaaaaaaa    4380
tgccagagga gttgttagct tccactgtcc agaaatagaa tagttacaat caagtgcatc    4440
tctgaatgaa aatggatcat tttctagtta attagagacc aattagatac ttcataaaca    4500
ggggagtatc aagtacgtat ctgctaccca taagaaagta cataactgcg atcttatgat    4560
tattttcctc ttgatgttca ggtgccattt cacggaggtg cattcaccaa cactattagc    4620
aatgaagcaa tcatgactat tgacacagag atgatggtgg ggcctgccca ttatcccaca    4680
atgcaggaga gagcagcgaa ggtgatgagg tatagggaga agaggaagag gcggcgctat    4740
gacaagcaaa tccgatacga gtccagaaaa gcttacgctg agcttcggcc atgggtcaac    4800
ggccgctttg tcaaggtacc cgaagccatg gcatcgccat catctccagc ttcgccctat    4860
gatcctagta aacttcacct cggatggttc cggtaattta tagcacaagc cagataaaat    4920
gataacatat ttccttctga ttgatccacc cgtgaagcag ttgttcctca agtaaaata     4980
agtcggttag tgattgatcg attggagcca ttatgttgac ttgactattt aaaatggtca    5040
gcagatcaat caaacaaaat gtatttattg aaacaagtct tgttatacta cgtgttgatt    5100
taaacatgta atttcaagag gatagctact ttgatgtgta ataaaattgt ctcaaaattg    5160
gtgacaagtg cgattgttgt tgtgatttat atggaattat gtcaatcata ctggaaaaat    5220
aatatgtaac cagttgaatt aagtcatcgc cgactcaaaa ttaaatacga atgaggcttt    5280
tatgtataaa gtttgttatt ttatcctgag gacttctcta ggggtggaaa acggattgag    5340
aaagtacacc atcacgattg ccgaacatgt acaatgctta tcttgagaaa gaaaattata    5400
tttcattcac caaatatgag gtgaaccttg caaccacatg tatattaaaa agctatgtgt    5460
cagctaacta atttgtggac ttatcatagg ttaaataacct ccaatgtgta cgaatgagga   5520
acttgagtag aatatgtgaa gttgcatgga aaactgtgaa catatcaaat tatcaagaca    5580
tcactacaga tgtacatcat ccgaagttca tgtattatat tgaaattgtg tgttccttat    5640
gttgttggat gtacttattg aagtgatcct tcatctatga ggtaagtatt aattaatttg    5700
tccatcgttt gatcaatcat gtgtatttaa ttagtttgtt ggatgtacta agttttaatt    5760
agtttgttgg atgtactgag tattaattag tttgtccatc ccaagcttca tctataaccc    5820
aatgacaaag gtgacaacgc tatgcacaca tacatacaca tgattgatca aacgatggac    5880
aaactaccaa tgacaaaggt gacaacgcta tgcacacata catacacaaa tagatgaagc    5940
ttggaatacg gcacgggtgg cagcctcgaa cctcaagctg gtgcgaaccc aatgagctag    6000
acaagataac aatgtctgtc caagataagg ggaagctatt gttgactgcc atgatctaat    6060
aggttgccaa atactaattg tcatgagatt tatttagtcc aatgtgttgg gtttagtccc    6120
acttcagttg tgggggaga cataacatga tttataaggg caggggtgtc ccctcctaac     6180
aggctagtcc tttggaggga gagggcccaa gacctctcat aagtcggtgt tactctctgg    6240
ttgagcctgg ttgacgcatg tgggtcggaa atgctagtgt tagcggaccc gaaattgcgt    6300
aacaagtggt accatgagct aggttgttcg aggttgcgat tgttaattca gaggaggtcg    6360
tgttcaatcg acggaggcgc tgcgagggtt tgccaggtgc ctgcggtgag atcgaagttg    6420
tccgattgaa ggtcaacgga agatcaaaa gcagtcaaag ctggatcggt ttggcagagg     6480
cagcaggccg agcaagctgc ggggacgcgc aggccaagca ggacccaagt gcgggtgact    6540
ggcctggtaa agcacgcggc tgctagtaga caggagcgcg tatgcggcag ccagacaagc    6600
ggatgcggtc tgcgatgtgg cacttggcag aggctgtttg gtacgtggtt ggctcaagga    6660
```

```
atggcctatt gatgctgctg gtgtgagcac aaagaggcga gatttcacgg gcaagtttgg    6720
ctgattcttg gagaagcggt gttgcatata aaagtctgtt tgttgatgtg cttaaagact    6780
gtaccaagaa gcaagttgac gggtcaaaaa aagaagcaa gttgagaaca ttaccaaggg     6840
tagtgacaag gcaaggacga caacgtgcga taaggcttga agcaagagtc tggagcttgt    6900
cgtggcagga tcatgcatac acagggcgtc aagcaatgca cggagatgtg cggggcggac    6960
acggcgcaga gtggagcatg gttgcagtcg aacatacacg gctggcttgg actggattgt    7020
ttaatggact ggcatggagg ttggtcaaag c                                   7051
```

<210> SEQ ID NO 75
<211> LENGTH: 996
<212> TYPE: DNA
<213> ORGANISM: Triticum monococcum

<400> SEQUENCE: 75

```
taactgcctc ttcttcttcc tcgacgtctc tcctcctcgg ctcctccacg caccagacca      60
caccagaaaa acaaacaag caagcaaacc ttggagctag ctagcagtat gtccatgtca     120
tgcggtttgt gcggcgccaa caactgcccg cgcctcatgg tctcgcccat tcaccatcat    180
catcaccatc atcaggagca ccagctgtgt gagtaccagt tcttcgccca tggcaaccac    240
caccaccacc accatggctc ggcagcagac tacccagtgc caccgccgcc agacaacttc    300
gaccaccgca gaacatggac cagaccattt catgaaacag cagcggcagg aacagcagc     360 aggctcacgc tggaggtggg cgcaggcggc aacacatgg ctcacctagt gcagccaccg     420
gcaagagccc acatcgtgcc atttcacgga ggtgcattca ccaacactat tagcaatgaa    480
gcaatcatga ctattgacac agagatgatg gtggggcctg cccattatcc cacaatgcag    540
gagagagcag cgaaggtgat gaggtatagg gagaagagga gaggcggcg ctatgacaag     600 caaatccgat acgagtccag aaaagcttac gctgagcttc ggccatgggt caacggccgc    660
tttgtcaagg tacccgaagc catggcatcg ccatcatctc cagcttcgcc ctatgatcct    720
agtaaacttc acctcggatg gttccggtaa tttatagcac aagccagata aaatgataac    780
atatttcctt ctgattgatc caccgtgaa gcagttgttc ctcaaagtaa aataagtcgg     840
ttagtgattg atcgattgga gccattatgt tgacttgact attaaaatg gtcagcagat     900 caatcaaaca aaatgtattt attgaaacaa gtcttgttat actacgtgtt gatttaaaca    960
tgtaatttca agaggatagc tactttgatg tgtaat                               996
```

<210> SEQ ID NO 76
<211> LENGTH: 213
<212> TYPE: PRT
<213> ORGANISM: Triticum monococcum

<400> SEQUENCE: 76

```
Met Ser Met Ser Cys Gly Leu Cys Gly Ala Asn Asn Cys Pro Arg Leu
 1               5                  10                  15

Met Val Ser Pro Ile His His His His His His Gln Glu His Gln
            20                  25                  30

Leu Cys Glu Tyr Gln Phe Phe Ala His Gly Asn His His His His
        35                  40                  45

His Gly Ser Ala Ala Asp Tyr Pro Val Pro Pro Pro Asp Asn Phe
    50                  55                  60

Asp His Arg Arg Thr Trp Thr Arg Pro Phe His Glu Thr Ala Ala Ala
65                  70                  75                  80
```

Gly Asn Ser Ser Arg Leu Thr Leu Glu Val Gly Ala Gly Gly Gln His
            85                  90                  95

Met Ala His Leu Val Gln Pro Pro Ala Arg Ala His Ile Val Pro Phe
                100                 105                 110

His Gly Gly Ala Phe Thr Asn Thr Ile Ser Asn Glu Ala Ile Met Thr
            115                 120                 125

Ile Asp Thr Glu Met Met Val Gly Pro Ala His Tyr Pro Thr Met Gln
130                 135                 140

Glu Arg Ala Ala Lys Val Met Arg Tyr Arg Glu Lys Arg Lys Arg Arg
145                 150                 155                 160

Arg Tyr Asp Lys Gln Ile Arg Tyr Glu Ser Arg Lys Ala Tyr Ala Glu
                165                 170                 175

Leu Arg Pro Trp Val Asn Gly Arg Phe Val Lys Val Pro Glu Ala Met
            180                 185                 190

Ala Ser Pro Ser Ser Pro Ala Ser Pro Tyr Asp Pro Ser Lys Leu His
            195                 200                 205

Leu Gly Trp Phe Arg
210

<210> SEQ ID NO 77
<211> LENGTH: 187
<212> TYPE: PRT
<213> ORGANISM: Triticum monococcum

<400> SEQUENCE: 77

Met Ser Met Ser Cys Gly Leu Cys Gly Ala Asn Asn Cys Pro Arg Leu
1               5                   10                  15

Met Val Ser Pro Ile His His His His His His Gln Glu His Gln
            20                  25                  30

Leu Cys Glu Tyr Gln Phe Phe Ala His Gly Asn His His His His
        35                  40                  45

His Gly Ser Ala Ala Asp Tyr Pro Val Pro Pro Pro Asp Asn Phe
    50                  55                  60

Asp His Arg Arg Thr Trp Thr Arg Pro Phe His Glu Thr Ala Ala Ala
65                  70                  75                  80

Gly Asn Ser Ser Arg Leu Thr Leu Glu Val Gly Ala Gly Gly Gln His
            85                  90                  95

Met Ala His Leu Val Gln Pro Pro Ala Arg Ala His Ile Val Pro Phe
                100                 105                 110

Tyr Gly Gly Ala Phe Thr Asn Thr Ile Ser Asn Glu Ala Ile Met Thr
            115                 120                 125

Ile Asp Thr Glu Met Met Val Gly Pro Ala His Tyr Pro Thr Met Gln
130                 135                 140

Glu Arg Ala Ala Lys Val Met Arg Tyr Arg Glu Lys Arg Lys Arg Arg
145                 150                 155                 160

Arg Tyr Asp Lys Gln Ile Arg Tyr Glu Ser Arg Lys Ala Tyr Ala Glu
                165                 170                 175

Leu Arg Pro Arg Val Asn Gly Arg Phe Val Lys
            180                 185

<210> SEQ ID NO 78
<211> LENGTH: 2913
<212> TYPE: DNA
<213> ORGANISM: Triticum dicoccoides

<400> SEQUENCE: 78

```
gagtttagtt tccatgccca tgataatagc atggatgccc catgacgaaa attgtttcac      60
agctggtagt acttttctat tttagtattg gcatggtttc cattttgttg tttttgtctc     120
cctcggactt ttgtgttagc atctccttt tgttttgacg ctgaccaaaa aaagctacac      180
aaatatctag cagtggcctt gtgtggacat aagatcatgt gggggattcc cagcaagcaa     240
ggtctgcatg gctccggctc ctccgcgtaa gaaagaaaga atcaacgat ggatcgaggg      300
atcatatcta ttccgaccca ctcattagtt gagcaatatt ttgatagttg ccatatcgaa     360
tatttttct ggcctgagag ctcacggctg cctatatgca gtgcatgtga gagagacaca     420
gtacggccct agctactact acaagtacct tggtagttac tggtactcat aactgcctct    480
tcttcttcct cgacatctct cctcctcggc ttctccacgc accagaccac agcagaaaaa    540
acaaaaaagc aagcaaacct tggagctagc tagcagtatg tccatgtcat gcggtttgtg    600
cggcgccaac aactgcccgc gcctcatggt ctcgcccatt catcatcgtc atcaccatca    660
tcaggagcac cagctgcgtc agcaccagtt cttcgcccaa ggcaaccacc accaccacca    720
cccagtgcca ctgccgccag ccaacttcga ccatagcaga acatggacca caccatttca    780
tgaaacagca gctgcaggga acagcagcag gctcacgctg gaggtgggcg caggcggccg    840
acccatggct cacctagtgc agccaccggc aagagcccac atcgtaagta gtagtaccgc    900
ttaattgttt catctcttgc cgatggatgc gtccctggct tcctccttaa aaatccccac    960
ctaatttatg tccatctata cccactacaa aaaaatagca ccatgtaacc atctcatata   1020
tctgtcacat aattctgtta atgtacgctc tcaattgtt ctcctgaaaa agatatgcgg     1080
gaatggatct tgatattctt taattttcta tggaggcata tatagagttt gtgttttgta   1140
ttagttgatg cagaattgta tgggttgtca aatcatcagt catacatata aacttatttc   1200
attttatttg accaacaaca aggtaatcag tcatacatgc atactgaaaa tttgacttgt   1260
gttcaataac taaccaactc gaccggcaca gctgggggaa gactttaatc aagctgctag   1320
ctagagctta ataatataac atatctcttt atgggatcaa gcaatacata tgcgctcaat   1380
tctcaacttg tcaatatcta tctggagtcc acactttatg gtaattaatt gacaaagttt   1440
tgtgaaatgg acaatataca tactggatcg atgcacccct tttctcattt tatgtggtca   1500
ttatgaattt gattgttatt tagtatttca atttatctt gagctagttt tgcaagtctg    1560
tagctcatat ataactgata ctactcccca cgatagcttg cgtagtggcc gggtgatcga   1620
tctaccgagt tcataaaact gatcgagatc gggtccaaaa aagaacaaac ccatacaaaa   1680
tggaaagaag atccttgttt agttagtttg catcagaaaa ttgcctaatt agttacttgc   1740
tatcaatctt ttgaacatgg catgttcacc ccaaacggac tcagatcaca attattgatg   1800
aagttacgcc ttttaaaaac tcataaaact gtacatacat gtacagggct acacacatgt   1860
acataataca cctaattaaa acgtatattc gtagaccaat tgttttggac ggtgcacatc   1920
tttgaaaaaa aatgccagag gagttgttag cttccactgt ccagaaatag aatagttaca   1980
atcaagtgca tctctgaatg aaaatggatc attttctagt taattagaga ccaattagat   2040
acttcataaa caggggagta tcaagtacgt atctgctacc ctaagaaagt acataactgc   2100
gatcttatga ttattttcct cttgatgttc aggtgccatt ttacggaggt gcattcacca   2160
acactattag caatgaagca atcatgacta ttgacacaga gatgatggtg gggcctgccc   2220
attatcccac aatgcaggag agagcagcga aggtgatgag gtatagggag aagaggaaga   2280
ggcggcgcta tgacaagcaa atcagatacg agtccagaaa agcttacgct gagcttcggc   2340
cacgggtcaa cggctgcttt gtcaaggtac ccgaagccat ggcgtcgcca tcatctccag   2400
```

-continued

```
cttcgcccta tgatcctagt aaacttcacc tcggatggtt ccggtaattt atagcacaag    2460
ccagataaaa tgataacata tttccttctg attgatccac ccgtgaagca gttgttcctc    2520
aaagtaaaat aagtcggtta gtgattgatc gattggagcc attatgttga cttgactatt    2580
taaaatggtc agcagatcaa tcaaacaaaa tgtatttatt gaaacaagtc ttgttatact    2640
acgtgttgat ttaaacatgt aatttcaaga ggatagctac tttgatgtgt aataaaattg    2700
tctcaaaatt ggtgacaagt gcgattgttg ttgtgattta tatggaatta tgtcaatcat    2760
attggaaaaa taattaacca gttgaattaa gtcatcgcca actcaaaatt aaatacgaat    2820
gaggctttta tgtataaagt ttgttatttt atcttgagga cttctctagg ggtggaaaac    2880
ggattgagaa agtacaccat cacgattgcc gaa                                 2913
```

<210> SEQ ID NO 79
<211> LENGTH: 975
<212> TYPE: DNA
<213> ORGANISM: Triticum dicoccoides

<400> SEQUENCE: 79

```
taactgcctc ttcttcttcc tcgacatctc tcctcctcgg cttctccacg caccagacca      60
cagcagaaaa aacaaaaaag caagcaaacc ttggagctag ctagcagtat gtccatgtca     120
tgcggtttgt gcggcgccaa caactgcccg cgcctcatgg tctcgcccat tcatcatcgt     180
catcaccatc atcaggagca ccagctgcgt cagcaccagt tcttcgccca aggcaaccac     240
caccaccacc acccagtgcc actgccgcca gccaacttcg accatagcag aacatggacc     300
acaccatttc atgaaacagc agctgcaggg aacagcagca ggctcacgct ggaggtgggc     360
gcaggcggcc gacccatggc tcacctagtg cagccaccgg caagagccca catcgtgcca     420
ttttacggag gtgcattcac caacactatt agcaatgaag caatcatgac tattgacaca     480
gagatgatgg tggggcctgc ccattatccc acaatgcagg agagagcagc gaaggtgatg     540 aggtatggg agaagaggaa gaggcggcgc tatgacaagc aaatcagata cgagtccaga     600
aaagcttacg ctgagcttcg gccacgggtc aacggctgct tgtcaaggt acccgaagcc     660 atggcgtcgc catcatctcc agcttcgccc tatgatccta gtaaacttca cctcggatgg     720
ttccggtaat ttatagcaca agccagataa aatgataaca tatttccttc tgattgatcc     780
acccgtgaag cagttgttcc tcaaagtaaa ataagtcggt tagtgattga tcgattggag     840
ccattatgtt gacttgacta tttaaaatgg tcagcagatc aatcaaacaa aatgtattta     900
ttgaaacaag tcttgttata ctacgtgttg atttaaacat gtaatttcaa gaggatagct     960
actttgatgt gtaat                                                     975
```

<210> SEQ ID NO 80
<211> LENGTH: 206
<212> TYPE: PRT
<213> ORGANISM: Triticum dicoccoides

<400> SEQUENCE: 80

```
Met Ser Met Ser Cys Gly Leu Cys Gly Ala Asn Asn Cys Pro Arg Leu
  1               5                  10                  15

Met Val Ser Pro Ile His His Arg His His His Gln Glu His Gln
             20                  25                  30

Leu Arg Gln His Gln Phe Phe Ala Gln Gly Asn His His His His
         35                  40                  45

Pro Val Pro Leu Pro Pro Ala Asn Phe Asp His Ser Arg Thr Trp Thr
```

```
                  50                  55                  60
Thr Pro Phe His Glu Thr Ala Ala Ala Gly Asn Ser Ser Arg Leu Thr
 65                  70                  75                  80

Leu Glu Val Gly Ala Gly Gly Arg Pro Met Ala His Leu Val Gln Pro
                 85                  90                  95

Pro Ala Arg Ala His Ile Val Pro Phe Tyr Gly Gly Ala Phe Thr Asn
            100                 105                 110

Thr Ile Ser Asn Glu Ala Ile Met Thr Ile Asp Thr Glu Met Met Val
            115                 120                 125

Gly Pro Ala His Tyr Pro Thr Met Gln Glu Arg Ala Ala Lys Val Met
130                 135                 140

Arg Tyr Arg Glu Lys Arg Lys Arg Arg Tyr Asp Lys Gln Ile Arg
145                 150                 155                 160

Tyr Glu Ser Arg Lys Ala Tyr Ala Glu Leu Arg Pro Arg Val Asn Gly
                165                 170                 175

Cys Phe Val Lys Val Pro Glu Ala Met Ala Ser Pro Ser Pro Ala
            180                 185                 190

Ser Pro Tyr Asp Pro Ser Lys Leu His Leu Gly Trp Phe Arg
            195                 200                 205

<210> SEQ ID NO 81
<211> LENGTH: 5734
<212> TYPE: DNA
<213> ORGANISM: Triticum monococcum

<400> SEQUENCE: 81
ttttcaccaa aagtaattac ctatgtacta tatgtatact tttttctgtg tgatttcat      60
gaccgatctt gtcgatagct agctaggatg agagaagtca atgcataatg tgtgtgatat    120
gtagctagct agccagtcct aaaagatcaa acatgtaatg gattgtgctg tgtgtgtggc    180
agtctgcatc acgccatcag atgacaaaaa tattctctac ctagctagtt cacatgaact    240
tgctggcctg catctataca tatacacacc agaacaaaga atacttggct tttctttctt    300
tttgtagcat agcctttgtt tctacttcag ggcagaagaa gatgaatcgc ctgtgtggtg    360
gtccgagata gcttagatgc atagatctgt gtggtagccc gcagggtgtg gtgctgatga    420
ggtcgcccac gcgggctact cctgcgagct caggattgtg tggactgtct ggccctgctt    480
tatgcaaagg aggaaatggc ggcggattcc aacgctccat ggctccagac tctcccgctg    540
cttcttgcgc ttttcgctgc ccagaaagat cgaccacatg tgtatctgga ttgaaatgtg    600
ctagctaatg gttgtttcgt tcttgatttt tgctcctttt catgtgctcc acatgtacac    660
aatagaaaga tcttgaaaac gactccgctg ccggtgatac ctcgatttgt ggatcagagt    720
tggtcgcaca gacaagggat cgatcgagat atatgcttgc caatggccat ccaaatacat    780
aaatggttcc atgtcaccga tgtgcgtgca agatagcaaa catgatcaaa ttgactgttt    840
aatctcttcg tctggtttaa ttatgaaact agtatatttt cgaaccctca actatatatt    900
ttgtgtggtg aacttttgtt ggttctcatt ttacagctaa attaatttcc acgcccatac    960
gtaacgcttt gttacgaggg gaggctcaca caattgaaaa agcctagccg cctttcccat   1020
cgccttcctt tctcgccgcc acgcaggttc aggagcagct tactgcggaa gttttgaagg   1080
tcttgggggg ttgttgtagc ttgacaagga gatgaaggct cgagtggagg tttccatcag   1140
ggagtgttca acagcagcat ttgtgaatcc ggcggcgccc gaaccaaccc aacatggtga   1200
gcttctacgg cggcgcagct tggctaggcc atcggagaag atgatgtgga tgcatggccc   1260
```

```
tggagggcgg cgagttcgat ctcaggtcca gacttggcgt acaacagcgt gataattttg   1320
tctcatgcat tctttatgct gtcttcgtgt tttgttaggt atggcttgcc ggctgcgctc   1380 cccccctgttg aaagaaatgt tgtccccgtc ttgcccctg ctgatgtgct caccaccgat   1440
ggagggtgtg tgtttttgtg tctccgtcga tgggtcttcc gggatccaga cggtttaggt   1500
tttccatgga ttcgcccgat tcggccagct tcgtgatct tcagagtttc tacaagtcct   1560
tatcgatgtt ctcttctctg gggtggcggt ttgctttgcg gatcacagtc tcgccgacgt   1620
ctcttggtct gcgtcaacga gttcctactc gttgcctctg caagctcctg ggtttgaaaa   1680
aaggttcgct acatcaaggc cgagacccaa aaacagcacc gagctttcat agtgcgccgc   1740
cgatgtatgc atgacgaaga agacttcggc acccttgaag tgttgattgt aattttttctt  1800 tgtatatggc tgtgtttgta aggtcctatg attcttaata tatggtttta agcctctttg   1860
ccaaaaaaaa gttcaacgcc catcacatta ctatttttat gatgaagagt gttttttgtta  1920 acttaaaatg tagcgtcaaa tggatacaga gcatgatgag caacacgcgg cctttgcaat   1980
accaactgtc tgtccaaact aaaaaaaaac tgacatattg acaatgctaa agtcatatag   2040
gaccaacact acaccattaa ttgttccaca acttgtactt ttctgtttta gtattgccat   2100
ggtttccact gtgttgtgtt tgtctccctc ggacctttgt gttagcatct ccttttttgtt  2160 tgacagtgac caaaaaagct acaaatatct agcagtggcc ttgcgtggac ataagatcat   2220
gtgggagatt cccggcaagc aaggcgtgca tgggtccagc tcctccgcgt aagaaagaaa   2280
gaaataaaaa atgaatcgag gggtagtatc tattccgacg cactcattag ttgggcctat   2340
ttgatttgat ccatcatctt ttgctaattc tcagatcgaa tcttttgcct ggtctgcagc   2400
tcactgctgc atatatgcag tgcagtggag gagggagaga cacaacacaa ccctagctat   2460
ttcaaggtgc cttagtagtt agtactcgtc gtcgtctctt cttcttcctc gacatctctc   2520
cccctccacg cgccaaacca caccagaaac aaacaagcaa gcaatcaaac gtagggcta   2580 gctgcagtat gtccatgtca tgcggtttgt gcggcgcaag cgactgcccg caccacatga   2640
tctcgcccgt tcttcagcat caggaacaac actggctgcg cgagtaccag ttcttcaccc   2700
aaggccacca ccaccaccac cacggcgcgg cggcggacta cccaccgcca ccgccaccgt   2760
cggccaattg ccaccactgc agatcatgga ccacaccgtt tcatgaaaca gcagctgcag   2820
ggaacagcag cagactcacg ctggaggtag atgcaggcgg ccaaaacatg gctcacctgc   2880
tgcagccacc ggcacggcca agaaccacca tcgtgagtag tactactgct taattgttcc   2940
agctcttgcc gatcgctggg gcctccttgt aacaaaagtt cccttttacg taatctccat   3000
ctactccccc cccccccccc ccccccccg cccctcccc gcatctcaaa aaaagttagc   3060
gccatgtaac cagctcatat atctgtcaca taattctgtt aatttatgct ggtcaattat   3120
aatctcccaa ggcagaaagt ttgtgttttg tatcagttga tgaacaagaa tgggaactca   3180
catcatcagt tacacataca tacttatttc attttatttg actaacaagg taatcagtta   3240
attcctttat gggaacaagc aatacatatg tccacgcctt catgttaatt ccttgacaaa   3300
gtttgtgaaa tggacaatat atatactgga tcaatgcacc ctctttctca ttttatgtgg   3360
tcatttatga attttagtgc tattttatat ttaaattttc tcttaagctt gttttgtaag   3420
cttatagctc atgtataaca gatactactc cccataattg cttccgtagt ggccgggtga   3480
tcaatctacc gagttcataa aactgatcgg gatcagatcc aaaacagacc aaaacctcac   3540
gaaatagaaa caagatccTT gtttaataag tttgcaccag gaaattgcct acttaattac   3600
tttctatcaa tcttatgaac atggcatgtt tctcacatat ggtgacccag atcacaattg   3660
```

```
ttgacggagt taaacatttt tagcaattca taaaaccatg cacagatgta cagggctacg    3720
cgtatgcaca tacataatac acctaattaa acatatatt catagagcga ttgagtttgg     3780
actgtgcgct tctttggaca caaaggcccg ggaagttgtt ctcttccatt gtctagaaaa    3840
atagaacagt tacaatcaag tgcaccactg aatgaaaatg ggtcaactct ggttaataag    3900
agaccaactg tacttcataa acagggaata tcatgtacat atctgcaacc cacaggaaaa    3960
gtacagagct gcactcttac agttattttc ctcttcatgt tcaggtgcca ttctgcgggg    4020
ctgcattcac cagcactatt agcaatgcaa caatcatgac tattgataca gagatgatgg    4080
tgggggctgc ccataatctg acgatgcagg agagagaggc gaaggtgatg aggtacaggg    4140
agaagaggaa gaggcggtgc tatgacaagc aaatccgcta cgagtccaga aaagcttacg    4200
ccgagctcag gccacgggtc aatggctgct tgtcaaggt accagaagcc gctgcatcgt      4260
cgtcaccccc agcttcgccc tatgatccta gtaaacttca cctcggatgg ttccagtagt    4320
ttttcatcaa agtaaaataa gttggttatt gattgaccga cggaggagt tatgttgatt     4380 tgactatttc aaaaggtcag caaaccaatc aaagaaaatg tatttgttga acaagtatt     4440 gttatgcttt atgttaattt aagcatgtaa tttgaggagg ctagctactt agatgtgttt    4500
attgtatgca accaattgaa tcaagtcatc accaactcaa agttaaatac ggacgagctt    4560
tttatgtata agttgttgt tttatcttga cgacttatca agagtgaaaa atggattggg      4620
agttatgagt aaaccatcac gaccgccaaa gatgtacaat gcttattttg agagagaaaa    4680
ttatatttca ctcaccaaat atgagttgaa ccttgtaacc acatgtatat tacaaagctg    4740
tgtgtcacct aactaatttg aggccttatc ataggtaaaa tacctccaat ctgcacgaat    4800
gagtcacttt aaaagaatat gtcacgttgc atggaaaact gtaaacatgt gtagacagca    4860
taatatatag ctgcaaatca tccaaagctt gtgtactata ttataattat gagttcctta    4920
tgctgttgca tgtacttatt gaagtgatcc ttcgtctatg aggtaagttt gtacattcat    4980
tcatccattt aacctcgcga atatagatag ctagttaatt cgtttgatcg atcatgtgta    5040
tgtgtgcgtc catagtgtca ccgcctttat cactgggaga tggcacacgg tggcagcctc    5100
caacctcaag ctggtgcaaa ccagatcagc tagacaagat aacaatgttt gtccaagata    5160
aagggaagct attgttgact accatgatcc agcaagttgc caaatactag gggccagttc    5220
ttttgttggc ttccaaaata agctgccccc tatctagctt tttctaaaag cccaaccaaa    5280
ttaatttttt agaagcttac taattaagac ttgatagtag gcttctaaaa agtatttttg    5340
gttgggcttc tagaataagc tgggtagggg gccgcttatt ctagaagccc aaaaaaccac    5400
taaaagaact gaccctaatt gtcatgagat ttattaagtc caaagctcga tggaagtgac    5460
tagattaatt gtttgttcct aaattcatgg gcggatgcca tgggtgaagg caaagtaagt    5520
ttaactatat acttaacact agttatctaa taagttaatg ctactagcta tttgttgata    5580
tcatgataat atttagactg aattatatta tggagtgtaa aatttcacaa tatttcagca    5640
gcggcacccc ggatattaag atcctaggtc cttcaccgcc ttaattaata tcaattcccc    5700
tgaacaagtt attacttggt tgttccatct tgta                               5734
```

<210> SEQ ID NO 82
<211> LENGTH: 639
<212> TYPE: DNA
<213> ORGANISM: Triticum monococcum

<400> SEQUENCE: 82

```
atgtccatgt catgcggttt gtgcggcgca agcgactgcc cgcaccacat gatctcgccc      60
gttcttcagc atcaggaaca acactggctg cgcgagtacc agttcttcac ccaaggccac     120
caccaccacc accacggcgc ggcggcggac tacccaccgc caccgccacc gtcggccaat     180
tgccaccact gcagatcatg gaccacaccg tttcatgaaa cagcagctgc agggaacagc     240
agcagactca cgctggaggt agatgcaggc ggccaaaaca tggctcacct gctgcagcca     300
ccggcacggc aagaaccac catcgtgcca ttctgcgggg ctgcattcac cagcactatt      360
agcaatgcaa caatcatgac tattgataca gagatgatgg tggggctgc ccataatctg      420 acgatgcagg agagagaggc gaaggtgatg aggtacagga gaagaggaa gaggcggtgc      480 tatgacaagc aaatccgcta cgagtccaga aaagcttacg ccgagctcag gccacgggtc     540
aatggctgct ttgtcaaggt accagaagcc gctgcatcgt cgtcaccccc agcttcgccc     600
tatgatccta gtaaacttca cctcggatgg ttccagtag                            639
```

<210> SEQ ID NO 83
<211> LENGTH: 212
<212> TYPE: PRT
<213> ORGANISM: Triticum monococcum

<400> SEQUENCE: 83

```
Met Ser Met Ser Cys Gly Leu Cys Gly Ala Ser Asp Cys Pro His His
 1               5                   10                  15

Met Ile Ser Pro Val Leu Gln His Gln Glu Gln His Trp Leu Arg Glu
            20                  25                  30

Tyr Gln Phe Phe Thr Gln Gly His His His His His Gly Ala Ala
        35                  40                  45

Ala Asp Tyr Pro Pro Pro Pro Ser Ala Asn Cys His His Cys
    50                  55                  60

Arg Ser Trp Thr Thr Pro Phe His Glu Thr Ala Ala Ala Gly Asn Ser
65                  70                  75                  80

Ser Arg Leu Thr Leu Glu Val Asp Ala Gly Gly Gln Asn Met Ala His
                85                  90                  95

Leu Leu Gln Pro Pro Ala Arg Pro Arg Thr Thr Ile Val Pro Phe Cys
            100                 105                 110

Gly Ala Ala Phe Thr Ser Thr Ile Ser Asn Ala Thr Ile Met Thr Ile
        115                 120                 125

Asp Thr Glu Met Met Val Gly Ala Ala His Asn Leu Thr Met Gln Glu
    130                 135                 140

Arg Glu Ala Lys Val Met Arg Tyr Arg Glu Lys Arg Lys Arg Arg Cys
145                 150                 155                 160

Tyr Asp Lys Gln Ile Arg Tyr Glu Ser Arg Lys Ala Tyr Ala Glu Leu
                165                 170                 175

Arg Pro Arg Val Asn Gly Cys Phe Val Lys Val Pro Glu Ala Ala Ala
            180                 185                 190

Ser Ser Ser Pro Pro Ala Ser Pro Tyr Asp Pro Ser Lys Leu His Leu
        195                 200                 205

Gly Trp Phe Gln
    210
```

<210> SEQ ID NO 84
<211> LENGTH: 3454
<212> TYPE: DNA
<213> ORGANISM: Triticum dicoccoides

<400> SEQUENCE: 84

-continued

```
tgttttgtta ggtatggcgt gccggctgtg ctcccccctg ttgaaagaaa tgttgtcccc      60
atcctgcccc ctggcgatgt gctcaccacc gatggagggt gtgtgttttt gtgtctccgt     120
cgatgggtct tctgggatcc ggtcggttta ggtttcccat ggattcgccc gaattcggcc     180
agctttcgtg atcttcagag tttctacaag tccttatcga cgttctcttc tctggggtgg     240
cggtttgctt tgcggatcac agtctcgccg acgtctcttg gtctgcgtcg acgagttcct     300
actcgttgcc tctgcaagct cctgggtttc aaaaaaggtt tgctacatca aggcggagac     360
ccaaagacag caccgagctt tcatagtgcg ccgccgatgt atgcatgacg aagaagactt     420
cggcacccct aaagttttga ttgtaatttt tcttttgtata tgggtgtatt tgtaaggtcc    480
tatgattctt aatatatggt tttaagcctc tttgccaaaa aaaaaagttc aacacccatc     540
acattactat ttttacgatg aagagtgttt ttgttaactt aaaatgtagc gtcaaatgga     600
tacagagcat gatgagcaac acgcggcctt tgcaatacca agtgtctgtc caaactaaaa     660
aaaactgaca tattgacaat gctaaagtca ataggacca acactacacc actaaatgtt      720
ccacaacttg tacttttctg tttagtattg ccatggtttc cattgtgttg tgtttgtctc     780
cctcggacct ttgtgttagc atctcctttt tgtttgacag tgaccaaaaa agctacaaat     840
atctagcagt ggccttgcgt ggacataaga tcatgtggga gattcccggc aagcaaggtg     900
tgcatggctc cagctcctcc gcgtaagaaa gaaagaaata aaaatgaat cgaggggtag      960
tatctattcc gacgcactca ttagttgggc ctatttgatt tgatccatca tcttttgcta    1020
attctcagat cgaatctttt gcctggtctg cagctcactg ctgcatacat gcagtgcagt    1080
ggaggaggga gagacacaac acaaccctag ctatttcaag gtgccttagt agttagtact    1140
cgtcgttgtc tcttcttctt cctcgacatc tctcccctc cacgcaccaa accacaccag     1200
aaacaaacaa gcaagcaagc aaacgtagga gctagctgca gtatgcccat gtcatgcggt    1260
ttgtgcggcg caagcgactg cccgcaccac atgatctcgc ccgttcttca gcatcaggaa    1320
caacaccggc tgcgcgagta ccagttcttc acccaaggcc accaccacca ccaccacgac    1380
gcggcggcg actacccacc gccaccgcca ccgtcagcca attgccacca ctgcagatca     1440
tggaccacac cgtttcatga acagcagct gcagggaaca gcagcaggct cacgctggag     1500
gtagacgcag cggccaaaaa catggctcac ctgctgcagc caccggcacg gccaagaacc    1560
accatcgtga gtagtactac tgcttaattg ttccagctct tgccgatcgc ttgggcctcc    1620
ttctaacaaa agttcccttt tacgtaatct ccatctactc cccccccccc ccccccccgg    1680
catctcaaaa aaagttagcg ccatgtaacc agctcatata tctgtcacgt aattctgtta    1740
atttatgctg gttgaatata atctcccaag gcagagtgtt tgtgttttgt atcagttgat    1800
gcacaagaat gggcactcac atcatcagtt acacatacat acttatttca ttttatttga    1860
ctaacaaggt aatcagttaa ttcctttatg ggaacaagca atacatatgt ccacgccttc    1920
atgttaattc cttgacaaag tttgtgaaat ggacaatata tatactggat cagtgcacca    1980
tctttttcat tttatgtggt catttatgaa ttttagtgct attttgtatt taaaattttc    2040
tcttaagctt gttttgtaag cttatagctc aagtataaca gatactactc cccataattg    2100
cttccgtagt ggccgggtga tcaatctacc gagttcataa aactgatcga aatcagatcc    2160
aaaacagacc aaaacctcac gaaatagaaa caagatcctt gtttaattag tttgcaccag    2220
gaaattgcct acttaattac tttctatcaa tcttatgaag atggtatgtt tctcacatat    2280
ggtgatccag atcacaattg ttgacggagt taaacatttt tagcaattca taaaaccgtg    2340
```

-continued

```
cacagatgta cagggctacg cgtatgcaca tacataatac acctaattaa aacatatatt    2400
catagagcga ttgagtttgg actgtgcgct tctttggaca caaaggcccg ggaagttgtt    2460
ctcttccatt gtctagaaaa atagaacagt tacaatcaag tgcaccactg aatgaaaatg    2520
ggtcaattct ggttaataag agaccaactg tacttcataa acaggaaata tcatgtacat    2580
atctgcaacc cacaggaaaa gtacagaact gcactcttac gattattttc ctcttcatgt    2640
tcaggtgcca ttctgcgggg ctgcattcac cagcactatt agcaatgcaa cgatcatgac    2700
tattgataca gagatgatgg tgggggctgc ccataatctg acgatgcagg agagagaggc    2760
gaaggtgatg aggtacaggg agaagaggaa gaggcggtgc tatgacaagc aaatccgcta    2820
tgagtccaga aaagcttacg ccgagctcag gccacgggtc aatggccgct tgtcaaggt     2880 accagaagcc gctgcatcgt cgtcaccccc agcttcgccc tatgatccta gtaaacttca    2940
cctcggatgg ttccggtagt ttttcatcaa agtaaaataa gttggttatt gtttgaccga    3000
tgggaggagt tatgttgatt tgactatttc aaaaggtcag cagaccaatc aaagaaaatg    3060
tatttgttga aacaagtatt gttatgcttt atgttaattt aagcatgtag tttgaggagg    3120
ctagctactt agatgtgttt attgtatgca accaattgaa tcaagtcatc accaactcaa    3180
agttaaatac ggacaagctt tttatgtata agttgttat tttatcttga cgacttatca    3240
agagtgaaaa atggattggg agttatgagt aaaccatcac gaccgccaaa gatgtacaat    3300 gcttatttg agagagaaaa attatatttc actcaccaaa tatgagttga accttgtaac     3360
cacatgtata ttacaaagct gtgtgtcacc taactaattt gaggccttat cataggtaaa    3420
atacctccaa tctgcacgaa tgaggcactt taaa                                3454
```

<210> SEQ ID NO 85
<211> LENGTH: 639
<212> TYPE: DNA
<213> ORGANISM: Triticum dicoccoides

<400> SEQUENCE: 85

```
atgcccatgt catgcggttt gtgcggcgca agcgactgcc cgcaccacat gatctcgccc      60
gttcttcagc atcaggaaca acaccggctg cgcgagtacc agttcttcac ccaaggccac     120
caccaccacc accacgacgc ggcggcggac tacccaccgc caccgccacc gtcagccaat     180
tgccaccact gcagatcatg gaccacaccg tttcatgaaa cagcagctgc agggaacagc     240
agcaggctca cgctggaggt agacgcaggc ggccaaaaca tggctcacct gctgcagcca     300
ccggcacggc caagaaccac catcgtgcca ttctgcgggg ctgcattcac cagcactatt     360
agcaatgcaa cgatcatgac tattgataca gagatgatgg tgggggctgc ccataatctg     420
acgatgcagg agagagaggc gaaggtgatg aggtacaggg agaagaggaa gaggcggtgc     480
tatgacaagc aaatccgcta tgagtccaga aaagcttacg ccgagctcag gccacgggtc     540
aatggccgct tgtcaaggt accagaagcc gctgcatcgt cgtcaccccc agcttcgccc     600
tatgatccta gtaaacttca cctcggatgg ttccggtag                            639
```

<210> SEQ ID NO 86
<211> LENGTH: 212
<212> TYPE: PRT
<213> ORGANISM: Triticum dicoccoides

<400> SEQUENCE: 86

```
Met Pro Met Ser Cys Gly Leu Cys Gly Ala Ser Asp Cys Pro His His
 1               5                   10                  15
```

```
Met Ile Ser Pro Val Leu Gln His Gln Glu Gln His Arg Leu Arg Glu
             20                  25                  30

Tyr Gln Phe Phe Thr Gln Gly His His His His Asp Ala Ala
         35                  40                  45

Ala Asp Tyr Pro Pro Pro Pro Ser Ala Asn Cys His His Cys
 50                  55                  60

Arg Ser Trp Thr Thr Pro Phe His Glu Thr Ala Ala Gly Asn Ser
65                   70                  75                  80

Ser Arg Leu Thr Leu Glu Val Asp Ala Gly Gly Gln Asn Met Ala His
             85                  90                  95

Leu Leu Gln Pro Pro Ala Arg Pro Arg Thr Thr Ile Val Pro Phe Cys
            100                 105                 110

Gly Ala Ala Phe Thr Ser Thr Ile Ser Asn Ala Thr Ile Met Thr Ile
            115                 120                 125

Asp Thr Glu Met Met Val Gly Ala Ala His Asn Leu Thr Met Gln Glu
130                 135                 140

Arg Glu Ala Lys Val Met Arg Tyr Arg Glu Lys Arg Lys Arg Arg Cys
145                 150                 155                 160

Tyr Asp Lys Gln Ile Arg Tyr Glu Ser Arg Lys Ala Tyr Ala Glu Leu
                165                 170                 175

Arg Pro Arg Val Asn Gly Arg Phe Val Lys Val Pro Glu Ala Ala Ala
            180                 185                 190

Ser Ser Ser Pro Pro Ala Ser Pro Tyr Asp Pro Ser Lys Leu His Leu
            195                 200                 205

Gly Trp Phe Arg
    210

<210> SEQ ID NO 87
<211> LENGTH: 1985
<212> TYPE: DNA
<213> ORGANISM: Hordeum vulgare

<400> SEQUENCE: 87
cctccgcgta aggaagaaat aaatcaaaaa tgcatcgagg gaccgtatct attccgacgc      60
gctcattagt tgggcctatt tgatttgatt tgatccatcg ttttttgctaa ttctcaggtc     120 gaatcttttg tttggcctgc agctcagtgc tgcatatatg cagtgcagtg cagtgcagga     180
gggagagaca caatacagcc ctagcttctt caaggtgtta gtagctagca ctcatcgctg     240
tctcttcttc ttcctcgaca tctctcttcc acgcaccaga ccacaccaga aacaaacaaa     300
ctagcaaaca agcaaacgtt ggagttagct gcagtatgtc catgtcatgt ggtttgtgcg     360
gcgccagcaa ctgcgcgtac cacatgatgt cgcccgttct tcttcatcat caccatcatc     420
aggaacaccc actgcacgag taccagttct tcgcccaagg tcaccaccac caccacagcg     480
cggcagcgga ctacccacca ccaccgccac cgccagacaa ttgccaccac cacagatcat     540
ggaccacgcc gtttcatgaa acagcagctc cagagaacag caccaggctc acacgggagg     600
tggacgcagg cggccaacac atggctcacc tgctgcagcc accggcgccg ccaagagcca     660
ccatcgtgag tagtactact gcttaatttt tctatctctt gccgatcgat gggacctgct     720
aacaaaaatc acactttctt aatttccatc tcaaaaaaag ctaccgccat gtgaccagct     780
catatatatg ccacataact ccttaatttt attctggtcg attgtaattt accaaggcag     840
aaagcttgta ttttgtatca gttgatgcac aagaatgggc gctcacgtca tcagtcgcac     900
atactatata cttatttcat tttatttgac taacaaggta actagttaat tccttatgg     960
```

-continued

```
ggtcaagcaa tacatatgtg cacgccttca tgttaattcc ttgacaaagt ttgtgaagtg    1020
gaaaatatat ttactttatc aatgcaccta ctctcatttt atgtggtcat ttatgaattt    1080
tattaatttt ctgttgagct agttttgtat gcttatagct catatataac tgatactact    1140
ccccataatt tttccgtagt ggtcgggtga tcgatctacc tagttcataa acttatcgag    1200
atcaggtcca aaacagacca aaacctcacg aaatggaaac aagatccttg tttaattagt    1260
ttgcatcagg aaattgctta ttacttgctg tcaatcttat gaagatggta ttttcctcac    1320
aaatggatcc agtcacaatt gttgatgaag ttaaacattt ttggcaattc ataaaaccgt    1380
gcatagatgt ccggctacac gcacacaagt acataataca cctagttaaa acatatatcc    1440
atagagcaat tgagtttgga ctatgcgctt cattggacac aaaggcccgg aagttgttc     1500 tcttccattg tctaaaaaaa tagaacagtt acagtcaagt gcaacactga atgaaaatgg    1560
atcaagtttt ggttaacaag agaccaactt atacttcata acaaggaat atcaagtaca     1620 tatctgctac ccacaagaaa agtacacctt atgactattt tcttcttgat gttcaggtgc    1680
cattctgcga gagtgcattc gccagcacta ttagcaacgc aacgatcatg actattgata    1740
cagaaatgat ggtggggcct gcctataatc aacgatgca ggagagagag gcgaaggtga     1800
tgaggtacag ggagaagagg aagaggcggc gctatgacaa gcaaatccgc tacgagtcca    1860
gaaaagctta cgccgagctc aggccacggg tcaatggccg ctttgccaag gtgcccgaag    1920
ccgttgtgtc tccatcaccc ccaacttccc cccatgatcc tagtaaactt cacctcggat    1980
ggttc                                                                1985
```

<210> SEQ ID NO 88
<211> LENGTH: 639
<212> TYPE: DNA
<213> ORGANISM: Hordeum vulgare

<400> SEQUENCE: 88

```
atgtccatgt catgtggttt gtgcggcgcc agcaactgcg cgtaccacat gatgtcgccc      60
gttcttcttc atcatcacca tcatcaggaa cacccactgc acgagtacca gttcttcgcc     120
caaggtcacc accaccacca cagcgcggca gcggactacc accaccacc gccaccgcca      180 gacaattgcc accaccacag atcatggacc acgccgtttc atgaaacagc agctccagag     240
aacagcacca ggctcacacg ggaggtggac gcaggcggcc aacacatggc tcacctgctg     300
cagccaccgg cgccgccaag agccaccatc gtgccattct gcgagagtgc attcgccagc     360
actattagca acgcaacgat catgactatt gatacagaaa tgatggtggg gcctgcctat     420
aatccaacga tgcaggagag agaggcgaag gtgatgaggt acaggagaa gaggaagagg      480 cggcgctatg acaagcaaat ccgctacgag tccagaaaag cttacgccga gctcaggcca     540
cgggtcaatg gccgctttgc caaggtgccc gaagccgttg tgtctccatc accccaact      600 tcccccatg atcctagtaa acttcacctc ggatggttc                              639
```

<210> SEQ ID NO 89
<211> LENGTH: 213
<212> TYPE: PRT
<213> ORGANISM: Hordeum vulgare

<400> SEQUENCE: 89

```
Met Ser Met Ser Cys Gly Leu Cys Gly Ala Ser Asn Cys Ala Tyr His
  1               5                  10                  15

Met Met Ser Pro Val Leu Leu His His His His Gln Glu His Pro
                 20                  25                  30
```

Leu His Glu Tyr Gln Phe Phe Ala Gln Gly His His His His Ser
    35                  40                  45

Ala Ala Ala Asp Tyr Pro Pro Pro Pro Pro Pro Asp Asn Cys His
    50                  55                  60

His His Arg Ser Trp Thr Thr Pro Phe His Glu Thr Ala Ala Pro Glu
65                  70                  75                  80

Asn Ser Thr Arg Leu Thr Arg Glu Val Asp Ala Gly Gly Gln His Met
                85                  90                  95

Ala His Leu Leu Gln Pro Pro Ala Pro Pro Arg Ala Thr Ile Val Pro
            100                 105                 110

Phe Cys Glu Ser Ala Phe Ala Ser Thr Ile Ser Asn Ala Thr Ile Met
            115                 120                 125

Thr Ile Asp Thr Glu Met Met Val Gly Pro Ala Tyr Asn Pro Thr Met
        130                 135                 140

Gln Glu Arg Glu Ala Lys Val Met Arg Tyr Arg Glu Lys Arg Lys Arg
145                 150                 155                 160

Arg Arg Tyr Asp Lys Gln Ile Arg Tyr Glu Ser Arg Lys Ala Tyr Ala
                165                 170                 175

Glu Leu Arg Pro Arg Val Asn Gly Arg Phe Ala Lys Val Pro Glu Ala
            180                 185                 190

Val Val Ser Pro Ser Pro Pro Thr Ser Pro His Asp Pro Ser Lys Leu
            195                 200                 205

His Leu Gly Trp Phe
    210

<210> SEQ ID NO 90
<211> LENGTH: 2043
<212> TYPE: DNA
<213> ORGANISM: Hordeum vulgare
<220> FEATURE:
<221> NAME/KEY: misc_feature
<222> LOCATION: 1105, 1156, 1190, 1197, 1209, 1237, 1238, 1239, 1240,
      1241, 1242, 1243, 1244, 1245, 1246, 1247, 1248, 1249, 1250, 1251,
      1252, 1253, 1254, 1255, 1256, 1257, 1258, 1259, 1260, 1261, 1262,
      1263, 1264, 1265, 1294, 1300, 1313, 1326, 1340
<223> OTHER INFORMATION: n = A,T,C or G
<220> FEATURE:
<221> NAME/KEY: misc_feature
<222> LOCATION: 1359, 1385
<223> OTHER INFORMATION: n = A,T,C or G

<400> SEQUENCE: 90
tcaaatattc tagcagtggc cttgcgtgga cataagatca tgtggtagat tcccggcaag      60
caaggtgtgc atggctccaa ctcctccgcg taaggaagaa ataaatcaaa aatgcatcga     120
gggaccgtat ctattccgac gcactcatta gttggattta tctgatttga ttttatccat    180
cgtcttttgc taattctcag atcgaatctt ttgtctggtc tgcagctcac tgctgcatat    240
atgcagtgca gtgcaggagg gagagacaca atacagccct agcttcttca aggtgcttta    300
gtagctagca ctcatcgctg tctcttcttc ttcctcgaca tctctcttcc acgcaccaga    360
ccacaccaga aacaaacaga caagcaagca agcaagcaaa cgttggagct agctgcagta    420
tgtccatggc atgcggtttg tgcggcgcca gcaattgccc gtatcacatg atgtcgcccg    480
ttcttcttca tcatcaccat catcaggaac atcggcagcg cgagtaccag ttcttcgccc    540
aaggtcacca ccaccaccac cacggcgcgg cagcagacta cccaccgcca cagccaccgc    600
cggccaattg ccaccaccgc agatcatggg ccacgctgtt tcatgaaaca gcagctccag    660
tgaatagcac caggctcaca caagaggtgg acgcaggcgg ccaacagatg gctcacctgc    720

```
tgcagccacc ggcgccgcca agagccacca tcgtgagtac tactgcttaa tcgttccatc    780
tcttcccgat cgatgtgact ccttctaaca aaaatcacac tttcttaatt tccatctcaa    840
aaaaagctag cgccatgtga ccagctcata tatctgtcac ataactccgt taatttatgc    900
tggtcgattg taatttacca aggcagaaag tttgtgtttt gtatcagttg atgcacaaga    960
ctggatgctc agatcatcag tcacacatac tatatattta tttcatttta tttgactaac   1020
aaggtaatca gttaattcct ttatggggtc aagcaacata tgtccacgcc ttcatgttaa   1080
ttccttggca gagtttgtga aatanaagat atatattggg atcaatgcac cctacctctt   1140
tctcatttta tgtggncatt taaaaatttg aatgctattt tgtatttaan tttctcntga   1200
gctagttgng aagcttatag ctcaatttaa ctggaannnn nnnnnnnnnn nnnnnnnnnn   1260
nnnnncgagt tcatgaaact gatcaagatc agtncaaaan aggccaaacc tcncgaaatg   1320
gaattncgat ccttgttaan tagtttgcat caggaaatng gctacttaat tacttgctac   1380
caatnttatg aagatggcat gtttcctcac aaatggatcc agctcacaat ttttggtgaa   1440
gttaaacatt tttagcaatt cataaaaggt gcatagatgt acagggctac acgtacacac   1500
gcacataata cgcctagtta aaacatatat gcatagagca attgagtttg acaatgcgc    1560 ttctttggac ataatggccc gggaaattgt tctcttccat tgtctaaaaa catgaacag    1620 ttagaatcaa gtgcaccact gaatgagaat gggtcaattt ttggttaacg agagaccaac   1680
tatacgttat aaaacactgta ctactctcac cattgttttc ctctcgatgt tcaggtgcca   1740
ttccgccgga gtgcattcac caacactatt agcaacgcaa cgatcatgac tattgataca   1800
gagatgatgg cggggactgc ctatagtcca cgatgcagg aaagagaagc aaaggtgatg    1860
aggtacaggg agaagaggaa gaagcggcgc tatgacaagc aaatccgcta cgagtccaga   1920
aaagcttacg ccgagcttag gccacgggtc aacggccgct tgtcaaggt acctgaagcc    1980 gctgcgtcac catcacccccc agcttcgccc catgatccta gtgaacttca cctcggatgg   2040
ttc                                                                 2043
```

<210> SEQ ID NO 91
<211> LENGTH: 642
<212> TYPE: DNA
<213> ORGANISM: Hordeum vulgare

<400> SEQUENCE: 91

```
atgtccatgg catgcggttt gtgcggcgcc agcaattgcc cgtatcacat gatgtcgccc      60
gttcttcttc atcatcacca tcatcaggaa catcggcagc gcgagtacca gttcttcgcc     120
caaggtcacc accaccacca ccacggcgcg gcagcagact acccaccgcc acagccaccg     180
ccggccaatt gccaccaccg cagatcatgg gccacgctgt tcatgaaac agcagctcca     240 gtgaatagca ccaggctcac acaagaggtg gacgcaggcg ccaacagat ggctcacctg      300 ctgcagccac cggcgccgcc aagagccacc atcgtgccat tccgccggag tgcattcacc     360
aacactatta gcaacgcaac gatcatgact attgatacag atgatggc ggggactgcc      420 tatagtccaa cgatgcagga agagaagca aggtgatga ggtacaggga gaagaggaag       480
aagcggcgct atgacaagca aatccgctac gagtccagaa aagcttacgc cgagcttagg     540
ccacgggtca acggccgctt gtcaaggta cctgaagccg ctgcgtcacc atcacccca      600 gcttcgcccc atgatcctag tgaacttcac ctcggatggt tc                        642
```

<210> SEQ ID NO 92

<211> LENGTH: 214
<212> TYPE: PRT
<213> ORGANISM: Hordeum vulgare

<400> SEQUENCE: 92

Met Ser Met Ala Cys Gly Leu Cys Gly Ala Ser Asn Cys Pro Tyr His
1               5                   10                  15

Met Met Ser Pro Val Leu Leu His His His His Gln Glu His Arg
            20                  25                  30

Gln Arg Glu Tyr Gln Phe Phe Ala Gln Gly His His His His His
        35                  40                  45

Gly Ala Ala Asp Tyr Pro Pro Gln Pro Pro Ala Asn Cys
    50                  55                  60

His His Arg Arg Ser Trp Ala Thr Leu Phe His Glu Thr Ala Ala Pro
65                  70                  75                  80

Val Asn Ser Thr Arg Leu Thr Gln Glu Val Asp Ala Gly Gly Gln Gln
                85                  90                  95

Met Ala His Leu Leu Gln Pro Pro Ala Pro Pro Arg Ala Thr Ile Val
            100                 105                 110

Pro Phe Arg Arg Ser Ala Phe Thr Asn Thr Ile Ser Asn Ala Thr Ile
        115                 120                 125

Met Thr Ile Asp Thr Glu Met Met Ala Gly Thr Ala Tyr Ser Pro Thr
130                 135                 140

Met Gln Glu Arg Glu Ala Lys Val Met Arg Tyr Arg Glu Lys Arg Lys
145                 150                 155                 160

Lys Arg Arg Tyr Asp Lys Gln Ile Arg Tyr Glu Ser Arg Lys Ala Tyr
                165                 170                 175

Ala Glu Leu Arg Pro Arg Val Asn Gly Arg Phe Val Lys Val Pro Glu
            180                 185                 190

Ala Ala Ala Ser Pro Ser Pro Pro Ala Ser Pro His Asp Pro Ser Glu
        195                 200                 205

Leu His Leu Gly Trp Phe
    210

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93
ccaacacatg gctcacctag tg                                            22

<210> SEQ ID NO 94
<211> LENGTH: 25
<212> TYPE: DNA
<213> ORGANISM: Artificial Sequence
<220> FEATURE:
<223> OTHER INFORMATION: Primer

<400> SEQUENCE: 94
aaatggcacg atgtgggctc ttgcc                                         25

<210> SEQ ID NO 95
<211> LENGTH: 25
<212> TYPE: DNA
<213> ORGANISM: Artificial Sequence
<220> FEATURE:
<223> OTHER INFORMATION: Primer

```
<400> SEQUENCE: 95
ttgcttcatt gctaatagtg ttggt                                     25

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
ccaccactgc agatcatgga                                           20

<210> SEQ ID NO 97
<211> LENGTH: 26
<212> TYPE: DNA
<213> ORGANISM: Artificial Sequence
<220> FEATURE:
<223> OTHER INFORMATION: Primer

<400> SEQUENCE: 97
ccaagaacca ccatcgtgcc attctg                                    26

<210> SEQ ID NO 98
<211> LENGTH: 23
<212> TYPE: DNA
<213> ORGANISM: Artificial Sequence
<220> FEATURE:
<223> OTHER INFORMATION: Primer

<400> SEQUENCE: 98
ttgctaatag tgctggtgaa tgc                                       23

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
ggctccaatc gatcaatcac                                           20

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
ttcttcctcg acgtctctcc                                           20

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
tgaggcgcgg gcagttgttg                                           20

<210> SEQ ID NO 102
```

```
<211> LENGTH: 20
<212> TYPE: DNA
<213> ORGANISM: Artificial Sequence
<220> FEATURE:
<223> OTHER INFORMATION: Primer

<400> SEQUENCE: 102
ggttaagctt gggggagaag                                             20

<210> SEQ ID NO 103
<211> LENGTH: 20
<212> TYPE: DNA
<213> ORGANISM: Artificial Sequence
<220> FEATURE:
<223> OTHER INFORMATION: Primer

<400> SEQUENCE: 103
gttgagtggc cctgtttctc                                             20

<210> SEQ ID NO 104
<211> LENGTH: 22
<212> TYPE: DNA
<213> ORGANISM: Artificial Sequence
<220> FEATURE:
<223> OTHER INFORMATION: Primer

<400> SEQUENCE: 104
cattgatcag cctaaccaaa ca                                          22

<210> SEQ ID NO 105
<211> LENGTH: 22
<212> TYPE: DNA
<213> ORGANISM: Artificial Sequence
<220> FEATURE:
<223> OTHER INFORMATION: Primer

<400> SEQUENCE: 105
caaattctaa tccccaatcc aa                                          22

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
ggcggtaagg atctgagcta                                             20

<210> SEQ ID NO 107
<211> LENGTH: 21
<212> TYPE: DNA
<213> ORGANISM: Artificial Sequence
<220> FEATURE:
<223> OTHER INFORMATION: Primer

<400> SEQUENCE: 107
agtgggtcta gagtcctgct t                                           21

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
```

```
ggcggtaagg atctgagcta                                               20

<210> SEQ ID NO 109
<211> LENGTH: 217
<212> TYPE: DNA
<213> ORGANISM: Triticum monococcum

<400> SEQUENCE: 109
atccctttaa aaacccctcc ccccctgccg aatcctcgt tttggcctgg ccatcctccc    60
tctcctcccc tctcttccac ctcacgtcct cacccaacca cctgatagcc atggctccgc   120
cgcctcgcct ccgcctgcgc cagtcggagt agccgtcgcg gtctgcgggt gttggagggt   180
aggggcgtag ggttggcccg gttctcgagc ggagatg                            217

<210> SEQ ID NO 110
<211> LENGTH: 210
<212> TYPE: DNA
<213> ORGANISM: Triticum monococcum

<400> SEQUENCE: 110
atccctttaa aaacccctcc ccccacttgc cggaaacctc gttttggcct ggccatcctc    60
cctctcctcc ctctcttccg cctcacccaa ccacctgaca gccatggctc cgccccccg    120 ccccgcctg cgcctgtcgg agtagccgtc gcggtctgcc ggtgttggag gcttggggtg    180
tagggttggc cccgttctcc agcggagatg                                    210

<210> SEQ ID NO 111
<211> LENGTH: 201
<212> TYPE: DNA
<213> ORGANISM: Triticum monococcum

<400> SEQUENCE: 111
atccctttaa aaacccctcc ccccctgccg gaaccctcgt tttggcctgg ccatcctccc    60
tctcctcccc ctctcttcca accacctgac agccatggct ccgccccctc gcctccgcct   120
gcgcctgtcg gagtagccgt cgcggtctgc cggtgttgga gggtaggggc gtagggttgg   180
cccggttctc gagcggagat g                                             201

<210> SEQ ID NO 112
<211> LENGTH: 357
<212> TYPE: DNA
<213> ORGANISM: Triticum monococcum

<400> SEQUENCE: 112
atccctttaa aaaccggaaa aaaattatat gagaccaggt ctcatataaa tcaggtgaga    60
cccgccctga tgaatgacat gtggcattca caaatcacaa agcatctaat ctctccccc    120 ctgatttcag gtgggggtg ttttccttaa aaacccctcc ccccctgccg gaatcctcgt    180
tttggcctgg ccatcctccc tctcctcccc tctcttccac ctcacgtcct cacccaacca   240
cctgatagcc atggctccgc cgcctcgcct ccgcctgcgc cagtcggagt agccgtcgcg   300
gtctgcgggt gttggagggt aggggcgtag ggttggcccg gttctcgagc ggagatg      357

<210> SEQ ID NO 113
<211> LENGTH: 269
<212> TYPE: DNA
<213> ORGANISM: Triticum monococcum

<400> SEQUENCE: 113
```

```
atcccttta aaaccggaaa aaaattctat gagaccaggt ctcatagaat ttttttcctt      60
aaaaacccct ccccccctgc cggaatcctc gttttggcct ggccatcctc cctctcctcc    120
cctctcttcc acctcacgtc ctcacccaac cacctgatag ccatggctcc gccgcctcgc    180
ctccgcctgc gccagtcgga gtagccgtcg cggtctgcgg gtgttggagg gtaggggcgt    240
agggttggcc cggttctcga gcggagatg                                      269
```

<210> SEQ ID NO 114
<211> LENGTH: 195
<212> TYPE: DNA
<213> ORGANISM: Triticum monococcum

<400> SEQUENCE: 114

```
atcccttaaa atccccccc ccctgccgga atcctcgttt tggcctggcc atcctcacct      60
cacgtcctca cccaaccacc tgatagccat ggctccgccg cctcgcctcc gcctgcgcca    120
gtcggagtag ccgtcgcggt ctgcgggtgt tggagggtag gggcgtaggg ttggcccggt    180
tctcgagcgg agatg                                                     195
```

<210> SEQ ID NO 115
<211> LENGTH: 165
<212> TYPE: DNA
<213> ORGANISM: Triticum monococcum

<400> SEQUENCE: 115

```
atcctcgttt tggcctggcc atcctcacct cacgtcctca cccaaccacc tgatagccat      60
ggctccgccg cctcgcctcc gcctgcgcca gtcggagtag ccgtcgcggt ctgcgggtgt    120
tggagggtag gggcgtaggg ttggcccggt tctcgagcgg agatg                    165
```

<210> SEQ ID NO 116
<211> LENGTH: 161
<212> TYPE: DNA
<213> ORGANISM: Triticum monococcum

<400> SEQUENCE: 116

```
atccctttaa aaacccctcc ccccccctgc cggacccctc gttttggcct ggccatcctc      60
cctctcctcc cctctcttcc acctcaccca accaccccgt cgcggtctgc cggtgttgga    120
gggtaggggc gtagggttgg cccggttttc gagcggagat g                        161
```

<210> SEQ ID NO 117
<211> LENGTH: 44
<212> TYPE: PRT
<213> ORGANISM: Triticum monococcum

<400> SEQUENCE: 117

```
Glu Arg Ala Ala Lys Val Met Arg Tyr Arg Glu Lys Arg Lys Arg Arg
 1               5                  10                  15

Arg Tyr Asp Lys Gln Ile Arg Tyr Glu Ser Arg Lys Ala Tyr Ala Glu
            20                  25                  30

Leu Arg Pro Trp Val Asn Gly Arg Phe Val Lys Val
        35                  40
```

<210> SEQ ID NO 118
<211> LENGTH: 44
<212> TYPE: PRT
<213> ORGANISM: Triticum monococcum

<400> SEQUENCE: 118

-continued

Glu Arg Ala Ala Lys Val Met Arg Tyr Arg Glu Lys Arg Lys Arg Arg
1               5                   10                  15

Arg Tyr Asp Lys Gln Ile Arg Tyr Glu Ser Arg Lys Ala Tyr Ala Glu
            20                  25                  30

Leu Arg Pro Arg Val Asn Gly Arg Phe Val Lys Val
        35                  40

<210> SEQ ID NO 119
<211> LENGTH: 44
<212> TYPE: PRT
<213> ORGANISM: Triticum dicoccoides

<400> SEQUENCE: 119

Glu Arg Ala Ala Lys Val Met Arg Tyr Arg Glu Lys Arg Lys Arg Arg
1               5                   10                  15

Arg Tyr Asp Lys Gln Ile Arg Tyr Glu Ser Arg Lys Ala Tyr Ala Glu
            20                  25                  30

Leu Arg Pro Arg Val Asn Gly Cys Phe Val Lys Val
        35                  40

<210> SEQ ID NO 120
<211> LENGTH: 44
<212> TYPE: PRT
<213> ORGANISM: Triticum monococcum

<400> SEQUENCE: 120

Glu Arg Glu Ala Lys Val Met Arg Tyr Arg Lys Arg Lys Arg Arg
1               5                   10                  15

Cys Tyr Asp Lys Gln Ile Arg Tyr Glu Ser Arg Lys Ala Tyr Ala Glu
            20                  25                  30

Leu Arg Pro Arg Val Asn Gly Cys Phe Val Lys Val
        35                  40

<210> SEQ ID NO 121
<211> LENGTH: 44
<212> TYPE: PRT
<213> ORGANISM: Triticum dicoccoides

<400> SEQUENCE: 121

Glu Arg Glu Ala Lys Val Met Arg Tyr Arg Lys Arg Lys Arg Arg
1               5                   10                  15

Cys Tyr Asp Lys Gln Ile Arg Tyr Glu Ser Arg Lys Ala Tyr Ala Glu
            20                  25                  30

Leu Arg Pro Arg Val Asn Gly Arg Phe Val Lys Val
        35                  40

<210> SEQ ID NO 122
<211> LENGTH: 44
<212> TYPE: PRT
<213> ORGANISM: Hordeum vulgare

<400> SEQUENCE: 122

Glu Arg Glu Ala Lys Val Met Arg Tyr Arg Lys Arg Lys Lys Arg
1               5                   10                  15

Arg Tyr Asp Lys Gln Ile Arg Tyr Glu Ser Arg Lys Ala Tyr Ala Glu
            20                  25                  30

Leu Arg Pro Arg Val Asn Gly Arg Phe Val Lys Val
        35                  40

<210> SEQ ID NO 123

```
<211> LENGTH: 44
<212> TYPE: PRT
<213> ORGANISM: Hordeum vulgare

<400> SEQUENCE: 123

Glu Arg Glu Ala Lys Val Met Arg Tyr Arg Glu Lys Arg Lys Arg Arg
 1               5                  10                  15

Arg Tyr Asp Lys Gln Ile Arg Tyr Glu Ser Arg Lys Ala Tyr Ala Glu
                20                  25                  30

Leu Arg Pro Arg Val Asn Gly Arg Phe Ala Lys Val
            35                  40

<210> SEQ ID NO 124
<211> LENGTH: 44
<212> TYPE: PRT
<213> ORGANISM: Oryza sativa

<400> SEQUENCE: 124

Glu Arg Glu Ala Lys Leu Met Arg Tyr Lys Glu Lys Arg Lys Lys Arg
 1               5                  10                  15

Cys Tyr Glu Lys Gln Ile Arg Tyr Ala Ser Arg Lys Ala Tyr Ala Glu
                20                  25                  30

Met Arg Pro Arg Val Arg Gly Arg Phe Ala Lys Glu
            35                  40

<210> SEQ ID NO 125
<211> LENGTH: 44
<212> TYPE: PRT
<213> ORGANISM: Hordeum vulgare

<400> SEQUENCE: 125

Leu Arg Glu Ala Lys Leu Met Arg Tyr Lys Glu Lys Arg Lys Arg Arg
 1               5                  10                  15

Arg Tyr Glu Lys Gln Ile Arg Tyr Ala Ser Arg Lys Ala Tyr Ala Glu
                20                  25                  30

Met Arg Pro Arg Val Lys Gly Arg Phe Ala Lys Val
            35                  40

<210> SEQ ID NO 126
<211> LENGTH: 43
<212> TYPE: PRT
<213> ORGANISM: Oryza sativa

<400> SEQUENCE: 126

Asp Arg Glu Ala Lys Val Met Arg Tyr Lys Glu Lys Arg Lys Arg Arg
 1               5                  10                  15

Arg Tyr Glu Lys Gln Ile Arg Tyr Ala Ser Arg Lys Ala Tyr Ala Glu
                20                  25                  30

Met Arg Pro Arg Val Lys Gly Arg Phe Ala Lys
            35                  40

<210> SEQ ID NO 127
<211> LENGTH: 44
<212> TYPE: PRT
<213> ORGANISM: Arabidopsis thaliana

<400> SEQUENCE: 127

Asp Arg Glu Ala Arg Val Leu Arg Tyr Arg Glu Lys Arg Lys Thr Arg
 1               5                  10                  15

Lys Phe Glu Lys Thr Ile Arg Tyr Ala Ser Arg Lys Ala Tyr Ala Glu
                20                  25                  30
```

```
Ile Arg Pro Arg Val Asn Gly Arg Phe Ala Lys Arg
        35                  40
```

<210> SEQ ID NO 128
<211> LENGTH: 44
<212> TYPE: PRT
<213> ORGANISM: Oryza sativa

<400> SEQUENCE: 128

```
Asp Arg Glu Ala Arg Val Leu Arg Tyr Arg Glu Lys Lys Ala Arg
1               5                   10                  15

Lys Phe Glu Lys Thr Ile Arg Tyr Glu Thr Arg Lys Ala Tyr Ala Glu
                20                  25                  30

Ala Arg Pro Arg Ile Lys Gly Arg Phe Ala Lys Arg
        35                  40
```

<210> SEQ ID NO 129
<211> LENGTH: 44
<212> TYPE: PRT
<213> ORGANISM: Hordeum vulgare

<400> SEQUENCE: 129

```
Glu Arg Glu Ala Arg Val Leu Arg Tyr Lys Glu Lys Lys Ser Arg
1               5                   10                  15

Lys Phe Glu Lys Thr Thr Arg Tyr Ala Thr Arg Lys Ala Tyr Ala Glu
                20                  25                  30

Ala Arg Pro Arg Ile Lys Gly Arg Phe Ala Lys Arg
        35                  40
```

<210> SEQ ID NO 130
<211> LENGTH: 44
<212> TYPE: PRT
<213> ORGANISM: Hordeum vulgare

<400> SEQUENCE: 130

```
Asp Arg Glu Ala Arg Val His Arg Tyr Arg Glu Lys Arg Lys Met Arg
1               5                   10                  15

Arg Phe Glu Lys Thr Ile Arg Tyr Ala Ser Arg Lys Ala Tyr Ala Glu
                20                  25                  30

Thr Arg Pro Arg Ile Lys Gly Arg Phe Ala Lys Arg
        35                  40
```

<210> SEQ ID NO 131
<211> LENGTH: 44
<212> TYPE: PRT
<213> ORGANISM: Oryza sativa

<400> SEQUENCE: 131

```
Asp Arg Glu Ala Arg Val His Arg Tyr Arg Glu Lys Arg Lys Thr Arg
1               5                   10                  15

Arg Phe Glu Lys Thr Ile Arg Tyr Ala Ser Arg Lys Ala Tyr Ala Glu
                20                  25                  30

Thr Arg Pro Arg Ile Lys Gly Arg Phe Ala Lys Arg
        35                  40
```

<210> SEQ ID NO 132
<211> LENGTH: 44
<212> TYPE: PRT
<213> ORGANISM: Hordeum vulgare

<400> SEQUENCE: 132

Glu Arg Glu Ala Arg Leu Met Arg Tyr Arg Glu Lys Arg Lys Ser Arg
1               5                   10                  15

Arg Phe Glu Lys Thr Ile Arg Tyr Ala Ser Arg Lys Ala Tyr Ala Glu
            20                  25                  30

Thr Arg Pro Arg Val Lys Gly Arg Phe Ala Lys Arg
        35                  40

<210> SEQ ID NO 133
<211> LENGTH: 44
<212> TYPE: PRT
<213> ORGANISM: Oryza sativa

<400> SEQUENCE: 133

Glu Arg Glu Ala Arg Leu Met Arg Tyr Arg Glu Lys Arg Lys Ser Arg
1               5                   10                  15

Arg Phe Glu Lys Thr Ile Arg Tyr Ala Ser Arg Lys Ala Tyr Ala Glu
            20                  25                  30

Thr Arg Pro Arg Ile Lys Gly Arg Phe Ala Lys Arg
        35                  40

<210> SEQ ID NO 134
<211> LENGTH: 44
<212> TYPE: PRT
<213> ORGANISM: Arabidopsis thaliana

<400> SEQUENCE: 134

Glu Arg Glu Ala Arg Val Leu Arg Tyr Arg Glu Lys Arg Lys Asn Arg
1               5                   10                  15

Lys Phe Glu Lys Thr Ile Arg Tyr Ala Ser Arg Lys Ala Tyr Ala Glu
            20                  25                  30

Met Arg Pro Arg Ile Lys Gly Arg Phe Ala Lys Arg
        35                  40

<210> SEQ ID NO 135
<211> LENGTH: 44
<212> TYPE: PRT
<213> ORGANISM: Hordeum vulgare

<400> SEQUENCE: 135

Gly Arg Glu Ala Arg Leu Met Arg Tyr Arg Glu Lys Arg Lys Asn Arg
1               5                   10                  15

Arg Phe Glu Lys Thr Ile Arg Tyr Ala Ser Arg Lys Ala Tyr Ala Glu
            20                  25                  30

Ser Arg Pro Arg Val Lys Gly Arg Phe Ala Lys Arg
        35                  40

<210> SEQ ID NO 136
<211> LENGTH: 44
<212> TYPE: PRT
<213> ORGANISM: Oryza sativa

<400> SEQUENCE: 136

Gly Arg Ala Ala Arg Leu Met Arg Tyr Arg Glu Lys Arg Lys Asn Arg
1               5                   10                  15

Arg Phe Glu Lys Thr Ile Arg Tyr Ala Ser Arg Lys Ala Tyr Ala Glu
            20                  25                  30

Thr Arg Pro Arg Val Lys Gly Arg Phe Ala Lys Arg
        35                  40

<210> SEQ ID NO 137
<211> LENGTH: 44
<212> TYPE: PRT
<213> ORGANISM: Hordeum vulgare

<400> SEQUENCE: 137

Asp Gly Ala Ala Arg Val Met Arg Tyr Arg Glu Lys Arg Lys Asn Arg
1               5                   10                  15

Lys Phe His Lys Thr Ile Arg Tyr Ala Ser Arg Lys Ala Tyr Ala Glu
            20                  25                  30

Ala Arg Pro Arg Leu Lys Gly Arg Phe Val Lys Arg
        35                  40

<210> SEQ ID NO 138
<211> LENGTH: 44
<212> TYPE: PRT
<213> ORGANISM: Oryza sativa

<400> SEQUENCE: 138

Ala Arg Glu Glu Arg Val Met Arg Tyr Arg Glu Lys Arg Lys Asn Arg
1               5                   10                  15

Lys Phe His Lys Thr Ile Arg Tyr Ala Ser Arg Lys Ala Tyr Ala Glu
            20                  25                  30

Ala Arg Pro Arg Leu Lys Gly Arg Phe Val Lys Arg
        35                  40

<210> SEQ ID NO 139
<211> LENGTH: 44
<212> TYPE: PRT
<213> ORGANISM: Arabidopsis thaliana

<400> SEQUENCE: 139

Gly Arg Glu Ala Arg Val Ser Arg Tyr Arg Glu Lys Arg Arg Thr Arg
1               5                   10                  15

Leu Phe Ser Lys Lys Ile Arg Tyr Glu Val Arg Lys Leu Asn Ala Glu
            20                  25                  30

Lys Arg Pro Arg Met Lys Gly Arg Phe Val Lys Arg
        35                  40

<210> SEQ ID NO 140
<211> LENGTH: 44
<212> TYPE: PRT
<213> ORGANISM: Oryza sativa

<400> SEQUENCE: 140

Glu Arg Glu Ala Arg Val Ser Arg Tyr Arg Glu Lys Arg Arg Thr Arg
1               5                   10                  15

Leu Phe Ala Lys Lys Ile Arg Tyr Glu Val Arg Lys Leu Asn Ala Glu
            20                  25                  30

Lys Arg Pro Arg Met Lys Gly Arg Phe Val Lys Arg
        35                  40

<210> SEQ ID NO 141
<211> LENGTH: 44
<212> TYPE: PRT
<213> ORGANISM: Arabidopsis thaliana

<400> SEQUENCE: 141

Thr Arg Asn Asn Ala Val Met Arg Tyr Lys Glu Lys Lys Lys Ala Arg
1               5                   10                  15

Lys Phe Asp Lys Arg Val Arg Tyr Ala Ser Arg Lys Ala Arg Ala Asp

```
                20                  25                  30
Val Arg Arg Arg Val Lys Gly Arg Phe Val Lys Ala
             35                  40

<210> SEQ ID NO 142
<211> LENGTH: 44
<212> TYPE: PRT
<213> ORGANISM: Oryza sativa

<400> SEQUENCE: 142

Ser Arg Asp Asn Ala Leu Thr Arg Tyr Lys Glu Lys Lys Arg Arg
 1               5                  10                  15

Lys Phe Asp Lys Lys Ile Arg Tyr Ala Ser Arg Lys Ala Arg Ala Asp
             20                  25                  30

Val Arg Lys Arg Val Lys Gly Arg Phe Val Lys Ala
             35                  40

<210> SEQ ID NO 143
<211> LENGTH: 33
<212> TYPE: PRT
<213> ORGANISM: Triticum dicoccoides

<400> SEQUENCE: 143

Met Ser Met Ser Cys Gly Leu Cys Gly Ala Asn Asn Cys Pro Arg Leu
 1               5                  10                  15

Met Val Ser Pro Ile His His Arg His His His Gln Glu His Gln
             20                  25                  30

Leu

<210> SEQ ID NO 144
<211> LENGTH: 33
<212> TYPE: PRT
<213> ORGANISM: Triticum monococcum

<400> SEQUENCE: 144

Met Ser Met Ser Cys Gly Leu Cys Gly Ala Asn Asn Cys Pro Arg Leu
 1               5                  10                  15

Met Val Ser Pro Ile His His His His His His Gln Glu His Gln
             20                  25                  30

Leu

<210> SEQ ID NO 145
<211> LENGTH: 33
<212> TYPE: PRT
<213> ORGANISM: Triticum monococcum

<400> SEQUENCE: 145

Met Ser Met Ser Cys Gly Leu Cys Gly Ala Asn Asn Cys Pro Arg Leu
 1               5                  10                  15

Met Val Ser Pro Ile His His His His His His Gln Glu His Gln
             20                  25                  30

Leu

<210> SEQ ID NO 146
<211> LENGTH: 33
<212> TYPE: PRT
<213> ORGANISM: Hordeum vulgare

<400> SEQUENCE: 146

Met Ser Met Ala Cys Gly Leu Cys Gly Ala Ser Asn Cys Pro Tyr His
```

-continued

```
                1               5                  10                 15
Met Met Ser Pro Val Leu Leu His His His His Gln Glu His Arg
                20                 25                 30
Gln
```

<210> SEQ ID NO 147
<211> LENGTH: 33
<212> TYPE: PRT
<213> ORGANISM: Hordeum vulgare

<400> SEQUENCE: 147

```
Met Ser Met Ser Cys Gly Leu Cys Gly Ala Ser Asn Cys Ala Tyr His
1               5                  10                 15
Met Met Ser Pro Val Leu Leu His His His His Gln Glu His Pro
                20                 25                 30
Leu
```

<210> SEQ ID NO 148
<211> LENGTH: 33
<212> TYPE: PRT
<213> ORGANISM: Triticum dicoccoides

<400> SEQUENCE: 148

```
Met Ser Met Ser Cys Gly Leu Cys Gly Ala Ser Asn Cys Pro His His
1               5                  10                 15
Met Ile Ser Pro Val Leu Gln His Gln His His Gln Glu His Arg
                20                 25                 30
Leu
```

<210> SEQ ID NO 149
<211> LENGTH: 33
<212> TYPE: PRT
<213> ORGANISM: Triticum monococcum

<400> SEQUENCE: 149

```
Met Ser Met Ser Cys Gly Leu Cys Gly Ala Ser Asp Cys Pro His His
1               5                  10                 15
Met Ile Ser Pro Val Leu Gln His Gln Glu Gln His Trp Leu Arg Glu
                20                 25                 30
Tyr
```

<210> SEQ ID NO 150
<211> LENGTH: 33
<212> TYPE: PRT
<213> ORGANISM: Triticum dicoccoides

<400> SEQUENCE: 150

```
Met Pro Met Ser Cys Gly Leu Cys Gly Ala Ser Asp Cys Pro His His
1               5                  10                 15
Met Ile Ser Pro Val Leu Gln His Gln Glu Gln His Arg Leu Arg Glu
                20                 25                 30
Tyr
```

<210> SEQ ID NO 151
<211> LENGTH: 57
<212> TYPE: PRT
<213> ORGANISM: Oryza sativa

<400> SEQUENCE: 151

```
Met Gly Met Ala Asn Glu Glu Ser Pro Asn Tyr Gln Val Lys Lys Gly
1               5                   10                  15

Gly Arg Ile Pro Pro Arg Ser Ser Leu Ile Tyr Pro Phe Met Ser Met
            20                  25                  30

Gly Pro Ala Ala Gly Glu Gly Cys Gly Leu Cys Gly Ala Asp Gly Gly
                35                  40                  45

Gly Cys Cys Ser Arg His Arg His Asp
    50                  55

<210> SEQ ID NO 152
<211> LENGTH: 28
<212> TYPE: PRT
<213> ORGANISM: Oryza sativa

<400> SEQUENCE: 152

Met Ser Ala Ala Ser Gly Ala Ala Cys Gly Val Cys Gly Gly Gly Val
1               5                   10                  15

Gly Glu Cys Gly Cys Leu Leu His Gln Arg Arg Gly
            20                  25

<210> SEQ ID NO 153
<211> LENGTH: 49
<212> TYPE: PRT
<213> ORGANISM: Hordeum vulgare

<400> SEQUENCE: 153

Met Asn Cys Val Ser Asn Gly Thr Val Tyr Glu Glu Ala Val Gly Arg
1               5                   10                  15

Glu Gly Arg Trp Ala Arg Leu Cys Asp Gly Cys Cys Thr Val Pro Ser
            20                  25                  30

Val Val Tyr Cys Arg Ala Asp Ser Ala Tyr Leu Cys Ala Ser Cys Asp
                35                  40                  45

Ala

<210> SEQ ID NO 154
<211> LENGTH: 52
<212> TYPE: PRT
<213> ORGANISM: Hordeum vulgare

<400> SEQUENCE: 154

Met Ile Lys Ala Glu Pro Asp Leu Arg Gly Gln Leu Arg Gly Ser Ala
1               5                   10                  15

Gly Val Gly Gly Met Gln Leu Gln Gln Arg Cys Asp Ser Cys Arg Ser
            20                  25                  30

Ala Pro Cys Ala Phe Tyr Cys Arg Ala Asp Ser Ala Ala Leu Cys Ala
                35                  40                  45

Ala Cys Asp Ala
    50

<210> SEQ ID NO 155
<211> LENGTH: 46
<212> TYPE: PRT
<213> ORGANISM: Hordeum vulgare

<400> SEQUENCE: 155

Met Glu Gly Glu Glu Lys Pro Val Val Gly Ala Tyr Trp Gly Val
1               5                   10                  15

Gly Ala Arg Ala Cys Asp Ser Cys Ala Thr Glu Ala Ala Arg Leu Phe
            20                  25                  30
```

```
Cys Arg Ala Asp Ala Ala Phe Leu Cys Ala Gly Cys Asp Ala
             35                  40                  45

<210> SEQ ID NO 156
<211> LENGTH: 40
<212> TYPE: PRT
<213> ORGANISM: Hordeum vulgare

<400> SEQUENCE: 156

Arg Ala His Gly Ser Gly Ser Arg His Ala Arg Val Trp Leu Cys Glu
 1               5                  10                  15

Val Cys Glu His Ala Pro Ala Ala Val Thr Cys Lys Ala Asp Ala Ala
                20                  25                  30

Val Leu Cys Ala Ser Cys Asp Ala
             35                  40

<210> SEQ ID NO 157
<211> LENGTH: 45
<212> TYPE: PRT
<213> ORGANISM: Oryza sativa

<400> SEQUENCE: 157

Met Ala Ser Ala Ala Ala Ala Thr Gly Ala Ala Leu Gly Ala Arg Thr
 1               5                  10                  15

Ala Arg Ala Cys Asp Gly Cys Met Arg Arg Arg Ala Arg Trp His Cys
                20                  25                  30

Pro Ala Asp Asp Ala Phe Leu Cys Gln Ala Cys Asp Ala
             35                  40                  45

<210> SEQ ID NO 158
<211> LENGTH: 54
<212> TYPE: PRT
<213> ORGANISM: Oryza sativa

<400> SEQUENCE: 158

Met Asp Ala Leu Cys Asp Phe Cys Arg Glu Gln Arg Ser Met Val Tyr
 1               5                  10                  15

Cys Arg Ser Asp Ala Ala Ser Leu Cys Leu Ser Cys Asp Arg Asn Val
                20                  25                  30

His Ser Ala Asn Ala Leu Ser Arg Arg His Thr Arg Thr Leu Leu Cys
             35                  40                  45

Asp Arg Cys Val Gly Gln
          50

<210> SEQ ID NO 159
<211> LENGTH: 43
<212> TYPE: PRT
<213> ORGANISM: Oryza sativa

<400> SEQUENCE: 159

Pro Ala Ala Val Arg Cys Leu Glu Glu Asn Thr Ser Leu Cys Gln Asn
 1               5                  10                  15

Cys Asp Trp Asn Gly His Gly Ala Ala Ser Ala Ala Gly His Lys
                20                  25                  30

Arg Gln Thr Ile Asn Cys Tyr Ser Gly Cys Pro
             35                  40
```